(12) United States Patent
Oertel

(10) Patent No.: US 8,471,063 B2
(45) Date of Patent: Jun. 25, 2013

(54) MICHAEL SYSTEMS AS TRANSGLUTAMINASE INHIBITORS

(75) Inventor: Kai Oertel, Frankfurt (DE)

(73) Assignee: Zedira GmbH, Darmstadt (DE)

( * ) Notice: Subject to any disclaimer, the term of this patent is extended or adjusted under 35 U.S.C. 154(b) by 749 days.

(21) Appl. No.: 12/513,476

(22) PCT Filed: Nov. 8, 2007

(86) PCT No.: PCT/DE2007/002014
§ 371 (c)(1),
(2), (4) Date: Feb. 4, 2010

(87) PCT Pub. No.: WO2008/055488
PCT Pub. Date: May 15, 2008

(65) Prior Publication Data
US 2011/0229568 A1  Sep. 22, 2011

Related U.S. Application Data

(60) Provisional application No. 60/874,246, filed on Dec. 12, 2006.

(30) Foreign Application Priority Data

Nov. 8, 2006  (DE) .......................... 10 2006 052 755

(51) Int. Cl.
*A61K 31/16* (2006.01)
(52) U.S. Cl.
USPC .......................................... 564/123; 514/1.1
(58) Field of Classification Search
USPC ....................................................... 564/123
See application file for complete search history.

(56) References Cited

U.S. PATENT DOCUMENTS
2006/0035838 A1   2/2006   Khosla et al.

FOREIGN PATENT DOCUMENTS
WO    90/06937    6/1990

OTHER PUBLICATIONS

Lazarova et al., J. Med. Chem. (2003), 46, 674-676.*
International Preliminary Report on Patentability issued for PCT application PCT/DE2007/002014.
Search Report issued for PCT application PCT/DE2007/002014.
Paris et al. "Post-synthesis modification of aspartyl or glutamyl residue side-chains on solid support" Tetrahedron Letters 40 (1999) 5179-5182.
Lazarova et al "Synthesis and biological evaluation of novel cyclosporin A analogues: Potential soft drugs for the treatment of autoimmune diseases", Journal of Medicinal Chemistry vol. 46, No. 5, Feb. 27, 2003, pp. 674-676.
Meinke et al: "Synthesis of side chain modified apicidin derivatives: Potent mechanism based histone deacetylase inhibitors" Tetrahedron Letters vol. 41, No. 41, Oct. 7, 2000, pp. 7831-7835.
Marrano et al "Evaluation of novel dipeptide bound alpha, beta-unsaturated amides and epoxides as irreversible inhibitors of guinea pig liver transglutaminase" Bioorganic & Medicinal Chemistry vol. 9, No. 7, Jul. 2001, pp. 1923-1928.
De Macedo et al "Synthesis of dipeptide bound epoxides and alpha, beta-unsaturated amides as potential irreversible transglutaminase inhibitors" Bioorganic & Medicinal Chemistry, vol. 10, No. 2, Feb. 2002, pp. 355-360.
Bycroft et al "Convenient syntheses of (3S,5S)-carbapenam-3-carboxylates and their biosynthetic relevance" Tetrahedron Letters vol. 44, No. 5, Jan. 27, 2003, pp. 973-976.
Wei et al "A regioselective tandem reduction—Wittig-Horner reaction involving the [alpha] ester moiety of diethyl aspartate or glutamate" Tetrahedron Letters vol. 35, No. 15, 1994, pp. 2305-2308.
Doyle et al. "Peptides incorporating electrophilic glutamine analogues as potential transglutaminase inhibitors" Biochemical Society Transactions, vol. 18, No. 6, Dec. 1990.
Barton et al. "Synthesis of Novel α-Amino Acids and Derivatives Using Radical Chemistry: Synthesis of L- and D-α-Amino Adipic Acids, L-α-Aminopimelic Acid and Appropriate Unsaturated Derivatives" Tetrahedron 1987, 43, 19, 4297-4308.
CAS RN 240436-49-1; Sep. 1999.
CAS RN 603127-32-8, Oct. 2003.
Diaper et al. "The Stereoselective Synthesis of Aziridine Analogues of Diaminopimelic Acid (DAP) and Their Interaction with DAP Epimerase"—Organic & Biomol. Chem. 2005, 3, 4402-4411.
Dunn et al. "Synthesis of Enatiomerically Pure Unsaturated α-Amino Acids Using Serine-Derived Zinc/Copper Reagents" JOC 1995, 60, 2210-2215.
Hernandez et al. "A New Selective Cleavage of N,N-Dicarbamoyl-Protected Amines Using Lithium Bromide" JOC 2003, 68, 743-746.
Jackson et al., "Stereospecific Allylation of a Serine-derived Zinc/Copper Reagent. Synthesis of Substituted Pipecolic Acid Derivatives" Synlett 1997, 7, 789-790.
Moloney et al. "trans-2,5-Disubstituted Pyrrolidines: Rapid Stereocontrolled Access from Sulfones" Organic & Biomol. Chem. 2006, 4, 3894-3897.
Shono et al. "Electro-organic Chemistry. Part 80. α-Hydroxylation of N-Acylated Cyclic Amines and Utilization of the Products as Amino-aldehyde Equivalents", J. Chem. Res., Synopses 1984, 10, 320-321.
Sutherland et al. "Unsaturated α-Aminopimelic Acids as Potent Inhibitors of meso-Diaminopimelic Acid (DAP) D-Dehydrogenase" Chem. Commun. 1999, 555-556.

* cited by examiner

Primary Examiner — Karlheinz R Skowronek
Assistant Examiner — Catherine Mader
(74) Attorney, Agent, or Firm — Meyertons, Hood, Kivlin, Kowert & Goetzel, P.C.; Eric B. Meyertons

(57) ABSTRACT

Described herein are peptide derivatives and peptidomimetics as inhibitors for transglutaminases, methods for their preparation, pharmaceutical compositions containing said compounds as well as uses of said transglutaminase inhibitors in particular for the treatment of coeliac disease and transglutaminase dependent diseases.

9 Claims, 18 Drawing Sheets

MICHAEL SYSTEMS AS TRANSGLUTAMINASE INHIBITORS

BACKGROUND OF THE INVENTION

1. Field of the Invention

The invention relates to peptide derivatives and peptidomimetics as inhibitors of transglutaminases, methods for the preparation thereof, pharmaceutical compositions containing said compounds as well as to the use of said transglutaminase inhibitors.

2. Description of the Relevant Art

Transglutaminases are part of the class of transferases and according to EC nomenclature they are correctly designated as "protein-glutamine amine γ-glutamyl transferases" and the EC number EC 2.3.2.13. was assigned to them.

The ε-amino group of the amino acid lysine and the γ-glutamyl group of the amino acid glutamine is linked by them while ammonia is released and an isopeptide bond is formed.

Transglutaminases play an important role in the stabilization of the extracellular matrix (e.g. Aeschlimann and Paulsson, Thromb. Haemostasis, 71, pp. 402-415, 1994) and in programmed cell death (apoptosis) in mammal cells (e.g. Fesus et al., FEBS Lett., 284, pp. 109-11, 1991).

Additionally, transglutaminases play an important role in many therapeutic areas such as the cardiovascular field (thrombosis), autoimmune diseases (coeliac disease, Duhring's disease), neurodegenerative diseases (Alzheimer's disease, Parkinson's disease, Huntington's disease), dermatological diseases (ichthyosis, psoriasis, acne) as well as in wound healing and inflammatory diseases (tissue fibrosis) (J. M. Wodzinska, Mini-Reviews in medical chemistry, 2005, 5, 279-292).

Coeliac disease, a gluten intolerance, however, is one of the most important indications. Coeliac disease is characterized by a chronic inflammation of the mucosa of the small intestine. In patients concerned, the intestine epithelium is successively destroyed after ingestion of gluten-containing food resulting in reduced absorption of nutrients which again has massive impact on the patients concerned and is associated with symptoms such as loss of weight, anemia, diarrhea, nausea, loss of appetite and fatigue. Due to these findings, there is a large demand for the development of inhibitors of said enzymes.

SUMMARY OF THE INVENTION

Described herein are new inhibitors of transglutaminases, pharmaceutical formulations containing said inhibitors and methods for the synthesis of said inhibitors. Furthermore, new uses for said inhibitors are presented.

Said objective is realized by the technical teaching of the independent claims. Further advantageous embodiments, aspects and details of the invention result from the dependent claims, the description and the examples.

Surprisingly, it has been found that compounds and particularly peptide derivatives and peptide-like structures, such as peptidomimetics having at least one acceptor-substituted double bond, are particularly useful inhibitors of transglutaminases. Preferably, such acceptor-substituted double bonds are Michael systems (MS) from a carbonyl function (C=O) and a carbon-carbon double bond (C=C) conjugated therewith, consequently a Michael acceptor system of the C=C—C=O type. In general, however, a conjugated system is not required. Compounds having at least one olefinic double bond, wherein the double bond carries at least one electron-withdrawing group, are perfectly suited transglutaminase inhibitors. Said compounds having acceptor-substituted double bonds or respectively Michael systems are likely to be suicide inhibitors, binding irreversibly to the transglutaminases. Furthermore, it is preferred that the acceptor-substituted double bond is bound to a backbone via an ethylene group (—C$_2$H$_4$—) or a carbonylethylene group (—CO—C$_2$H$_4$—), wherein said backbone preferably has a peptidic, peptide-like or peptidomimetic structure. The inventive residue of the backbone has the following structure:

acceptor-substituted double bond —C$_2$H$_4$— backbone or acceptor-substituted double bond —CO—C$_2$H$_4$— backbone The term "acceptor-substituted double bond" designates a double bond which is conjugated with an electron-withdrawing group (as e.g. C=O, C=S, P=O, P=S, N=O, S=O, N=N, C≡N) and is able to make a nucleophilic addition with nucleophiles as well as to form a covalent bond with atoms like oxygen, sulfur and nitrogen.

TG1, TG2, TG3, TG4, TG5, TG6, TG7 and FXIII or FXIIIa, respectively, are classified among the human transglutaminases. Additionally, non-human transglutaminases may be targets of interest in anti-parasite treatments.

Therefore, the compounds suitable as transglutaminase inhibitors can be described by the following general structure [TGI1]:

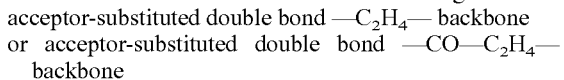

acceptor-substituted double bond-(CO)$_m$—C$_2$H$_4$-backbone wherein
m can equal to 0 or 1 and
the acceptor-substituted double bond has at least one electron-withdrawing residue able to conjugate, preferably with an electronegativity $\geq 2.20$, further preferred $\geq 2.50$, particularly preferred $\geq 2.80$, and
the backbone is a peptide or peptidomimetic formed by at least two amino acids or at least a dipeptidomimetic and/or the backbone has at least one amide bond. The backbone will also be designated herein as residue A.

Another embodiment applies therefore to compounds according to the general formula [TGI1] as pharmaceuticals as well as their use in medicine.

The acceptor-substituted double bond will also be designated as follows:

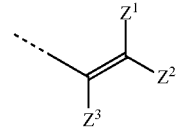

whereas at least one of the substituents $Z^1$, $Z^2$ and $Z^3$ is an electron-withdrawing residue able to conjugate and whereas two out of the three substituents $Z^1$, $Z^2$ and $Z^3$ can be hydrogen or any other electron-drawing or electron-releasing residue. Thus the general formula [TGI2] of transglutaminase inhibitors can also be presented as follows:

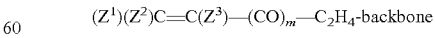

$(Z^1)(Z^2)C=C(Z^3)$—$(CO)_m$—C$_2$H$_4$-backbone whereas m and $Z^1$, $Z^2$ and $Z^3$ have the meaning described herein and whereas, however, at least one of the three moieties $Z^1$, $Z^2$ and $Z^3$ is an electron-withdrawing residue able to conjugate.

If the acceptor-substituted double bond has two or three moieties—designed as $Z^1$, $Z^2$ and $Z^3$—which are not hydrogen it is preferred that the mean electronegativity of the two or three residues is ≧2.20, further preferred ≧2.40, particularly preferred ≧2.60. When assessing the electronegativity the linker to the backbone in form of an ethylene group or a carbonyl ethylene group is not taken into account.

The backbone is preferably a peptide of 2 to 20 amino acids wherein amino acids include also non-proteinogenic amino acids, or a peptidomimetic of 2 to 20 amino acids wherein preferably 1 to 10, further preferred 1 to 5 and particularly preferred 1 to 3 amino acid mimetics are included. Furthermore, the backbone has preferably 1 to 19, further preferred 1 to 10, still further preferred 1 to 6 and particularly 1 to 4 amide bonds.

The vinyl group substituted with at least one electron-drawing group or respectively the Michael acceptor system, seems to be a significant component of the transglutaminase inhibitors and, in combination with the peptidic or at least peptide-like backbone, it is responsible for the formation of potent transglutaminase inhibitors. Surprisingly, it has been found that said combination of a preferably peptidic, peptide-like or peptidomimetic backbone from, preferably, only few amino acids or amino acid derivatives or analogues in combination with the side group carrying the acceptor-substituted double bond have a higher activity and selectivity with respect to known inhibitors with Michael systems. Thus, not only the presence of a Michael acceptor system or respectively an acceptor-substituted double bond seems to be important, but also its precise structure. It has been proven to be advantageous that the side group with acceptor-substituted double bond or respectively Michael system is bioisosteric with respect to glutamine.

Peptides, peptide derivatives as well as peptidomimetics are suitable backbones for the at least one Michael system. The peptidic or peptide-like backbone may include 2 to 20 amino acids or mimetics for amino acids which are preferably linked to each other via peptide bonds or, for example, ester bonds, carbonate bonds, urethane linkages, carbamate linkages and/or urea linkages. The backbone carrying the Michael system should be provided with at least one carbonyl group vicinal to the carbon atom carrying the side chain with the Michael system.

As shown in the following structure, it was surprisingly found that for the inhibitory potence of the transglutaminase inhibitors seemingly three features are characteristic: First, the presence of an electrophilic acceptor-substituted double bond which additionally is bond to the backbone via an ethylene or a carbonyl ethylene linker and third, the backbone displays a peptide-like or proteinogenic structure.

The inventive group with acceptor-substituted double bond has the following general structure:

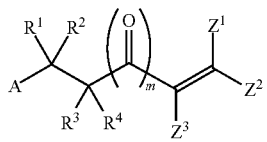

wherein the compound includes at least one acceptor-substituted olefin with the residues $Z^1$, $Z^2$ and $Z^3$, which olefin is bound to an at least secondarily substituted group A via an ethylene group with the residues $R^1$, $R^2$, $R^3$ and $R^4$ or via a carbonyl ethylene group with the residues $R^1$, $R^2$, $R^3$ and $R^4$, wherein A represents a peptide residue, a peptide derivative or a peptidomimetic residue;
m is 0 or 1;
the residues $Z^1$, $Z^2$, $Z^3$ independently of each other represent the following groups: —H, —CO—($C_1$-$C_6$ alkyl), —CO—$R^6$, —CO—$R^7$, —CO—($C_1$-$C_6$ halogenalkyl), —CO—($C_3$-$C_{10}$ heteroaryl), —CO—($C_6$-$C_{15}$ aryl), —COO—($C_1$-$C_6$ halogenalkyl), —COO—($C_3$-$C_{10}$ heteroaryl), —COO—($C_6$-$C_{15}$ aryl), —COO—($C_1$-$C_6$ alkyl), —COO—$R^8$, —COO—$R^9$, —CN, —COOH, —CO—NH($C_1$-$C_6$ alkyl), —CO—N($C_1$-$C_6$ alkyl)($C_1$-$C_6$ alkyl), —CO—$NR^{10}R^{11}$, —CO—$NH_2$, —CO—N($CR^{12}R^{13}R^{14}$)($CR^{15}R^{16}R^{17}$), —$NO_2$, —CS—($C_1$-$C_6$ alkyl), —CS—$R^{18}$, —CS—$R^{19}$, —CS—O—($C_1$-$C_6$ alkyl), —CS—O—$R^{20}$, —CS—O—$R^{21}$, —CS—N($C_1$-$C_6$ alkyl)($C_1$-$C_6$ alkyl), —CS—$NR^{22}R^{23}$, —CS—$NH_2$, —CS—N($CR^{24}R^{25}R^{26}$)($CR^{27}R^{28}R^{29}$), —SO—$R^{30}$, —SO—$R^{31}$, —$SO_2$—$R^{32}$, —$SO_2$—$R^{33}$, —SO—$CR^{34}R^{35}R^{36}$, —SO—$CR^{37}R^{38}R^{39}$, —$SO_2$—$CR^{40}R^{41}R^{42}$, —$SO_2$—$CR^{43}R^{44}R^{45}$, —SO—N($C_1$-$C_6$ alkyl)($C_1$-$C_6$ alkyl), —SO—$NR^{46}R^{47}$, —SO—$NH_2$, —SO—N($CR^{48}R^{49}R^{50}$)($CR^{51}R^{52}R^{53}$), —$SO_2$—N($C_1$-$C_6$-alkyl)($C_1$-$C_6$ alkyl), —$SO_2$—$NR^{54}R^{55}$, —$SO_2$—$NH_2$, —$SO_2$—N($CR^{56}R^{57}R^{58}$)($CR^{59}R^{60}R^{61}$), —$SO_2$—OH, —$SO_2$—$OR^{62}$, —$SO_2$—$CR^{63}R^{64}R^{65}$, —$SO_2$—$OCR^{66}R^{67}R^{68}$, —O—P(O)$(OH)_2$, —O—P(O)($OR^{69}$)($OR^{70}$), —O—P(O)(O—$C_1$-$C_6$-alkyl)(O—$C_1$-$C_6$-alkyl), —P(O)($OR^{71}$)($OR^{72}$), —P(O)(O—$C_1$-$C_6$ alkyl)(O—$C_1$-$C_6$ alkyl), —$CF_2$—P(O)($OR^{73}$)($OR^{74}$), —$CF_2$—P(O)(O—$C_1$-$C_6$ alkyl)(O—$C_1$-$C_6$ alkyl);
at least one of the residues $Z^1$, $Z^2$ and $Z^3$ is different from hydrogen,
the residues $Z^1$ and $Z^2$ together may also form a residue —CO—O—CO—$CH_2$— or —CO—O—$CH_2$—$CH_2$—,
the residues $Z^2$ and $Z^3$ together may also form a residue —CO—Z'—$CH_2$—, —CO—O—$CH_2$—, —CO—O—CO—, —CO—NH—CO— or —Z'—$CH_2$—$CH_2$— wherein Z' represents one of the following groups: —$CH_2$—, —$CF_2$—, —$C_2H_4$—, —$CF_2$—$CH_2$—, —$CH_2$—$CH_2$—, —O—, —O—$CH_2$—, —NH— or —NH—$CH_2$—;
and the residues $R^1$-$R^{74}$ independently of each other represent one of the groups described below.

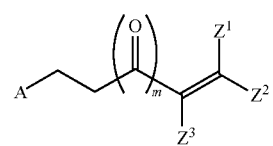

Formula [G]

Compounds, in which $R^1$, $R^2$, $R^3$ and $R^4$ represent hydrogen are preferred, which leads to the general formula [G], in which the residues A and $Z^1$ to $Z^3$ have the meaning indicated above and m is 0 or 1.

In the case that m=1 it is not mandatory that $Z^1$, $Z^2$ or $Z^3$ represent a group able to conjugate since already one carbonyl group is conjugated with the double bond. In such a case it is preferred that at least one of the residues $Z^1$, $Z^2$ or $Z^3$ represents an electron-drawing group. Preferred compounds are especially those where m=1 and at least one of the residues $Z^1$, $Z^2$ or $Z^3$, preferably $Z^1$ or $Z^2$, represent an additional group able to conjugate.

A preferred form of the acceptor-substituted double bond is a Michael system formed of a carbonyl function in conjugation with a double bond having the following general structure [A]:

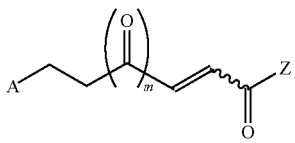

[A]

wherein

Z represents a hydroxy group, amino group, $C_1$-$C_6$ alkylamino group (—NH($C_1$-$C_6$ alkyl)), $C_1$-$C_6$ dialkylamino group (—N($C_1$-$C_6$ alkyl)($C_1$-$C_6$ alkyl)), $C_1$-$C_6$ alkoxy group (—O—($C_1$-$C_6$ alkyl)), $C_1$-$C_6$ alkyl group, $C_1$-$C_6$ halogenalkyl group, $C_3$-$C_{10}$ heteroaryl group or a $C_6$-$C_{15}$ aryl group.
m is 0 or 1; and
A represents the residue of the compound to which the Michael system is bound.

A is also the peptidic or the peptide-like backbone derived therefrom, wherein A, however, does not have to contain amino acids or peptide bonds, but may also include a carbon backbone optionally including heteroatoms, aromatic compounds, heteroaromatic compounds, heterocycles or carbocycles and can optionally contain amino acid analogues or peptide analogues. Residue A may include up to 30, preferably 20, heteroatoms such as N, S, O, P, F, Cl, Br, and up to 80, preferably up to 70, further preferred up to 60 and particularly preferred up to 50 carbon atoms which may be contained in linear, branched, saturated, unsaturated as well as substituted carbon chains and carbocycles or heterocycles.

Preferably, residue A includes a secondarily substituted atom, preferably a carbon atom to which the olefinic side chain is bound. Preferably, a carbonyl group (C=O) is bound to said preferably secondarily substituted carbon atom. The carbon atom of residue A, which atom carries the side chain, can also be substituted tertiarily and is preferably bound to three or four carbon atoms, wherein one of said carbon atoms is part of the side chain. Furthermore, the side chain may also be bound to a sulfur or nitrogen atom of residue A.

The zigzag line means that both isomeric forms (Z-isomer, E-isomer) are covered by the general formula [A], consequently both of the following isomers are included:

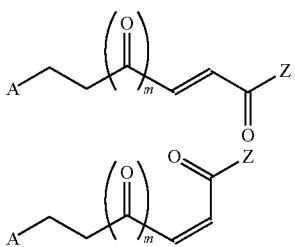

The term "$C_1$-$C_6$ alkyl group" used herein includes the following residues: —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(OH$_3$)$_2$—O$_2$H$_5$, —CH$_2$—C(CH$_3$)$_3$, —CH(C$_2$H$_5$)$_2$, —C$_6$H$_{13}$, —C$_2$H$_4$—CH(CH$_3$)$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —O$_2$H$_4$—C(CH$_3$)$_3$, —CH(CH$_3$)—C(CH$_3$)$_3$, -cyclo-C$_3$H$_5$, -cyclo-C$_4$H$_7$, -cyclo-C$_5$H$_9$ and -cyclo-C$_6$H$_{11}$.

The residues —CH$_3$, —O$_2$H$_5$, —C$_3$H$_7$, —CH(CH$_3$)$_{23}$— C$_4$H$_9$, —CH$_2$—CH(CH$_3$)$_2$, —CH(CH$_3$)—O$_2$H$_5$, —C(OH$_3$)$_3$, and —C$_5$H$_{11}$ are preferred. The residues —CH$_3$, —O$_2$H$_5$, —C$_3$H$_7$ and —CH(CH$_3$)$_2$ are particularly preferred.

The term $C_1$-$C_6$ alkoxy group refers to —O—($C_1$-$C_6$ alkyl group) and the term $C_1$-$C_6$ alkylamino group refers to —NH—($C_1$-$C_6$) alkyl group. The term $C_1$-$C_6$ dialkylamino group describes a —N[($C_1$-$C_6$ alkyl group)($C_1$-$C_6$ alkyl group)] group, wherein the two alkyl residues can be identical or different. —CH$_3$, —O$_2$H$_5$, —C$_3$H$_7$, —CH(CH$_3$)$_2$ and —C$_4$H$_9$ are preferred $C_1$-$C_6$ alkyl groups. —O—CH$_3$, —O—C$_2$H$_5$, —O—C$_3$H$_7$, —O—CH(CH$_3$)$_2$, —O—C(CH$_3$)$_3$ are particularly preferred.

The term $C_1$-$C_6$ halogenalkyl group refers to a $C_1$-$C_6$ alkyl group, in which one, two, three, four, five to all hydrogen atoms are replaced by halogen atoms (—F, —Cl, —Br, —I). The following are preferred: —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$.

The term $C_6$-$C_{15}$ aryl group preferably refers to groups such as a phenyl, tolyl, benzyl, styryl, dimethylphenyl, trimethylphenyl, dimethylbenzyl, trimethyl-benzyl or naphthyl group which can be substituted with up to 5 substituents selected from the group comprising the residues $R^6$-$R^{50}$. The substituents $R^6$ bis $R^{66}$ are as defined below.

Group Z can refer to the following residues: $CR^7R^8R^9$, $CR^{10}R^{11}$—$CR^{12}R^{13}R^{14}$, —$CR^{15}R^{16}$—$CR^{17}R^{18}$— $CR^{19}R^{20}R^{21}$, —O—$CR^{22}R^{23}R^{24}$, —O—$CR^{25}R^{26}$— $CR^{27}R^{28}R^{29}$, —O—$CR^{30}R^{31}$—$CR^{32}R^{33}$—$CR^{34}R^{35}R^{36}$, —NH—$CR^{37}R^{38}R^{39}$, —NH—$CR^{40}R^{41}CR^{42}R^{43}R^{44}$, —NH—$CR^{45}R^{46}$—$CR^{47}R^{48}$—$CR^{49}R^{50}R^{51}$ wherein the substituents $R^7$ to $R^{45}$ can be independently selected form the list below.

The term $C_3$-$C_{10}$ heteroaryl group refers to cyclic, bicyclic or tricyclic aromatic residues having at least three carbon atoms and at least one heteroatom, selected from nitrogen, oxygen and/or sulfur.

The following are preferred examples for $C_3$-$C_{10}$ heteroaryl groups:

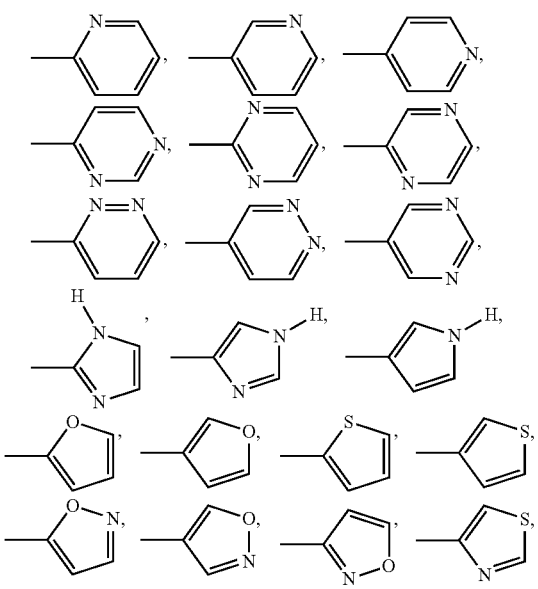

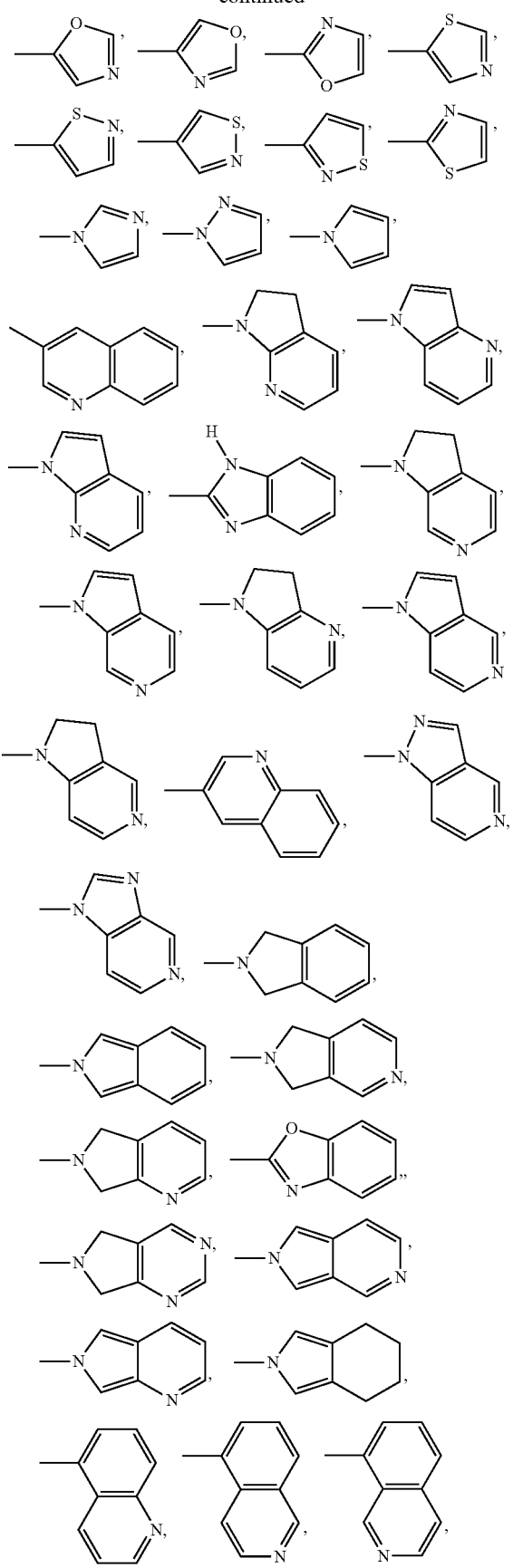
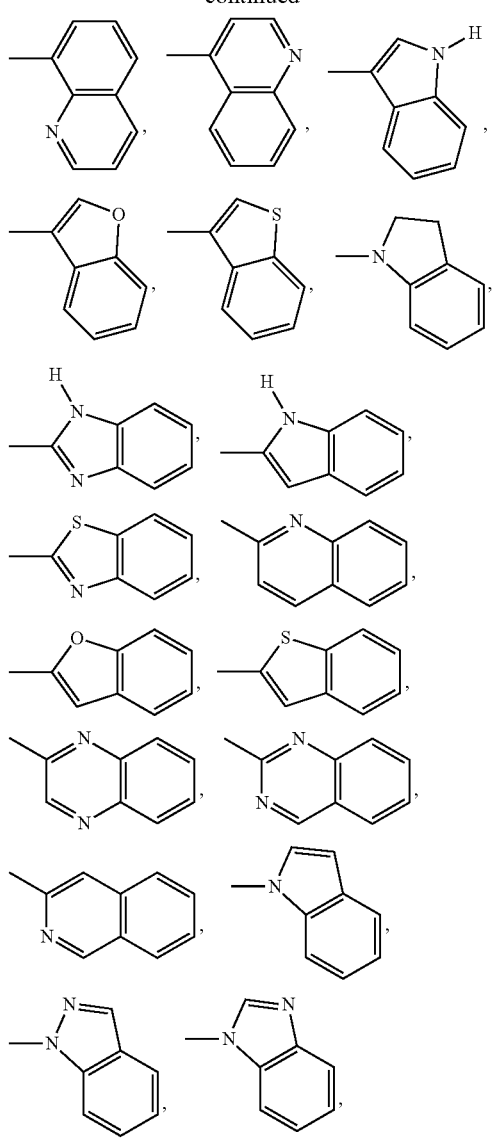
wherein these groups can be substituted with up to 5 substituents $R^{52}$ to $R^{56}$ or $R^{80}$ to $R^{84}$ selected form the list below,
Additional preferred Michael systems have the following structure:
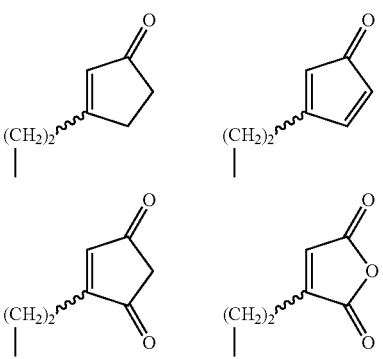

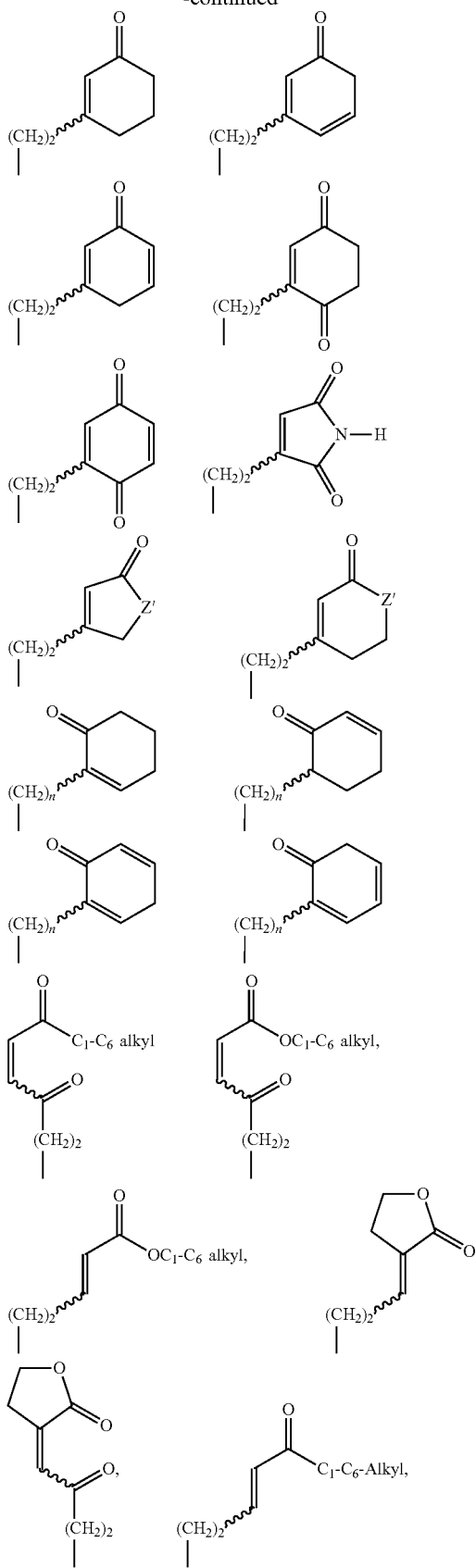

wherein

Z' represents one of the following groups: —CH₂—, —CF₂—, —C₂H₄—, —CF₂—CH₂—, —CH₂—CH₂—, —O—, —O—CH₂—, —NH— or —NH—CH₂—;

The zigzag line is intended to symbolize that the configuration of the double bond may be both "Z" and "E".

If the particularly preferred Michael systems of the following structure:

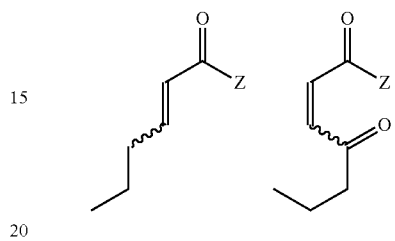

are contemplated, wherein Z has the meaning defined herein, the Michael system represents the side chain of an amino acid or an amino acid derivative or analogue, wherein the amino acid is part of the peptidic or peptide-like residue of the molecule.

The whole molecule can be represented schematically as follows:

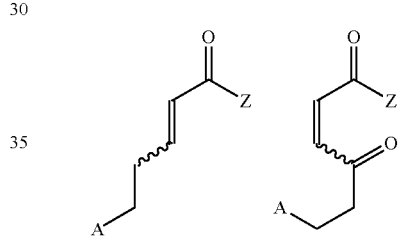

wherein A represents the peptide, peptide derivative or peptidomimetic and the compound can be represented as follows:

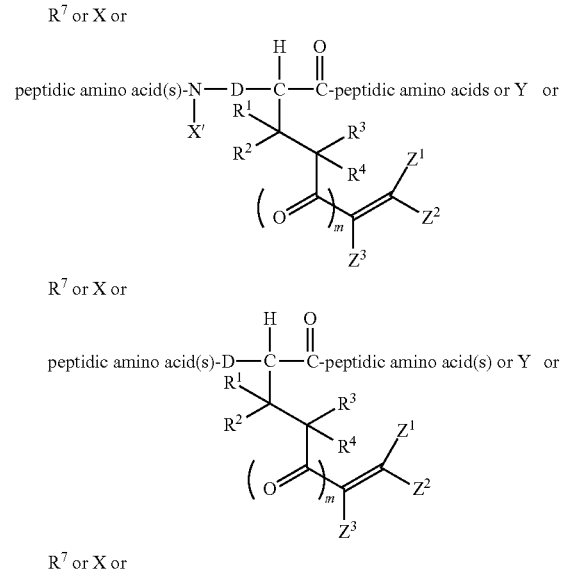

-continued

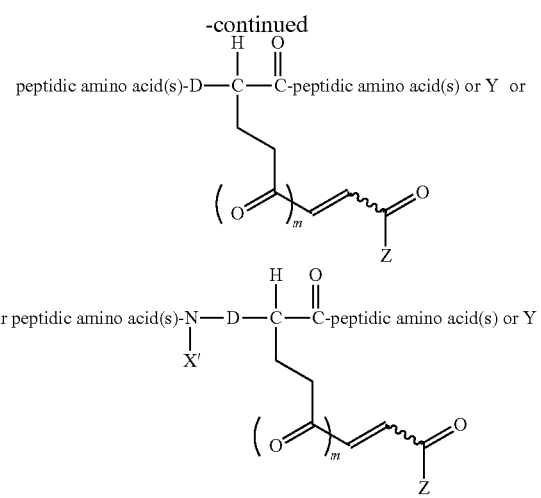

wherein D can represent a chemical bond or one of the following groups:
—CH$_2$—, —CL$^1$L$^2$-, —CF$_2$—, —C$_2$H$_4$—, —CH$_2$—CF$_2$—, —CF$_2$—CH$_2$—, —CH=CH—, —CH(OH)—CH$_2$—, —C(=O)—CH$_2$—, —CH$_2$—NH—, —CH$_2$—O—, —CH(OH)—CH$_2$—NH—, —CHQ-C$_2$H$_4$—, —CHQ-CH$_2$—CF$_2$—, —CHQ-CF$_2$—CH$_2$—, —CHQ-CH=CH—, —CHQ-CH(OH)—CH$_2$—, —CHQ-C(=O)—CH$_2$—, —CHQ-CH$_2$—NH—, —CHQ-CH$_2$—O—, —CHQ-P(=O)(OH)—NH—, —CHQ-P(=O)(OH)—O—, —CHQ-P(=O)(OH)—S—, —CHQ-P(=O)(OH)—CH$_2$—, or —CHQ-CH(OH)—CH$_2$—NH—, wherein L$^1$, L$^2$ and Q independently of each other represent a side chain residue of a natural amino acid or a residue —R$^{59}$, —R$^{60}$, —R$^{61}$ and the residues R$^1$ to R$^4$ and R$^{59}$, R$^{60}$, R$^{61}$, X, X' and Y have the meanings as defined below. The variable m can be 0 or 1.

Amongst others, the following formula is the result of D representing a chemical bond:

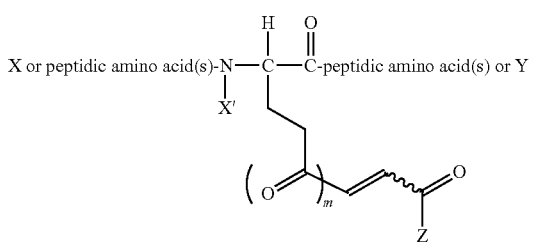

Group A represents the backbone of the peptide, peptide derivative or peptidomimetic, to which at least one acceptor-substituted olefin (MS) or respectively one Michael system (MS) of the type described herein is bound.

Obviously, a peptidic or peptide-like compound can also have two or three identical or different acceptor-substituted olefins or Michael systems. The side chain(s) carrying the Michael acceptor or respectively the side chain(s) having an acceptor-substituted olefin can be attached at any position of A.

In the simplest embodiment, A preferably represents a dipeptide or respectively a dipeptide derivative, symbolized by the two amino acids AS1 and AS2, linked to each other via a peptide bond (amide bond): AS1-AS2

AS1 or AS2 or AS1 and AS2 carry an acceptor-substituted olefin (MS) as side chain, preferably a Michael system and the dipeptide (dipeptide derivative) preferably has the group Y attached at the C-terminal end and the groups X and X' attached at the N-terminus.

The peptides, peptide derivatives and the peptidomimetics are indicated in the usual notation, i.e. from the N-terminus in direction of the C-terminus- Thus, the dipeptide can be represented as follows:

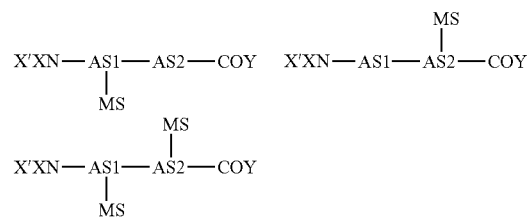

In one embodiment, tri-, tetra-, penta-, hexa-, septa-, octa-, nona- and decapeptides and peptides of up to 20 amino acids or amino acid-like compounds can also be used. Tripeptides, tetrapeptides and pentapeptides, however, are preferred and tetrapeptides are particularly preferred.

The tripeptides (tripeptide derivatives) can have the following structures:

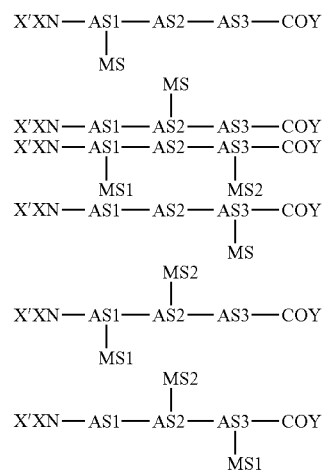

The tetrapeptides (tetrapeptide derivatives) can have the following structure:

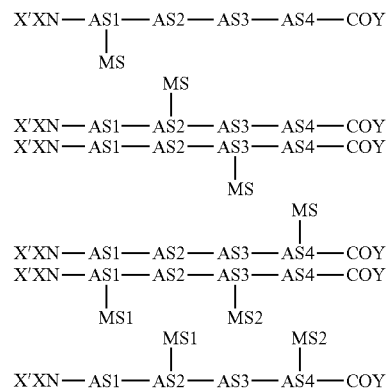

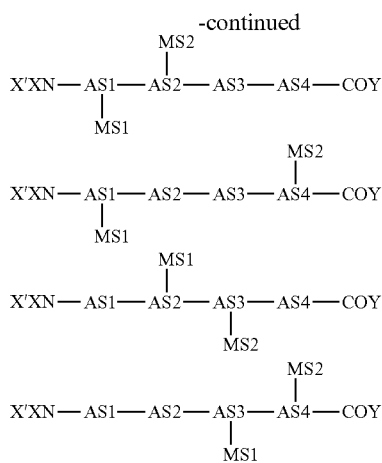

The pentapeptides (pentapeptide derivatives) can have the following structure:

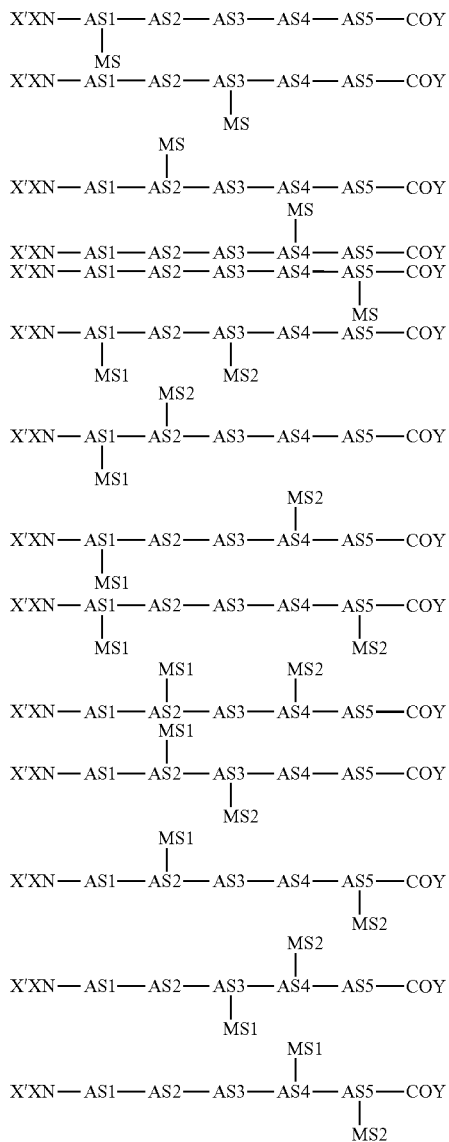

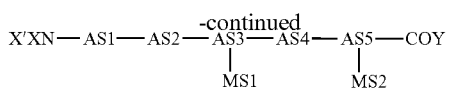

MS1 and MS2 may refer to two identical or two different acceptor-substituted olefins and the tri-, tetra- and pentapeptides can also carry more than two acceptor-substituted olefins and preferably more than two Michael systems.

However, in all peptides, peptide derivatives or peptidomimetics, maximally one acceptor-substituted olefin or Michael system is present per amino acid.

The natural amino acids such as alanine (Ala, A), cysteine (Cys, C), aspartic acid (Asp, D), glutamic acid (Glu, E), phenylalanine (Phe, F), glycine (Gly, G), histidine (H is, H), isoleucine (Ile, I), lysine (Lys, K), leucine (Leu, L), methionine (Met, M), asparagine (Asn, N), proline (Pro, P), glutamine (Gln, Q), arginine (Arg, R), serine (Ser, S), threonine (Thr, T), valine (Val, V), tryptophan (Trp, W) and tyrosine (Tyr, Y) as well as amino acid derivatives such as 4-hydroxyproline, N,N,N-trimethyllysine, 3-methylhistidine, 5-hydroxylysine, O-phosphoserine, γ-carboxyglutamate, ε-N-acetyllysine, ω-N-methylarginine, citrulline or ornithine can be used as amino acids (AS, AS1, AS2, ... AS19, AS20).

In addition to the L-amino acids, D-amino acids as well as combinations of L- and D-amino acids can also be used in a peptide or peptide derivative.

The term "amino acid" or "amino acids" is intended to include not only the natural amino acids or derivatives thereof, but also a general chemical compound having at least one amino function or at least one ammonium function or at least one carboxylic acid function or at least one carboxylate function. Such compounds should or have to be capable of forming a betaine structure and/or should or have to be capable of forming peptide bonds or respectively amide bonds.

Thus, compounds of the following formulas are also defined by the term "amino acid" or "amino acids"

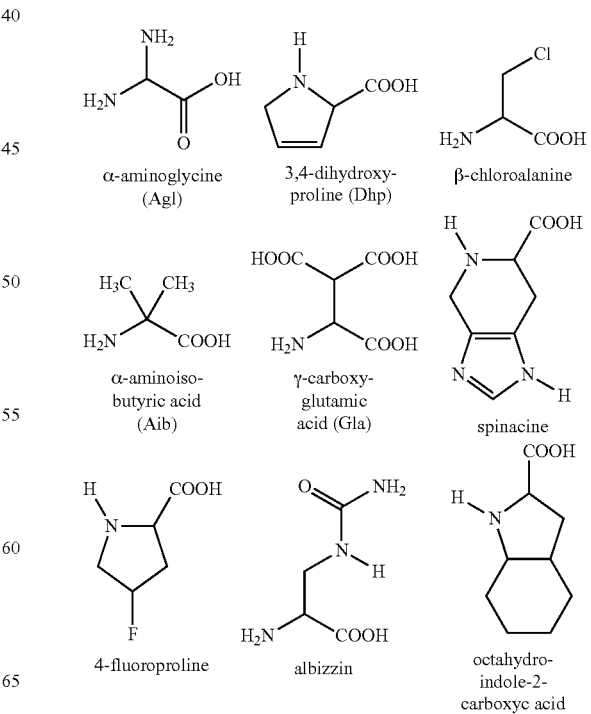

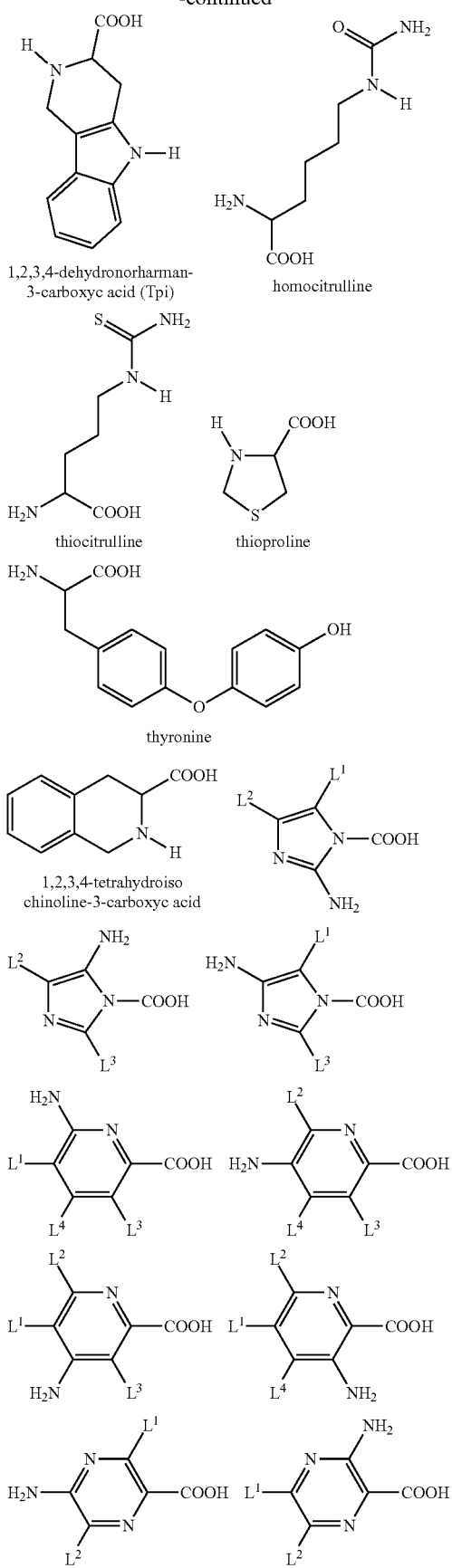

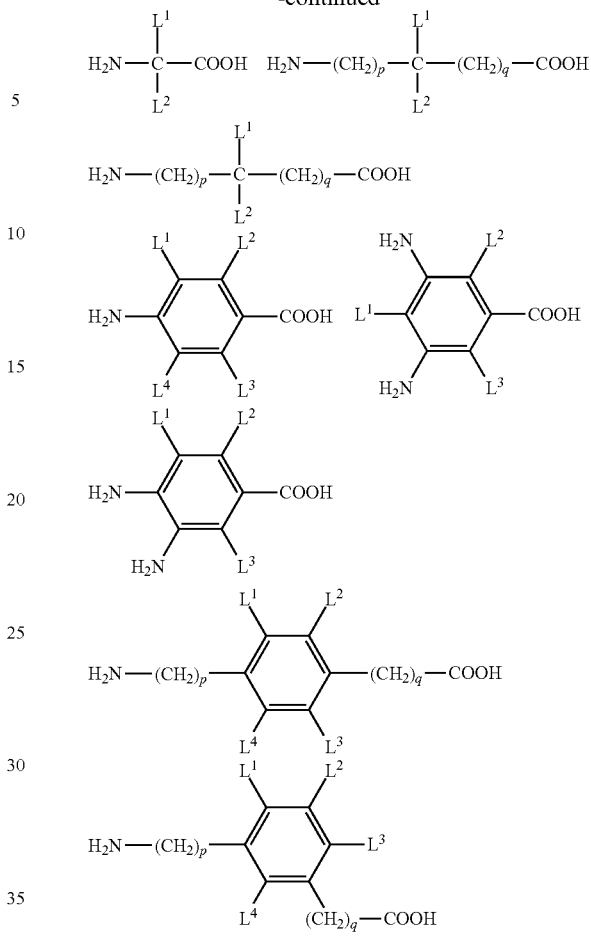

wherein p and q independently of each other are 0, 1, 2, 3, 4, 5.

$L^1$, $L^2$, $L^3$, $L^4$ independently of each other represent a side chain residue of a natural amino acid or a residue —$R^{57}$, —$R^{59}$, $R^{60}$, $R^{61}$, $CR^{62}R^{63}R^{64}$, —$CR^{65}R^{66}CR^{67}R^{68}R^{69}$, —$CR^{70}R^{71}$—$CR^{72}R^{73}$—$CR^{74}R^{75}R^{76}$, wherein $R^{57}$ to $R^{76}$ have the meaning indicated below. In one embodiment the residues $L^1$ to $L^4$ represent hydrogen.

In the case of the peptidomimetics, the amide bond (—NH—CO—) is preferably replaced by a different functionality. For example, the amide nitrogen can be alkylated so that the peptidomimetics contain the following structural fragment:

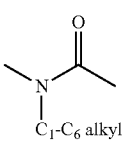

As amino acid analogues which can be used as amino acid components in the peptidic background should be named e.g. thiocarbonyl amino acids, β-amino acids, γ-amino acids or δ-amino acids, whereas non-proteinogenic amino acids are generally tagged as amino acid analogues. Further examples for amino acid analogues are:

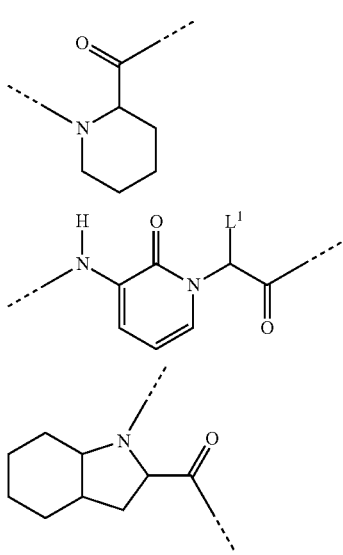

Furthermore, the peptidomimetics may contain amino acids of the following form, which are also designated as dipeptide analogues:

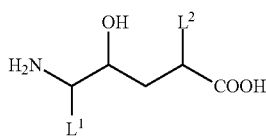

hydroxyethylene dipeptide analogue

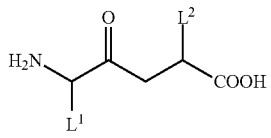

ketomethlyene dipeptide analogue

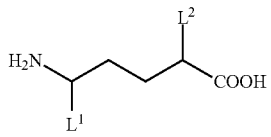

carba- dipeptide analogue

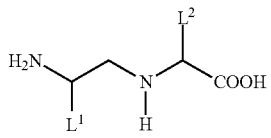

reduced dipeptide analogue

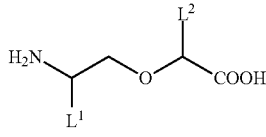

methyloxy dipeptide analogue

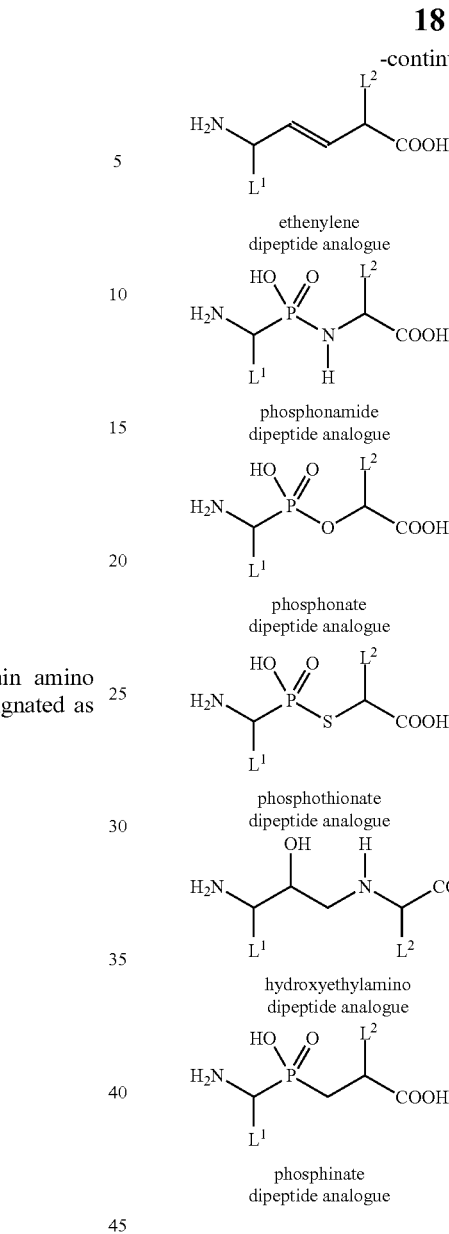

wherein the residues $L^1$ and $L^2$ independently of each other have the meanings indicated above under "amino acids". Herein, the aforementioned compounds are designated as dipeptide analogues, but are to be considered one amino acid (AS). Consequently, a residue defined herein composed of 4 amino acids can include 4 of the aforementioned dipeptide-analogues and not only a maximum of 2 of said dipeptide analogues, given that a dipeptide analogue is to be counted as one amino acid and not as two amino acids.

Stereochemistry regarding the natural amino acids, the unnatural amino acids and the peptide analogues or respectively stereochemistry regarding the inventive peptides or peptidomimetics may be L and D or respectively R and S, so that enantiomeric forms and diasteromeric forms and mixtures of enantiomers and/or diastereomers fall within the definition of the inventive peptides, peptide derivatives and peptidomimetics disclosed herein.

Inventive peptides as well as the use of the following inventive peptides as transglutaminase inhibitors are preferred, wherein the peptide or peptidomimetic is a compound of the following general formula (I), (II) or (III):

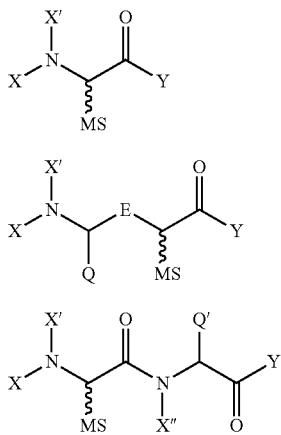

wherein

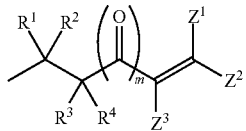

MS is the acceptor-substituted olefin, preferably the Michael system of the following structure:
and E represents the following group —$CH_2$—, —$CF_2$—, —$C_2H_4$—, —$CH_2$—$CF_2$—, —$CF_2$—$CH_2$—, —CH=CH—, —CH(OH)—$CH_2$—, —C(=O)—$CH_2$—, —$CH_2$—NH—, —$CH_2$—O—, —CH(OH)—$CH_2$—NH—, —P(=O)(OH)—NH—, —P(=O)(OH)—O—, —P(=O)(OH)—S—, —P(=O)(OH)—$CH_2$—, —CH(OH)—$CH_2$—NH—, —C(=O)—NH—, —C(=O)—O— or —C(=O)—NX''—;

Q and Q' independently of each other represent a side chain residue of a natural amino acid or Q together with X' forms a propylenyl residue or Q' together with X" forms a propylenyl residue;

Y represents a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group; or Y represents a peptide residue of up to 6 amino acids and bound via an amide bond, the C-terminal carbonyl function of which peptide residue carries a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group; or Y represents a peptidomimetic residue of up to 60 carbon atoms, preferably of up to 30 carbon atoms; and X" represents hydrogen or a $C_1$-$C_6$ alkyl group; and —NXX' is an amino group, —NH—CHO, $C_1$-$C_{10}$ alkylamino group, $C_1$-$C_8$ alkyloxycarbonyl amino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group; or the group —NXX' is part of a peptidomimetic residue composed of up to 60 carbon atoms, preferably of up to 30 carbon atoms or X' represents hydrogen or a $C_1$-$C_6$ alkyl group; and X represents a peptide residue of up to 6 amino acids and bound via an amide bond, the N-terminus of which peptide residue carries an amino group, —NH—CHO, $C_1$-$C_{10}$ alkylamino group, $C_1$-$C_8$ alkyloxycarbonyl amino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group;

wherein any of the $C_1$-$C_6$ alkoxy groups, $C_1$-$C_6$ alkyl groups, $C_1$-$C_{10}$ alkylamino groups,
$C_1$-$C_8$ alkyloxycarbonyl amino groups, $C_6$-$C_{12}$ aralkyloxycarbonyl amino group, $C_1$-$C_{10}$ dialkylamino groups, $C_2$-$C_6$ nitrogen heterocycles as well as $C_3$-$C_5$ nitrogen heteroaryl groups can be independently substituted with up to 5 residues selected from $R^{80}$, $R^{81}$, $R^{82}$, $R^{83}$, $R^{84}$.

The residues $R^1$ to $R^{84}$ as well as the residues $L^1$, $L^2$, $L^3$, $L^4$ independently of each other represent the following groups:
—H, —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —OPh, —$OCH_2$-Ph, —$OCPh_3$, —SH, —$SCH_3$, —$SC_2H_5$, —$SC_3H_7$, —S-cyclo-$C_3H_5$, —$SCH(CH_3)_2$, —$SC(CH_3)_3$, —$NO_2$, —F, —Cl, —Br, —I, —$N_3$, —CN, —OCN, —NCO, —SCN, —NCS, —CHO, —$COCH_3$, —$COC_2H_5$, —$COC_3H_7$, —CO-cyclo-$C_3H_5$, —$COCH(CH_3)_2$, —$COC(CH_3)_3$, —COOH, —COCN, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —$CONH[CH(CH_3)_2]$, —$CONH[C(CH_3)_3]$, —$CON(CH_3)_2$, —$CON(C_2H_5)_2$, —$CON(C_3H_7)_2$, —CON(cyclo-$C_3H_5)_2$, —$CON[CH(CH_3)_2]_2$, —$CON[C(CH_3)_3]_2$, —$NHCOCH_3$, —$NHCOC_2H_5$, —$NHCOC_3H_7$, —NHCO-cyclo-$C_3H_5$, —NHCO—$CH(CH_3)_2$, —NHCO—$C(CH_3)_3$, —NHCO—$OCH_3$, —NHCO—$OC_2H_5$, —NHCO—$OC_3H_7$, —NHCO—O-cyclo-$C_3H_5$, —NHCO—$OCH(CH_3)_2$, —NHCO—$OC(CH_3)_3$, —$NH_2$, —$NHCH_3$, —$NHC_2H_5$, —$NHC_3H_7$, —NH-cyclo-$C_3H_5$, —$NHCH(CH_3)_2$, —$NHC(CH_3)_3$, —$N(CH_3)_2$, —$N(C_2H_5)_2$, —$N(C_3H_7)_2$, —N(cyclo-$C_3H_5)_2$, —$N[CH(CH_3)_2]_2$, —$N[C(CH_3)_3]_2$, —$SOCH_3$, —$SOC_2H_5$, —$SOC_3H_7$, —SO-cyclo-$C_3H_5$, —$SOCH(CH_3)_2$, —$SOC(CH_3)_3$, —$SO_2CH_3$, —$SO_2C_2H_5$, —$SO_2C_3H_7$, —$SO_2$-cyclo-$C_3H_5$, —$SO_2CH(CH_3)_2$, —$SO_2C(CH_3)_3$, —$SO_3H$, —$SO_3CH_3$, —$SO_3C_2H_5$, —$SO_3C_3H_7$, —$SO_3$-cyclo-$C_3H_5$, —$SO_3CH(CH_3)_2$, —$SO_3C(CH_3)_3$, —$OCF_3$, —$OC_2F_5$, —O—$COOCH_3$, —O—$COOC_2H_5$, —O—$COOC_3H_7$, —O—COO-cyclo-$C_3H_5$, —O—$COOCH(CH_3)_2$, —O—$COOC(CH_3)_3$, —NH—CO—$NH_2$, —NH—CO—$NHCH_3$, —NH—CO—$NHC_2H_5$, —NH—CO—$NHC_3H_7$, —NH—CO—NH-cyclo-$C_3H_5$, —NH—CO—$NH[CH(CH_3)_2]$, —NH—CO—$NH[C(CH_3)_3]$, —NH—CO—$N(CH_3)_2$, —NH—CO—$N(C_2H_5)_2$, —NH—CO—$N(C_3H_7)_2$, —NH—CO—N(cyclo-$C_3H_5)_2$, —NH—CO—$N[CH(CH_3)_2]_2$, —NH—CO—$N[C(CH_3)_3]_2$, —NH—CS—$NH_2$, —NH—CS—$NHCH_3$, —NH—CS—$NHC_2H_5$, —NH—CS—$NHC_3H_7$, —NH—CS—NH-cyclo-$C_3H_5$, —NH—CS—$NH[CH(CH_3)_2]$, —NH—CS—$NH[C(CH_3)_3]$, —NH—CS—$N(CH_3)_2$, —NH—CS—$N(C_2H_5)_2$, —NH—CS—$N(C_3H_7)_2$, —NH—CS—N(cyclo-$C_3H_5)_2$, —NH—CS—$N[CH(CH_3)_2]_2$, —NH—CS—$N[C(CH_3)_3]_2$, —NH—C(=NH)—$NH_2$, —NH—C(=NH)—$NHCH_3$, —NH—C(=NH)—$NHC_2H_5$, —NH—C(=NH)—$NHC_3H_7$, —$OC_6H_4$—$OCH_3$, —NH—C(=NH)—NH-cyclo-$C_3H_5$, —NH—C(=NH)—$NH[CH(CH_3)_2]$, —$CF_2Cl$, —NH—C(=NH)—$NH[C(CH_3)_3]$, —NH—C(=NH)—$N(CH_3)_2$, —NH—C(=NH)—N($C_2H_5$)$_2$, —NH—C(=NH)—N($C_3H_7$)$_2$, —NH—C(=NH)—N(cyclo-$C_3H_5$)$_2$, —O$C_6H_4$—$CH_3$, —NH—C(=NH)—N[CH($CH_3$)$_2$]$_2$, —NH—C(=NH)—N[C($CH_3$)$_3$]$_2$, —O—CO—$NH_2$, —O—CO—$NHCH_3$, —O—CO—NH$C_2H_5$, —O—CO—NH$C_3H_7$, —O—CO—NH-cyclo-$C_3H_5$, —O—CO—NH[CH($CH_3$)$_2$], —O—CO—NH[C($CH_3$)$_3$], —O—CO—N($CH_3$)$_2$, —O—CO—N($C_2H_5$)$_2$, —O—CO—N($C_3H_7$)$_2$, —O—CO—N(cyclo-$C_3H_5$)$_2$, —O—CO—N[CH($CH_3$)$_2$]$_2$, —O—CO—N[C($CH_3$)$_3$]$_2$, —O—CO—O$CH_3$, —O—CO—O$C_2H_5$, —O—CO—O$C_3H_7$, —O—CO—O-cyclo-$C_3H_5$, —O—CO—OCH($CH_3$)$_2$, —O—CO—OC($CH_3$)$_3$, —$CH_2$F, —$CHF_2$, —$CF_3$, —$CH_2$Cl, —$CH_2$Br, —$CH_2$I, —$CH_2$—$CH_2$F, —$CH_2$—$CHF_2$, —$CH_2$—$CF_3$, —$CH_2$—$CH_2$Cl, —$CH_2$—$CH_2$Br, —$CH_2$—$CH_2$I, cyclo-$C_3H_5$, cyclo-$C_4H_7$, cyclo-$C_5H_9$, cyclo-$C_6H_{11}$ cyclo-$C_7H_{13}$, cyclo-$C_8H_{15}$, -Ph, —$CH_2$-Ph, —C$Ph_3$, —$CH_3$, —$C_2H_5$, —$C_3H_7$, —CH($CH_3$)$_2$, —$C_4H_9$, —$CH_2$—CH($CH_3$)$_2$, —CH($CH_3$)—$C_2H_5$, —C($CH_3$)$_3$, —$C_5H_{11}$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —CH($C_2H_5$)$_2$, —$C_2H_4$—CH($CH_3$)$_2$, —$C_6H_{13}$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —CH=$CH_2$, —$CH_2$—CH=$CH_2$, —C($CH_3$)=$CH_2$, —CH=CH—$CH_3$, —$C_2H_4$—CH=$CH_2$, —$C_7H_{15}$, —$C_5H_{17}$, —$CH_2$—CH=CH—$CH_3$, —CH=CH—$C_2H_5$, —$CH_2$—C($CH_3$)=$CH_2$, —CH($CH_3$)—CH=CH, —CH=C($CH_3$)$_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$C_2H_4$—C($CH_3$)=$CH_2$, —$CH_2$—CH($CH_3$)—CH=$CH_2$, —CH($CH_3$)—$CH_2$—CH=$CH_2$, —$CH_2$—CH=C($CH_3$)$_2$, —$CH_2$—C($CH_3$)=CH—$CH_3$, —CH($CH_3$)—CH=CH—$CH_3$, —CH=CH—CH($CH_3$)$_2$, —CH=C($CH_3$)—$C_2H_5$, —C($CH_3$)=C($CH_3$)$_2$, —C($CH_3$)$_2$—CH=$CH_2$, —CH($CH_3$)—C($CH_3$)=$CH_2$, —C($CH_3$)=CH—CH=$CH_2$, —CH=C($CH_3$)—CH=$CH_2$, —CH=CH—C($CH_3$)=$CH_2$, —$C_4H_8$—CH=$CH_2$, —$C_3H_6$—CH=CH—$CH_3$, —$C_2H_4$—CH=CH—$C_2H_5$, —$CH_2$—CH=CH—$C_3H_7$, —CH=CH—$C_4H_9$, —$C_3H_6$—C($CH_3$)=$CH_2$, —$CH_2$—$CH_2$—$CH_2$—O$CH_3$, —$C_2H_4$—CH($CH_3$)—CH=$CH_2$, —$CH_2$—CH($CH_3$)—$CH_2$—CH=$CH_2$, —$CH_2NH_2$, —CH($CH_3$)—$C_2H_4$—CH=$CH_2$, —$C_2H_4$—CH=C($CH_3$)$_2$, —$C_2H_4$—C($CH_3$)=CH—$CH_3$, —$CH_2$—CH($CH_3$)—CH=CH—$CH_3$, —CH($CH_3$)—$CH_2$—CH=CH—$CH_3$, —$CH_2OH$, —$CH_2SH$, —$CH_2$—CH=CH—CH($CH_3$)$_2$, —$CH_2$—CH=C($CH_3$)—$C_2H_5$, —$CH_2$—$CH_2$—$CH_2NH_2$, —$CH_2$—C($CH_3$)=CH—$C_2H_5$, —CH($CH_3$)—CH=CH—$C_2H_5$, —$CH_2$—$CH_2NH_2$, —CH=CH—$CH_2$—CH($CH_3$)$_2$, —CH=CH—CH($CH_3$)—$C_2H_5$, —CH=C($CH_3$)—$C_3H_7$, —C($CH_3$)=CH—$C_3H_7$, —$CH_2$—CH($CH_3$)—C($CH_3$)=$CH_2$, —$CH_2$—$CH_2SH$, —CH($CH_3$)—$CH_2$—C($CH_3$)=$CH_2$, —CH($CH_3$)—CH($CH_3$)—CH=$CH_2$, —$CH_2$—$CH_2OH$, —$CH_2$—C($CH_3$)$_2$—CH=$CH_2$, —C($CH_3$)$_2$—$CH_2$—CH=$CH_2$, —$CH_2$—C($CH_3$)=C($CH_3$)$_2$, —CH($CH_3$)—CH=C($CH_3$)$_2$, —C($CH_3$)$_2$—CH=CH—$CH_3$, —$CH_2$—$CH_2$—$CH_2SH$, —CH($CH_3$)—C($CH_3$)=CH—$CH_3$, —CH=C($CH_3$)—CH($CH_3$)$_2$, —C($CH_3$)=CH—CH($CH_3$)$_2$, —C($CH_3$)=C($CH_3$)—$C_2H_5$, —CH=CH—C($CH_3$)$_3$, —C($CH_3$)$_2$—C($CH_3$)=$CH_2$, —CH($CH_3$)—C($C_2H_5$)=$CH_2$, —C($CH_3$)$_2$—CH=$CH_2$, —CH($CH_3$)—C($C_2H_5$)=$CH_2$, —$CH_2$—C($C_3H_7$)=$CH_2$, —$CH_2$—C($C_2H_5$)=CH—$CH_3$, —CH($C_2H_5$)—CH=CH—$CH_3$, —C($C_4H_9$)=$CH_2$, —C($C_3H_7$)=CH—$CH_3$, —C($C_2H_5$)=CH—$C_2H_5$, —C($C_2H_5$)=C($CH_3$)$_2$, —C[C($CH_3$)$_3$]=$CH_2$, —C[CH($CH_3$)($C_2H_5$)]=$CH_2$, —C[$CH_2$—CH($CH_3$)$_2$]=$CH_2$, —$C_2H_4$—CH=CH—CH=$CH_2$, —$C_6H_4$—O$CH_3$, —$CH_2$—CH=CH—$CH_2$—CH=$CH_2$, —CH=CH—$C_2H_4$—CH=$CH_2$, —$C_6H_4$—OH, —$CH_2$—CH=CH—CH=CH—$CH_3$, —CH=CH—$CH_2$—CH=CH—$CH_3$, —$CH_2$—$CH_2$—O$CH_3$, —CH=CH—CH=CH—$C_2H_5$, —$CH_2$—CH=CH—C($CH_3$)=$CH_2$, —$CH_2$—$CH_2OH$, —$CH_2$—CH=C($CH_3$)—CH=$CH_2$, —$CH_2$—C($CH_3$)=CH—CH=$CH_2$, —$CH_2$—O$CH_3$, —CH($CH_3$)—CH=CH—CH=$CH_2$, —CH=CH—$CH_2$—C($CH_3$)=$CH_2$, —CH=CH—CH($CH_3$)—CH=$CH_2$, —CH=C($CH_3$)—$CH_2$—CH=$CH_2$, —C($CH_3$)=CH—$CH_2$—CH=$CH_2$, —CH=CH—CH=C($CH_3$)$_2$, —$CH_2$—$C_6H_4$—O$CH_3$, —CH=CH—C($CH_3$)=CH—$CH_3$, —CH=C($CH_3$)—CH=CH—$CH_3$, —$CH_2$—$C_6H_4$—OH, —C($CH_3$)=CH—CH=CH—$CH_3$, —CH=C($CH_3$)—C($CH_3$)=$CH_2$, —C($CH_3$)=$CH_2$, —C($CH_3$)=CH—C($CH_3$)=$CH_2$, —C($CH_3$)=C($CH_3$)—CH=$CH_2$, —CH=CH—CH=CH—$CH_2$, —CH=$CH_2$, —C≡CH, —C≡C—$CH_3$, —$CH_2$—C≡CH, —$C_2H_4$—C≡CH, —$CH_2$—C≡C—$CH_3$, —C≡C—$C_2H_5$, —$C_3H_6$—C≡CH, —$C_2H_4$—C≡C—$CH_3$, —$CH_2$—C≡C—$C_2H_5$, —C≡C—$C_3H_7$, —CH($CH_3$)—C≡CH, —$CH_2$—CH($CH_3$)—C≡CH, —CH($CH_3$)—$CH_2$—C≡CH, —CH($CH_3$)—C≡C—$CH_3$, —$C_4H_8$—C≡CH, —$C_3H_6$—C≡C—$CH_3$, —$C_2H_4$—C≡C—$C_2H_5$, —$CH_2$—C≡C—$C_3H_7$, —C≡C—$C_4H_9$, —C≡C—C($CH_3$)$_3$, —$C_2H_4$—CH($CH_3$)—C≡CH, —$CH_2$—CH($CH_3$)—$CH_2$—C≡CH, —$CH_2$—C≡C—CH($CH_3$)$_2$, —CH($CH_3$)—$C_2H_4$—C≡CH, —CH($CH_3$)—$CH_2$—C≡C—$CH_3$, —CH($CH_3$)—C≡C—$C_2H_5$, —C≡C—CH($CH_3$)—$C_2H_5$, —C≡C—$CH_2$—CH($CH_3$)$_2$, —CH($C_2H_5$)—C≡C—$CH_3$, —C($CH_3$)$_2$—C≡C—$CH_3$, —CH($C_2H_5$)—$CH_2$—C≡CH, —$CH_2$—C($CH_3$)$_2$—C≡CH, —$CH_2$—C≡CH, —CH($CH_3$)—CH($CH_3$)—C≡CH, —CH($C_3H_7$)—C≡CH, —C($CH_3$)($C_2H_5$)—C≡CH, —C≡C—C≡CH, —$CH_2$—C≡C—C≡C—$CH_3$, —CH(C≡CH)$_2$, —$C_2H_4$—C≡C—C≡CH, —$CH_2$—C≡C—$CH_2$—C≡CH, —C≡C—$C_2H_4$—C≡CH, —$CH_2$—C≡C—C≡C—$CH_3$, —C≡C—$CH_2$—C≡C—$CH_3$, —C≡C—C≡C—$C_2H_5$, —CH($CH_3$)—C≡C—C≡CH, —C(C≡CH)$_2$—$CH_3$, as well as stereoisomeric forms, E/Z isomers, enantiomers, enantiomeric mixtures, diastereomers, diastereomeric mixtures, racemates, tautomers, anomers, keto-enol forms, betaine forms, prodrugs, solvates, hydrates and pharmacologically acceptable salts of the aforementioned compounds.

No absolute substance protection is claimed for the compounds of the general formula (I) wherein X and X' represent hydrogen and Y represents a hydroxy group.

Particularly for the residues $R^1$, $R^2$, $R^3$, $R^4$ it is preferred if none, one, two, three or all four residues represent fluorine and the remaining residues represent hydrogen.

The inventive compounds with m=0 can be prepared by attaching a protective group (PG1 and PG2) to the amino acid Glu (glutamic acid) at the C-terminus and the N-terminus (1), subsequently reducing the carboxyl function of the side chain to aldehyde (2) and transforming the resulting aldehyde in an acceptor-substituted electrophilic double bond (3). Thereafter, the protective groups are removed and the N-terminus prolongated with a peptide fragment or a peptidomimetic, if desired (optional) (4). After activating the C-terminal carbonyl function the C-terminus can also optionally be prolongated with a peptide fragment or a petidomimetic (5). The orderly course of the synthesis is depicted in the following scheme:

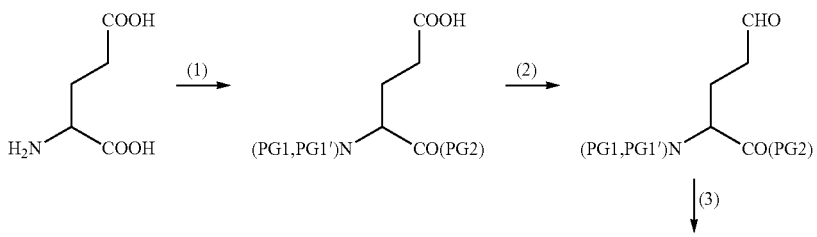

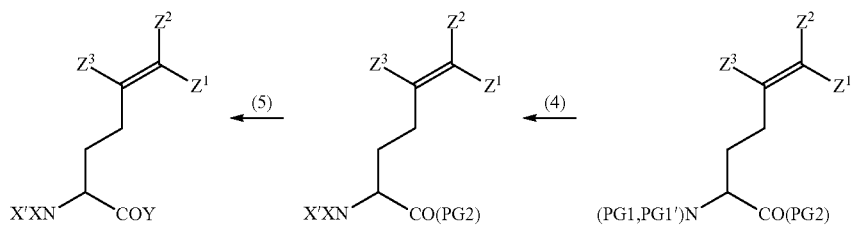

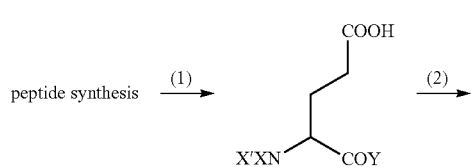

Alternatively, the backbone can be shaped first and the acceptor-substituted electrophilic double bond at the side chain of glutamic acid is generated subsequently. To this aim, a peptide or peptidomimetic protected at the C-terminus and the N-terminus is prepared (1), the carboxyl function of the side chain of glutamic acid is reduced to aldehyde (2) and the resulting aldehyde is transformed in an acceptor-substituted electrophilic double bond (3). Finally, the protective groups can be removed.

-continued

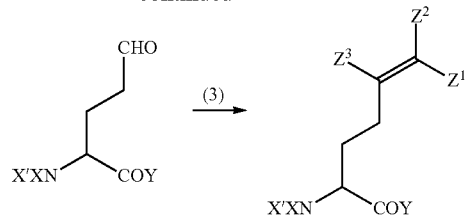

The inventive compounds with m=1 can be prepared by attaching a protective group (PG1 and PG2) to the amino acid Glu (glutamic acid) at the C-terminus and the N-terminus (1), subsequently transforming the carboxyl function of the side chain to a keto group (2), and the terminal carbonyl function of the resulting keto group is transformed transformed in an acceptor-substituted electrophilic double bond (3). Thereafter, the protective groups are removed and the N-terminus prolongated with a peptide fragment or a peptidomimetic, if desired (optional) (4). After activating the C-terminal carbonyl function the C-terminus can also optionally be prolongated with a peptide fragment or a petidomimetic (5). The orderly course of the synthesis is depicted in the following scheme:

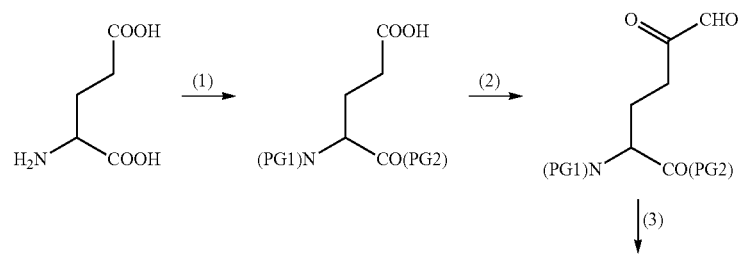

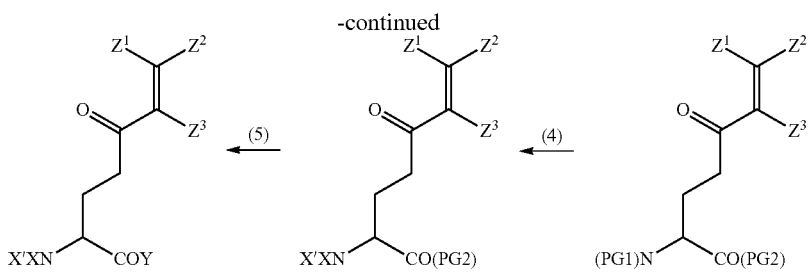

Alternatively, the backbone can be shaped first and the acceptor-substituted electrophilic double bond at the side chain of glutamic acid is generated subsequently. To this aim, a peptide or peptidomimetic protected at the C-terminus and the N-terminus is prepared (1), the carboxyl function of the side chain of glutamic acid is transformed to a diketo group (2) and the terminal carbonyl function of the resulting diketo group is transformed in an acceptor-substituted electrophilic double bond (3). Finally, the protective groups can be removed.

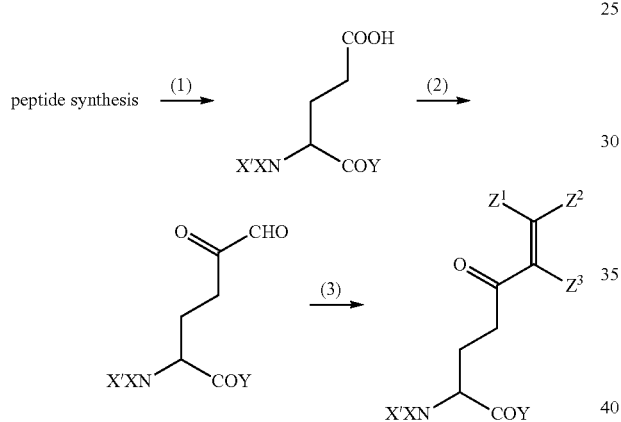

The term "prodrug" describes a precursor of the active ingredient containing a compound according to general formulas (I), (II), (III), [A] or [B] and further includes groups which can be cleaved under physiological conditions or releases a compound according to general formulas (I), (II), (III), [A] or [B] under physiological conditions.

Preferred acceptor-substituted olefins are in particular Michael systems of at least one conjugated double bond and one carbonyl function and in particular such Michael systems which are selected from the types of Michael systems mentioned above.

Other acceptor-substituted olefins (MS) have the following structures:

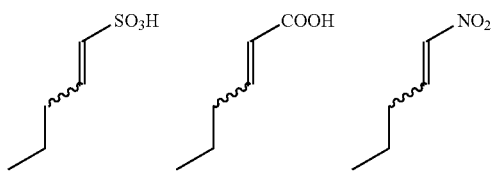

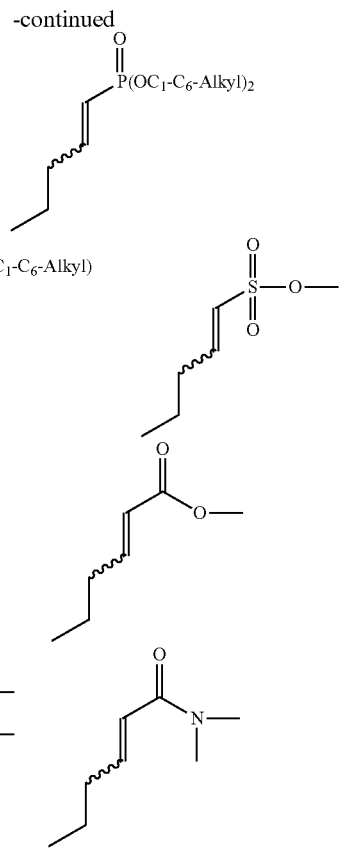

The sulfoxide, sulfone, sulfonic acid, ester, amide and phosphonate groups capable to conjugate can be attached with any other residues wherein alkyl, aryl and alkaryl residues are preferred. The presence of further residues including hydrogen in the above chemical structures is indicated by a continuing bond at the sulfur, nitrogen and oxygen atom.

The peptidomimetic residues may contain heteroatoms such as S, N, O, P, as well as heterocycles, carbocycles, aromatic compounds, heteroaromatic compounds and functional groups selected from the list of $R^1$ to $R^{84}$ and can include up to 80, preferably of up to 60, further preferred of up to 50 and particularly preferred of up to 40 carbon atoms.

It is particularly preferred that the groups $L^1$-$L^4$, $R^6$-$R^{76}$ and Q, Q', Q'', Q''', Q'''' independently of each other represent a side chain of a natural amino acid or a derivative derived therefrom.

Said particularly preferred side chains are: —H, —$CH_3$, —$CH(CH_3)_2$, —$CH_2$—$CH(CH_3)_2$, —$CH(CH_3)$—$CH_2$—$CH_3$, —$CH_2$—$CH_2$—S—$CH_3$, —$CH_2$—$CH_2$—$CH_2$-(proline chain), —$CH_2$-Ph, —$CH_2$—OH, —CH(OH)—$CH_3$, —CH$_2$—CO—NH$_2$, —CH$_2$—CH$_2$—CO—NH$_2$, —CH$_2$—SH, —CH$_2$—CH$_2$—CH$_2$—CH$_2$—NH$_2$, —CH$_2$—CH$_2$—CH$_2$—NH—C(=NH)—NH$_2$, —CH$_2$—COOH, —CH$_2$—CH$_2$—COOH,

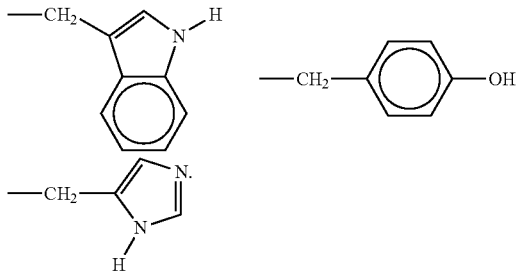

The inventive peptides or peptidomimetics have the general formulas (I), (II) or (III)

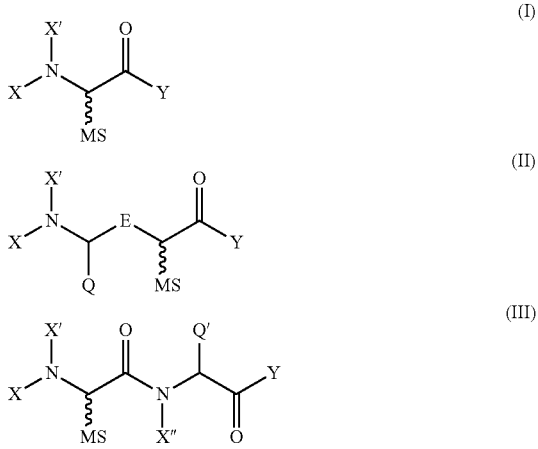

wherein
formula (I) includes at least one amino acid carrying the Michael acceptor system or respectively the acceptor-substituted double bond (MS). Residue Y can include an amino acid chain (peptide residue) of 1 to 6 amino acids or amino acid analogues, preferably of 1 to 4, further preferred of 1 to 3 and particularly preferred of 1 to 2 amino acids or amino acid analogues. The dipeptide analogues described above are also designated as amino acids analogues. If at least one amino acid analogue or amino acid derivative is used, the peptidomimetic residue Y is obtained which may include 2 to 40 carbon atoms, preferably 3 to 30, further preferred 4 to 25 and particularly preferred 5 to 20 carbon atoms. On the other hand, Y may also represent a hydroxy group, amino group, $C_1$-$C_6$ alkylamino group, $C_1$-$C_6$ dialkylamino group, $C_1$-$C_6$ alkoxy group, $C_6$-$C_{19}$ aryloxy group, $C_1$-$C_6$ alkyl group, $C_1$-$C_6$ halogenalkyl group, $C_3$-$C_{10}$ heteroaryl group or a $C_6$-$C_{15}$ aryl group as defined above and preferably a $C_1$-$C_4$ alkoxy group.

As $C_6$-$C_{19}$ aryloxy group are designated preferably the following residues: -Ph, —CL$^5$L$^6$-Ph, wherein L$^5$ and L$^6$ can be selected independently from: —H, —CH$_3$, —C$_2$H$_5$, —C$_3$H$_7$, —CH(CH$_3$)$_2$, —C$_4$H$_9$, -Ph and —CH$_2$-Ph.

If Y represents a peptide residue, the C-terminal end of said peptide residue can also carry one of the aforementioned groups.

As already described, the term "amino acid" as used herein not only includes natural amino acids but also derivatives of natural amino acids and amino acid analogues such as the dipeptide analogues described above.

In particular natural amino acids, the side chain of which has been modified and amino acids with unnatural side chains such as for example allyl or propinyl side chains are designated as amino acid derivatives or amino acid analogues. Further examples for modified side chains are —CH$_2$—CH$_2$—S—(C$_2$-C$_6$ alkyl), —CH$_2$—S—(C$_1$-C$_6$ alkyl), substitution of the cyclic proline —CH$_2$—CH$_2$—CH$_2$ chain by a —CH$_2$—CH$_2$ chain or a —CH$_2$—CH$_2$—CH$_2$—CH$_2$ chain, substitution at the phenyl residue of phenylalanine by one or more nucleophiles, etherification or esterification of the hydroxy group of tyrosine, threonin and serine to form —CH$_2$—O—(C$_1$-C$_6$ alkyl), —CH$_2$—O—CO—(C$_1$-C$_6$ alkyl), —CH$_2$—O—CO—O—(C$_1$-C$_6$ alkyl), —CH$_2$—O—CO—NH—(C$_1$-C$_6$ alkyl), —CH(CH$_3$)—O—(C$_1$-C$_6$ alkyl), —CH(CH$_3$)—O—CO—(C$_1$-C$_6$ alkyl), —CH(CH$_3$)—O—CO—O—(C$_1$-C$_6$ alkyl), —CH(CH$_3$)—O—CO—NH—(C$_1$-C$_6$ alkyl), ortho, meta or para-CH$_2$—C$_6$H$_4$—O—(C$_1$-C$_6$ alkyl), ortho, meta or para-CH$_2$—C$_6$H$_4$—O—CO—(C$_1$-C$_6$ alkyl), ortho, meta or para-CH$_2$—C$_6$H$_4$—O—CO—O—(C$_1$-C$_6$ alkyl), ortho, meta or para-CH$_2$—C$_6$H$_4$—O—CO—NH—(C$_1$-C$_6$ alkyl), substitution at the imidazole ring of histidine, substitution of the phenyl ring of tryptophan or addition at the heterocycle of tryptophan, reduction of asparagine or glutamine to —CH$_2$—CH$_2$—NH$_2$, —CH$_2$—CH$_2$—CH$_2$—NH$_2$, derivatization of asparagine or glutamine to —CH$_2$—CO—NH(C$_1$-C$_6$ alkyl), —CH$_2$—CH$_2$—CO—NH (C$_1$-C$_6$ alkyl), —CH$_2$—CO—N(C$_1$-C$_6$ alkyl)(C$_1$-C$_6$ alkyl), —CH$_2$—CH$_2$—CO—N(C$_1$-C$_6$ alkyl)(C$_1$-C$_6$ alkyl), derivatization of lysine to —CH$_2$—CH$_2$—CH$_2$—CH$_2$—NH(C$_1$-C$_6$ alkyl), —CH$_2$—CH$_2$—CH$_2$—CH$_2$—N(C$_1$-C$_6$ alkyl)(C$_1$-C$_6$ alkyl), —CH$_2$—CH$_2$—CH$_2$—CH$_2$—NH—CO—(C$_1$-C$_6$ alkyl), —CH$_2$—CH$_2$—CH$_2$—CH$_2$—NH—CO—O—(C$_1$-C$_6$ alkyl), derivatization of arginine to —CH$_2$—CH$_2$—CH$_2$—NH—C(=NH)—NH(C$_1$-C$_6$ alkyl), —CH$_2$—CH$_2$—CH$_2$—NH—C(=NH)—N(C$_1$-C$_6$ alkyl)(C$_1$-C$_6$ alkyl), —CH$_2$—CH$_2$—CH$_2$—NH—C(=O)—NH$_2$, —CH$_2$—CH$_2$—CH$_2$—NH—C(=O)—NH(C$_1$-C$_6$ alkyl), —CH$_2$—CH$_2$—CH$_2$—NH—C(=O)—N(C$_1$-C$_6$ alkyl)(C$_1$-C$_6$ alkyl), —CH$_2$—CH$_2$—CH$_2$—NH$_2$, or cyclization of the guanidino group to imidazole, esterification or reduction of aspartic acid and glutamic acid to —CH$_2$—CH$_2$—OH, —CH$_2$—CH$_2$—CH$_2$—OH, —CH$_2$—CH$_2$—O—(C$_1$-C$_6$ alkyl), —CH$_2$—OH$_2$—OH$_2$—O—(C$_1$-C$_6$ alkyl), —CH$_2$—OH$_2$—O—CO—(C$_1$-C$_6$ alkyl), —CH$_2$—OH$_2$—OH$_2$—O—CO—(C$_1$-C$_6$ alkyl), —CH$_2$—OH$_2$—O—CO—NH(C$_1$-C$_6$ alkyl), —CH$_2$—OH$_2$—OH$_2$—O—CO—NH(C$_1$-C$_6$ alkyl), —CH$_2$—OH$_2$—O—CO—N(C$_1$-C$_6$ alkyl)(C$_1$-C$_6$ alkyl), —CH$_2$—OH$_2$—OH$_2$—O—CO—N(C$_1$-C$_6$ alkyl)(C$_1$-C$_6$ alkyl), —CH$_2$—COO(C$_1$-C$_6$ alkyl), —CH$_2$—OH$_2$—COO(C$_1$-C$_6$ alkyl).

Similar facts as for group Y representing the C-terminal end of the inventive compounds are true for group —NXX' representing the N-terminal end of the inventive compounds.

The groups X, X', X", X''' and X'''' can represent hydrogen atoms or a $C_1$-$C_6$ alkyl group and the group —NXX' can represent an amino group, $C_1$-$C_{10}$ alkylamino group, $C_6$-$C_{12}$ aralkyloxycarbonyl amino group, $C_1$-$C_{10}$ dialkylamino group, $C_2$-$C_6$ nitrogen heterocycle or a $C_3$-$C_6$ nitrogen heteroaryl group wherein the residues have the meaning defined above and include the definitions for e.g. the $C_1$-$C_6$ alkyl residues. The preferred residue $C_7$ is a heptyl residue, the preferred residue $C_8$ is an octyl residue, the preferred residue $C_9$ is a nonyl residue and the preferred residue $C_{10}$ is a decyl residue, wherein other alkyl residues as well as cycloalkyl residues and branched alkyl residues are possible residues, too.

Preferably, group —NXX' represents amides and amino protecting groups such as acetyl amides, benzoic acid amides or carboxylic acids carrying heterocycles. X' can furthermore represent residues such as a benzyloxycarbonyl, a tert.-butyloxycarbonyl, cyclopentyloxycarbonyl, ethylthiocarbonyl, isopropylthiocarbonyl, benzylthiocarbonyl, methylthiocarbonyl, ethylthiocarbonyl, isopropylcarbonyl, cyclopropylcarbonyl, 2-pyridylthiomethyl carbonyl, hydroxyethylcarbonyl, thiophene-3-carbonyl, isoxazole-5-carbonyl or a nicotinic acid residue.

Furthermore, it is preferred if X stands for the following residues:

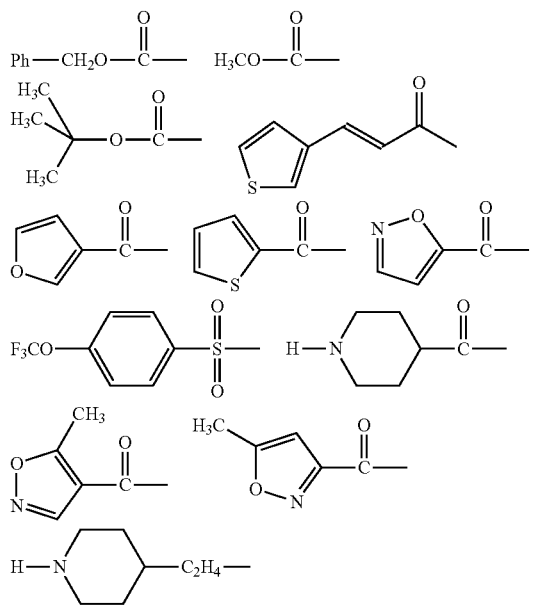

If the group —NXX' is a nitrogen heterocycle then the following nitrogen heterocycles are preferred:

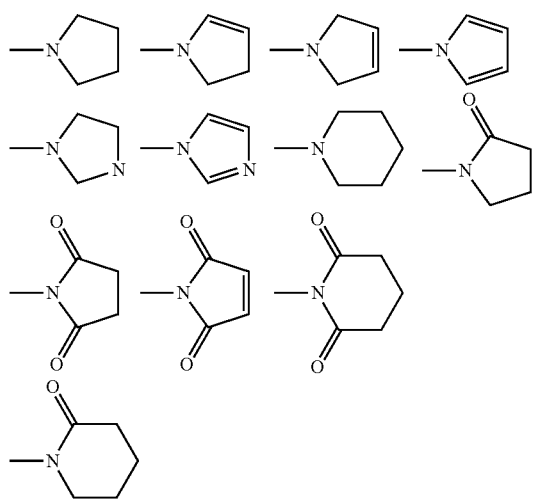

Surprisingly, it was found that the group —NXX' should not be an unsubstituted amino group (—NH$_2$) as long as it is in the immediate proximity to the Michael system, i.e. if the amino group (—NXX') and the ethylene linker leading to the electrophilic double bond are bound to the same carbon atom of an amino acid or an amino acid analogue. If the ethylene linker and the amino group —NXX' are located at the same carbon atom at least one of the residues X and X' should be different from hydrogen and preferably represent an alkyl group or an acyl group, such as shown above for X.

Furthermore, the group —NXX' can be part of a peptidomimetic residue composed of 2 to 30 carbon atoms, preferably 2 to 40, further preferred 3 to 30, still further preferred 4 to 25 and particularly preferred 5 to 20 carbon atoms. Furthermore, X may represent a peptide residue of 1 to 6 amino acids or amino acid analogues bond, preferably 1 to 4, further preferred 1 to 3 and particularly preferred 1 to 2 amino acids or amino acid analogues, which residue is bound via an amide bond, wherein the N-terminus of said peptide residue or peptidomimetic residue can carry an amino group, $C_1$-$C_{10}$ alkylamino group, $C_1$-$C_8$ alkyloxycarbonyl amino group, $C_6$-$C_{12}$ aralkyloxycarbonyl amino group, dialkylamino group, $C_2$-$C_6$ nitrogen heterocycle or a $C_3$-$C_5$ nitrogen heteroaryl group, wherein any of the $C_1$-$C_6$ alkoxy groups, $C_1$-$C_6$ alkyl groups, $C_1$-$C_{10}$ alkylamino groups, $C_1$-$C_8$ alkyloxycarbonyl amino groups, $C_6$-$C_{12}$ aralkyloxycarbonyl amino groups, dialkylamino groups, $C_2$-$C_6$ nitrogen heterocycles and $C_3$-$C_5$ nitrogen heteroaryl groups can be independently substituted with up to 5 residues selected from $R^{80}$, $R^{81}$, $R^{82}$, $R^{83}$, $R^{84}$ as defined above.

If Y and X represent peptide residues or peptidomimetic residues, a total number of the amino acids contained in X and Y of 1 to 5 is preferred and a number of 1 to 4 is further preferred, while a number of 2 to 3 is particularly preferred.

The following formulas are additional preferred general formulas for the inventive compounds:

(IA)

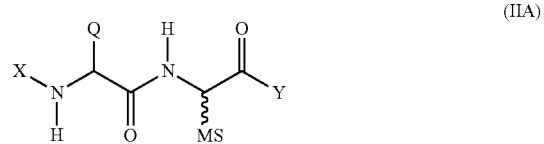

(IIA)

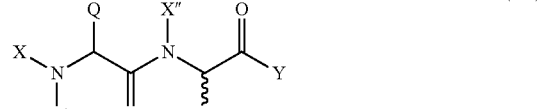

(IIB)

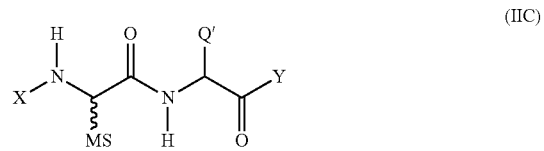

(IIC)

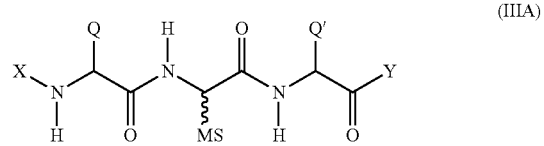

(IIIA)

wherein MS, E, Q, Q', X and Y have the meaning disclosed herein.

In a special embodiment, the side chain residues Q or Q', Q", Q''' and/or Q'''', respectively, together with the vicinal nitrogen atom, form a pyrrolidine ring so that at least one amino acid proline or a proline derivative or proline mimetic is present in the inventive compound. It is also possible that two, three, four or more proline amino acids are present in a compound, wherein one amino acid as proline is preferred.

Tripeptides and tetrapeptides are particularly preferred so that the present application preferably also relates to peptides of the general formula (IV) and the tetrapeptides derived therefrom.

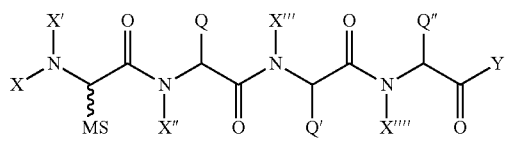

(IV)

wherein
MS is an acceptor-substituted olefin as described herein and MS is preferably a Michael system of at least one conjugated double bond and a carbonyl function as described herein;
Q, Q' and Q" independently of each other represent a side chain residue of a natural amino acid; or Q together with X" forms a propylenyl residue; or Q' together with X''' forms a propylenyl residue; or Q" together with X'''' forms a propylenyl residue;
Y represents a hydroxy group, amino group, $C_1$-$C_6$ alkylamino group, $C_1$-$C_6$ dialkylamino group, $C_1$-$C_6$ alkoxy group, $C_6$-$C_{19}$ aryloxy group, $C_1$-$C_6$ alkyl group, $C_1$-$C_6$ halogen alkyl group, $C_3$-$C_{10}$ heteroaryl group or a $C_6$-$C_{19}$ aryl group; or Y represents a peptide residue of up to 6 amino acids and bound via an amide bond, the C-terminal carbonyl function of which peptide residues carries a hydroxy group, amino group, $C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group; or Y represents a peptidomimetic residue of up to 60 carbon atoms, preferably of up to 30 carbon atoms and
X", X''', X'''' independently of each other represent hydrogen or a $C_1$-$C_6$ alkyl group; and
—NXX' is a amino group, —NH—CHO, $C_1$-$C_{10}$ alkylamino group, $C_1$-$C_8$ alkyloxycarbonyl amino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group or the group —NXX' is part of a peptidomimetic residue of up to 60 carbon atoms, preferably of up to 30 carbon atoms
or
X' represents hydrogen or a $C_1$-$C_6$ alkyl group; and
X represents a peptide residue of up to 6 amino acids and bound via an amide bond, the N-terminus of which peptide residue carries an amino group, —NH—CHO, $C_1$-$C_{10}$ alkylamino group, $C_1$-$C_8$ alkyloxycarbonyl amino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group,
wherein any of the $C_1$-$C_6$ alkoxy groups, $C_1$-$C_6$ alkyl groups, $C_1$-$C_{10}$ alkylamino groups, $C_1$-$C_8$ alkyloxycarbonyl amino groups, $C_6$-$C_{12}$ aralkyloxycarbonyl amino group, $C_1$-$C_{10}$ dialkylamino groups, $C_2$-$C_6$ nitrogen heterocycles as well as $C_3$-$C_5$ nitrogen heteroaryl groups can be independently substituted with up to 5 residues selected from $R^{80}$, $R^{81}$, $R^{82}$, $R^{83}$, $R^{84}$,
wherein the residues $R^{80}$, $R^{81}$, $R^{82}$, $R^{83}$, $R^{84}$ independently of each other have the above meaning.

In the case that neither X nor Y represent a peptide residue or an amino acid residue (comprising amino acid analogues and peptidomimetic residues), formula (IV) leads to tetrapeptides having a preferred structure.

According to formula (IV), only such an acceptor-substituted olefin (MS) or respectively only such a Michael system (MS) is present which is located in terminal position at the N-terminus of the inventive compound. Also, two, three or four identical or different acceptor-substituted olefins or respectively Michael acceptor systems may be present. Besides, the acceptor-substituted olefin or respectively the Michael system can be located at any of the amino acids, as can be seen from the following general formulas IVA-IVD:

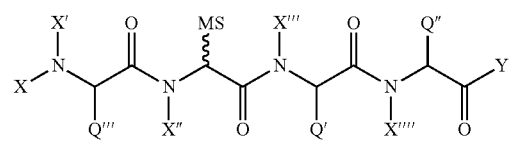

IVA

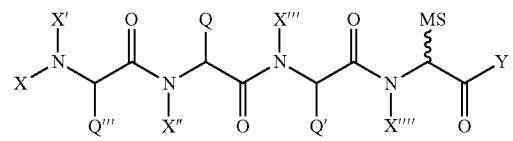

IVB

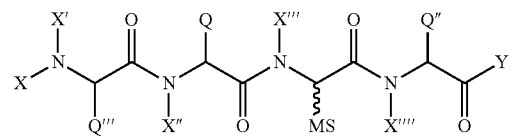

IVC

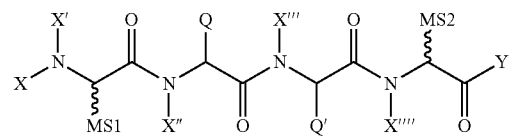

IVD

The side chain Q together with the residue X", the nitrogen bound to X" and the carbon bound to Q may form a pyrrolidine ring so that the compounds contain a proline amino acid.

Similarly, the side chain Q' together with the group X''' and the nitrogen bound to X''' and the carbon bound to Q' can form a pyrrolidine ring.

The side chain Q" together with the residue X'''', the nitrogen bound to X'''' and the carbon bound to Q" may form a pyrrolidine ring, just as Q''' can form a heterocyclyl residue with the chiral carbon atom bound to Q''' and the group X and the oxygen atom bound to X.

This leads to the formation of the following tetrapeptides VA to VD with a proline amino acid:

Additional preferred structures:

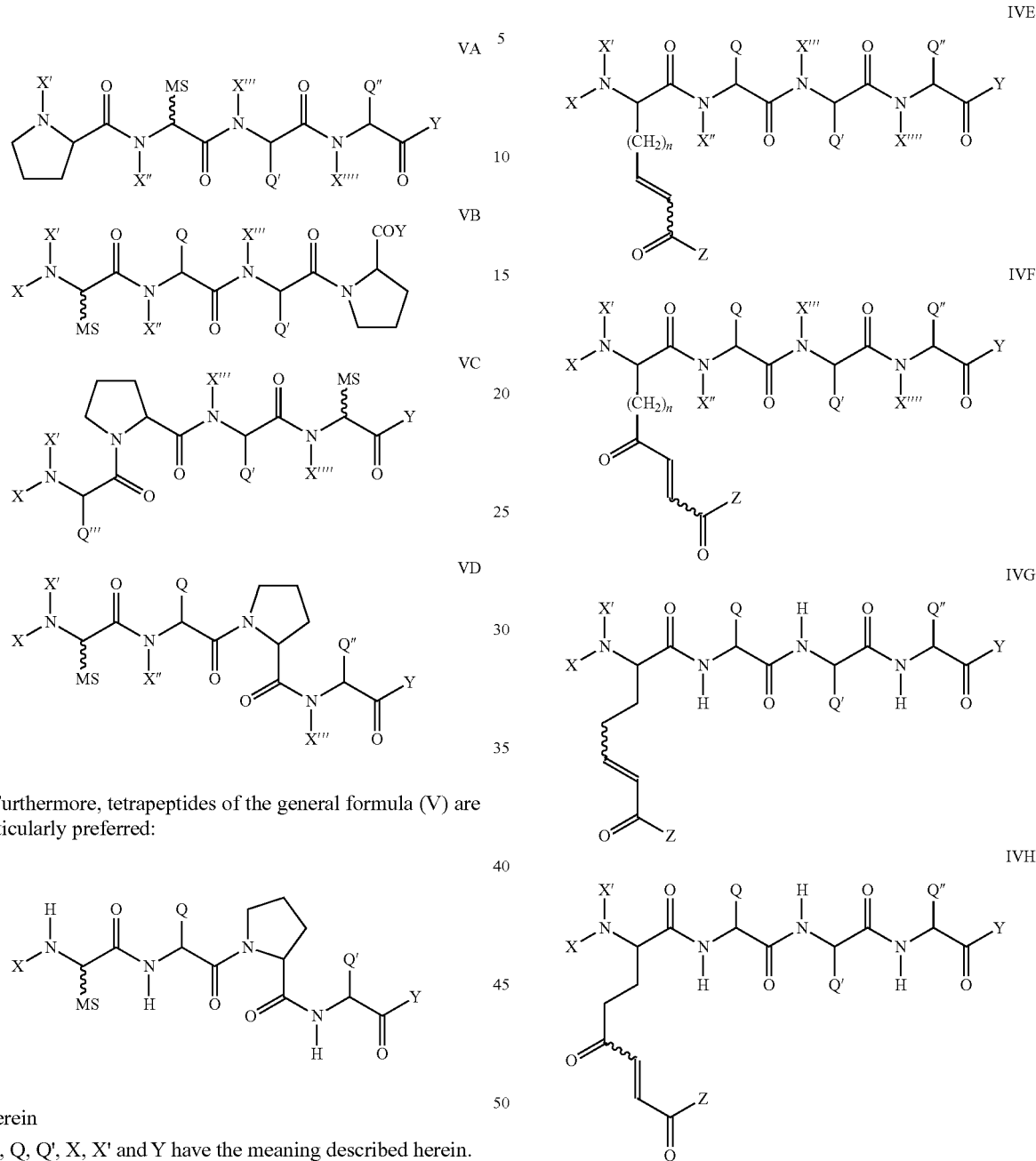

Furthermore, tetrapeptides of the general formula (V) are particularly preferred:

wherein
MS, Q, Q', X, X' and Y have the meaning described herein.

Michael systems (MS) of the following structure are particularly preferred:

wherein Z and Z' have the meaning disclosed herein.

Furthermore, it is preferred that the peptides, peptide derivatives or peptidomimetics contain the amino acid glutamine, proline, valine and/or leucine and in particular the sequence proline-leucine.

The following substructures of the general formulas VE to V are preferred:

VE

VF

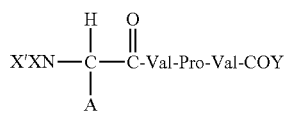

VG

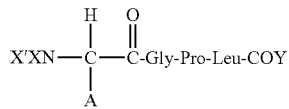

VH

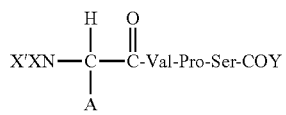

VJ

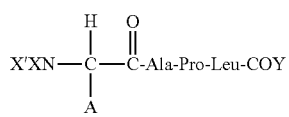

VK

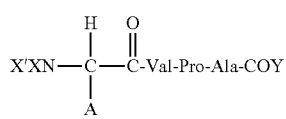

VL

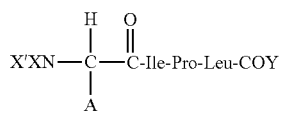

VM

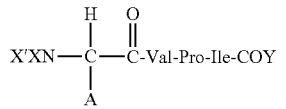

Preferably, Y is a hydroxyl group, $C_1$-$C_6$ alkoxy group or a $C_6$-$C_{19}$ aryloxy group. Preferably, X' is hydrogen and X is a phenyl or alkyloxycarbonyl group.

The compound of the formulas VN and VO as well as the compounds 1 and 2 (?) are particularly preferred:

VN

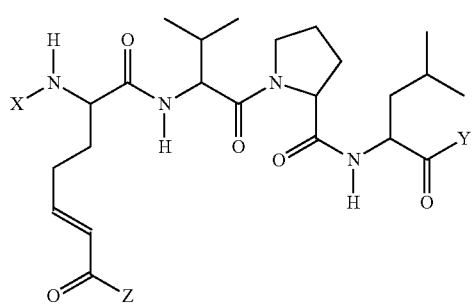

VO

[structure]

compound 1

[structure]

VK $N^\alpha$-benzyloxycarbonyl-{[(E)-(L)-6-amino-hept-2-ene dicarboxylic acid]-1-ethanoyl}-L-valinyl-L-prolinyl-L-leucine methyl ester

VL compound 7

[structure]

$N^\alpha$-acetyl-L-asparaginyl-{[(E)-(L)-6-amino-hept-2-ene dicarboxylic acid]-1-methanoyl}-L-glutamyl-L-alaninyl-L-valine methyl ester Additional inventive compounds are mentioned in the following:

$N^\alpha$-benzyloxycarbonyl-{[(E)-(L)-6-amino-hept-2-ene-dicarboxylic acid]-1-ethanoyl}-L-glutaminyl-L-prolinyl-L-leucine methyl ester (compound 2);

$N^\alpha$-benzyloxycarbonyl-{[(E)-(L)-6-amino-hept-2-ene-dicarboxylic acid]-1-ethanoyl}-L-phenylalanine methyl ester (compound 3);

$N^\alpha$-benzyloxycarbonyl-{[(E)-(L)-6-amino-hept-2-ene-dicarboxylic acid]-1-methanoyl}-L-glutaminyl-L-proline methyl ester (compound 4);

N$^\alpha$-benzyloxycarbonyl-{[(E)-(L)-6-amino-hept-2-ene-dicarboxylic acid]-1-ethanoyl}-L-glutaminyl-L-prolinyl-L-isopentyl amide (compound 5);

[(E)-(L)-6-(2-oxo-pyrrolidon-1-yl)-hept-2-ene-dicarboxylic-acid-1-ethanoyl]-L-valinyl-L-proline methyl ester (compound a);

N$^\alpha$-acetyl-L-leucinyl-glycinyl-L-prolinyl-glycinyl-{[(E)-(L)-6-amino-hept-2-ene-dicarboxylic acid]-1-ethanoyl}-L-serinyl-L-leucinyl-L-valinyl-L-isoleucinyl-glycine methyl ester (compound 8);

N$^\alpha$-benzyloxycarbonyl-{[L-7-amino-4-oxo-oct-2-ene-dicarboxylic acid]-1-ethanoyl}-L-valinyl-L-prolinyl-leucine-methyl ester (compound 9);

N$^\alpha$-Acetyl-{[(E)-(L)-6-amino-hept-2-ene-dicarboxylic acid]-1-methanoyl}-L-glutaminyl-L-glutamyl-L-alanine methyl ester (compound 10);

N$^\alpha$-acetyl-{[(E)-(L)-6-amino-hept-2-ene-dicarboxylic acid]-1-methanoyl}-L-glutaminyl-L-glutamyl methyl ester (compound 11);

N$^\alpha$-acetyl-{[(E)-(L)-6-Amino-hept-2-ene dicarboxylic acid]-1-methanoyl}-L-phenylalaninyl-L-prolinyl-L-leucine methyl ester (compound 12);

N$^\alpha$-benzyloxycarbonyl-{[(E)-(L)-6-amino-hept-2-ene dicarboxylic acid]-1-methanoyl}-L-phenylalaninyl-L-prolinyl-L-leucine methyl ester (compound 13);

N$^\alpha$-acetyl-{[(E)-(L)-6-amino-hept-2-ene-dicarboxylic acid]-1-methanoyl}-L-(p-fluoro)-phenylalaninyl-L-prolinyl-L-leucine methyl ester (compound 14);

N$^\alpha$-benzyloxycarbonyl-{[(E)-(L)-6-amino-hept-2-ene-dicarboxylic acid]-1-methanoyl}-L-(p-fluoro)-phenylalaninyl-L-prolinyl-L-leucine methyl ester (compound 15);

[(E)-(L)-6-(2-Oxo-pyrrolidon-1-yl)hept-2-ene-dicarboxylic acid 1-ethanoyl]-L-valinyl-L-homoprolinyl-L-leucine methyl ester (compound 16);

[(E)-(L)-6-(2-oxo-pyrrolidon-1-yl)-hept-2-ene-dicarboxylic acid-1-ethanoyl]-L-cyclohexylglycinyl-L-homoprolinyl-L-leucine methyl ester (compound 17);

[(E)-(L)-6-(2-oxo-pyrrolidon-1-yl)-hept-2-ene-dicarboxylic acid-1-ethanoyl]-L-cyclohexylglycinyl-L-prolinyl-L-leucine methyl ester (compound 18);

N$^\alpha$-benzyloxycarbonyl-{[(E)-(L)-6-amino-hept-2-ene-dicarboxylic acid]-1-ethanoyl}-L-glutaminyl-L-proline-L-tyrosine methyl ester (compound 19);

N$^\alpha$-benzyloxycarbonyl-{[(E)-(L)-6-amino-hept-2-ene-dicarboxylic acid]-1-ethanoyl}-L-glutaminyl-L-prolinyl-L-leucine methyl ester (compound 20);

N$^\alpha$-benzyloxycarbonyl-{[(E)-(L)-6-amino-hept-2-ene-dicarboxylic acid]-1-ethanoyl}-L-leucinyl-L-prolinyl-L-glutamine methyl ester (compound 21);

N$^\alpha$-acetyl-{[L-7-Amino-4-oxo-oct-2-ene-dicarboxylic acid]-1-ethanoyl}-L-glutaminyl-L-prolinyl-L-leucine methyl ester (compound 22);

N$^\alpha$-(5-methylisoxazol-3-carbonyl)-{[L-7-amino-4-oxo-oct-2-ene-dicarboxylic acid]-1-isopropanoyl}-L-valinyl-L-prolinyl-leucine methyl ester (compound 23);

N$^\alpha$-(2-fluorobenzoyl)-{[L-7-amino-4-oxo-oct-2-ene-dicarboxylic acid]-1-methanoyl}-L-valinyl-L-4-fluoroprolinyl-leucine isopropyl ester (compound 24);

N$^\alpha$-benzyloxycarbonyl-{[(E)-(L)-6-amino-hept-2-ene-dicarboxylic acid]-1-ethanoyl}-L-phenylalaninyl-L-prolinyl-L-leucine methyl ester (compound 25);

N$^\alpha$-benzyloxycarbonyl-{[(E)-(L)-6-amino-hept-2-ene-dicarboxylic acid]-1-ethanoyl}-glycinyl-L-prolinyl-L-leucine methyl ester (compound 26);

N$^\alpha$-benzyloxycarbonyl-{[(E)-(L)-6-amino-hept-2-ene-dicarboxylic acid]-1-ethanoyl}-L-alaninyl-L-prolinyl-L-leucine methyl ester (compound 27);

N$^\alpha$-tert.butyloxycarbonyl-{[(E)-(L)-6-amino-hept-2-ene-dicarboxylic acid]-1-ethanoyl}-L-glutaminyl-L-prolinyl-L-leucine methyl ester (compound 28);

N$^\alpha$-thiophene-2-carbonyl-{[(E)-(L)-6-amino-hept-2-ene-dicarboxylic acid]-1-ethanoyl}-L-glutaminyl-L-prolinyl-L-leucine methyl ester (compound 29);

N$^\alpha$-furane-3-carbonyl-{[(E)-(L)-6-amino-hept-2-ene-dicarboxylic acid]-1-ethanoyl}-L-glutaminyl-L-prolinyl-L-leucine methyl ester (compound 30);

N$^\alpha$-isoxazole-5-carbonyl-{[(E)-(L)-6-amino-hept-2-ene-dicarboxylic acid]-1-ethanoyl}-L-glutaminyl-L-prolinyl-L-leucine methyl ester (compound 31);

??? (compound 32 fehlt!)

N$^\alpha$-(5-methyl-isoxazole-3-carbonyl)-{[(E)-(L)-6-amino-hept-2-ene-dicarboxylic acid]-1-ethanoyl}-L-glutaminyl-L-prolinyl-L-leucine methyl ester (compound 33);

N$^\alpha$-(trans-3-(3-thienyl)acryloyl)-{[(E)-(L)-6-amino-hept-2-ene-dicarboxylic acid]-1-ethanoyl}-L-glutaminyl-L-prolinyl-L-leucine methyl ester (compound 34);

N$^\alpha$-acetyl-{[(E)-(L)-6-amino-hept-2-ene-dicarboxylic acid]-1-ethanoyl}-L-glutaminyl-L-prolinyl-L-leucine methyl ester (compound 35);

N$^\alpha$-(4-trifluoromethoxy-benzolsulfonyl)-{[(E)-(L)-6-amino-hept-2-ene-dicarboxylic acid]-1-ethanoyl}-L-glutaminyl-L-prolinyl-L-leucine methyl ester (compound 36);

N$^\alpha$-benzyloxycarbonyl)-{[(E)-(L)-6-amino-hept-2-ene-dicarboxylic acid]-1-ethanoyl}-L-cyclohexyl glycine-L-prolinyl-L-leucine methyl ester (compound 37);

N$^\alpha$-benzyloxycarbonyl)-{[(E)-(L)-6-amino-hept-2-ene-dicarboxylic acid]-1-ethanoyl}-L-valinyl-L-homoprolinyl-L-leucine methyl ester (compound 38);

(E)-(S)-6-benzyloxycarbonyl amino-6-[3-((R)-2-phenylcarbamoyl-pyrrolidine-1-carbonylphenylcarbamoyl]-hex.2-ene acid ethyl ester (compound 39);

(E)-(S)-6-benzyloxycarbonyl amino-6-{1-[(S)-3-carboxy-1-(3-methyl-butylcarbamoyl)-propyl]-2-oxo-1,2-dihydro pyridine-3-ylcarbamoyl}-hex-2-enoyl acid isopropyl ester (compound 40);

N$^\alpha$-benzyloxycarbonyl)-{[(E)-(L)-2-amino-6-methansulfonyl]-hex-5-enyl]-L-glutaminyl-L-prolinyl-L-leucine methyl ester (compound 3.2.1);

N$^\alpha$-benzyloxycarbonyl)-[(E)-(L)-2-amino-6-dimethylsulfamoyl)-hex-5-enyl]-L-glutaminyl-L-prolinyl-L-leucine methyl ester (compound 3.2.2);

N$^\alpha$-benzyloxycarbonyl)-[(L)-2-amino-4-(3-oxo-cyclopent-1-enyl]-butyryl-L-glutaminyl-L-prolinyl-L-leucine methyl ester (compound 3.2.3);

N$^\alpha$-benzyloxycarbonyl)-[(L)-2-amino-5-(2-oxo-dihydro-furane-(3E)-ylidene)]-pentanoyl-L-glutaminyl-L-prolinyl-L-leucine methyl ester (compound 3.2.4);

N$^\alpha$-benzyloxycarbonyl)-[(E)-(L)-6-amino-hept-2-ene-dicarboxylic acid]-L-glutaminyl-L-prolinyl-L-leucine methyl ester (compound 3.2.5);

Nr-acetyl-{[(E)-(L)-6.amino-hept-2-ene-dicarboxylic acid]-1-pentylamido}-L-glutaminyl-L-asparatyl-L-proline methyl ester (compound 3.2.6);

N$^\alpha$-benzyloxycarbonyl)-{[(E)-(L)-6-amino-hept-2-ene-dicarboxylic acid]-1-isopropanoyl}-L-(p-fluoro-phenylalaninyl)-L-proline (compound 3.2.7);

N$^\alpha$-benzyloxycarbonyl)-{[(E)-(L)-6-amino-hept-2-ene-dicarboxylic acid]-1-benzoyl}-L-phenylalaninyl-L-homoprolinyl-L-leucinyl amide (compound 3.2.8);

N$^\alpha$-benzyloxycarbonyl)-{[(E)-(L)-7-amino-2-oxo-oct-3-ene-dicarboxylic acid]-1-ethanoyl}-L-phenylalanine methyl ester (compound 3.2.9);

N$^\alpha$-benzyloxycarbonyl)-[(Z)-(L)-2-amino-7-oxo-oct-5-ene-dicarboxylic acid]-L-glutaminyl-L-prolinyl-L-leucine methyl ester (compound 3.2.10);

N$^\alpha$-benzyloxycarbonyl)-[(Z)-(L)-2-amino-6-cyano-hex-5-ene-dicarboxylic acid]-L-glutaminyl-L-prolinyl-L-leucine methyl ester (compound 3.2.11);

N$^\alpha$-benzyloxycarbonyl)-{[(E)-(L)-6-amino-hept-2-ene-dicarboxylic acid]-1-ethanoyl}-L-valinyl-L-(octahydroindol-2-carboxyl)-L-leucinyl amide (compound 4A);

N$^\alpha$-(piperidinyl-4-carbonyl)-{[(E)-(L)-2-amino-6-phenylsulfonyl]-hex-5-enyl}-L-phenylalaninyl-L-prolinyl-L-1-cyclopentylmethyl-2-oxo-2-(1H-tetrazole-5-yl)-ethyl amide (compound 4.2);

N$^\alpha$-benzyloxycarbonyl)-[(E)-(L)-2-amino-6-benzyloxysulfonyl-hex-5-enyl]-L-valinyl-L-prolinylbenzyl sulfonamide (compound 4.3);

(E)-(S)-6-[(S)-1-((S)-2-ethylcarbamoyl pyrrolidine-1-carbonyl)-2-methyl-propylcarbamoyl]-6-(2-piperidine-4-yl-ethylamino)-hex-2-ene-carboxylic acid isopropyl ester (compound 5.1);

(S)-2-[((S)-1-{(E)-2R,5S)-2-(4-fluorobenzyl)-9-methansulfonyl-5-[(5-methyl-isoxazole-3-carbonyl)-amino]-4-oxo-non-8-enoyl}pyrrolidine-2-carbonyl)-amino]-4-methyl-valeric acid methyl ester (compound 5.3.b);

(E)-(6R,9S)-9-benzyloxycarbonylamino-6-[2-(2-ethylcarbamoyl-octahydroindole-1-yl)-1-methyl-2-oxoethylcarbamoyl]-8-oxo-10-phenyl-dec-2-enyl acid-isopropyl ester (compound 5.4);

Piperidine-4-carbonyl-((E)-(S)-5-benzylsulfonyl-1-{2-[2-((S)-2-benzylsulfonylaminocarbonyl-octahydro indole-1-yl)-2-oxo-ethylamino]-acetyl}-4-enyl)amide (compound 5.6);

(E)-5-(N'-acetyl-N-carboxy-hydrazino)-[pent-2-enoyl)-1-ethanoly]-L-valinyl-L-prolinyl-L-leucine methyl ester (compound 5.7);

The compounds described herein having at least one acceptor-substituted olefin or respectively at least one Michael system of a conjugated double bond and a carbonyl function as well as the compounds according to the general formulas [A], [B], [α], [D], [E], [F], (I), (II), (III), (IV) and (V) are particularly useful in the treatment and prophylaxis of coeliac disease and other transglutaminase associated diseases.

Coeliac disease is also designated as coeliac sprue, non-tropical or endemic sprue, gluten-sensitive enteropathy, gluten intolerance or intestinal infantilism. Coeliac disease is characterized by an intolerance to "gluten" leading to a chronic inflammation of the small bowel mucosa.

Gluten is a mixture of prolamin and glutenin and is present in many cereals, such as wheat, bulgur (wheat variety), spelt (wheat variety), einkorn (wheat variety), emmer (wheat variety), kamut (wheat variety), barley, Grunkern (unripe spelt grains), oats, rye, triticale (hybrid between wheat and rye). Said types of cereals include proteins to an content of about 7-15% wherein about 90% of the proteins are gluten. In the case of wheat, the prolamin is referred to as gliadin and in the case of rye as secalin, in the case of barley as hordein and in the case of avenna as avenin.

Among the other diseases associated with transglutaminases are diseases such as fibroses, thrombosis, neurodegenerative diseases, cataract, acne, psoriasis, skin ageing and candidosis.

The most important examples for neurodegenerative diseases include Huntington's disease, Parkinson's disease and Alzheimer's disease, wherein other examples for neurodegenerative diseases which can be treated by the compounds described herein also include hemiparkinson-hemiatrophy, parkinsonian syndrome, amyotrophic lateral sclerosis, dementia, AIDS related dementia, senile dementia, retinitis pigmentosa, muscular atrophy, spinal muscular atrophy, paraneoplastic cerebellar degeneration (PCD), cerebellar atrophy, extrapyramidal atrophy, ataxia, multiple sclerosis, phakomatoses, FXTAS (fragile X-associated tremor/ataxia syndrome), also designated as fragile X syndrome, progressive supranuclear palsy (PSP), striatonigral degeneration (SND), olivopontocerebellar degeneration (OPCD), Shy Drager syndrome (SDS), corticobasal degeneration, Lewy body dementia, Lewy body disease, idiopathic orthostatic hypotension (IOH), multisystem atrophies, frontotemporal dementia, Lytico-Bodig disease (parkinsonism/dementia/amyotrophic lateral sclerosis), progressive pallidal atrophy, Hallervorden-Spatz disease, X-linked dystonia (Lubag), mitochondrial cytopathy with striatal necrosis, neuroacanthocytosis, Restless Legs Syndrome, Wilson's disease and multiple system atrophy (MSA), polyneuropathies, Inflammatory Bowel Diseases, Crohn's disease, ulcerative colitis, inflammations, rheumatoid diseases, ADHD (Attention-Deficit Hyperactivity Disorder).

For the most part, the compounds described herein have basic and acidic characteristics and are mostly present in their betaine structure. Thus, the use of salts of the peptides, peptide derivatives and peptidomimetics described herein is preferred.

Consequently, the compounds of formula (I) or [A] may be administered per se or in form of a pharmacologically effective salt. Since the compounds of the general formulas [A] or (I) can have basic characteristics and acidic characteristics, salts of said compounds can be obtained by conventional methods.

Suitable examples of the salts of the compounds of the formulas [A], [B], [α], [D], [E], [F], (I), (II), (III), (IV) and (V) include acid addition salts, alkali metal salts as well as salts with amines. Thus, alkali metal salts such as sodium salt or potassium salt, lithium salt or magnesium salt, calcium salt, alkylamino salts or amino acid salts, e.g. with amino acids such as methionine, tryptophan, lysine or arginine can be mentioned. The following acids are acids forming an acid addition salt of the compounds of formulas [A], [B], [C], [D], [E], [F], (I), (II), (III), (IV) and (V): sulfuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid (glyconic acid, dextronic acid), lactic acid, malic acid, tartaric acid, tartronic acid (hydroxymalonic acid, hydroxypropane diacid), fumaric acid, citric acid, ascorbic acid, maleic acid, malonic acid, hydroxymaleic acid, pyruvic acid, phenylacetic acid, (o, m, p)-toluic acid, benzoic acid, p-aminobenzoic acid, p-hydroxybenzoic acid, salicylic acid, p-aminosalicylic acid, methanesulfonic acid, ethanesulfonic acid, hydroxyethanesulfonic acid, ethylenesulfonic acid, p-toluenesulfonic acid, naphthylsulfonic acid, naphthylamine sulfonic acid, sulfanilic acid, camphersulfonic acid, quinic acid, o-methylmandelic acid, hydrogen-benzenesulfonic acid, picric acid (2,4,6-trinitrophenol), adipic acid, d-o-tolyltartaric acid, amino acids such as methionine, tryptophan, arginine and especially acidic amino acids such as glutamic acid or aspartic acid.

In the compounds disclosed herein salts can be prepared by the addition of bases. Thus, salts can be formed with inorganic and organic bases, such as for example NaOH, KOH, NH$_4$OH, tetraalkylammonium hydroxide and the like.

Furthermore, embodiments herein relate to pharmaceutical compositions comprising at least one compound according to the general formula [A], [B], [C], [D], [E], [F], (I), (II), (III), (IV), (V), and/or pharmacologically acceptable salts thereof and at least one pharmacologically acceptable carrier, adjuvant or at least one pharmacologically acceptable solvent.

The pharmaceutical compositions can be provided in form of drops, mouth spray, nose spray, pills, tablets, film tablets, multi-layered tablets, suppositories, gels, ointments, syrup, inhalation powders, granulates, emulsions, dispersions, microcapsules, capsules, powders or injection solutions.

Furthermore, combination preparations with other substances can be prepared, wherein the one or more additional active ingredients of at least one compound of the general formula [A], [B], [C], [D], [E], [F], (I), (II), (III), (IV) or (V) are administered either in mixed or in combined form. Preferably, the transglutaminase blockers are used for complementing the gluten-free diet. Obviously, supplementary administration of vitamins, minerals and trace elements can be indicated. Administration of enzyme preparations in which, for example, prolyl endopeptidases or other peptidases are used is recommended. Moreover, combinations with antiphlogistics (steroidal and non-steroidal), T-cell silencers or cytokines or with monoclonal antibodies or zonulin can also be considered.

The pharmaceutical compositions are used in particular for the treatment and prophylaxis of coeliac disease and other diseases associated with transglutaminases or caused by transglutaminases.

Furthermore, the compounds of the general formulas [A], [B], [C], [D], [E], [F], (I), (II), (III), (IV) or (V) can be administered in form of their pharmaceutically active salts, optionally using essentially non-toxic pharmaceutically acceptable carriers, adjuvants or diluents. Medications are prepared in a known manner in a conventional solid or fluid carrier or in diluents and a conventional pharmaceutically acceptable adjuvant/expedient in a suitable dose. The preferred preparations are provided in an administrable form suitable for oral application, such as pills, tablets, film tablets, coated tablets, capsules, powders, deposits and sustained release forms.

Tablets, film tablets, coated tablets, gelatin capsules and opaque capsules are the preferred pharmaceutical formulations. Any pharmaceutical compositions contains at least one compound of the general formulas [A], [B], [C], [D], [E], [F], (I), (II), (III), (IV) or (V) and/or pharmaceutically acceptable salts thereof in an amount of 5 mg to 500 mg, preferably 10 mg to 250 mg and most preferred in an amount of 10 to 100 mg per formulation.

Besides, embodiments include pharmaceutical preparations for oral, parenteral, dermal, intradermal, intragastric, intracutaneous, intravascular, intravenous, intramuscular, intraperitoneal, intranasal, intravaginal, intrabuccal, percutaneous, rectal, subcutaneous, sublingual, topic, transdermal or inhalative application, containing, in addition to typical vehicles and diluents, a compound of the general formulas [A], [B], [C], [D], [E], [F], (I), (II), (III), (IV) or (V) and/or a pharmaceutically acceptable salt thereof as active component.

The pharmaceutical compositions include one of the peptides or peptidomimetics disclosed herein as active component, typically mixed with suitable carrier materials, selected with respect to the intended form of administration, i.e. dosage forms which can be administered orally such as tablets, capsules (filled either with a solid, a semi-solid or a liquid), powders, orally administrable gels, elixirs, dispersible granulates, syrups, suspensions and the like in accordance with conventional pharmaceutical practices. For example, the active ingredient component can be combined with any oral, non-toxic, pharmaceutically acceptable, inert carrier, such as lactose, starch, sucrose, cellulose, magnesium stearate, dicalcium phosphate, calcium sulfate, talc, mannitol, ethyl alcohol (liquid forms) and the like for the oral administration in form of tablets or capsules. Moreover, suitable binders, lubricants, disintegrants and colorants can be added to the mixture if required. Powders and tablets may include inert carriers to an extent from about 5% per weight to about 95% per weight of the inventive composition.

Suitable binders include starch, gelatin, natural sugars, sweeteners made of corn, natural and synthetic gums, such as acacia gum, sodium alginate, carboxymethylcellulose, polyethylene glycol and waxes. Possible lubricants for the use in said dosage forms include boric acid, sodium benzoate, sodium acetate, sodium chloride and the like. Disintegrants include starch, methylcellulose, guar gum and the like. If required, sweeteners and flavor additives and preservatives can also be included. Some of the terms used above, namely disintegrants, diluents, lubricants, binders and the like are discussed in greater detail below.

Additionally, the compositions may be formulated in a form with sustained release to provide for a controlled release rate of any one or more components or active components, in order to optimize the therapeutic effect, i.e. the antihistaminic activity and the like. Suitable dosage forms for sustained release include layered tablets containing layers with varying degradation rates or controlled release polymeric matrices impregnated with the active components and in the form of a tablet or capsule containing such impregnated or encapsulated porous polymeric matrices.

Preparations in fluid form include solutions, suspensions and emulsions, such as water or water propylene glycol solutions for parenteral injections or the addition of sweeteners and opacifiers for oral solutions, suspensions and emulsions.

Aerosol preparations which are suitable for inhalation may include solutions and solids in the form of powders which can be combined with a pharmaceutically acceptable carrier, such as a compressed inert gas, e.g. nitrogen.

For the preparation of suppositories a low melting wax, such as a mixture of fatty acid glycerides, e.g. cocoa butter, is melted and the active component therein is homogenously dispersed by stirring or similar mixing operations. The melted homogenous mixture is then poured in fitting forms, cooled and thus hardened.

Furthermore, preparations in solid form which are to be converted into preparations in fluid form for either oral or parenteral administration shortly before use are included. Such preparations in fluid forms include solutions, suspensions and emulsions.

Furthermore, the compounds may be administered via transdermal application. The transdermal compositions can have the form of crèmes, lotions, aerosols and/or emulsions.

The term capsule refers to a special container or casing composed of methylcellulose, polyvinyl alcohols or denatured gelatins or starches, in which the active ingredients can be contained. Typically, hard shell capsules are prepared from mixtures of bones and porcine skin gelatins having a comparatively high gel strength. The capsule itself can contain small amounts of colorants, opacifiers, softening agents and preservatives.

The term tablet describes a compressed or cast solid dosage form containing the active components with suitable diluents. The tablet can be produced by compressing mixtures or granulates obtained by wet granulation, dry granulation or compaction, which methods are known to the one skilled in the art.

Oral gels refer to the active components dispersed or solubilized in a hydrophilic semi-solid matrix.

Powders for compositions refer to powder mixtures containing the active components and suitable diluents which mixtures can be suspended in water or juices.

Suitable diluents are substances which usually form the largest part of the composition or dosage form. Suitable diluents include sugars such as lactose, sucrose, mannitol and sorbitol; starches derived from wheat, corn, rice and potatoes; and celluloses such as microcrystalline cellulose. The amount of diluents in the composition can range from about 5 to about 95% per weight of the total composition, preferably form about 25 to about 75% per weight and further preferred from about 30 to about 60% per weight.

The term disintegrants refers to materials added to the composition in order to support disintegration and release of the medicinal substance. Suitable disintegrants include starches, modified starches which are soluble in cold water, such as sodium carboxymethyl starch; natural and synthetic gums such as locust bean gum, caraya, guar gum, tragacanth and agar; cellulose derivatives such as methylcellulose and sodium carboxymethylcellulose, microcrystalline celluloses and crossl inked microcrystalline celluloses such as croscarmellose sodium; alginates such as alginic acid and sodium alginate; clays such as bentonites and foaming mixtures. The amount of disintegrants used in the composition can range from about 2 to 20% per weight of the composition and further preferred from about 5 to about 10% per weight.

Binders characterize substances binding or "gluing" powders and they consequently serve as "glue" in the formulation. Binders add a cohesion starch which is already available in the diluents or the disintegrant. Suitable binders include sugar, such as sucrose; starches derived form wheat, corn, rice and potatoes; natural gums such as acacia gum, gelatin and tragacanth; derivatives of sea weed such as alginic acid, sodium alginate and ammonium calcium alginate, cellulose materials such as methyl cellulose and sodium carboxymethylcellulose and hydroxypropyl methylcellulose, polyvinylpyrrolidone and inorganic compounds, such as magnesium aluminum silicate. The amount of binders in the composition can range from about 2 to about 20% per weight of the total composition, preferably form about 3 to about 10% per weight and further preferred from about 3 to about 6% per weight.

The term lubricant refers to a substance added to the dosage form in order to allow for the tablet, granulate, etc. to be released from the casting mold or pressing mold, after compression, by reducing the friction. Suitable lubricants include metallic stearates such as magnesium stearate, calcium stearate or potassium stearate; stearic acid; waxes with high melting points and water soluble lubricants such as sodium chloride, sodium benzoate, sodium acetate, sodium oleate, polyethylene glycols and D,L-leucine. Due to the fact that lubricants have to be present on the surface of the granulates as well as between the granulates and parts of the tablet press they are typically added during the last step prior to compression. The amount of lubricants in the composition can range from about 0.2 to about 5% per weight of the total composition, preferably form about 0.5 to about 2% per weight and further preferred from about 0.3 to about 1.5% per weight.

Lubricants are materials preventing caking and improving the flow characteristics of granulates so that the flow is smooth and uniform. Suitable lubricants include silicon dioxide and talc. The amount of lubricants in the composition can range from about 0.1 to about 5% per weight of the total composition, preferably form about 0.5; to about 2 per weight.

Colorants are adjuvants coloring the composition or dosage form. Such adjuvants can include colorants having food quality which are adsorbed on a suitable adsorption means, such as clay or aluminum oxide. The amount of the colorant used can vary from about 0.1 to about 5% per weight of the composition and preferably from about 0.1 to about 1% per weight.

As used herein, a "pharmaceutically effective amount" of a transglutaminase inhibitor is the amount or activity effective for achieving the desired physiological result, either in cells treated in vitro or in a patient treated in vivo. Specifically, a pharmaceutical effective amount is such an amount which is sufficient for inhibiting, for a certain period of time, one or more of the clinically defined pathological processes associated with transglutaminase. The effective amount can vary according to the specific inhibitor and additionally depends on a plurality of factors and conditions related to the subject to be treated and the severity of the disease. If, for example, an inhibitor is to be administered in vivo, factors such as age, weight and health of the patients as well as dose reaction curves and data regarding toxicity obtained from preclinical animal studies are to be considered. If the inhibitor in form of the peptides or peptidomimetics described herein is to be brought in contact in with the cells in vivo, a plurality of preclinical in vitro studies would be designed in order to determine parameters such as absorption, half-life, dose, toxicity, etc. Determining a pharmaceutically effective amount for a given pharmaceutically active ingredient is part of the ordinary skills of the one skilled in the art.

The following examples are intended to illustrate the invention with the help of selected compounds, without restricting the scope of the present invention to said precise examples. It will be apparent to the one skilled in the art that the analogous compounds and compounds produced according to analogous methods of synthesis fall within the scope of the present invention.

BRIEF DESCRIPTION OF THE DRAWINGS

In FIG. 3 the following abbreviations have the respective meaning:

EWG: electron-withdrawing group

TBTU: O-(benzotriazole-1-yl)-N—N—N'—N'-tetramethyloronium tetrafluoroborate

HOBt: 1-hydroxybenzotriazole

DIPEA: N-ethyldiisopropylamine

TFA: Trifluoroacetic acid

DMD: Dimethyldioxirane

Figure 4:
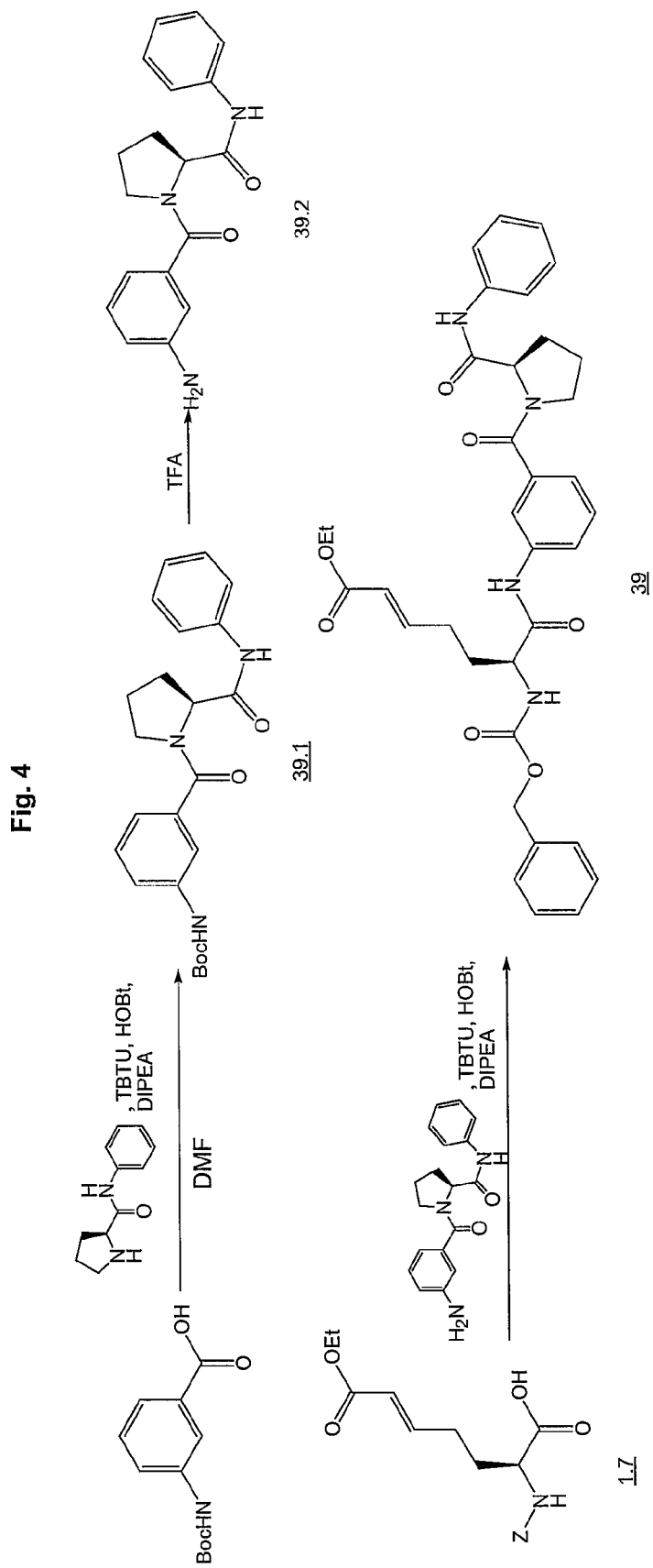

FIG. 4 shows the preparation of inhibitors with non-proteinogenic amino acids.

Figure 5:
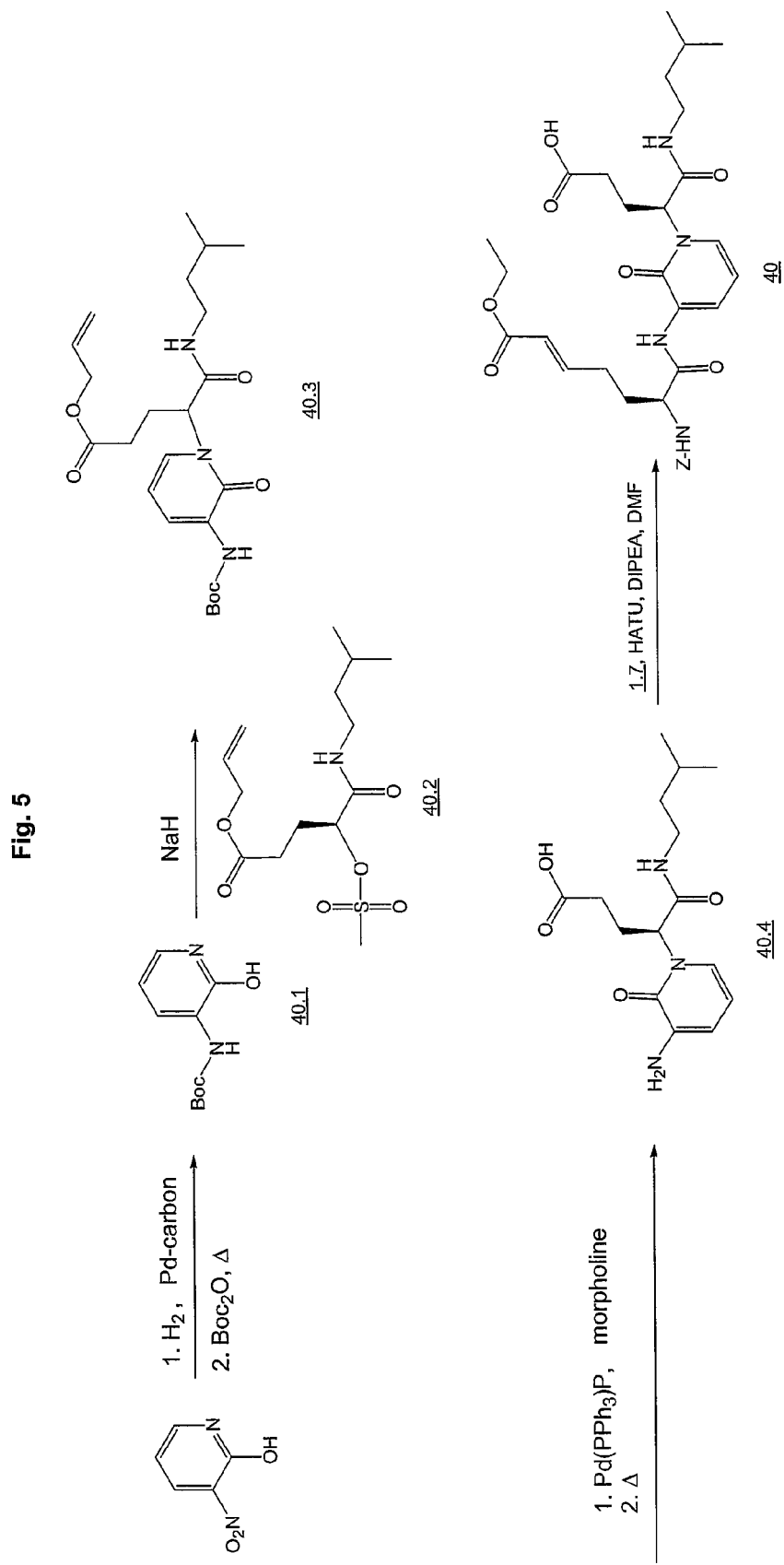
Figure 6:
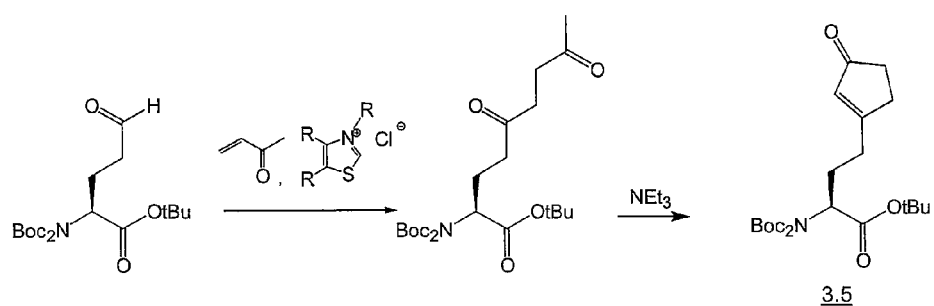
Figure 7:
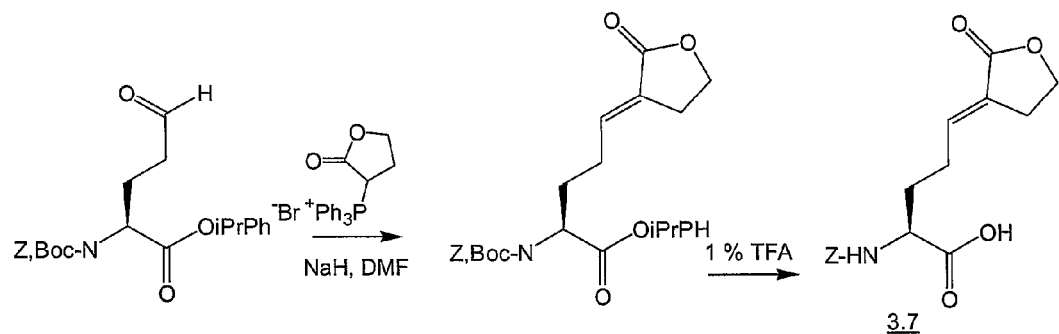
Figure 8:
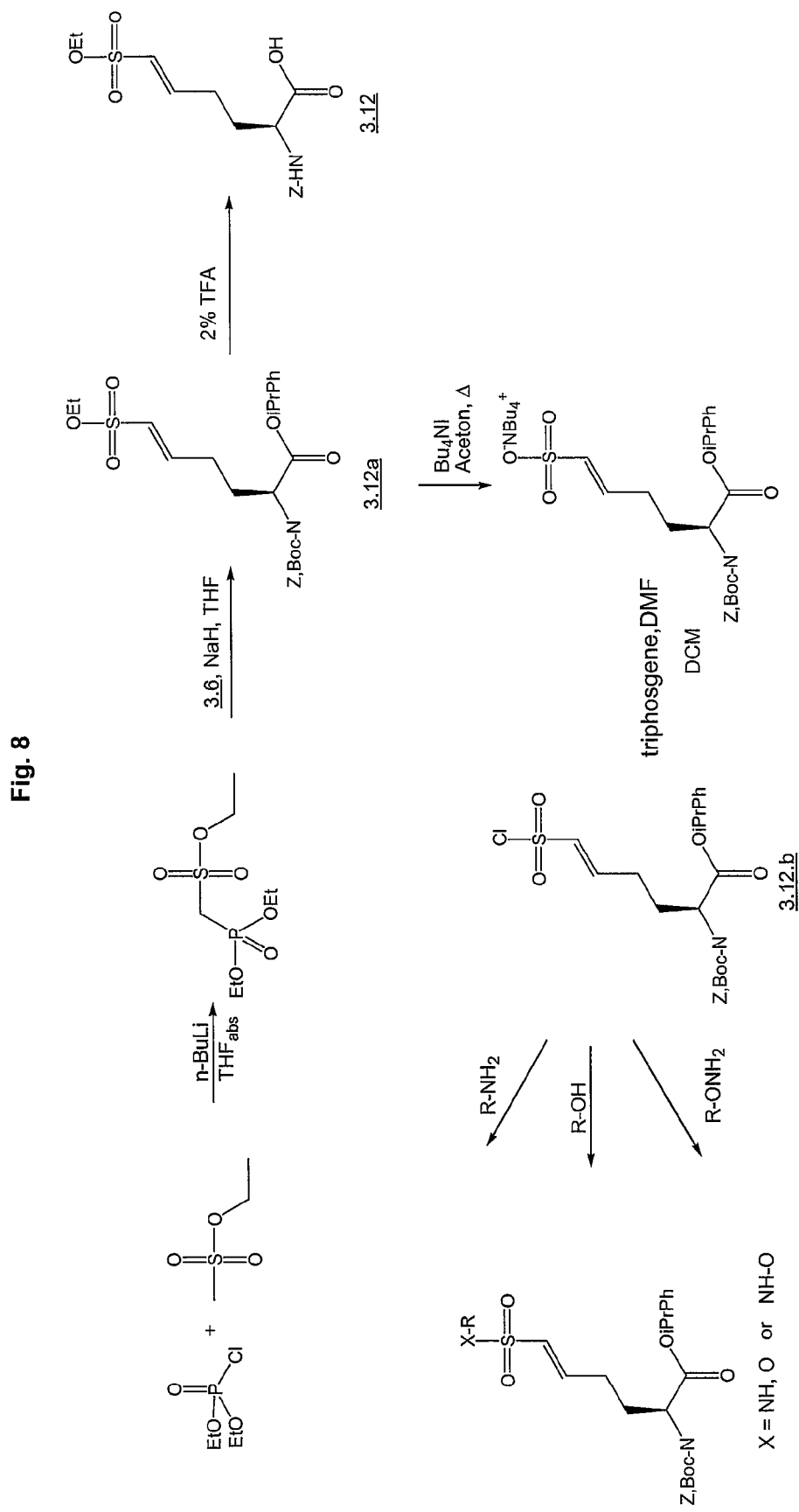

HATU: O-(7-azabenzotriazole-1-yl)-N—N—N'—N'-tetramethyloronium hexafluorophosphate FIG. 5 shows the preparation of pyridone-containing peptides FIG. 6 shows the preparation of Michael acceptor compounds with an endocyclic double bond FIG. 7 shows the preparation of inventive Michael acceptor compounds with an exocyclic double bond FIG. 8 shows the preparation of inventive vinyloguous sulfonic acid derivatives.

Figure 9:
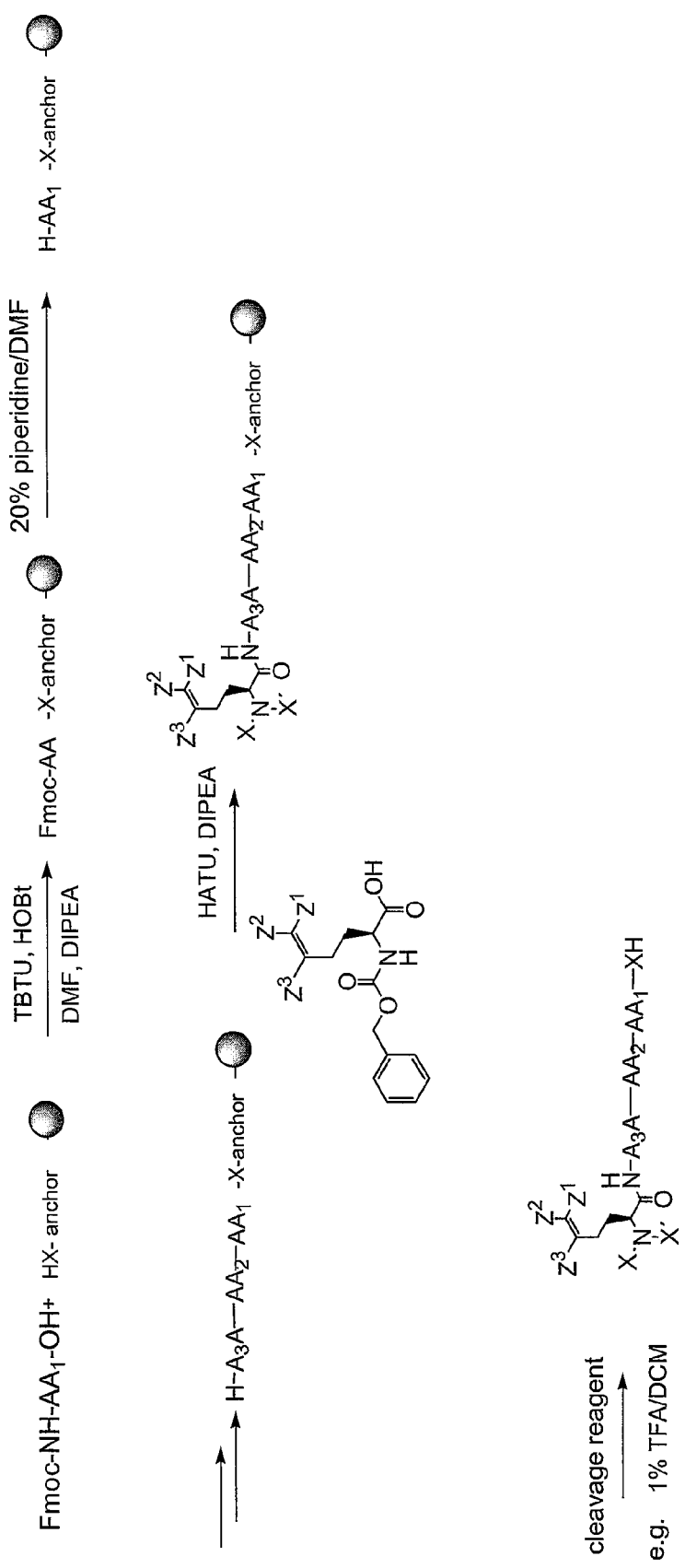

FIG. 9 shows the solid phase synthesis of inhibitors with a variable C-terminal residue.

Anchor means e.g. trityl(X=O), 2-chlorotrityl(X=O), Sieber amid(X=NH)

Figure 10:
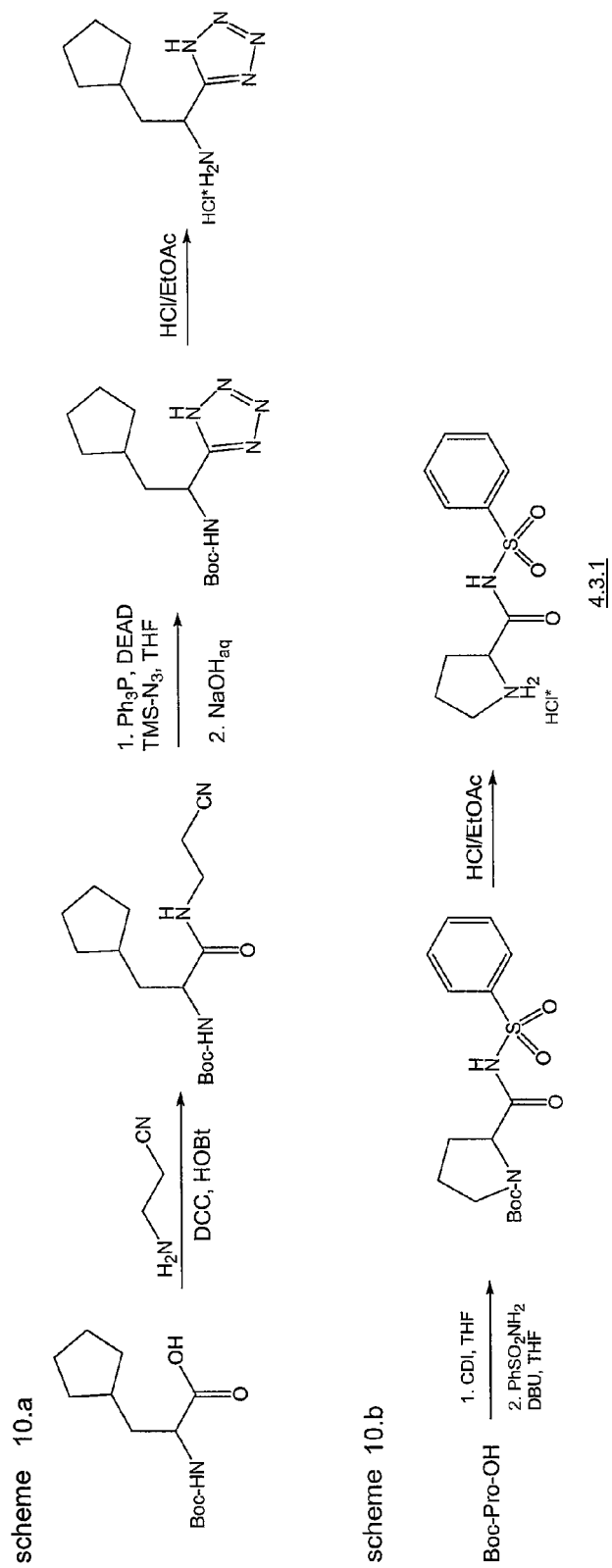

FIG. 10 shows carbonyl group surrogates and the synthesis of C-terminal residues using the example of tetrazoles (10a) and sulfonamides (10b).

Figure 11:
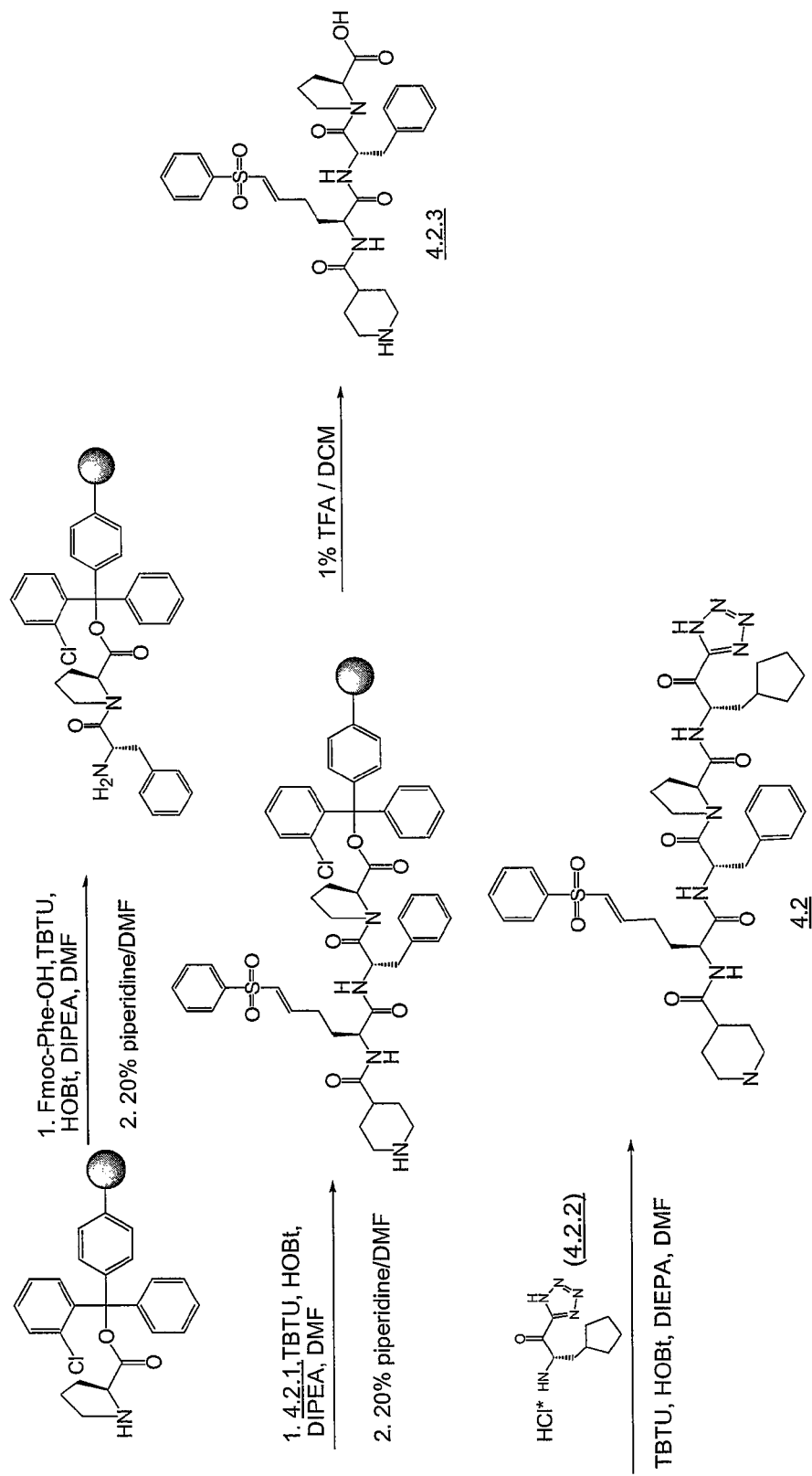

FIG. 11 shows the convergent synthesis of inhibitors containing carboxylic acid surrogates.

Figure 12:
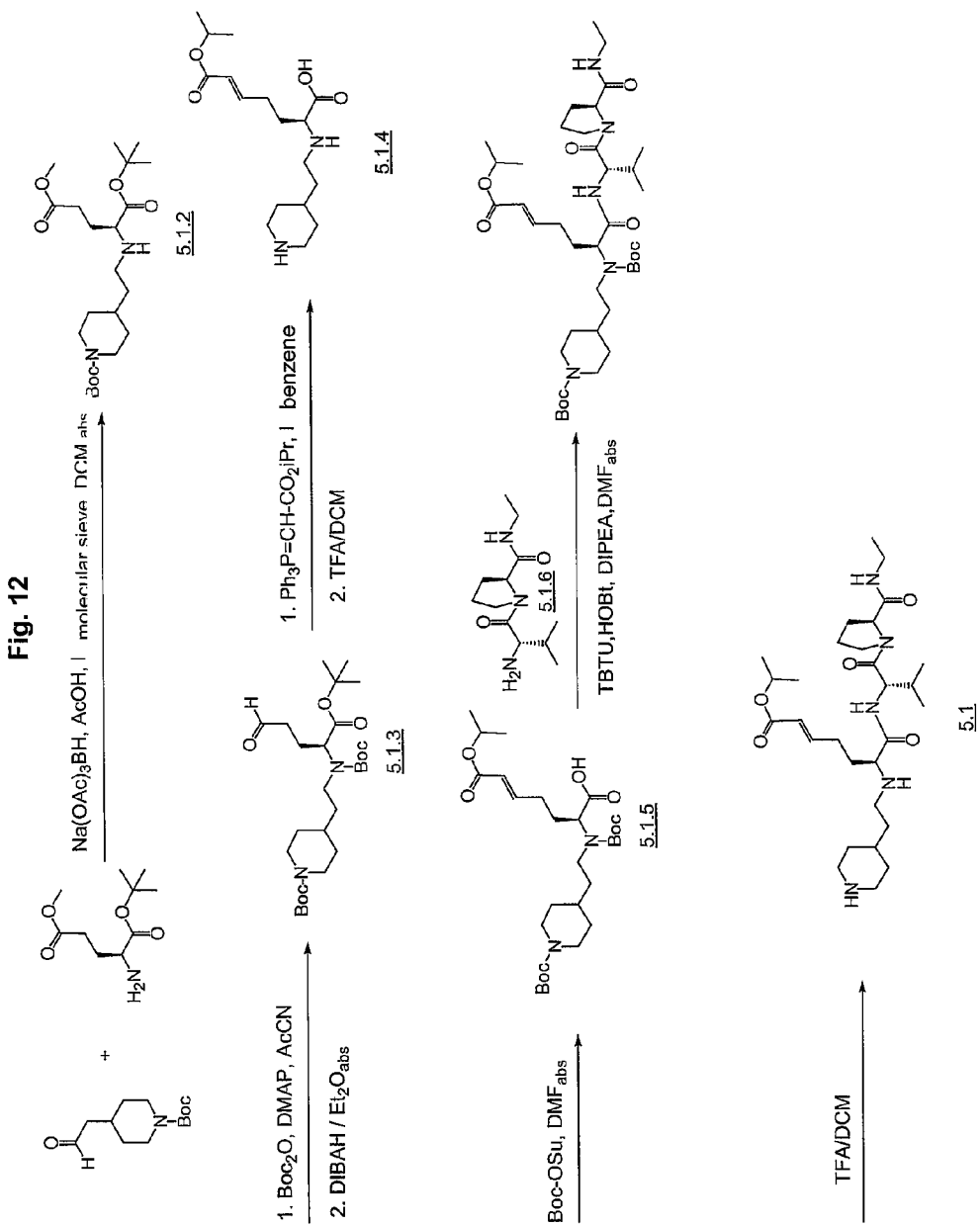

FIG. 12 shows an overview of the reaction for the preparation of compound: 5.1.

Figure 13:
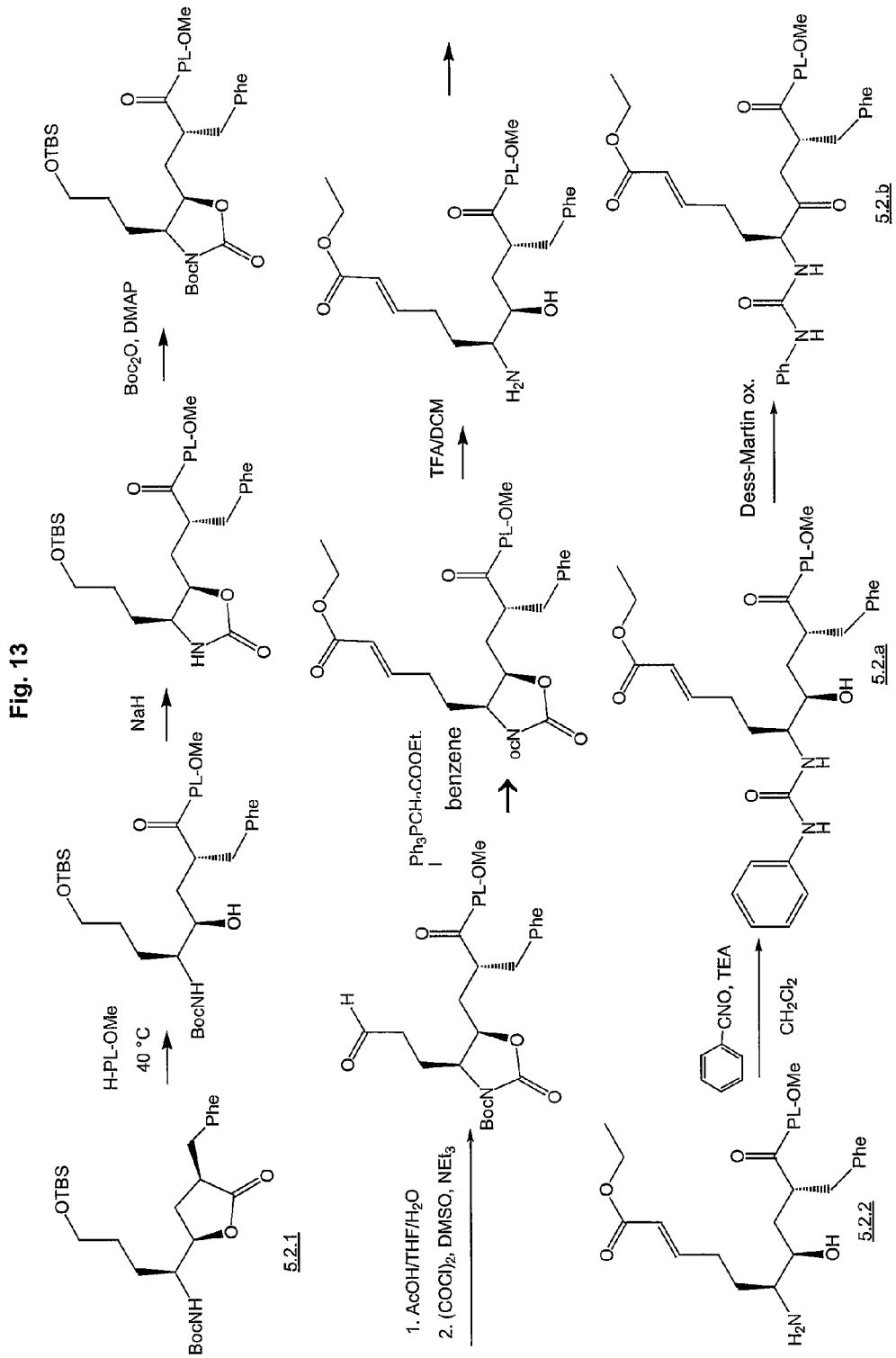

FIG. 13 shows an overview of the reaction for the preparation of inhibitors with hydroxymethylene (5.2.a) or ketomethylene isosters (5.2.b).

Figure 14:
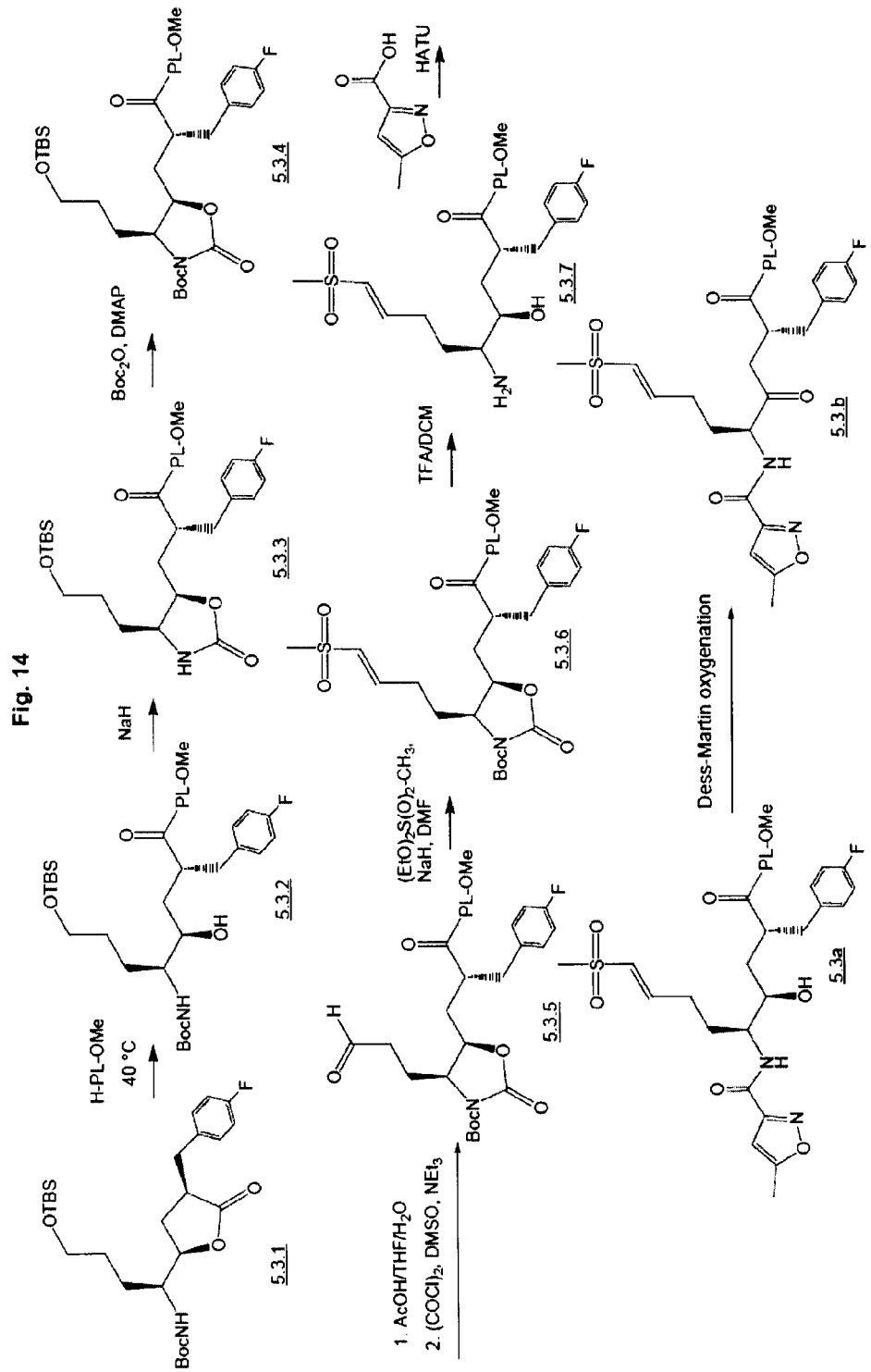

FIG. 14 shows an overview of the reaction for the preparation of compounds 5.3.a and 5.3.b.

Figure 15:
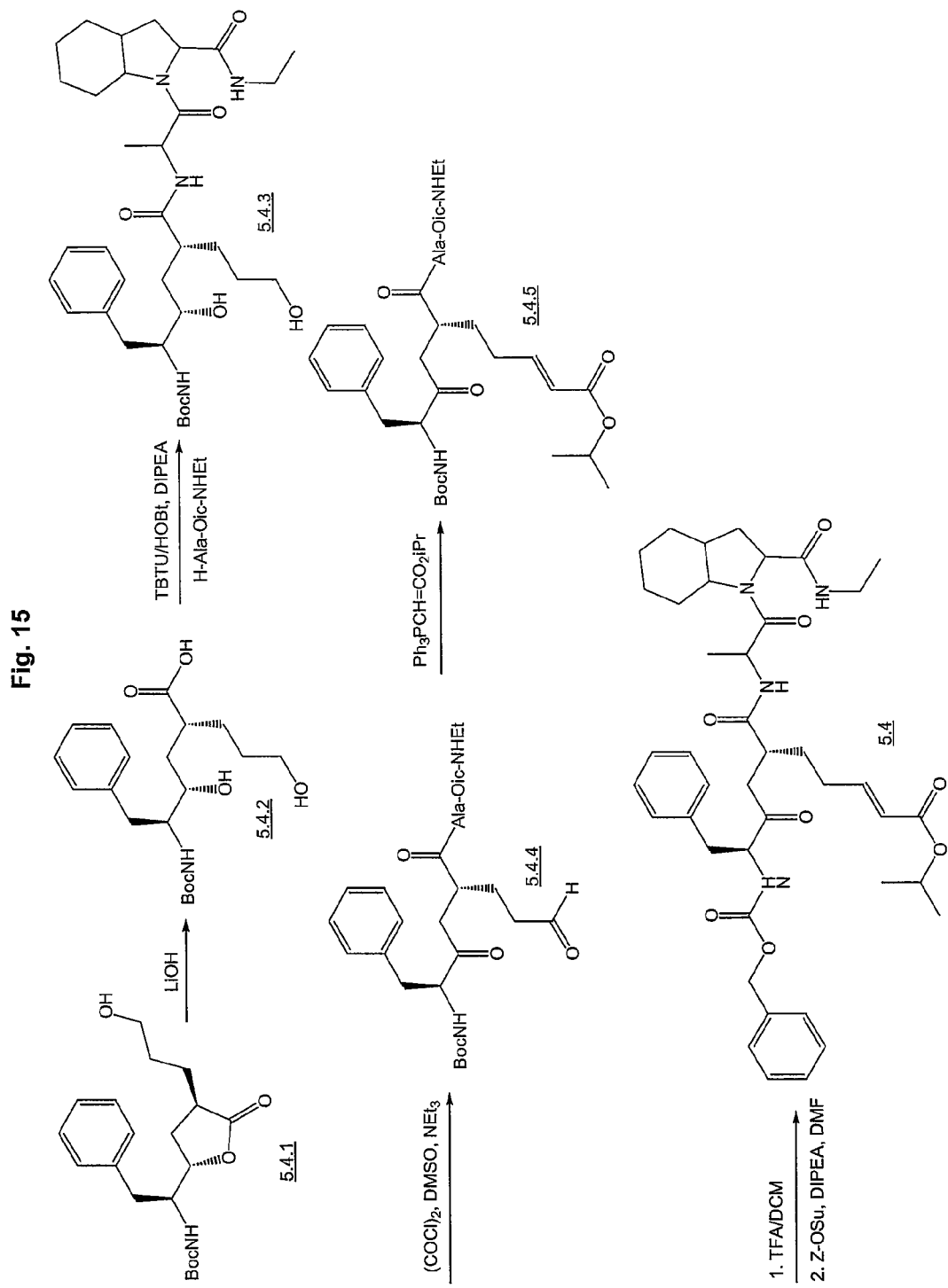

FIG. 15 shows an overview of the reaction for the preparation of compound 5.4.

Figure 16:
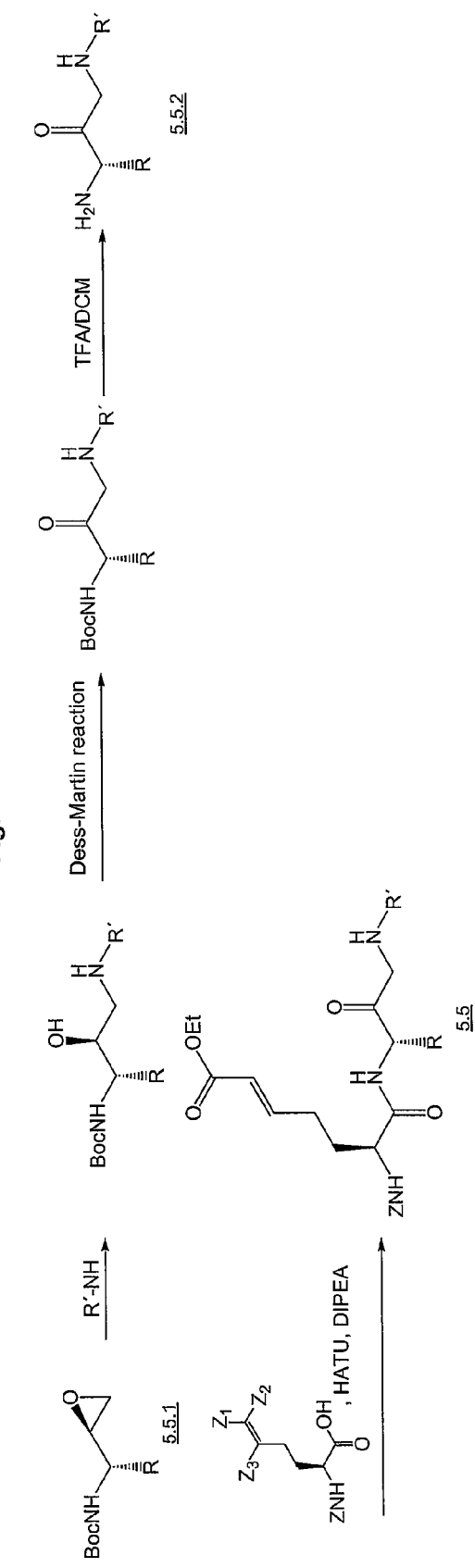

FIG. 16 shows a general synthesis scheme for the preparation of hydroxyethylamino isosters.

Figure 17:
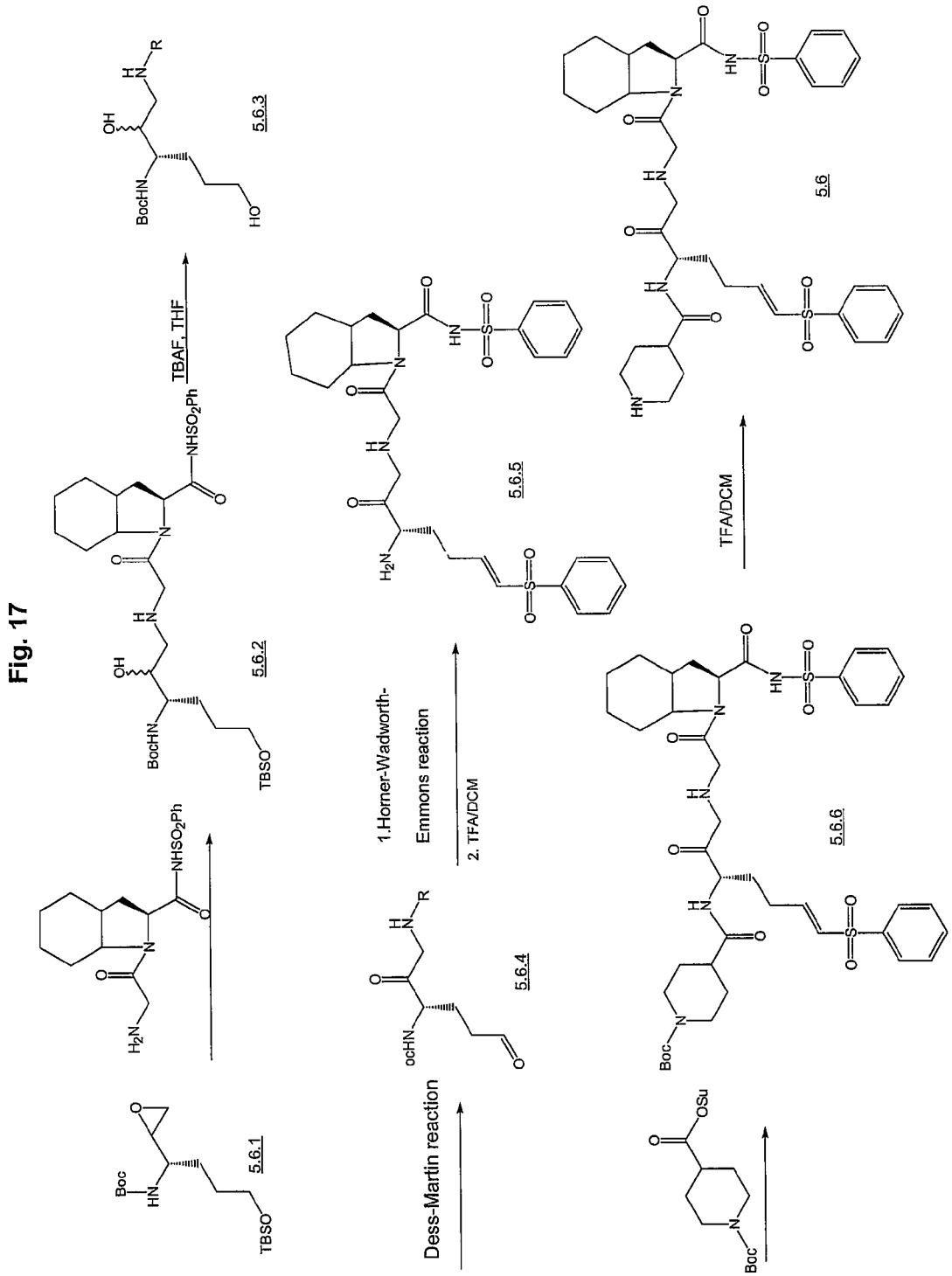

FIG. 17 shows an overview of the reaction for the preparation of compound 5.6.

Figure 18:
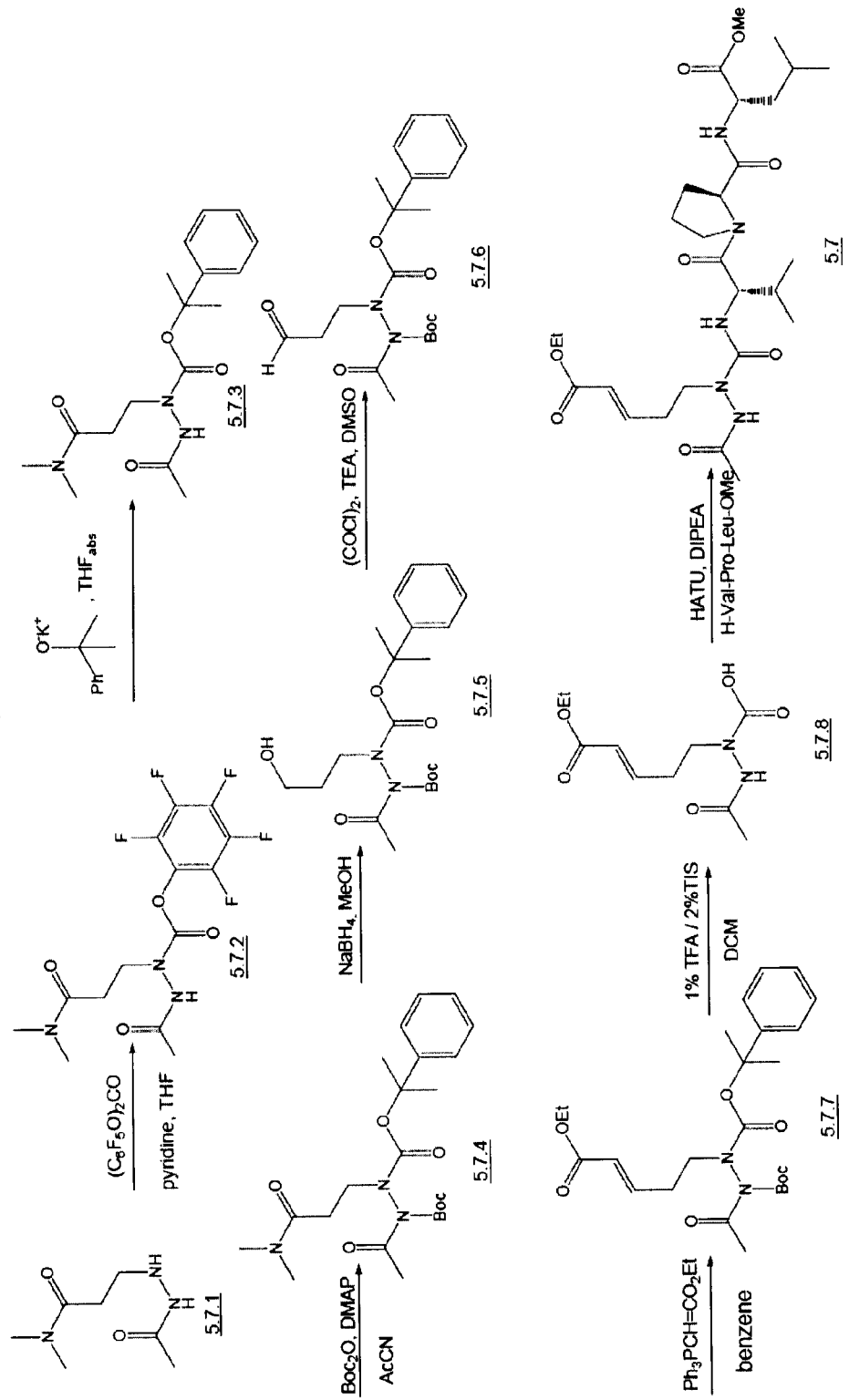

FIG. 18 shows an overview of the reaction for the preparation of compound 5.7.

Figure 19:
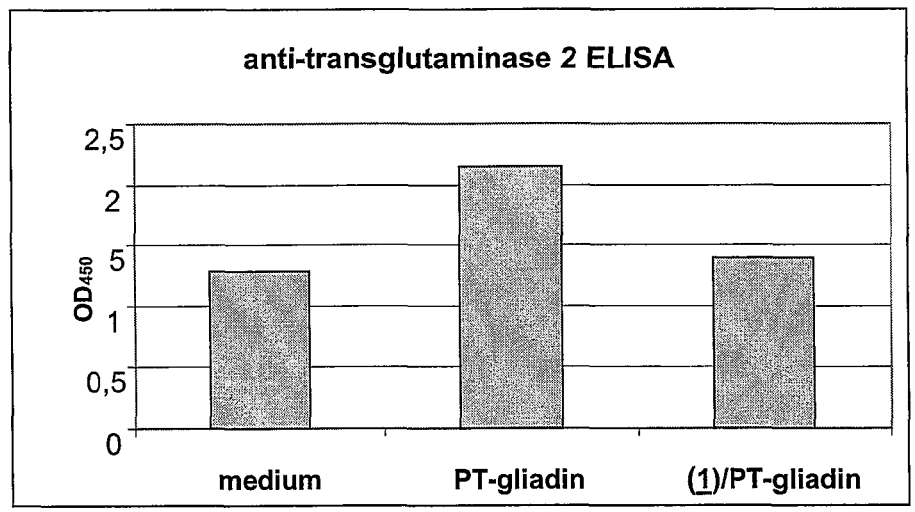

FIG. 19 shows values of the optical density $OD_{450}$ determined in the anti-TG2 ELISA for analyzing the concentration of antibodies and autoantibodies. In the anti-TG2-ELISA an $OD_{450}$ of 1.285 could be determined for the media control. In the supernatant of the PT-gliadin stimulated biopsy a clearly increased antibody concentration was determined ($OD_{450}$=2.144), while in the biopsy preincubated with the inhibitor (1) the antibody concentration was only slightly augmented ($OD_{450}$=1.401).

In patients suffering from coeliac disease the intake of gliadin (a cereal protein, e.g. in bread) leads to an increased autoantibody production in comparison with TG2.

The extinction determined in the anti-TG2-ELISA ($OD_{450}$) correlates with the autoantibody concentration in the sample. The clearly increased autoantibody concentration after treatment with PT-gliadin proves that the biopsy model (respectively the autoantibody production) can be stimulated and thus is suitable for the evaluation of transglutaminase inhibitors.

The slight increase of $OD_{450}$ corresponding to the autoantibody concentration after preincubation with inhibitor (1) shows that the inhibitors have the desired effects in the biological model. They clearly reduce the stimulation of the autoantibody production after treatment with PT-gliadin.

Figure 20:
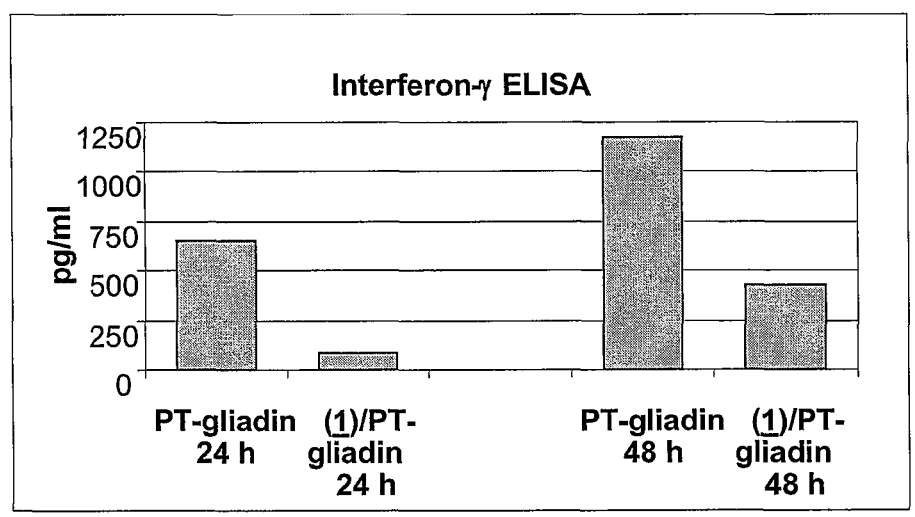

FIG. 20 shows the data measured in the interferon-γ ELISA for determining the interferon-γ values.

In the biopsy preincubated with inhibitor (1) only 86 pg/ml interferon-γ could be measured after 24 h, and only 426 pg/ml after 48 h.

With interferon-γ ELISA the concentration of interferon-γ is assessed in a sample.

Interferon-γ belongs to the so-called lead cytokines (transmitters) for inflammatory reactions. This means for patients suffering from coeliac disease that after the intake of cereal protein the lead cytokine interferon-γ is produced. Increased interferon-γ concentrations lead to an inflammation of the small bowel mucosa, a major symptom of coeliac disease.

In FIG. 20 it is shown that the incubation of the biopsies leads to the production of interferon-γ whereas a longer incubation time results—as expected—in a higher interferon-γ concentration. The preincubation with transglutaminase inhibitor (1) leads to a drastic drop of the interferon-γ concentration, after 24 h as well as after 48 h. Thus it could be shown in the biopsy model that transglutaminase inhibitor (1) inhibits the production of the lead cytokine interferon-γ. In combination with the data from example 1 the proof-of-principle for the therapy of coeliac disease with transglutaminase inhibitors is given.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

Structure of the Michael acceptor system

Michael acceptors are olefins which are conjugated with at least one electron-drawing substituent. Thus for the makeup of such Michael acceptors all reactions are suitable which generate such an olefin. Examples (but not limited to) are alkenylation reactions on metal organyls, Corey-Winter olefin syntheses, Horner-Wadworth-Emmons reactions, Knoevenagel condensations, Wittig reactions, Wittig-Horner reactions, Julia-Lythgoe olefinations and Peterson olefinations. These and other olefin-forming reactions is part of the ordinary skills of the one skilled in the art. Particularly preferred herein are reactions in which an aldehyde reacts with a suitably substituted Phosphory ylide or a corresponding phosphonate (Wittig reaction, Wittig-Horner reaction, Horner-Wadworth-Emmons reaction). Dragovich et al. could show the broad application of this reaction type for the synthesis of Michael acceptor systems (Dragovich et al., J. Med. Chem. 1998, 41, 15, 2806-2818). The reagents needed therefore are commercially available on a large scale (e.g. Sigma-Aldrich) or described in the literature. In the following general synthesis instructions for these olefination reactions of aldehydes are given. Concrete execution examples are given further below.

The starting point is a suitably substituted aldehyde, i.e. an aldehyde of the general structure wherein X is any residue:

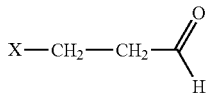

This aldehyde for example can be prepared from derivatives of glutamic acid as disclosed herein for compound 1.4.

An equivalent of a phosphor ylide (e.g. Triphenylphosphonium ylide) is solved with a suitable solvent (e.g. benzol, toluol or DMF) and deprotonated with a base (e.g. NaH, n-BuLi, NaNH$_2$). After the end of the reaction an equivalent of the respective aldehyde is added. After the end of the reaction the solvent is removed under vacuum and the resulting olefin is purified with chromatographic methods.

General Rule 1:

General rule for the synthesis of compounds with an alkyloxycarbonyl ethenyl Michael system:

The parent compound is the amino acid Glu (glutamic acid) which is provided with protecting groups at the C-terminus and at the N-terminus. Acid-labile protecting groups, such as tert.-butyloxycarbonyl, tert.-butyl ester or 2-phenyl-isopropyl ester can be used as protecting groups. The side chain is selectively reduced to an aldehyde by diisobutylaluminum hydride and subsequently reacted with a phosphorane to form the Michael system. After acid-induced cleavage of the protecting groups, for example by means of trifluoroacetic acid, a peptide residue or a peptide analogue or an amino acid analogue or one or two alkyl residues are attached to the N-terminal end. Preferably, said process is performed using an activated carboxylic acid, for example as active ester or carboxylic acid anhydride and the C-terminal end is subsequently reacted with an amino group of a peptide residue or of a peptide analogue or an amino acid analogue or an esterification is performed. These reactions can be employed universally, are well known to the one skilled in the art and consequently, any peptidic or peptide-like residue can be added to both the C-terminus and the N-terminus of the amino acid having the Michael system.

Instead of initially forming the Michael system at the amino acid glutamic acid and then modifying the C-terminus as described above, a desired synthetic peptide can be synthesized which is afterwards provided with protecting groups and at which the modification of the glutamic acid side chain or the glutamic acid side chains is carried out in order to form the Michael system or several Michael systems. Subsequent to the generation of the Michael system(s) the protecting groups may be partially or completely removed.

General Rule 2:

General rule for the synthesis of compounds with a alkyloxycarbonyl ethenyl Michael system:

Again, the parent compound is the amino acid Glu (glutamic acid) provided with a protecting group at the C-terminus and at the N-terminus and the side chain is converted to a vicinal diketo compound (glyoxal) by means of diazomethane and subsequently dimethyl dioxirane. The diketo side chain is subsequently reacted with a desired phosphorane in order to form the Michael system. After acid-induced cleavage of the protecting groups, for example by means of trifluoroacetic acid, a peptide residue or a peptide analogue or a amino acid analogue or one or two alkyl residues are attached to the N-terminal end. Preferably, said process is performed using an activated carboxylic acid, for example as active ester or carboxylic acid anhydride and the C-terminal end is subsequently reacted with an amino group of a peptide residue or of a peptide analogue or an amino acid analogue or otherwise an esterification is carried out. These reactions can be universally performed, are well known to the one skilled in the art and consequently, any peptidic or peptide-like residue can be added to both the C-terminus and the N terminus of the amino acid having the Michael system.

Instead of initially forming the Michael system at the amino acid glutamic acid and then modifying the C-terminus as described above, a desired synthetic peptide can be synthesized which is afterwards provided with protecting groups and at which modification of the glutamic acid side chain or the glutamic acid side chains to the Michael system or to several Michael systems is carried out. Subsequent to the formation of the Michael system(s) the protecting groups may be partially or completely removed.

EXAMPLES

General Method for Inactivating Human Tissue Transglutaminase

250 µg of lyophilized his-tagged recombinant human tissue transglutaminase (His$_6$-rh-TG2) are reconstituted by the addition of 150 µl of water (resulting buffer 50 mM of NaH$_2$PO$_4$, 150 mM of NaCl, pH=8).

A 10 mM inhibitor stock solution in DMSO is prepared and diluted with buffer (50 mM of Tris-HCl, 10 mM of CaCl$_2$, 5 mM of DTT, pH=7.5, respectively) to the 20-fold of the concentration desired for the inhibition mixture (at least 1/50 dilution resulting in 2% DMSO concentration).

900 µl of an assay solution composed of 55.56 mM of Tris, 11.11 mM of CaCl$_2$, 0.11% PEG$_{8000}$, 5.56 mM of DTT, 5.56 mM of glycine methyl ester and 50 µM of Abz-APE(CAD-DNP)QEA-OH, (patent number:), pH=7.5 are placed in a cuvette and brought to a temperature of 37° C. in the measuring cell of a spectrophotometer. 50 µl of the respective inhibitor solution are added to said solution (resulting in a concentration of less than 0.2% of DMSO in the mixture).

7 µl of the transglutaminase solution reconstituted above are diluted with 51 µl of buffer (50 mM of Tris, 100 mM of NaCl, 5 mM of DTT, pH=7.5). 50 µl of said enzyme solution (10 µg His$_6$-rhTG2) are added to the assay solution containing the respective inhibitor concentration. The mixture is incubated for 5 min at 37° C. before the measurement is performed. $\lambda_{exc}$=313 nm and $\lambda_{em}$=418 nm, 15 min)

The resulting enzyme activity was measured by analyzing the slope of the straight line obtained by the increase in fluorescence.

DMSO is used instead of inhibitor stock solution in order to determine the non-inhibited enzyme activity. IC$_{50}$ values are determined by plotting the resulting enzyme activity against the logarithm of the inhibitor concentration. IC$_{50}$ is defined as the concentration of an inhibitor at which enzyme activity is reduced to 50% after 5 min of preincubation.

Biopsy Example 1

Biopsies with a diameter of about 2 mm were stored for a maximum of 30 min in ice-cold PBS after removal from the lower duodenum of patients suffering from coeliac disease. The single biopsies were transferred into the cavities of a 24-well cell culture dish and coated with 500 µl of Trowell T8 medium.

For preincubation, the transglutaminase inhibitor (1) in a final concentration of 5 µM was added to the biopsies and they were incubated for 30 min at a temperature of 37° C. in the incubator under gassing with CO$_2$ (5%). Subsequently, stimulation with gliadin after peptic-tryptic digest (PT gliadin) used in a final concentration of 1 mg/ml was performed. PT gliadin was produced as described by Wieser and Belitz (Wieser H and Belitz HD (1992), Z Lebenm Unters Forsch 194: 229-234). The treatment with the proteases pepsin and trypsin simulates the digestion in the gastrointestinal tract. Thus the resulting gliadin peptides correspond to those which occur in the duodenum after the intake of cereal protein. The biopsies were then incubated for another 48 hrs in the incubator under the above conditions.

Controls were incubated with inhibitor-free medium and without or respectively with PT gliadin.

After 48 hrs, 50 µl samples were taken and analyzed by means of an anti-TG2 ELISA kit.

An OD$_{450}$ of 1.285 for the medium control could be measured in the anti-TG2 ELISA. A significantly increased antibody concentration was measured in the supernatant of the biopsy stimulated with PT gliadin (OD$_{450}$=2.144), while only a minor increase in antibody concentration could be observed in the biopsy preincubated with the inhibitor (1) having an OD$_{450}$ of 1.401 (see FIG. 19).

Biopsy Example 2

Biopsies were cultivated and treated as described in biopsy example 1. After 24 and 48 hrs, 50 µl samples were taken both from the biopsy stimulated with PT gliadin and from the biopsy preincubated with inhibitor (1), which subsequently was also stimulated with PT gliadin and the samples were analyzed by means of an interferon-γ Elisa. A very high interferon-γ value of 653 pg/ml could already be measured in the biopsy stimulated with PT gliadin after 24 hrs, which value increased to 1177 pg/ml after 48 hrs. In the biopsy preincubated with inhibitor (1), the interferon-γ value measured after 24 hrs was only 86 pg/ml, and after 48 hrs only 426 pg/ml, despite the stimulation (see FIG. 20).

Synthesis of Required Peptide Sequences:

Standard methods are used for the synthesis of the non-modified peptide sequences. Generally, all methods known in literature can be used for peptide synthesis. (see also: Bodanzky M, Bodanzky A., The practice of peptide synthesis, Springer Verlag, 1994). By way of example, two methods are described which are most frequently used.

1. Synthesis of a peptide sequence in solution: α-amino function of the amino acids to be coupled protected by the tert.-butyloxycarbonyl protecting group (Boc protecting group); coupling to a free amine by 0-(benzotriazole-1-yl)-N,N,N'',N''-tetramethyluronium hexafluoroborate (TBTU), 1-hydroxybenzotriazole (HOBt) and N,N-diethylisopropylamine, cleavage of the Boc protecting group by trifluoroacetic acid (TFA) in dichloromethane (DCM). Subsequently, coupling of the next amino acid was performed.
2. Synthesis of a peptide sequence on solid phase: Starting with commercially available starting amino acids bound via a 2-chlorotrityl linker 9-fluorenylmethyl (Fmoc) protected amino acids of the sequence are coupled accordingly. Other reagents used are TBTU, HOBt and DIPEA. The reaction conditions are known to the one skilled in the art. For further information see e.g. *Fmoc Solid Phase Peptide Synthesis, A practical approach*, Chan, W. C., White P. D., Oxford University Press.

In the following description some exemplary peptides required for the synthesis of different inhibitors are described.

L-valinyl-L-prolinyl-isopentylamide (5.1)

Boc-L-prolinyl-isopentylamide 479 mg (5.5 mmol) of isopentylamide are dissolved in 5 ml of DMF A solution of 1.06 g of Boc-proline (5 mmol), 1.57 g of TBTU (4.9 mmol), 675 mg of HOBt (5 mmol) and 1.71 ml of DIPEA (10 mmol) in 15 ml of DMF is added to said solution. After one hour, the solvent is removed under vacuum and the oily residue is taken up in 200 ml of ethyl acetate. The organic phase is washed three times with 50 ml of 10% citric acid, 10% NaHCO$_3$ and saturated NaCl-solution, respectively. The organic phase is dried over Na$_2$SO$_4$ and the solvent is removed under vacuum.

Yield: 1.38 g

Cleavage of the N$^α$-tert.-butyloxycarbonyl protecting group

The intermediate compound synthesized that way is dissolved in 25 ml of dichloromethane and 25 ml of TFA are added. The mixture is stirred for one hour at room temperature. The solvent is removed under vacuum and residues of TFA are removed by co-distilling with methanol and drying under high vacuum.

Boc-L-valinyl-prolinyl-isopentylamide

The trifluoroacetate salt (TFA*pro-isopentylamide) is dissolved in DMF and a solution of 1.15 g of Boc-valine (5.33 mmol), 1.6 g of TBTU (5.1 mmol), 719 mg of HOBt (5.33 mmol) and 1.88 ml of DIPEA (11 mmol) in 20 ml of DMF is added. After one hour, the solvent is removed under vacuum and the oily residue is taken up in 200 ml of ethyl acetate. The organic phase is washed three times with 50 ml of 10% citric acid, 10% NaHCO$_3$ and saturated NaCl solution, respectively. The organic phase is dried over Na$_2$SO$_4$ and the solvent is removed under vacuum.

Yield: 1.75 g

ESI-MS: 406.4 [M+Na]$^+$

L-serinyl-L-leucinyl-L-valinyl-L-isoleucinyl-glycine methyl ester (8.1)

The compound given in the title is synthesized according to the above-mentioned standard method starting with glycine methyl ester in solution.

The first coupling is described below by way of example. The subsequent couplings are carried out under identical conditions.

N$^α$-tert.-butyloxycarbonyl-Lisoleucinyl-glycine methyl ester 850 mg of N$^α$-tert-butyloxycarbonyl-L-isoleucine (3.68 mmol) together with 1.18 g of TBTU (3.68 mmol) and 497 mg of HOBt (3.68 mmol) are dissolved in 10 ml of DMF. By adding 1.9 ml of DIPEA (11.1 mmol) the solution is adjusted to a pH of ~11 and the reaction mixture is mixed with a solution of 461.4 mg of glycine methyl ester hydrochloride (3.68 mmol) in 5 ml DMF. The mixture is stirred for 45 min at room temperature and subsequently the solvent is removed under vacuum. The oily residue obtained is taken up in 200 ml of ethyl acetate and washed three times with 50 ml of 10% citric acid, 10% NaHCO$_3$ and water, respectively. The organic phase is dried with Na$_2$SO$_4$ and the solvent is removed under vacuum. A colorless solid is obtained.

Yield: 1.08 g (97% theoretical yield)

Cleavage of the N$^\alpha$-tert.-butyloxycarbonyl Protecting Group

The protected peptide is dissolved in dichloromethane and mixed with the same volume of trifluoroacetic acid. After one hour, the solvent is removed under vacuum. Acid residues are removed by co-distilling with methanol for several times. The amine thus obtained can be directly coupled with the next amino acid.

The compound given in the title (8.1) is obtained in form of a light brown solid by means of several coupling and deprotection reactions.

ESI-MS: 502.2 [M+Na]$^+$

N$^\alpha$-acetyl-L-leucinyl-glycinyl-L-prolinyl-glycine (8.2)

The compound given in the title is synthesized by means of solid phase peptide synthesis. Starting with commercially available H-glycine-2-chlorotrityl ester (polymer bound), the Fmoc-protected amino acids of the sequence are coupled accordingly by means of TBTU, HOBt and DIPEA. The reaction conditions are known to the one skilled in the art. For further information see e.g. *Fmoc Solid Phase Peptide Synthesis, A practical approach*, Chan, W. C., White P. D., Oxford University Press.

After cleavage from the polymeric carrier and purification of the crude product obtained by washing with diethyl ether, the compound given in the title is obtained in its pure form.

ESI-MS: 407.2 [M+Na]$^+$

Below, the syntheses of the inhibitors are described. Unless otherwise defined, the peptides used in that context are synthesized according to one of the above methods.

1. Synthesis of the 6-amino-hept-2-ene-dicarboxylic Acid Derivatives 1.2. N$^\alpha$-tert.-butyloxycarbonyl-L-glutamic acid 5-methyl ester 1-tert.-butyl ester 2.3 g of N-tert.butyloxycarbonyl-L-glutamic acid 1-tert.-butyl ester (7.58 mmol) are dissolved in 80 ml of methanol and a freshly prepared diazomethane solution (23 mmol of Diazald®) is added dropwise at room temperature. After one hour, the solvent is removed under vacuum. The compound is purified using chromatography on silica gel. (column: 18.5*4 cm, DCM/MeOH=99/1, R$_f$=0.99).

Yield: 1.3 g
ESI-MS: 340.2 [M+Na]$^+$ 1.3 N,N-di-(tert.-butyloxycarbonyl)-L-glutamic acid 5-methyl ester 1-tert.-butyl ester

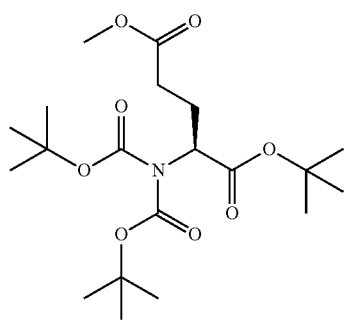 [SMILES: COC(=O)CC[C@@H](C(=O)OC(C)(C)C)N(C(=O)OC(C)(C)C)C(=O)OC(C)(C)C]

1.3 g of N-tert.-butyloxycarbonyl-L-glutamic acid 5-methyl ester 1-tert.-butyl ester (1.2., 4.12 mmol) are dissolved in 15 ml of acetonitrile and mixed with 100 mg of N,N-dimethyl-4-aminopyridine (DMAP). A solution of 1.79 g of di-tert.-butyl-bicarbonate (8.2 mmol) in 7 ml of acetonitrile is added under nitrogen atmosphere. After stirring overnight, the solvent is removed under vacuum and the crude product obtained is purified by means of chromatography on silica gel.

(column: 33*3.5 cm, petrol ether/ethyl acetate=92/8, R$_f$=0.32)

Yield: 1.3 g
ESI-MS: 440.3 [M+Na]$^+$ 1.4 N,N-di-(tert.-butyloxycarbonyl)-L-2-amino-5-oxopentanoic acid tert.-butyl ester

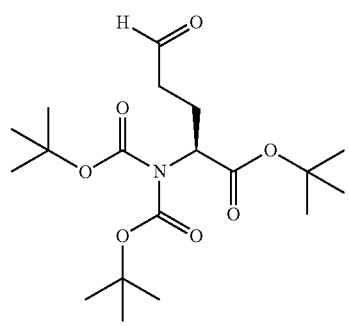 [SMILES: CC(C)(C)OC(=O)[C@H](CCC=O)N(C(=O)OC(C)(C)C)C(=O)OC(C)(C)C]

1.31 g of N,N-di-(tert.-butyloxycarbonyl)-L-glutamic acid 5-methyl ester 1-tert.-butyl ester (1.3, 3.14 mmol) are dissolved in 40 ml of absolute diethyl ether and cooled to −78° C. under argon atmosphere. At said temperature, 3.45 ml of a solution of diisobutylaluminum hydride (1M in hexane) are slowly added dropwise. Subsequent to the addition, the mixture is stirred for another 15 min at −78° C., before the reaction mixture is quenched at said temperature by the addition of 1.5 ml of water. The mixture is thawed to room temperature under vigorous stirring and the opaque solution is filtered over celite. The filtrate is concentrated to dryness and residual water is removed by co-distillation with toluene. The compound is purified using chromatography on silica gel (column: 37*3.2 cm, petrol ether/ethyl acetate=92/8 on 90/10).

Yield: 890 mg

500-MHz-$^1$H-NMR-cosy (DMSO$_{d6}$): δ[ppm]=9.65 (s, 1H, H-4), 4.63 (dd, 1H, H-1, J$_{1/2a}$=4.8 Hz, J$_{1/2b}$=9.85 Hz), 2.51-2.50 (m, 1H, H-3$_a$), 2.48-4.40 (m, 1H, H-3$_b$), 2.27-2.20 (m, 1H, H-2a), 1.98-1.91 (m, 1H, H-2$_b$), 1.44 (s, 18H, 6*CH$_3$ (Boc)), 1.92 (s, 9H, 3*CH$_3$(O-tBu))

ESI-MS: 410.4 [M+Na]$^+$, 428.4 [M+H$_2$O+Na]$^+$

1.5 N,N-di-(tert.-butyloxycarbonyl)-{(E)-(L)-6-amino-hept-2-ene-dicarboxylic acid}-1-ethanoyl-7-tert.-butyl ester

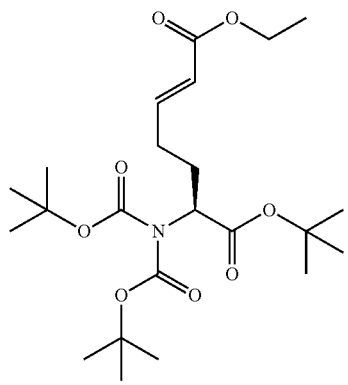 [SMILES: CCOC(=O)/C=C/CC[C@@H](C(=O)OC(C)(C)C)N(C(=O)OC(C)(C)C)C(=O)OC(C)(C)C]

160 mg of N,N-di-(tert.-butyloxycarbonyl)-L-2-amino-5-oxopentanoic acid 1-tert.-butyl ester (1.4, 0.413 mmol) are placed in 8 ml of dry benzene and a solution of 152 mg of (ethoxycarbonylmethylene)-triphenylphosphorane (0.413 mmol) is added at room temperature under argon atmosphere. After stirring overnight, the solvent is removed under vacuum and the oily residue obtained is purified by means of preparative HPLC. (Synergie Max, 4 μm, 250×21.2 mm, eluent A: 0.1% TFA/water; eluent B: 90% AcCN/10% water/0.1% TFA. Gradient: 8 ml/min, 5% B on 100% B, 1%/min)

$R_t$: 98-103.6 min

Yield: 80 mg

ESI-MS: 480.3 [M+Na]$^+$

1.7 N$^\alpha$-benzyloxycarbonyl-{(E)-(L)-6-amino-hept-2-ene-dicarboxylic acid}-1-ethyl ester

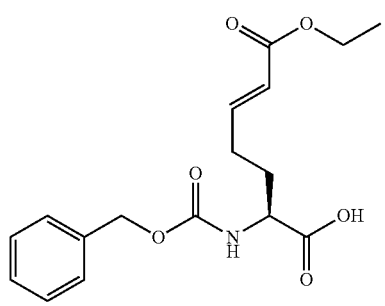 [SMILES: CCOC(=O)/C=C/CC[C@H](NC(=O)OCc1ccccc1)C(=O)O]

80 mg of N,N-di-(tert.-butyloxycarbonyl)-{(E)-(L)-6-amino-hept-2-ene-dicarboxylic acid}-1-ethanoyl-7-tert.-butyl ester (1.5, 0.175 mmol) are dissolved in 7.5 ml of dichloromethane and cooled to 0° C. under nitrogen atmosphere. 5 ml of TFA are slowly added to said solution. After two hours of stirring at said temperature, the solvent is removed under vacuum. The residual TFA is removed from the brown residue obtained (L-6-amino-hept-2-ene-dicarboxylic acid 1-ethyl ester, 1.6) under high vacuum. 64 mg of brown solid (116% with respect to the TFA salt) are obtained.

The product thus obtained is further reacted by adding it to a solution of 65.4 mg of N-(benzyloxycarbonyl)-succinimide (0.262 mmol) in 4 ml of DMF. DIPEA is added under nitrogen atmosphere so that the pH value is adjusted to about 6. After one hour, the clear solution obtained is concentrated to dryness under vacuum and the solid residue is purified by preparative HPLC (Synergie Max, 4 μm, 250×21.2 mm, eluent A: 0.1% TFA/water; eluent B: 90% AcCN/10% water/0.1% TFA. Gradient: 8 ml/min, 5% B on 100% B, 1%/min)

$R_t$: 64.0-66.5 min

Yield: 64 mg

500-MHz-$^1$H-NMR-cosy (DMSO$_{d6}$): δ[ppm]=7.62 (d, 1H, NH), 7.37-7.30 (m, 5H, aryl-H), 6.87 (dt, 1H, H-4, $J_{4/3}$=6.9 Hz $J_{4/5}$=15.6 Hz), 5.84 (d, 1H, H-5, $J_{5/4}$=15.6 Hz), 5.02 (s, 2H, benzyl-CH$_2$), 4.11 (q, 2H, H-6$_a$, H-6$_b$, $J_{6/7}$=7.1 Hz), 4.08-4.00 (m, 1H, H-1), 2.30-2.23 (m, 2H, H-3$_a$, H-3$_b$), 1.90-1.80 (m, 1H, H-2$_a$, H-2$_b$), 1.20 (t, 3H, CH$_3$-7)

ESI-MS: 358.2 [M+Na]$^+$

1.8 N,N-di-(tert.-butyloxycarbonyl)-{(E)-(L)-6-amino-hept-2-ene-dicarboxylic acid}-1-methanoyl-7-tert.-butyl ester

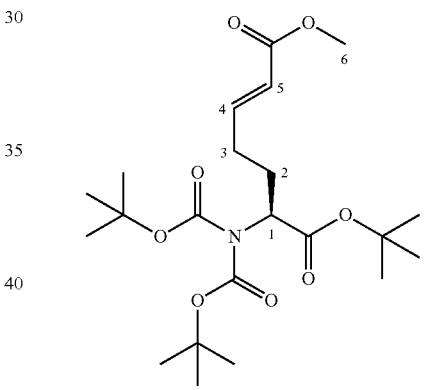

445 mg of N,N-di-(tert.-butyloxycarbonyl)-L-2-amino-5-oxopentanoic acid 1-tert.-butyl ester (1.4, 1.15 mmol) are placed in 20 ml of dry benzene and a solution of 385 mg (methoxycarbonylmethylene)-triphenylphosphorane (1.15 mmol) is added at room temperature under argon atmosphere. After stirring overnight, the solvent is removed under vacuum and the oily residue obtained is purified by means of chromatography on silica gel. (column: 29*2.4 cm, petrol ether/ethyl acetate=99.5/0.5)

Yield: 424 mg

500-MHz-$^1$H-NMR-cosy (DMSO$_{d6}$): δ[ppm]=6.66 (dt, 1H, H-4, $J_{4/3}$=6.8 Hz $J_{4/5}$=15.9 Hz), 5.64 (d, 1H, H-5, $J_{5/4}$=15.9 Hz), 4.45-4.2 (m, 1H, H-1), 3.44 (s, 3H, CH$_3$-6), 2.01-1.95 (m, 2-H, H-3$_a$, H-3$_b$), 1.95-1.86 (m, 1H, H-2$_b$), 1.78-1.67 (m, 1H, H-2$_b$), 1.24 (s, 18H, 6*CH$_3$(Boc)), ESI-MS: 466.3 [M+Na]$^+$

1.9 N$^\alpha$-tert.-butyloxycarbonyl-{(E)-(L)-6-amino-hept-2-ene-dicarboxylic acid}-1-ethyl ester

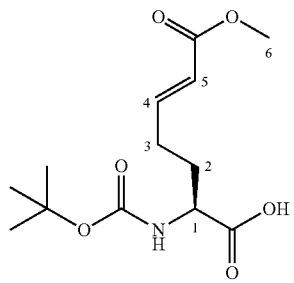 [SMILES: COC(=O)/C=C/CC[C@H](NC(=O)OC(C)(C)C)C(=O)O]

50 mg of N,N-di-(tert.-butyloxycarbonyl)-{(E)-(L)-6-amino-hept-2-ene-dicarboxylic acid}-1-methanoyl-7-tert.-butyl ester (1.8, 0.11 mmol) are dissolved in 5 ml of dichloromethane and cooled to 0° C. under nitrogen atmosphere. At said temperature, 5 ml of trifluoroacetic acid are added and the mixture is stirred for two hours at room temperature. The solvent is removed under vacuum and the greenish residue obtained (L-6-amino-hept-2-ene-dicarboxylic acid 1-methyl ester) is co-distilled several times with methanol to remove residual TFA. 88 mg of the trifluoroacetate salt are obtained (139% theoretical yield). The oily residue is absorbed in 4 ml of DMF and mixed with 36 mg of Boc-OSu (1.65 mmol). By adding DIPEA the pH is adjusted to about 6. After stirring overnight at room temperature, the solvent is removed under vacuum and the product in its pure form is obtained by preparative HPLC. (Synergie Max, 4 μm, 250×21.2 mm, eluent A: 0.1% TFA/water; eluent B: 90% AcCN/10% water/0.1% TFA. Gradient: 8 ml/min, 5% B on 100% B, 1%/min).

$R_t$: 53.5-56.5 min
Yield: 23 mg
ESI-MS: 310.1 [M+Na]$^+$

1.10 N$^\alpha$-acetyl-{(E)-(L)-6-amino-hept-2-ene-dicarboxylic acid}-1-methyl ester

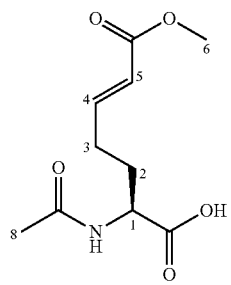

As described under 1.9, L-6-amino-hept-2-ene-dicarboxylic acid 1-methyl ester is initially prepared (0.1 mmol). The intermediate product is taken up in 10 ml of DMF and a solution of 68 mg of pentafluorophenyl acetate (0.3 mmol) in 4 ml of DMF is added under nitrogen atmosphere. The mixture is stirred overnight at room temperature before the solvent is removed under vacuum. The pure product is obtained by preparative HPLC.

(Synergie Max, 4 μm, 250×21.2 mm, eluent A: 0.1% TFA/water; eluent B: 90% AcCN/10% water/0.1% TFA. Gradient: 8 ml/min, 5% B on 100% B, 1%/min).

$R_t$: 54.6-56.8 min
Yield: 19 mg
ESI-MS: 252.1 [M+Na]

1.11 N$^\alpha$-benzyloxycarbonyl-{(E)-(L)-6-amino-hept-2-ene-dicarboxylic acid}-1-methyl ester

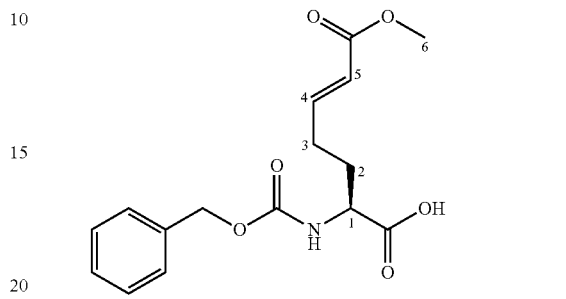

As described under 1.10, L-6-amino-hept-2-ene-dicarboxylic acid 1-methyl ester*TFA (0.02 mmol) is initially prepared. The intermediate product is taken up in 20 ml of DMF and a solution of 75 mg of N-(benzyloxycarbonyl)-succinimide (0.3 mmol) in 7 ml of DMF is added under nitrogen atmosphere. The mixture is stirred overnight at room temperature before the solvent is removed under vacuum. The pure product is obtained by preparative HPLC (Synergie Max, 4 μm, 250×21.2 mm, eluent A: 0.1% TFA/water; eluent B: 90% AcCN/10% water/0.1% TFA. Gradient: 8 ml/min, 5% B on 100% B, 1%/min).

$R_t$: 38.4-42.4 min
Yield: 25 mg
ESI-MS: 344.1 [M+Na]$^+$

1.12 L-2-(4-chloro-butyrylamino)-pentanedicarboxylic acid 1-tert.-butyl ester 5-methyl ester 933 mg of L-glutamic acid 5-methyl ester 1-tert.-butyl ester hydrochloride (3.68 mmol) are dissolved in 20 ml of dichloromethane$_{abs}$ and cooled to 0° C. after 1.28 ml of DIPEA (7.5 mmol) have been added. 518.5 mg of 4-chlorobutyric acid chloride are added to said solution. The mixture is stirred overnight while being slowly heated to room temperature. The solution is diluted to 100 ml with dichloromethane and washed with 10% citric acid as well as saturated NaCl solution (three times, respectively). The organic phase is dried over Na$_2$SO$_4$ and the solvent is removed under vacuum. The product in its pure form is obtained as a colorless oil.

Yield: 1.15 g
ESI-MS: 344.1 [M+Na]$^+$

1.13 L-2-(2-oxo-pyrrolidin-1-yl)-pentanedicarboxylic acid 1-tert.-butyl ester 5-methyl ester 1.15 g of 2-(4-chloro-butyrylamino)-pentanedicarboxylic acid 1-tert.-butyl ester 5-methyl ester (1.12, 3.58 mmol) are dissolved in 10 ml of DMF. The mixture is cooled to 0° C. under argon atmosphere and 173 mg of sodium hydride (60% on mineral oil) are added. After a period of 15 min, the ice bath is removed and the mixture is stirred for four hours at room temperature. The solvent is removed under high vacuum and the residue is taken up in 200 ml of ethyl acetate. After washing with 1 N HCl, 10% NaHCO$_3$ and saturated NaCl solution, the product is dried over $Na_2SO_4$ and the solvent is removed again under vacuum.

The pure product is obtained in form of a pale yellow oil.
Yield: 908 mg
ESI-MS: 308.3 [M+Na]$^+$, 252.3 [M-t-Bu+Na]$^+$

1.14 (E)-(L)-6-(2-oxo-pyrrolidin-1-yl-)hept-2-ene-dicarboxylic acid 1-ethyl ester 100 mg of 2-(2-oxo-pyrrolidin-1-yl)-pentanedicarboxylic acid 1-tert.-butyl ester 5-methyl ester (1.13, 0.35 mmol) are dissolved in 10 ml diethyl ether$_{abs}$ and cooled to −78° C. under argon atmosphere. At said temperature, 0.385 ml of a monomolar solution of diisobutylaluminum hydride in hexane are slowly added dropwise. After 30 min, the mixture is quenched by the addition of 1 ml of water and subsequently thawed to room temperature. The reaction solution is filtrated using diatomaceous earth, rewashed twice with diethyl ether and the combined organic phases were concentrated.
Yield: 83 mg
ESI-MS: 278.2 [M+Na]$^+$

1.15 (L)-(E)-(L)-6-(2-oxo-pyrrolidon-1-yl)-hept-2-ene-dicarboxylic acid 1-ethyl ester

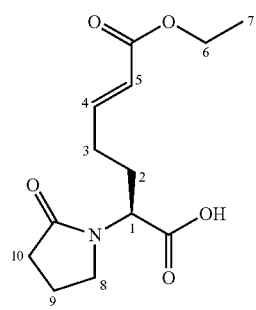

70 mg of (E)-6-(2-oxo-pyrrolidin-1-yl-)hept-2-ene-dicarboxylic acid 1-ethyl ester (1.14, 0.27 mmol) are dissolved in 5 ml of benzene dried over a molecular sieve (4 Å). A solution of 95 mg of carboxymethylene triphenylphosphorane is added under nitrogen atmosphere and the mixture is stirred overnight at room temperature. The solvent is removed under vacuum and the oily residue obtained is taken up in 10 ml of dichloromethane and mixed with 10 ml of trifluoroacetic acid. After one hour, the solvent is removed under vacuum and the crude product obtained is purified by means of chromatography on silica gel. (column: 21×1.2 cm, petrol ether/ethyl acetate: 8/2)
ESI-MS: 292.1 [M+Na]$^+$ Alternative Protecting Group Strategy for the Preparation of 6-amino-hept-2-ene-dicarboxylic Acid For the realization of an orthogonal protecting group strategy, the following steps can be performed:

A derivative of glutamic acid protected at the nitrogen, by way of example Z-Glu(OMe)-OH, is dissolved in dichloromethane and mixed with 2-phenylisopropanol and N,N-dimethyl-4-aminopyridine (DMAP) with 1.5 equivalents dicyclohexylcarbodiimide. After stirring overnight at room temperature, the product is removed from the precipitated solid by filtration and the crude product obtained is purified by means of chromatography on silica gel. The product (Z-Glu(OMe)-OiPrPh) is obtained in pure form.

Figure 1:
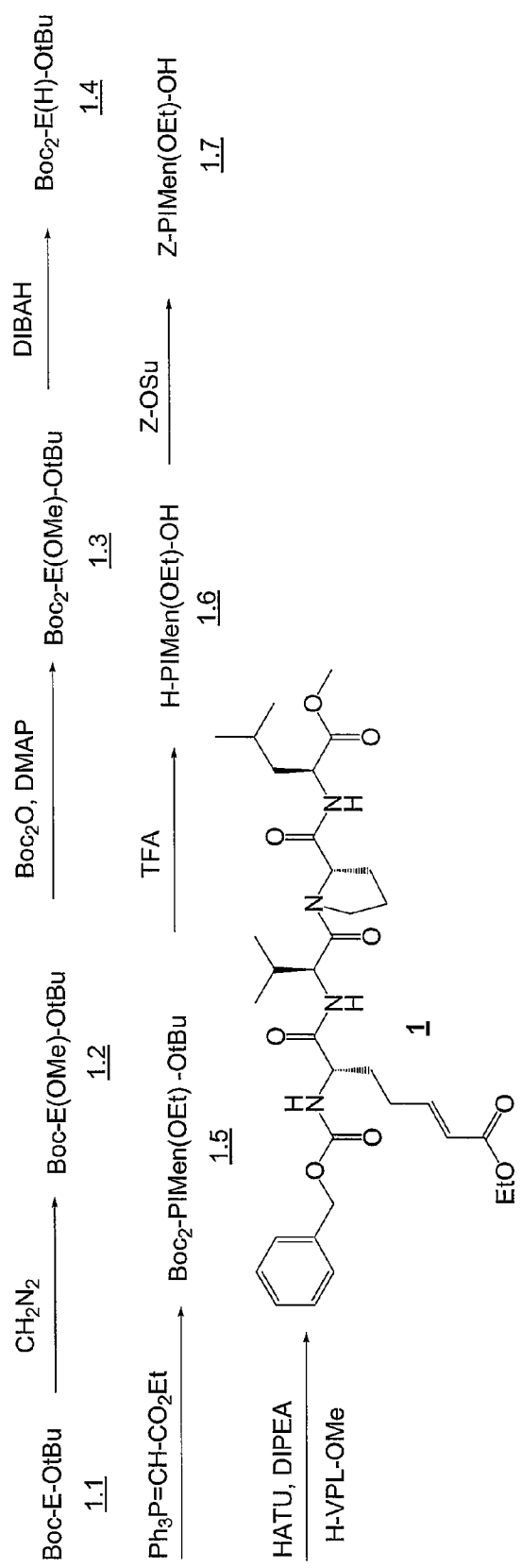
FIG. 1 shows the synthesis scheme for the preparation of L-2-amino-hept-5-ene-dicarboxylic acid derivatives.
Figure 2:
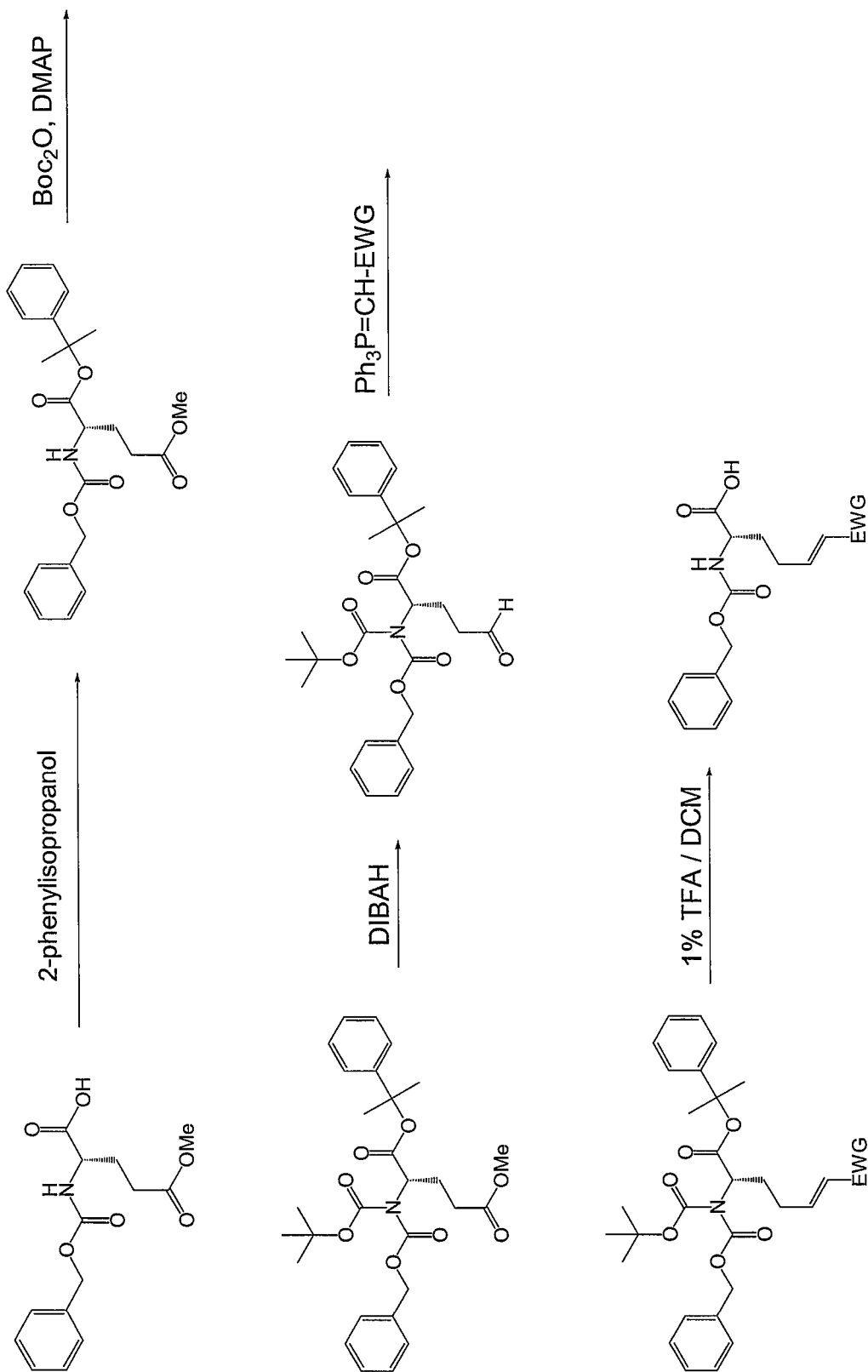
FIG. 2 shows the synthesis scheme for an alternative preparation of L-2-amino-hept-5-ene-dicarboxylic acid derivatives.

As described in section 1.3, Z-Glu(OMe)-iPrPh is protected by a tert.-butyloxycarbonyl protecting group at the nitrogen and the product is reduced to the aldehyde Z,Boc-Glu(H)—IPrPh as described in section 1.4. The conversion to olefin under the conditions of the Wittig reaction is performed as described, for example, in section 1.8, before the cleavage of the carboxyl protecting group together with one of the two amino protecting groups can be achieved due to the treatment with 1% TFA in dichloromethane. Thereby, compounds as 1.7 or 1.8 can be obtained directly depending on the choice of the Wittig reagent, which are available for further reactions, such as coupling to an amine (FIG. 2). An execution example is given under 3.6.

2. Synthesis of the Inhibitors with a Peptidic Environment of the Pharmacophoric Group A preferred embodiment of the inhibitors is a peptide sequence of proteinogenic α-amino acids to which a pharmacophoric group is added at a suitable site. In the following several of these peptidic inhibitors are presented.

N$^\alpha$-benzyloxycarbonyl-{[(E)-(L)-6-amino-hept-2-ene-dicarboxylic acid]-1-ethanoyl}-L-valinyl-L-prolinyl-L-leucine methyl ester (compound 1)

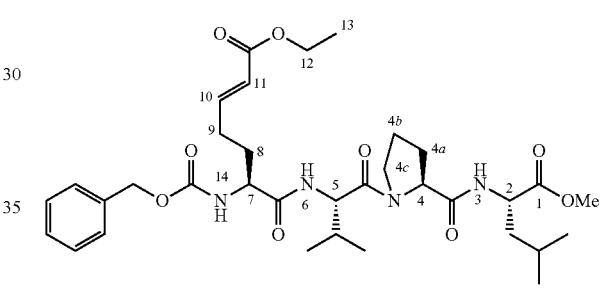

15 mg of N$^\alpha$-benzyloxycarbonyl-{(E)-(L)-6-amino-hept-2-ene-dicarboxylic acid}-1-ethyl ester (1.7, 44.7 μmol) together with HATU are dissolved in 5 ml of DMF 22.8 μl of DIPEA (134.2 μl) are added to said solution and the yellow solution obtained is immediately added to a solution of 20.4 mg (44.7 μmol) of the trifluoroacetate salt of L-valinyl-L-prolinyl-L-leucine methyl ester (prepared according to method 1). The pH (determined with the help of a moistened indicator stick) is adjusted to 9. For this purpose, 44.7 μmol of additional DIPEA are required. After ten minutes, the solvent is removed under vacuum and the oily brown residue is purified by preparative HPLC (Synergie Max, 4 μm, 250×21.2 mm, eluent A: 0.1% TFA/water; eluent B: 90% AcCN/10% water/0.1% TFA. Gradient: 8 ml/min, 40% B on 100% B, 1")/0/min).
$R_t$: 37.8-40.32 min
Yield: 17 mg 500-MHz-$^1$H-NMR-cosy (DMSO$_{d6}$): δ[ppm]=8.19 (d, 1H, H-3), 7.88 (d, 1H, H-6), 7.47 (d, 1H, H-14), 7.37-7.31 (m, 5H, aryl-H), 6.87 (dt, 1H, H-10, $J_{10/9}$=6.6 Hz, $J_{11/10}$=15.4 Hz), 5.81 (d, 1H, H-11, $J_{11/10}$=15.4 Hz), 5.02 (s, 2H, benzyl-CH$_2$), 4.37-4.28 (m, 2H, H-5, H-4), 4.28-4.20 (m, 1H, H-2), 4.10 (q, 2H, H-12$_a$, H-12$_b$), 4.08-4.00 (m, 1H, H-7), 3.73-3.67 (m, 1H, H-4c$_a$), 3.61 (s, 3H, OMe), 3.60-3.52 (m, 1H, H-4c$_b$), 2.27-2.15 (m, 2H, H-9$_a$, H-9$_b$), 2.10-2.00 (m, 1H, 2.00-1.90 (m, 2H, H-4$_{b/1}$, methine-H (Val)), 1.88-1.78 (m, 3H, H-4$_{a/2}$, H-4$_{b/2}$), 1.78-1.65 (m, 2H, methine-H (Leu)), 1.65-1.60 (m, 1H, H-8$_b$), 1.58-1.50 (m, 1H, CH$_{2a}$-Leu), 1.50-

1.43 (m, 1H, CH$_{2b}$-Leu), 1.22 (t, 3H, CH$_3$-16), 0.89 (dd, 6H, 2×CH$_3$-Val), 0.84 (dd, 6H, 2×CH$_3$-Leu)

ESI-MS: 681.4 {M+Na}$^+$

N$^\alpha$-benzyloxycarbonyl-{[(E)-(L)-6-amino-hept-2-ene-dicarboxylic acid]-1-ethanoyl}-L-glutaminyl-L-prolinyl-L-leucine methyl ester (compound 2)

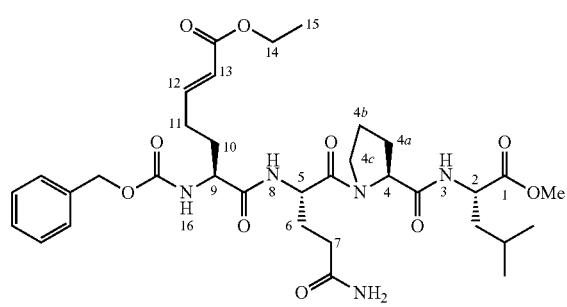 [SMILES: CCOC(=O)/C=C/CC[C@H](NC(=O)OCc1ccccc1)C(=O)N[C@@H](CCC(N)=O)C(=O)N1CCC[C@H]1C(=O)N[C@@H](CC(C)C)C(=O)OC]

33.5 mg of N$^\alpha$-benzyloxycarbonyl-{(E)-(L)-6-amino-hept-2-ene-dicarboxylic acid}-1-ethyl ester (1.7, 0.1 mmol) are dissolved in 7.5 ml of DMF and successively mixed with 38 mg of HATU (0.1 mmol) and 51 µl of DIPEA (0.3 mmol) and immediately added to a solution of the trifluoroacetate salt of 0.1 mmol of H-Gln-Pro-Leu-OMe (synthesized according to method 1) in 7.5 ml of DMF. By gradually adding DIPEA the pH is adjusted to 9. Further processing is as described for compound 1 (Synergie Max, 4 µm, 250×21.2 mm, eluent A: 0.1% TFA/water; eluent B: 90% AcCN/10% water/0.1% TFA.

Gradient: 8 ml/min, 30% B on 100% B, 1%/min).

R$_t$=33.9-36.1 min

Yield: 28 mg

500-MHz-$^1$H-NMR-cosy (DMSO$_{d6}$): δ[ppm]=8.19 (d, 1H, H-3), 8.11 (d, 1H, H-8), 7.45 (d, 1H, H-16), 7.37-7.28 (m, 5H, aryl-H), 7.20 (br. s., 1H, CONH$_2$), 6.87 (dt, 1H, H-12, J$_{12/13}$=15.6 Hz), 6.78 (br. s., 1H, CONH$_2$), 5.82 (d, 1H, H-11, J$_{13/12}$=15.6 Hz), 5.03 (s, 2H, benzyl-CH$_2$), 4.50-4.43 (m, 1H, H-5), 4.37-4.34 (m, 1H, H-4), 4.27-4.22 (m, 1H, H-2), 4.10 (q, 2H, H-14$_a$, H-14$_b$), 4.05-4.00 (m, 1H, H-9), 3.65-3.57 (m, 2H, H-4c$_a$, H-4c$_b$), 3.61 (s, 3H, OMe), 2.25-2.19 (m, 2H, H-11$_a$, H-11$_b$), 2.16-2.10 (m, 2H, H-7$_a$, H-7$_b$), 2.10-2.00 (m, 1H, H-4$_{a/1}$), 1.95-1.70 (m, 5H, H-4$_{a/2}$, H-4$_{b/1}$, H-4$_{b/2}$, H-6$_a$, H-10$_a$), 1.71-1.60 (m, 3H, H-10$_b$, methine-H (Leu), H-6$_b$), 1.65-1.60 (m, 1H, H-8$_b$), 1.60-1.51 (m, 1H, CH$_{2a}$-Leu), 1.51-1.45 (m, 1H, CH$_{2b}$-Leu), 1.21 (t, 3H, CH$_3$-16), 0.87 (dd, 6H, 2×CH$_3$-Leu)

ESI-MS: 710.4 {M+Na}$^+$

N$^\alpha$-benzyloxycarbonyl-{[(E)-(L)-6-amino-hept-2-ene-dicarboxylic acid]-1-ethanoyl}-L-phenylalanine methyl ester (compound 3)

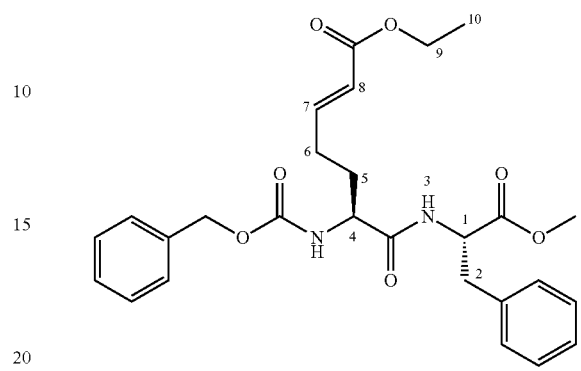

33.5 mg of N$^\alpha$-benzyloxycarbonyl-{(E)-(L)-6-amino-hept-2-ene-dicarboxylic acid}-1-ethyl ester (1.7, 0.1 mmol) are dissolved in 7.5 ml of DMF and successively mixed with 38 mg of HATU (0.1 mmol) and 51 µl of DIPEA (0.3 mmol). The amino acid activated that way is added to a solution of 21.5 mg of phenylalanine methyl ester hydrochloride (commercially available) in 7.5 ml of DMF. By gradually adding DIPEA the pH is adjusted to about 9. The mixture is stirred for 30 minutes at room temperature. Further processing is carried out as described for compound 1: (Synergie Max, 4 µm, 250×21.2 mm, eluent A: 0.1% TFA/water; eluent B: 90% AcCN/10% water/0.1% TFA.

Gradient: 8 ml/min, 30% B on 100% B, 1%/min).

R$_t$=39.6-42.0 min

Yield: 29 mg

ESI-MS: 519.2 {M+Na}$^+$

N$^\alpha$-benzyloxycarbonyl-{[(E)-(L)-6-amino-hept-2-ene-dicarboxylic acid]-1-methanoyl}-L-glutaminyl-L-proline methyl ester (compound 4)

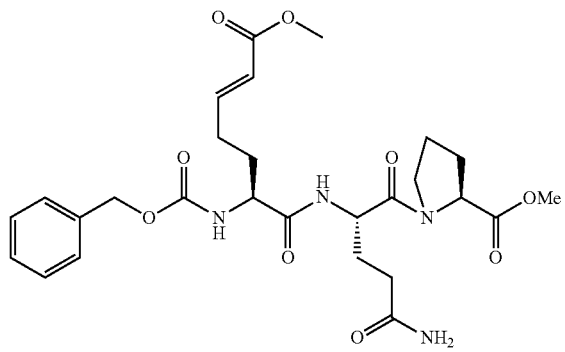 [SMILES: COC(=O)/C=C/CC[C@H](NC(=O)OCc1ccccc1)C(=O)N[C@@H](CCC(N)=O)C(=O)N1CCC[C@H]1C(=O)OC]

32 mg (1.11, 0.1 mmol) are dissolved in 7 ml of DMF and successively mixed with 38 mg of HATU (0.1 mmol) and 51 µl of DIPEA (0.3 mmol). Said solution is added to a solution of the trifluoroacetate salt of Gln-Pro-OMe. Further treatment and processing are carried out as described for compound 1.

R$_t$=28.8-31.2 min

ESI-MS: 583.3 {M+Na}$^+$

Nα-benzyloxycarbonyl-{[(E)-(L)-6-amino-hept-2-ene-dicarboxylic acid]-1-ethanoyl}-L-glutaminyl-L-prolinyl-isopentylamide (compound 5)

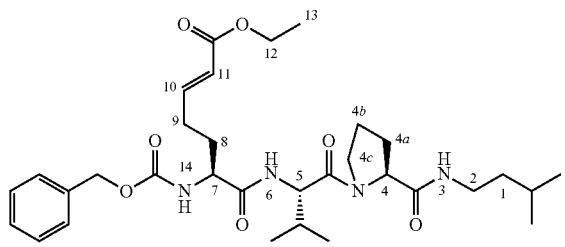 [SMILES: CCOC(=O)/C=C/CC[C@H](NC(=O)OCc1ccccc1)C(=O)N[C@H](C(=O)N1CCC[C@H]1C(=O)NCCC(C)C)C(C)C]

22 mg of Nα-benzyloxycarbonyl-{(E)-(L)-6-amino-hept-2-ene-dicarboxylic acid}-1-ethyl ester (1.7, 0.066 mmol) are dissolved in 5 ml of DMF and successively mixed with 25 mg of HATU (0.066 mmol) and 33.5 µl of DIPEA (0.0196 mmol) and immediately added to a solution of the trifluoroacetate salt of 0.0657 mmol of H-Val-Pro-isopropylamide (5.a) in 5 ml of DMF. By gradually adding DIPEA, the pH is adjusted to 9. Further processing is carried out as described for compound 1: (Synergie Max, 4 µm, 250×21.2 mm, eluent A: 0.1% TFA/water; eluent B: 90% AcCN/10% water/0.1% TFA.
Gradient: 8 ml/min, 30% B on 100% B, 1%/min).
$R_t$=37.3-40.3 min
Yield: 20 mg
500-MHz-$^1$H-NMR-cosy (DMSO$_{d6}$): δ[ppm]=7.86 (d, 1H, H-6), 7.69 (t, 1H, H-3), 7.48 (d, 1H, H-14), 7.39-7.28 (m, 5H, aryl-H), 6.88 (dt, 1H, H-10, $J_{10/9}$=7.0 Hz, $J_{10/11}$=14.3 Hz), 5.80 (d, 1H, H-11, $J_{11/10}$=14.3 Hz), 5.02 (s, 2H, benzyl-CH$_2$), 4.33-4.30 (m, 1H, H-5), 4.30-4.22 (m, 1H, H-4), 4.10 (q, 2H, H-12$_a$, H-12$_b$), 4.08-4.03 (m, 1H, H-7), 3.73-3.67 (m, 1H, H-4c$_a$), 3.60-3.54 (m, 1H, H-4c$_b$), 3.14-3.06 (m, 1H, H-2$_a$), 3.05-2.95 (m, 1H, H-2$_b$) 2.25-2.17 (m, 2H, H-9$_a$, H-9$_b$), 2.04-1.90 (m, 3H, H-4$_{a/1}$, H-4$_{b/1}$, methine-H (Val)), 1.85-1.70 (m, 3H, H-4$_{a/2}$, H-4$_{b/2}$, H-10$_a$), 1.68-1.60 (m, 1H, H-10$_b$), 1.60-1.50 (m, 1H, methine-H(isopropylamide)), 1.31-1.24 (m, 2H, H-3$_a$, H-3$_b$), 1.21 (t, 3H, CH$_3$-13), 0.89 (d, 12H, 4×CH$_3$)
ESI-MS: 623.5 {M+Na}$^+$

[(E)-(L)-6-(2-oxo-pyrrolidon-1-yl)-hept-2-ene-dicarboxylic acid 1-ethanoyl]-L-valinyl-L-proline methyl ester (compound 6)

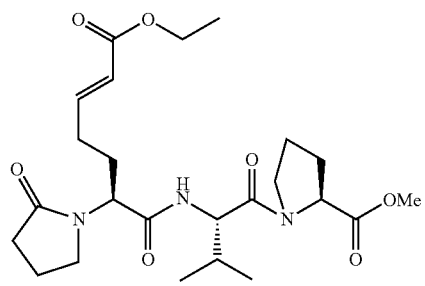 [SMILES: CCOC(=O)/C=C/CC[C@@H](C(=O)N[C@H](C(=O)N1CCC[C@H]1C(=O)OC)C(C)C)N1CCCC1=O]

27 mg of (L)-(E)-(L)-6-(2-oxo-pyrrolidon-1-yl)-hept-2-ene-dicarboxylic acid 1-ethyl ester (1.15, 0.1 mmol) are dissolved in 7.5 ml of DMF and successively mixed with 38 mg of HATU (0.1 mmol) and 51 µl of DIPEA (0.3 mmol). The amino acid activated that way is added to a solution of 0.1 mmol of the trifluoroacetate salt of H-Val-Pro-OMe in 7.5 ml of DMF. By gradually adding DIPEA the pH is adjusted to about 9. The mixture is stirred for 30 minutes at room temperature. Further processing is carried out as described for compound 1: (Synergie Max, 4 µm, 250×21.2 mm, eluent A: 0.1% TFA/water; eluent B: 90% AcCN/10% water/0.1% TFA. Gradient: 8 ml/min, 30% B on 100% B, 1%/min).
ESI-MS: 502.3 [M+Na]$^+$

L-glutamyl-L-alaninyl-L-valine methyl ester (7.1)

The compound given in the title is synthesized according to standard methods of peptide synthesis.
ESI-MS: 332.1 [M+H]$^+$

Nα-tert.-butyloxycarbonyl-{[(E)-(L)-6-amino-hept-2-ene-dicarboxylic acid]-1-methanoyl}-L-glutamyl-L-alaninyl-L-valine methyl ester (7.2)

29 mg of Nα-tert.-benzyloxycarbonyl-{(E)-(L)-6-amino-hept-2-ene-dicarboxylic acid}-1-methyl ester (1.9., 0.1 µmol) together with 38 mg of HATU (0.1 mmol) are dissolved in 5 ml of DMF. 51 µl of DIPEA (0.3 mmol) are added to said solution and the yellow solution obtained is immediately added to a solution of 44 mg (of the trifluoroacetate salt of L-glutamyl-L-alaninyl-L-valine methyl ester (7.1, 0.1 mmol)). By gradually adding DIPEA the pH is set to 9. After 30 minutes, the solvent is removed under vacuum and the oily brown residue is purified by preparative HPLC (Synergie Max, 4 µm, 250×21.2 mm, eluent A: 0.1% TFA/water; eluent B: 90% AcCN/10% water/0.1% TFA. Gradient:
8 ml/min, 40% B on 100% B, 1%/min).
Yield: 38 mg
ESI-MS: 623.2 [M+Na]$^+$

Nα-acetyl-L-asparaginyl-{[(E)-(L)-6-amino-hept-2-ene-dicarboxylic acid]-1-methanoyl}-L-glutamyl-L-alaninyl-L-valine methyl ester (compound 7)

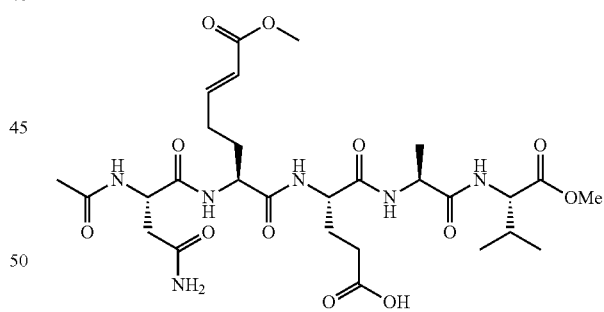

38 mg of Nα-tert-butyloxycarbonyl-{[(E)-(L)-6-amino-hept-2-ene-dicarboxylic acid]-1-methanoyl}-L-glutamyl-L-alaninyl-L-valine methyl ester (7.2, 63 µmol) are dissolved in 5 ml of dichloromethane, mixed with the same volume of trifluoroacetic acid and stirred for one hour at room temperature. After said period of time, the solvent is removed under vacuum. Acid residues are removed by co-distilling with methanol for several times. The oily residue obtained is dissolved in 4 ml of DMF. A solution of 11 mg of Nα-acetyl-L-asparagine, 24 mg of HATU and 33 µl of DIPEA is added to said solution. The pH of the resulting solution is adjusted to about 7 with DIPEA.

After one hour, the solvent is removed under vacuum. Purification is performed by means of preparative HPLC.

(Synergie Max, 4 µm, 250×21.2 mm, eluent A: 0.1% TFA/water; eluent B: 90% AcCN/10% water/0.1% TFA. Gradient: 8 ml/min, 40% B on 100% B, 1%/min).

R$_t$: 37.0-39.8 min
Yield: 27 mg
ESI-MS: 679.3 [M+Na]$^+$

N$^\alpha$-tert.-butyloxycarbonyl-{[(E)-(L)-6-amino-hept-2-ene-dicarboxylic acid]-1-methanoyl}-L-serinyl-L-leucinyl-L-valinyl-L-isoleucinyl-glycine methyl ester (8.3) 29 mg of N$^\alpha$-tert.-benzyloxycarbonyl-{(E)-(L)-6-amino-hept-2-ene-dicarboxylic acid}-1-methyl ester (1.9, 0.1 mmol) together with 38 mg of HATU (0.1 mmol) are dissolved in 5 ml of DMF. 51 µl of DIPEA (0.3 mmol) are added to said solution and the yellow solution obtained is immediately added to a solution of 64 mg (0.1 mmol) of the trifluoroacetate salt of L-serinyl-L-leucinyl-L-valinyl-L-isoleucinyl-glycine methyl ester (8.1). By gradually adding DIPEA the pH is adjusted to 9. After 30 minutes, the solvent is removed under vacuum and the oily brown residue is purified by preparative HPLC (Synergie Max, 4 µm, 250×21.2 mm, eluent A: 0.1% TFA/water; eluent B: 90% AcCN/10% water/0.1% TFA. Gradient: 8 ml/min, 40% B on 100% B, 1%/min).

Yield: 39 mg
ESI-MS: 807.5 {M+Na}$^+$

N$^\alpha$-acetyl-L-leucinyl-glycinyl-L-prolinyl-glycinyl-{[(E)-(L)-6-amino-hept-2-ene-dicarboxylic acid]-1-ethanoyl}-L-serinyl-L-leucinyl-L-valinyl-L-isoleucinyl-glycine methyl ester (compound 8)

21.2 mm, eluent A: 0.1% TFA/water; eluent B: 90% AcCN/10% water/0.1% TFA. Gradient: 8 ml/min, 40% B on 100% B, 1%/min).

R$_t$: 13.6-15.4 min
Yield: 15 mg
500-MHz-$^1$H-NMR-cosy (DMSO$_{d6}$): δ[ppm]=8.34 (t, 1H), 8.25-8.16 (m, 2H), 8.09 (d, 1H), 8.01 (d, 1H), 7.99 (d, 1H), 7.89 (t, 1H), 7.81-7.73 (m, 2H), 6.68 (dt, 1H), 5.85 (d, 1H), 4.49-3.65 (several multiplets, 13H), 3.64 (s, 3H), 3.61 (s, 3H), 3.56 (m, 2H), 3.55-3.42 (m, 2H), 2.18-2.12 (m, 2H), 2.07-1.55 (several multiplets, 7H), 1.84 (s, 3H), 1.51-1.38 (m, 4H), 1.13-1.04 (m, 1H), 0.89-0.78 (several multiplets, 18H)
ESI-MS: 1059.8 [M+Na]$^+$ Preparation of Inhibitors with m=1

Surprisingly, it resulted that effective inhibitors can also be obtained when the ethylene group as a linker between the electrophilic double bond, i.e. the acceptor-substituted double bond, and the peptidic backbone is expanded with a carbonyl group. This completely novel pharmacophoric group, i.e. the electrophilic double bond linked via a ethylene carbonyl group as an integral part of the inhibitor, hasn't been described yet neither for other enzymes. The synthesis sequence of these inventive inhibitors is given in FIG. 3.

N$_\alpha$-benzyloxycarbonyl-L-glutamyl-L-valinyl-L-prolinyl-leucine methyl ester (9.1)

The compound given in the title is synthesized according to standard methods of peptide synthesis.
ESI-MS: 627.3 [M+Na]

N$^\alpha$-benzyloxycarbonyl-(5-oxo-6-diazo)-L-norleucinyl-L-valinyl-L-prolinyl-leucine methyl ester (9.2)

1.83 g of N$^\alpha$-benzyloxycarbonyl-L-glutamyl-L-valinyl-L-prolinyl-leucine methyl ester (9.1, 2.12 mmol) are dissolved

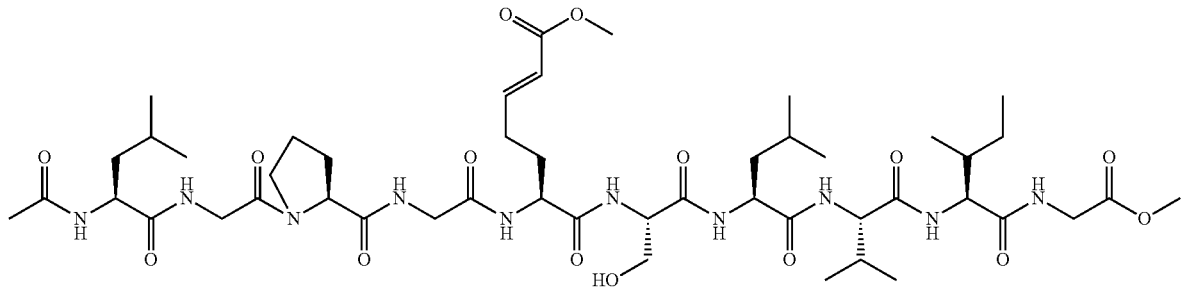 [SMILES: CCC(C)[C@H](NC(=O)[C@@H](NC(=O)[C@H](CC(C)C)NC(=O)[C@H](CO)NC(=O)[C@H](CC/C=C/C(=O)OC)NC(=O)CNC(=O)[C@@H]1CCCN1C(=O)CNC(=O)[C@H](CC(C)C)NC(C)=O)C(C)C)C(=O)NCC(=O)OC]

39 mg of N$^\alpha$-tert.-butyloxycarbonyl-{[(E)-(L)-6-amino-hept-2-ene-dicarboxylic acid]-1-ethanoyl}-L-serinyl-L-leucinyl-L-valinyl-L-isoleucinyl-glycine methyl ester (8.3, 49 µmol) are dissolved in 5 ml of dichloromethane. Once the same volume of trifluoroacetic acid has been added, the mixture is stirred for one hour at room temperature and subsequently the solvent is removed under vacuum. Acid residues are removed by co-distilling with methanol for several times. The oily residue obtained is dissolved in 4 ml of DMF.

A solution of 20 mg (50 µmol) of N$^\alpha$-acetyl-L-leucinyl-glycinyl-L-prolinyl-glycine (8.2) in DMF, 19 mg of HATU (50 µmol) is activated by the addition of 26 µl of DIPEA and is subsequently added to the solution synthesized above of the trifluoroacetate salt of deprotected 8.3. By gradually adding DIPEA the pH is adjusted to about 7. After one hour, the solvent is removed under vacuum. Purification is performed by means of preparative HPLC. (Synergie Max, 4 µm, 250× in 40 ml of THF$_{(abs)}$ and cooled to −15° C. 1.8 ml of diisopropylethylamine (10.6 mmol) and 1.43 ml of isobutyl chloroformate (10.6 mmol) are successively added to said solution under argon atmosphere. After 10 minutes, a freshly prepared solution of diazomethane in diethyl ether (about 33 mmol) is added. The reaction mixture is stirred overnight and the solvent is removed under vacuum.

Purification is performed by means of chromatography on silica gel.
ESI-MS: 651.4 [M+Na], 623.4 [M-N$_2$+Na]

N$^\alpha$-benzyloxycarbonyl-(L-7-amino-1,2-dioxo-hexanoyl)-L-valinyl-L-prolinyl-leucine methyl ester (9.3)

100 mg of N$^\alpha$-benzyloxycarbonyl-(5-oxo-6-diazo)-L-norleucinyl-L-valinyl-L-prolinyl-leucine methyl ester (9.2, 0.16 mmol) are dissolved in 20 ml of absolute acetone. 3 ml of a freshly prepared dimethyldioxirane solution (~0.1 M) are added at 0° C. under argon atmosphere. After ten minutes, the solvent is removed under vacuum, the residue is taken up in dichloromethane$_{abs}$ and dried over Na$_2$SO$_4$ (1%/min).

ESI-MS: 639.4 [M+Na], 657.4 [M+H$_2$O]

N$^\alpha$-benzyloxycarbonyl-{[L-7-amino-4-oxo-oct-2-ene-dicarboxylic acid]-1-ethanoyl}-L-valinyl-L-prolinyl-leucine methyl ester (compound 9)

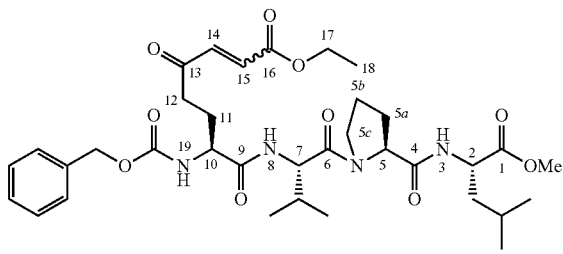 [SMILES: CCOC(=O)C=CC(=O)CC[C@H](NC(=O)OCc1ccccc1)C(=O)N[C@H](C(=O)N1CCC[C@H]1C(=O)N[C@@H](CC(C)C)C(=O)OC)C(C)C]

98 mg of N$^\alpha$-benzyloxycarbonyl-(L-2-amino-5,6-dioxo-hexanoyl)-L-valinyl-L-prolinyl-leucine methyl ester (9.3, 0.16 mmol) are dissolved in absolute benzene. 52 mg of (carbethoxymethylene)triphenylphosphorane (0.15 mmol) are added to said solution The mixture is stirred for one hour at room temperature under argon atmosphere. The solvent is removed under vacuum and the solid residue is purified by preparative HPLC (Synergie Max, 4 μm, 250×21.2 mm, eluent A: 0.1% TFA/water; eluent B: 90% AcCN/10% water/0.1% TFA. Gradient: 8 ml/min, 40% B on 100% B, 1%/min). During this process, two products are isolated. The solvent is removed under vacuum and the residue is dried under high vacuum.

R$_t$: 37-40 min 7 mg
R$_t$: 40-43 min 27 mg

Z isomer (fraction 37-40 min)
500-MHz-$^1$H-NMR-cosy (DMSO$_{d6}$): δ[ppm]=8.24 (d, 1H, H-3), 7.89 (d, 1H, H-8), 7.51 (d, 1H, H-19), 7.43-7.30 (m, 5H, aryl-H), 6.76 (d, 1H, H-14, J$_{14/15}$=12.1 Hz), 6.18 (d, 1H, H-15, J$_{14/15}$=12.1 Hz), 5.06 (s, 1H, benzyl-CH$_2$), 4.43-4.34 (m, 2H, H-5, H-7), 4.32-4.26 (m, 1H, H-2), 4.15 (q, 2H, H-17$_a$, H-17$_b$), 4.12-3.96 (m, 1H, H-10), 3.76-3.70 (m, 1H, H-5c$_a$), 3.65 (s, 3H, OMe), 3.63-3.55 (m, 1H, H-5c$_b$), 2.60-2.66 (m, 2H, H-12$_a$, H-12$_b$), 2.13-2.03 (m, 1H, H-5$_{a/1}$), 2.03-1.92 (m, 2H, H-5$_{b/1}$, methine-H (Val)), 1.92-1.81 (m, 3H, H-5$_{a/2}$, H-5$_{b/2}$, H-11$_a$), 1.81-1.70 (m, 2H, H-11$_b$, methine-H (Leu)), 1.63-1.55 (m, 1H, CH$_{2a}$-Leu)), 1.55-1.47 (m, 1H, CH$_{2b}$-Leu), 1.21 (t, 3H, CH$_3$-18), 0.94 (d, 6H, 2×CH$_3$-Val), 0.90 (d, 6H, 2×CH$_3$-Leu)
ESI-MS: 709.5 {M+Na}$^+$ E isomer (fraction 40-43 min)
500-MHz-$^1$H-NMR-cosy (DMSO$_{d6}$): δ[ppm]=8.22 (d, 1H, H-3), 7.90 (d, 1H, H-8), 7.51 (d, 1H, H-19), 7.43-7.30 (m, 5H, aryl-H), 6.97 (d, 1H, H-14, J$_{14/15}$=16.1 Hz), 6.72 (d, 1H, H-15, J$_{14/15}$=16.1 Hz), 5.07 (s, 1H, benzyl-CH$_2$), 4.43-4.33 (m, 2H, H-5, H-7), 4.30-4.28 (m, 1H, H-2), 4.25 (q, 2H, H-17$_a$, H-17$_b$), 4.15-3.97 (m, 1H, H-10), 3.77-3.71 (m, 1H, H-5c$_a$), 3.65 (s, 3H, OMe), 3.63-3.58 (m, 1H, H-5c$_b$), 2.85-2.73 (m, 2H, H-12$_a$, H-12$_b$), 2.13-2.03 (m, 1H, H-5$_{a/1}$), 2.03-1.92 (m, 2H, H-5$_{b/1}$, methine-H (Val)), 1.92-1.81 (m, 3H, H-5$_{a/2}$, H-5$_{b/2}$, H-11$_a$), 1.81-1.70 (m, 2H, H-11$_b$, methine-H (Leu)), 1.63-1.55 (m, 1H, CH$_{2a}$-Leu)), 1.55-1.47 (m, 1H, CH$_{2b}$-Leu), 1.28 (t, 3H, CH$_3$-18), 0.96 (dd, 6H, 2×CH$_3$-Val), 0.90 (dd, 6H, 2×CH$_3$-Leu)
ESI-MS: 709.5 {M+Na}$^+$ N$^\alpha$-benzyloxycarbonyl-{[(E)-(L)-6-amino-hept-2-ene-dicarboxylic acid]-1-ethanoyl}-L-phenylalaninyl-L-prolinyl-L-leucine methyl ester (compound 25)

500-MHz-$^1$H-NMR-cosy (DMSO$_{d6}$): δ[ppm]=8.53 (d, 1H), 8.19 (d, 1H), 7.37-7.17 (m, 11H), 6.83 (dt, 1H), 5.78 (d, 1H), 5.01 (s, 1H), 4.73-4.65 (m, 1H), 4.42-4.35 (m, 1H), 4.32-4.25 (m, 1H), 4.10 (q, 2H), 3.99-3.92 (m, 1H), 3.56 (s, 3H), 3.55-3.43 (m, 2H), 3.00 (dd, 1H), 2.76 (dd, 1H), 2.21-2.10 (m, 2H), 2.10-2.00 (m, 1H), 1.95-1.75 (m, 3H), 1.72-1.42 (m, 5H), 1.19 (t, 3H), 0.91 (d, 3H), 0.87 (d, 3H)

N$^\alpha$-benzyloxycarbonyl-{[(E)-(L)-6-amino-hept-2-ene-dicarboxylic acid]-1-ethanoyl}-glycinyl-L-prolinyl-L-leucine methyl ester (compound 26)

500-MHz-$^1$H-NMR-cosy (DMSO$_{d6}$): δ[ppm]=8.20 (d, 1H), 8.01 (d, 1H), 7.50 (d, 1H), 7.37-7.25 (m, 5H), 6.87 (dt, 1H), 5.81 (d, 1H), 5.02 (s, 1H), 4.39-4.35 (m, 1H), 4.28-4.22 (m, 1H), 4.11 (q, 2H), 4.07-4.03 (m, 1H), 4.01 (dd, 1H), 3.80 (dd, 1H), 3.61 (s, 3H), 3.61-3.42 (m, 2H), 2.32-2.20 (m, 2H), 2.08-2.01 (m, 1H), 1.95-1.88 (m, 1H), 1.88-1.73 (m, 2H), 1.81-1.60 (m, 3H), 1.59-1.45 (m, 2H), 1.21 (t, 3H), 0.88 (d, 3H), 0.83 (d, 3H)

N$^\alpha$-benzyloxycarbonyl-{[(E)-(L)-6-amino-hept-2-ene-dicarboxylic acid]-1-ethanoyl}-L-alaninyl-L-prolinyl-L-leucine methyl ester (compound 27)

500-MHz-$^1$H-NMR-cosy (DMSO$_{d6}$): δ[ppm]=8.14 (d, 1H), 8.10 (d, 1H), 7.42 (d, 1H), 7.37-7.31 (m, 5H), 6.87 (dt, 1H), 5.82 (d, 1H), 5.02 (s, 1H), 4.53-4.45 (m, 1H), 4.40-4.35 (m, 1H), 4.25-4.18 (m, 1H), 4.10 (q, 2H), 4.05-3.97 (m, 1H), 3.60 (s, 3H), 3.56-3.50 (m, 1H), 2.28-2.18 (m, 2H), 2.09-2.00 (m, 1H), 1.98-1.87 (m, 2H), 1.87-1.73 (m, 2H), 1.73-1.55 (m, 2H), 1.55-1.50 (m, 1H), 1.50-1.49 (m, 1H), 1.21 (m, 6H), 0.89 (d, 3H), 0.84 (d, 3H)

2.1 Preparation of Inhibitors with Peptidic Environment of the Pharmacophoric Group. Reactions at Amino Functions at the Example of (E)-(L)-6-amino-hept-2-ene-dicarboxylic Acid Pharmacophoric groups can be prepared by way of example, but not limited to, from amino acids as glutamic acid. Thus inventive inhibitors with an α-amino group are obtained, for example when using carboxymethyl Wittig reagents, (E)-(L)-6-amino-hept-2-ene-dicarboxylic acid. This amino group can be modified by any reaction that can be carried out on an amino group.

Surprisingly it resulted that potent inhibitors can mainly be obtained when such amino groups (—NXX'), provided that they are located in the immediate vicinity to the pharmacophoric group, are acylated or alkylated. In particular they should not be present as a free primary amine. If e.g. (E)-(L)-6-amino-hept-2-ene-dicarboxylic acid is used as a bioisosteric pharmacophore then the amino function must be rendered to a less polar compound through the substitution of at least one of the two hydrogens at the nitrogen atom, for example by an acylation. Examples, but not limited to, for the synthesis of inhibitors with varying unpolar groups at this nitrogen are given below. Furthermore, apart of acylation reactions all other known reactions at amino groups can be realized, as long as no extremely high pH values or other conditions are present that would ensue a degradation of the Michael acceptor structural element.

General description of the synthesis for the modification of amino functions in inhibitors:

The modification of amino groups in inventive inhibitors can normally be performed without difficulties, according to the common procedures in such cases. A special case is given when—as in the example of (E)-(L)-6-amino-hept-2-ene-dicarboxylic acid derivatives—the amino group reacts preferably itself with the pharmacophoric group under the given conditions. A quick access to several derivatives of such inhibitors is given for example (but not limited to) by the following sequence of synthesis: $N^\alpha$-tert.-butyloxycarbonyl-{[(E)-(L)-6-amino-hept-2-ene-dicarboxylic acid]-1-ethyl ester, the ester analogue to 1.9 is linked to a suitable amine with the here described methods. From the resulting amide the Boc protective group is cleaved acidolytically. The salt is stable at low pH values. The further conversion of the amino group meets no problems when the pH value of the medium is not higher than 9.

$N^\alpha$-tert.-butyloxycarbonyl-{[(E)-(L)-6-amino-hept-2-ene-dicarboxylic acid]-1-ethanoyl}-L-glutaminyl-L-prolinyl-L-leucine methyl ester (compound 28)

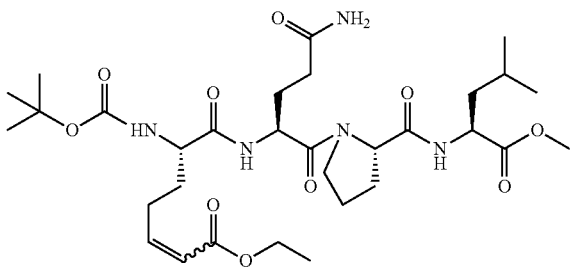 [SMILES: CCOC(=O)C=CCC[C@H](NC(=O)OC(C)(C)C)C(=O)N[C@@H](CCC(N)=O)C(=O)N1CCC[C@H]1C(=O)N[C@@H](CC(C)C)C(=O)OC]

Starting with 283 mg Boc-Gln-Pro-Leu-OMe (0.6 mmol) the salt of the free amine (H-Gln-Pro-Leu-OMe) is prepared through the treatment with trifluoroacetic acid. The resulting yellowish oil is dissolved in 10 ml DMF. $N^\alpha$-tert-butyloxycarbonyl-{[(E)-(L)-6-amino-hept-2-ene-dicarboxylic acid]-1-ethyl ester (0.6 mmol) is dissolved in 10 ml DMF and 229 mg HATU (0.6 mmol) and 307 µl DIPEA are added. The resulting solution is immediately added to the solution of the amine described above (H-Gln-Pro-Leu-OMe) and through continuous addition of DIPEA brought to ~pH 9.

After stirring for one hour at room temperature the solvent is removed under vacuum and the product is purified by means of chromatography on silica. gel. (column: 32.5×3.2. cm, dichlormethane/methanol: 95/5)

Yield: 345 mg

500-MHz-$^1$H-NMR-cosy (DMSO$_{d6}$): δ[ppm]=8.10 (d, 1H), 7.86 (d, 1H), 7.07 (s, 1H), 6.78-6.72 (m, 2H), 6.66 (s, 1H), 5.71 (d, 1H), 4.42-4.33 (m, 1H), 4.29-4.21 (m, 1H), 4.19-4.10 (m, 1H), 4.00 (q, 2H), 3.85-3.79 (m, 1H), 3.57-3.45 (m, 5H), 3.49 (s, 3H), 2.15-2.05 (m, 2H), 2.05-2.01 (m, 2H), 1.95-1.88 (m, 1H), 1.80-1.72 (m, 2H), 1.72-1.65 (m, 2H), 1.65-1.45 (m, 3H), 1.45-1.37 (m, 1H), 1.37-1.31 (m, 1H), 1.08 (t, 3H), 0.78 (d, 3H), 0.73 (d, 3H)

ESI-MS: 676.4 {M+Na}$^+$ $N^\alpha$-thiophene-2-carbonyl-{[(E)-(L)-6-amino-hept-2-ene-dicarboxylic acid]-1-ethanoyl}-L-glutaminyl-L-prolinyl-L-leucine methyl ester (compound 29)

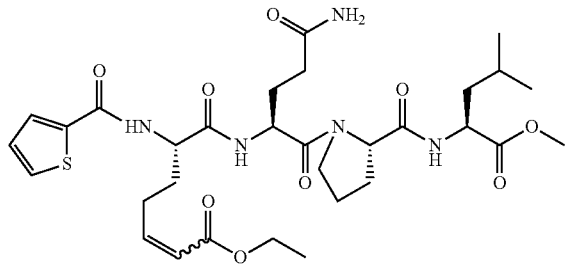 [SMILES: CCOC(=O)C=CCC[C@H](NC(=O)c1cccs1)C(=O)N[C@@H](CCC(N)=O)C(=O)N1CCC[C@H]1C(=O)N[C@@H](CC(C)C)C(=O)OC]

100 mg $N^\alpha$-tert.-butyloxycarbonyl-{[(E)-(L)-6-amino-hept-2-ene-dicarboxylic acid]-1-ethanoyl}-L-glutaminyl-L-prolinyl-L-leucine methyl ester (28, 0.152 mmol)) are dissolved in 5 ml dichloromethane and 5 ml trifluoroacetic acid are added. The mixture is stirred for one hour at room temperature and subsequently the solvent is removed under vacuum. The resulting amine H-{[(E)-(L)-6-amino-hept-2-ene-dicarboxylic acid]-1-ethanoyl}-L-glutaminyl-L-prolinyl-L-leucine methyl ester is dissolved in 5 ml DMF. To a solution of 19.6 mg 2-thiophene carboxylic acid (0.153 mmol) and 58.2 mg HATU (0.1553 mmol) in 5 ml DMF 52 µl DIPEA (=0.306 mmol) are added. The mixture is immediately given to the solution of the amine described above. Through continuous addition of DIPEA the pH is adjusted at ~9. After 30 minutes the solvent is removed under vacuum and the resulting residue is purified by means of preparative HPLC chromatography (Synergy Max, 4 µm, 250×21.2 mm, A-eluent: 0.1% FTA/water, B-eluent: 90% AcCN/10% water/ 0.1% FTA. Gradient: 8 ml/min, 40% B on 100% B, 1%/min).

500-MHz-$^1$H-NMR-cosy (DMSO$_{d6}$): δ[ppm]=8.44 (de, 1H), 8.24 (d, 1H), 8.22 (d, 1H), 7.88 (dd, 1H), 7.77 (dd, 1H), 7.24 (br. s., 1H), 7.16 (dd, 1H), 6.95-6.87 (m, 1H), 6.80 (br. S., 1H), 5.83 (d, 1H), 4.49-4.41 (m, 2H), 4.37-4.33 (m, 1H), 4.26-4.21 (m, 1H), 4.08 (q, 2H), 3.65-3.59 (m, 5H), 2.31-2.23 (m, 2H), 2.19-2.11 (m, 2H), 2.09-1.99 (m, 1H), 1.95-1.75 (several multiplets, 6H), 1.73-1.63 (m, 2H), 1.59-1.51 (m, 1H), 1.51-1.44 (m, 1H), 1.19 (t, 3H), 0.89 (d, 3H), 0.83 (d, 3H)

ESI-MS: 686.4 {M+Na}$^+$

According to the same method the following compounds were prepared and purified:

$N^\alpha$-furane-3-carbonyl-{[(E)-(L)-6-amino-hept-2-ene-dicarboxylic acid]-1-ethanoyl}-L-glutaminyl-L-prolinyl-L-leucine methyl ester (compound 30)

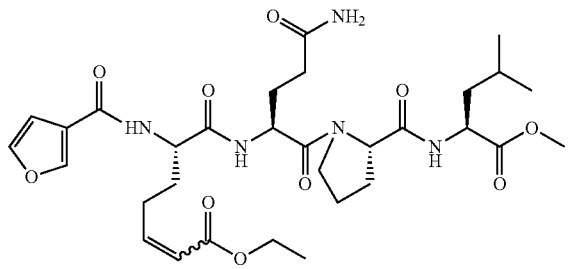 [SMILES: CCOC(=O)C=CCC[C@H](NC(=O)c1ccoc1)C(=O)N[C@@H](CCC(N)=O)C(=O)N1CCC[C@H]1C(=O)N[C@@H](CC(C)C)C(=O)OC]

500-MHz-¹H-NMR-cosy (DMSO$_{d6}$): δ[ppm]=8.24 (m, 3H), 8.14 (d, 1H), 7.73 (t, 1H), 7.25 (br. s, 1H), 6.94-6.86 (m, 2H), 6.79 (br. S., 1H), 5.83 (d, 1H), 4.49-4.41 (m, 2H), 4.37-4.33 (m, 1H), 4.28-4.21 (m, 1H), 4.09 (q, 2H), 3.66-3.59 (m, 5H), 2.30-2.23 (m, 2H), 2.18-2.11 (m, 2H), 2.08-2.00 (m, 1H), 1.95-1.64 (several multiplets, 8H), 1.59-1.51 (m, 1H), 1.51-1.44 (m, 1H), 1.20 (t, 3H), 0.89 (d, 3H), 0.84 (d, 3H)

ESI-MS: 648.5 {M+Na}⁺

N$^\alpha$-isoxazole-5-carbonyl-{[(E)-(L)-6-amino-hept-2-ene-dicarboxylic acid]-1-ethanoyl}-L-prolinyl-L-leucine methyl ester (compound 31)

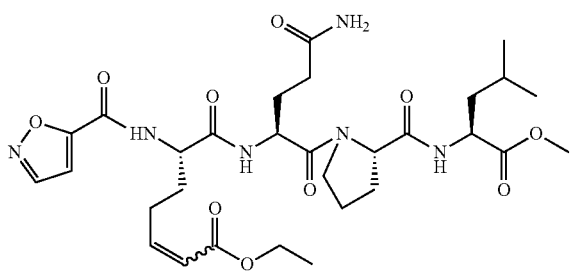 [SMILES: CCOC(=O)C=CCC[C@H](NC(=O)c1ccno1)C(=O)N[C@@H](CCC(N)=O)C(=O)N1CCC[C@H]1C(=O)N[C@@H](CC(C)C)C(=O)OC]

500-MHz-¹H-NMR-cosy (DMSO$_{d6}$): δ[ppm]=8.70 (d, 1H), 8.56 (d, 1H), 8.13 (d, 1H), 8.02 (d, 1H), 7.03 (br. s, 1H), 6.95 (d, 1H), 6.71 (dt, 1H), 6.59 (br. S., 1H), 5.65 (d, 1H), 4.33-4.24 (m, 2H), 4.18-4.15 (m, 1H), 4.09-4.04 (m, 1H), 3.91 (q, 2H), 3.47-3.40 (m, 5H), 2.13-2.04 (m, 2H), 2.00-1.93 (m, 2H), 1.90-1.82 (m, 1H), 1.78-1.60 (several multiplets, 6H), 1.55-1.45 (m, 2H), 1.39-1.34 (m, 1H), 1.34-1.24 (m, 1H), 1.01 (t, 3H), 0.71 (d, 3H), 0.65 (d, 3H)

ESI-MS: 671.4 {M+Na}⁺

N$^\alpha$-(5-methyl-isoxazole-4-carbonyl)-{[(E)-(L)-6-amino-hept-2-ene-dicarboxylic acid]-1-ethanoyl}-L-glutaminyl-L-prolinyl-L-leucine methyl ester (compound 32)

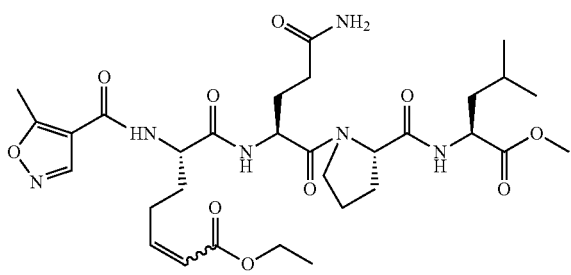 [SMILES: CCOC(=O)C=CCC[C@H](NC(=O)c1cnoc1C)C(=O)N[C@@H](CCC(N)=O)C(=O)N1CCC[C@H]1C(=O)N[C@@H](CC(C)C)C(=O)OC]

The used 5-methyl-isoxazole-4-carboxylic acid is prepared according to Street et al., J. Med. Chem. 2004, 3642-3657.

500-MHz-¹H-NMR-cosy (DMSO$_{d6}$): δ[ppm]=8.97 (s, 1H), 8.27 (d, 2H), 8.22 (d, 1H), 7.21 (br. s, 1H), 6.90 (dt, 1H), 6.77 (br. S., 1H), 5.83 (d, 1H), 4.50-4.41 (m, 2H), 4.38-4.33 (m, 1H), 4.28-4.21 (m, 1H), 4.08 (q, 2H), 3.65-3.58 (m, 5H), 2.61 (s, 3H), 2.28-2.20 (m, 2H), 2.18-2.11 (m, 2H), 2.09-2.00 (m, 1H), 1.95-1.77 (several multiplets, 6H), 1.72-1.61 (m, 2H), 1.59-1.52 (m, 1H), 1.52-1.45 (m, 1H), 1.19 (t, 3H), 0.89 (d, 3H), 0.83 (d, 3H ESI-MS: 685.5 {M+Na}⁺

N$^\alpha$-(5-methyl-isoxazole-3-carbonyl)-{[(E)-(L)-6-amino-hept-2-ene-dicarboxyc acid]-1-ethanoyl}-L-glutaminyl-L-prolinyl-L-leucine methyl ester (compound 33)

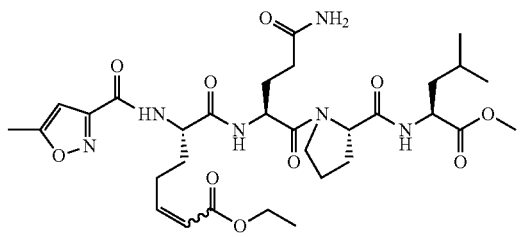

500-MHz-¹H-NMR-cosy (DMSO$_{d6}$): δ[ppm]=8.51 (d, 1H), 8.27 (d, 1H), 8.21 (d, 1H), 7.21 (br. s, 1H), 6.88 (dt, 1H), 6.77 (br. s., 1H), 5.83 (d, 1H), 4.50-4.43 (m, 2H), 4.38-4.33 (m, 1H), 4.27-4.21 (m, 1H), 4.09 (q, 2H), 3.65-3.59 (m, 5H), 2.50 (s, 3H), 2.28-2.21 (m, 2H), 2.19-2.10 (m, 2H), 2.09-2.00 (m, 1H), 1.95-1.77 (several multiplets, 6H), 1.72-1.61 (m, 2H), 1.59-1.52 (m, 1H), 1.52-1.45 (m, 1H), 1.19 (t, 3H), 0.88 (d, 3H), 0.84 (d, 3H ESI-MS: 685.5 {M+Na}⁺

N$^\alpha$-(trans-3-(3-thienyl)acryloyl)-{[(E)-(L)-6-amino-hept-2-ene-dicarboxyc acid]-1-ethanoyl}-L-glutaminyl-L-prolinyl-L-leucine methyl ester (compound 34)

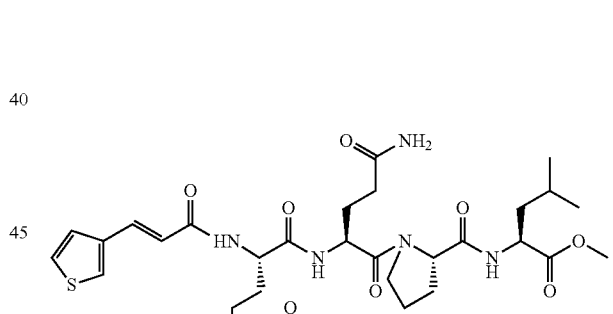

500-MHz-¹H-NMR-cosy (DMSO$_{d6}$): δ[ppm]=8.20 (m, 2H), 8.14 (d, 1H), 7.87 (s, 1H), 7.60 (s, 1H), 7.42 (d, 1H), 7.33 (s, 1H), 7.21 (br. s., 1H), 6.88 (dt, 1H), 6.76 (br. s., 1H), 6.56 (d, 1H), 5.83 (d, 1H), 4.55-4.40 (m, 2H), 4.40-4.31 (m, 1H), 4.29-4.20 (m, 1H), 4.08 (q, 2H), 3.70-3.48 (m, 5H), 2.28-2.21 (m, 2H), 2.19-2.10 (m, 2H), 2.09-2.00 (m, 1H), 1.95-1.77 (several multiplets, 6H), 1.72-1.61 (m, 2H), 1.59-1.52 (m, 1H), 1.52-1.45 (m, 1H), 1.18 (t, 3H), 0.88 (d, 3H), 0.83 (d, 3H)

ESI-MS: 712.5 {M+Na}⁺

N$^\alpha$-acetyl-{[(E)-(L)-6-amino-hept-2-ene-dicarboxyc acid]-1-ethanoyl}-L-glutaminyl-L-prolinyl-L-leucine methyl ester (compound 35)

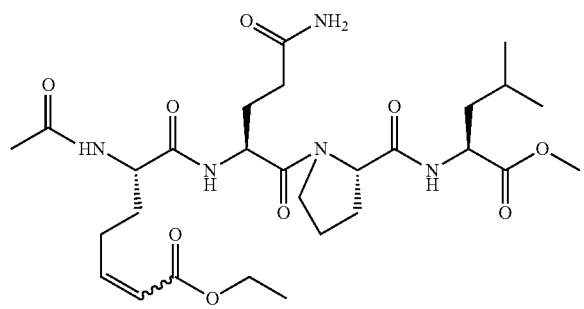 [SMILES: CCOC(=O)C=CCC[C@H](NC(C)=O)C(=O)N[C@@H](CCC(N)=O)C(=O)N1CCC[C@H]1C(=O)N[C@@H](CC(C)C)C(=O)OC]

500-MHz-$^1$H-NMR-cosy (DMSO$_{d6}$): δ[ppm]=8.21 (d, 1H), 8.13 (d, 1H), 7.95 (d, 1H), 7.21 (br. s, 1H), 6.86 (dt, 1H), 6.77 (br. s., 1H), 5.83 (d, 1H), 4.46-4.42 (m, 2H), 4.37-4.33 (m, 1H), 4.29-4.22 (m, 1H), 4.11 (q, 2H), 3.68-3.59 (m, 5H), 2.25-2.16 (m, 2H), 2.16-2.10 (m, 2H), 2.08-2.00 (m, 1H), 1.94-1.78 (several multiplets, 3H), 1.84 (s, 3H), 1.78-1.45 (several multiplets, 6H) 1.20 (t, 3H), 0.89 (d, 3H), 0.84 (d, 3H)

ESI-MS: 618.5 {M+Na}$^+$

N$^\alpha$-(4-trifluoromethoxy-benzolsulfonyl)-{[(E)-(L)-6-amino-hept-2-ene-dicarboxyc acid]-1-ethanoyl}-L-glutaminyl-L-prolinyl-L-leucine methyl ester (compound 36)

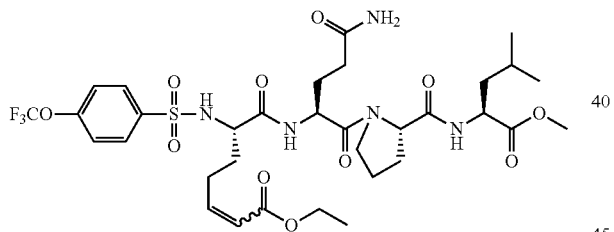

500-MHz-$^1$H-NMR-cosy (DMSO$_{d6}$): δ[ppm]=8.24 (d, 1H), 8.19 (d, 1H), 8.14 (d, 1H), 7.88 (d, 2H), 7.54 (d, 2H), 7.21 (br.s., 1H), 6.80 (br.s.), 6.76 (dt, 1H), 5.70 (d, 1H), 4.34-4.30 (m, 1H), 4.26-4.20 (m, 1H), 4.18-4.13 (m, 1H), 4.09 (q, 2H), 3.84-3.79 (m, 1H), 3.60 (s, 3H), 3.58-3.47 (m, 2H), 2.18-1.97 (several multiplets, 3H), 1.91-1.84 (m, 1H), 1.84-1.76 (several multiplets, 4H), 1.70-1.44 (several multiplets, 6H), 1.20 (t, 3H), 0.88 (d, 3H), 0.82 (d, 3H)

ESI-MS: 800.5 {M+Na}$^+$

Preparation of Inhibitors Containing Non-Proteinogenic Amino Acids

Under the term "amino acid" or "amino acids" should not only be understood the naturally occurring amino acids or their derivatives, but in general chemical compounds which have at least one amino function and at least one carboxyc acid function. The amino acids in a broader sense should be capable to form a betaine structure and/or should be capable to form amide bonds. A particularly preferred form are non-proteinogenic α-amino acids. The in vivo metabolization of active principles can be reduced by such non-proteinogenic amino acids.

General synthesis description of the preparation of inhibitors containing non-proteinogenic amino acids:

The amino acids can be treated analoguous to proteinogenic amino acids in respect of their protective group and coupling chemistry. Thus the synthesis sticks in general to the methods described above.

Here, the amino function of commercially available, non-natural amino acids is protected with the Boc- or the Fmoc protective group according to methods well known to the person skilled in the art. The formation of the respective peptide residue takes place in solution or on a solid phase. The peptide fragment is subsequently released from its protective group and coupled with a pharmacophore-carrying acid.

If a further prolongation at the N-terminal end is intended the derivative 1.9 is used. The resulting product can be prolonged further as described in examples 7 and 8.

By using derivatives as 1.10 or 1.11 shorter inhibitors with stable end groups can be obtained.

In the following two embodiments of such inventive inhibitors containing non-proteinogenic amino acids are given in 37 and 38.

N$^\alpha$-benzyloxycarbonyl-{[(E)-(L)-6-amino-hept-2-ene-dicarboxyc acid]-1-ethanoyl}-L-cyclohexylglycin-L-prolinyl-L-Ieucine methyl ester (compound 37)

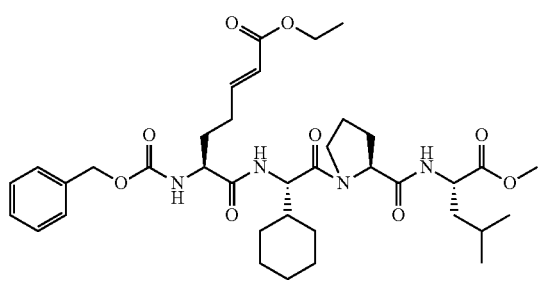 [SMILES: CCOC(=O)/C=C/CC[C@H](NC(=O)OCc1ccccc1)C(=O)N[C@H](C(=O)N1CCC[C@H]1C(=O)N[C@@H](CC(C)C)C(=O)OC)C1CCCCC1]

500-MHz-$^1$H-NMR-cosy (DMSO$_{d6}$): δ[ppm]=8.19 (d, 1H), 7.90 (d, 1H), 7.45 (d, 1H), 7.36-7.30 (m 5H), 6.86 (dt, 1H), 5.81 (d, 1H), 5.02 (s, 2H), 4.37-4.28 (m, 2H), 4.28-4.18 (m, 1H), 4.08 (q, 2H), 4.06-4.00 (m, 1H), 3.54 (s, 3H), 3.56-3.44 (m, 2H), 2.28-2.15 (m, 2H), 2.09-1.98 (m, 1H), 1.98-1.87 (m, 1H), 1.87-1.56 (several multiplets, 11H), 1.56-1.51 (m, 1H), 1.51-1.45 (m, 1H) 1.20 (t, 3H), 1.08-1.02 (m, 3H), 1.01-0.95 (m, 2H), 0.89 (d, 3H), 0.83 (d, 3H)

ESI-MS: 721.6 {M+Na}$^+$

N$^\alpha$-benzyloxycarbonyl-{[(E)-(L)-6-amino-hept-2-ene-dicarboxyc acid]-1-ethanoyl}-L-valinyl-L-homoprolinyl-L-leucine methyl ester (compound 38)

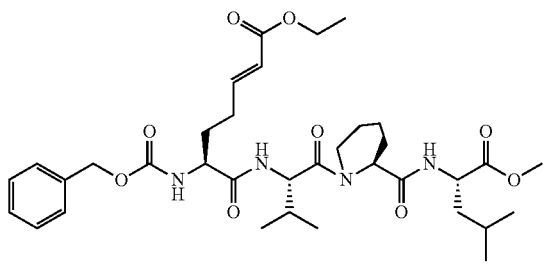 [SMILES: CCOC(=O)/C=C/CC[C@H](NC(=O)OCc1ccccc1)C(=O)N[C@H](C(=O)N1CCCC[C@H]1C(=O)N[C@@H](CC(C)C)C(=O)OC)C(C)C]

500-MHz-$^1$H-NMR-cosy (DMSO$_{d6}$): δ[ppm]=8.06 (d, 1H), 7.86 (d, 1H), 7.54 (d, 1H), 7.3-7.25 (m 5H), 6.86 (dt, 1H), 5.81 (d, 1H), 5.11-5.05 (m, 1H), 5.02 (s, 2H), 4.72-4.66 (m, 1H), 4.32-4.24 (m, 1H), 4.09 (q, 2H), 4.09-4.01 (m, 1H), 3.92-3.83 (m, 1H), 3.61 (s, 3H), 3.45-3.37 (m, 1H), 2.31-2.18 (m, 2H), 2.18-2.09 (m, 1H), 2.07-1.99 (m, 1H), 1.83-1.70 (m, 1H), 1.70-1.46 (several multiplets, 6H), 1.32-1.27 (m, 1H), 1.20 (t, 3H), 0.93-0.74 (m, 12H)

ESI-MS: 695.6 {M+Na}$^+$

A further preferred form of inventive inhibitors containing non-natural amino acids can be prepared by using aromatic or aliphatic molecules the amino and the carboxyc acid function of which are not positioned at the same carbon atom and therefore are not α-amino acids.

Surprisingly, also such structurally highly diverse inhibitors display a good to high inhibitory potence.

As embodiment for this class of inventive inhibitors compound 39 is given. In compound 39 m-amino-benzoic acid is linked to the pharmacophore-carrying amino acid 1.9. The synthesis of inventive inhibitors containing "non-α-amino acids" follows the same route as described herein for inhibitors containing proteinogenic amino acids. (FIG. 4). On pages XXX of the description more amino acid analogues as well as dipeptide mimetics are disclosed which can be employed according to the general synthesis instruction described herein or can be integrated into the non-proteinogenic backbone.

(E)-(S)-6-benzyloxycarbonylamino-6-[3-((R)-2-phenylcarbamoyl-pyrrolidine-1carbonyl)-phenylcarbamoyl]-hex-2-ene acid ethyl ester (compound 39)

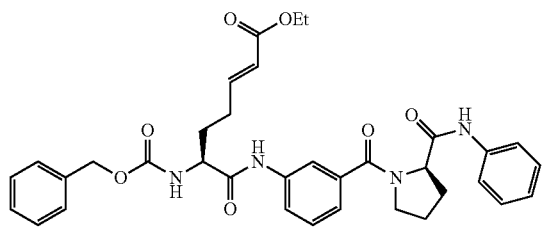 [SMILES: CCOC(=O)/C=C/CC[C@H](NC(=O)OCc1ccccc1)C(=O)Nc1cccc(C(=O)N2CCC[C@@H]2C(=O)Nc2ccccc2)c1]

215 mg boc-proline (1 mmol), 135 mg HOBt (1 mmol) and 305 mg TBTU are dissolved in 10 ml DMF. 342 µl DIPEA (2 mmol) are added to the solution and immediately added to a solution of 93 mg aniline in 5 ml DMF. After stirring for one hour at room temperature the solvent is removed under vacuum and the resulting residue is taken up in 200 ml ethyl acetate. The solution is washed three times each with 30 ml of 10% citric acid solution, saturated NaHCO$_3$ solution and water. The organic phase is dried over Na$_2$SO$_4$ and the solvent is removed under vacuum. This yields 213 mg of N$^\alpha$-tert.-butyloxycarbonyl-L-prolinylanilide. After treatment with 10 ml of a solution of TFA in dichloromethane (1/1) for one hour the solvent is removed under vacuum the oily residue is treated with diethyl ether 111 mg L-prolinylanilide is yielded.

100 mg L-prolinylanilide (0.52 mmol) are dissolved in DMF. To this a solution of 118 mg boc-3-amino-benzoic acid (0.5 mmol), 71 mg HOBt (0.5 mmol), 157 mg TBTU (0.5 mmol) and 170 µl DIPEA (1 mmol) is added. The mixture is stirred at room temperature for one hour and subsequently the solvent is removed under vacuum. The residue is taken up in 200 ml ethyl acetate. The solution is washed three times each with 30 ml of 10% citric acid solution, saturated NaHCO$_3$ solution and water. The organic phase is dried over Na$_2$SO$_4$ and the solvent is removed under vacuum. This yields 174 mg of compound 39.1 as a white solid.

From 160 mg of compound 39.1 (0.39 mmol) the boc protective group is cleaved by treatment with TFA in dichloromethane (see above). After treating the residue with diethyl ether 145 mg of the TFA salt of the primary amine (39.2) is yielded.

42 mg of 39.2 (0.1 mmol) are dissolved in 3 ml DMF. 29 mg N$^\alpha$-tert.-butyloxycarbonyl-{(E)-(L)-6-amino-hept-2-ene-dicarboxyc acid}-1-methyl ester (1.9, 0.1 mmol) are dissolved with 38 mg HATU (0.1 mmol) in 5 ml DMF. To this solution 51 µl DIPEA (0.3 mmol) are added and to this resulting solution the solution of 39.2 is added immediately. Through continuous addition of DIPEA the pH is adjusted at 9. After 30 minutes the solvent is removed under vacuum and the oily brown residue is purified by means of preparative HPLC (synergy max, 4 µm, 250×21.2 mm, A-eluent: 0.1% TFA/water, B-eluent: 90% AcCN/10% water/0.1% TFA. gradient: 8 ml/min, 40% B on 100% B, 1%/min).

Yield: 43 mg

ESI-MS: 649.3 {M+Na}$^+$

Example 40 contains a pyridone as a peptidomimetic structural element. Pyridone is another example (but not limited to) for a non-proteinogenic amino acid. The synthesis pathway corresponds to that published by Dragovich et al. (Dragovich P. S. et al., J. Med. Chem. 2002, 45, 1607-1623).

General description of the synthesis of pyridine-containing peptidomimetics (see FIG. 5): The pyridine group is built in the form of a dipeptide analogue. The key step herewith is the formation of a C—N-bond between the nitrogen of a pyridine derivative (e.g. 40.1) and a suitably substituted α-hydroxy-carboxyc acid (e.g. 40.2). The resulting dipeptide analogue (e.g. 40.3) can be modified further in a subsequent or previous reaction at the carboxyc acid as well as at the amino function. All methods included herein or known by literature can be used herewith.

(E)-(S)-6-benzyloxycarbonylamino-6-{1-[(S)-3-carboxy-1-(3-methyl-butylcarbamoyl)-propyl]-2-oxo-1,2-dihydro-pyridine-3-ylcarbamoyl}-hex-2-enoyl acid isopropyl ester (compound 40)

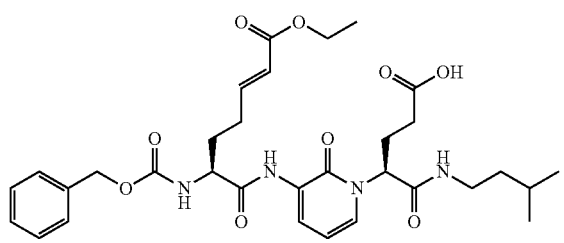 [SMILES: CCOC(=O)/C=C/CC[C@H](NC(=O)OCc1ccccc1)C(=O)Nc1cccn([C@@H](CCC(=O)O)C(=O)NCCC(C)C)c1=O]

The synthesis is run convergingly. Compound 40.1 (see scheme 5) is prepared as described in literature starting with the commercially available 2-hydroxy-3-nitropyridine. N-boc-(2-hydroxy-3-aminopyridine) is obtained (40.1). The preparation of 40.2 is achieved as follows: 671 mg of commercially available D—$N^\alpha$-tert.-butyloxycarbonyl-glutamic acid-5-allyl ester (Boc-Glu(OAllyl)-OH, 2.34 mmol) are dissolved in 10 ml DMF and 738 mg TBU (2.3 mmol), 316 mg HOBT (2.34 mmol) and 605 mg (800 µl) are added one after the other. This resulting solution is immediately added to a solution of 224 mg of isopentylamine (2.57 mmol) in 5 ml DMF. The mixture is stirred for one hour at room temlerature and subsequently the solvent is removed under vacuum. The oily residue is taken up in 200 ml dichloromethane and washed with 10% citric acid solution, 10% $NaHCO_3$ solution and saturated NaCl solution. After drying the organic phase and removing the solvent under vacuum 589 mg Boc-Glu(OAllyl)-isopentylamide are yielded in pure form. After treatment with TFA in dichloromethane the boc protective group is cleaved and the released amino group is converted into a hydroxy group via diazotization, as described in literature (Winitz et al., J. Am. Soc. Chem., 1956, 78, 2423-2428). After purification by means of chromatography on silica gel (column 18*2.3 cm, DCM/methanol=98/2) 221 mg (D)-4-hydroxy-4-(3-methylbutylcarbamoyl)-butyric acid allyl ester are yielded.

200 mg of the resulting (D)-4-hydroxy-4-(3-methylbutyl-carbamoyl)-butyric acid allyl ester (0.77 mmol) and 140 mg DIPEA (1.08 mmol) are dissolved in dichloromethane and cooled to −10° C. under argon atmosphere. To this solution 132.9 mg methanesulfonyl chloride (0.92 mmol) are added dropwise. After 30 minutes the solution is diluted with dichloromethane and washed with a saturated NaCl solution. The organic phase is dried over $Na_2SO_4$ and the solvent is removed under vacuum. This yields 183 mg of the mesyl ester 40.2 which can be used without further purification.

237 mg of the hydroxypyridine 40.1 (1.13 mmol) described above are dissolved in 10 ml of absolute THF. 43 mg NaH (60% on mineral oil, 1.08 mmol) are added and stirred for 20 minutes at room temperature under nitrogen atmosphere. 165 mg of the mesylate 40.2 (0.49 mmol) are added to this solution and the reaction batch is boiled under reflux for 48 hours. The reaction batch is subsequently diluted with 200 ml diethyl ether and washed two times with 10% $KHSO_4$ solution and two times with a saturated NaCl solution. The resulting residue is purified by means of chromatography on silica gel. (column: 22*1.8 cm, DCM/methanol=99/1). This yields 138 mg of compound 40.3 in pure form.

125 mg of 40.3 (0.28 mmol) are dissolved in $THF_{abs}$.242 mg morpholine (2.8 mmol) and subsequently 32 mg tetrakis (triphenylphosphine)palladium are added under argon atmosphere. The mixture is stirred for 45 minutes at room temperature. The solvent is removed under vacuum and the resulting carboxyc acid is purified by means of preparative HPLC (synergy max, 4 µm, 250*21.2 mm, A-eluent: 0.1% TFA/water, B-eluent: 90% AcCN/10% water/0.1% TFA. Gradient: 8 ml/min, 5% B on 100% B, VA/min). After cleavage of the boc protective group through treatment with TFA in dichloromethane 101 mg of the free amino acid 4.4 are yielded in form of its TFA salt.

35.8 mg of the carboxyc acid 1.7 (0.1 mmol) are dissolved together with 38 mg HATU (0.1 mmol) in 5 ml DMF. 51 µl DIPEA (0.3 mmol) are added to this solution and to the resulting yellow solution a solution of 42 mg of the amino acid 4.4 (0.1 mmol) is added. By continuously adding DIPEA the pH is adjusted at 9. After 30 minutes the solvent is removed under vacuum and the oily brown residue is purified by means of preparative HPLC (synergy max, 4 µm, 250*21.2 mm, A-eluent: 0.1% TFA/water, b-eluent: 90% AcCN/10% water/0.1°)/0 TFA. Gradient: 8 ml/min, 40% B on 100% B, 1%/min).

Yield: 23 mg

ESI-MS: 649.2 {M+Na}$^+$

3. Preparation of Inhibitors with Alternative Vinyloguous Electron Acceptor Groups Inhibitors contain a vinyloguous electron acceptor group. Such Michael acceptor systems can be obtained when a suitable aldehyde (e.g. 1.4) is reacted with a suitable phosphonium ylide in a Wittig reaction or a Horner-Wadsworth-Emmons reaction (J. Am. Chem. Soc, 1961, 83, 1733).

Other examples (but not limited to) for the preparation of inventive vinyloguous electron acceptor compounds (Michael systems) according to which an olefin can be prepared are: Deacylations (Tetrahedon 2004, 2337), Knoevenagel condensations (J. Chem. Soc. Perkin Trans. 1986, 2137) or Peterson olefinations (J. Chem. Soc. Perkin. Trans1, 1985, 1949). Particularly preferred are reactions with phosphonium ylides. Suitably substituted phosphonium ylides are either commercially available, or can be prepared easily (e.g. J. Chem. Soc., Perkin Trans1, 1985, 1481; J. Med. Chem., 1987, 1995). Synthesis examples (but not limited to) for the respective precursors of inventive inhibitors according to formula G with varying Z and Z' are presented in the following. The further conversion of these precursors can be done with the procedures described under 1.7 or 1.9 as well as with the examples 1 to 38.

3.1 Preparation of Pharmacophore-Carrying Amino Acids

N,N-Di-(tert.-butyloxycarbonyl)-[(E)-(L)-6-amino-hept-2-ene-dicarboxyc acid]-7-tert.-butyl ester (compound 3.1)

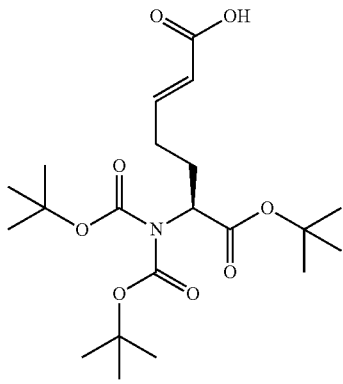 [SMILES: CC(C)(C)OC(=O)[C@H](CC/C=C/C(=O)O)N(C(=O)OC(C)(C)C)C(=O)OC(C)(C)C]

100 mg N,N-Di-(tert.-butyloxycarbonyl)-{(E)-(L)-6-amino-hept-2-ene-dicarboxyc acid}-1-ethanoyl-7-tert-butyl ester (1.8, 0.22 mmol) are dissolved in 1 ml ethanol and 503 µl of a one-molar NaOH solution are added. The mixture is stirred for 3 hours at room temperature. The solution is diluted by adding 20 ml water and diethyl ether respectively and subsequently the pH is adjusted to ~2 with a two-molar HCl solution. The hydrous phase is extracted two times each with 20 ml ethyl acetate and the combined organic phases are dried over $Na_2SO_4$. After removing the solvent under vacuum the free carboxyc acid is yielded as a colourless oil.

Yield: 94 mg
ESI-MS: 452.4 {M+Na}+

N,N-di-(tert.-butyloxycarbonyl)-[(E)-(L)-6-amino-hept-2-ene-dicarboxyc acid]-1-pentylamido-7-tert.-butyl ester (compound 3.2)

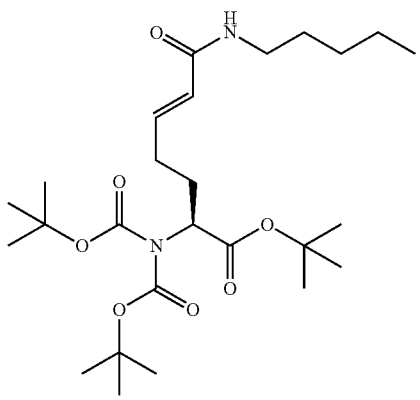 [SMILES: CCCCCNC(=O)/C=C/CC[C@@H](C(=O)OC(C)(C)C)N(C(=O)OC(C)(C)C)C(=O)OC(C)(C)C]

90 mg of the product obtained under 3.2 are dissolved in 3.5 ml of dry dichloromethane. 42 mg dicyclohexylcarbodiimide and 30 mg 1-aminopentane are added one after the other.

The mixture is stirred over night at room temperature. Subsequently the solvent is removed under vacuum and the resulting residue is purified by means of chromatography on silica gel. (column: 21*1.8 cm, petrol ether/ethyl acetate=9/1).

Yield: 80 mg
ESI-MS: 521.2 {M+Na}+

N,N-di-(tert.-butyloxycarbonyl)-[(E)-(L)-6-amino-hept-2-ene-dicarboxyc acid]-1-isopropanoyl-7-tert.-butyl ester (compound 3.3)

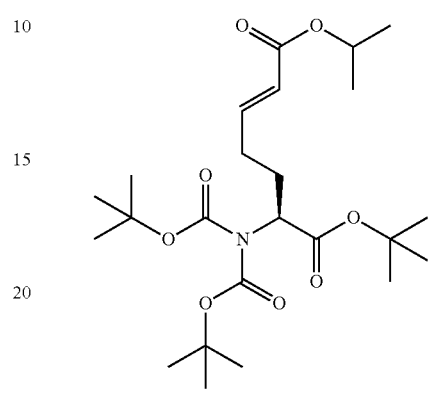

100 mg N,N-di-(tert.-butyloxycarbonyl)-L-2-amino-5-oxo-valeric acid-1-tert.-butyl ester (1.4, 0.258 mmol) are dissolved in 3 ml of dry benzene and 93.5 mg (isopropoxycarbonylmethylene)-triphenylphosphorane (0.258 mmol) (prepared by the common procedures known by literature) are added. The mixture is stirred for five hours at room temperature. Subsequently the solvent is removed under vacuum and the resulting oily residue is purified by means of chromatography on silica gel. (column: 29*2.3 cm, DCM/methanol=99.5/0.5).

Yield: 91 mg
ESI-MS: 494.4 {M+Na}+

N,N-di-(tert.-butyloxycarbonyl)-[(E)-(L)-6-amino-hept-2-ene-dicarboxyc acid]-1-benzoyl-7-tert.-butyl ester (compound 3.4)

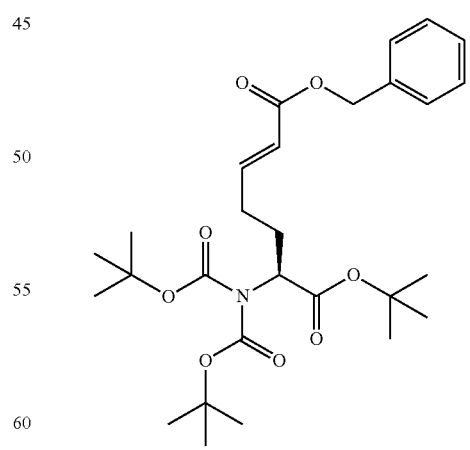

100 mg N,N-di-(tert.-butyloxycarbonyl)-L-2-amino-5-oxo-valeric acid-1-tert.-butyl ester (1.4, 0.258 mmol) are dissolved in 3 ml dry benzene and 109.2 mg and (benzyloxycarbonylmethylene)-triphenylphosphorane (Sigma Aldrich, 0.258 mmol) are added. The mixture is stirred for 18 hours at room temperature. Subsequently the solvent is removed under vacuum and the resulting oily residue is purified by means of chromatography on silica gel (column: 28*2.3 cm, DCM/methanol=99/1).

Yield: 94 mg

ESI-MS: 542.4 {M+Na}+

Michael acceptors can be prepared also in form of endo- and exocyclic systems. FIG. 6 shows the preparation of a cyclopentenone (3.5, Novák et al. Liebigs Ann. Chem. 1986, 509-524).

N,N-di-(tert.-butyloxycarbonyl)-[((L)-2-amino-4-(3)-oxo-cyclopent1-enyl)-butyric acid]-1-tert.-butyl ester (compound 3.5)

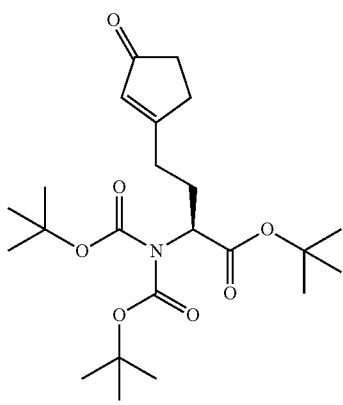 [SMILES: CC(C)(C)OC(=O)[C@H](CCC1=CC(=O)CC1)N(C(=O)OC(C)(C)C)C(=O)OC(C)(C)C]

The preparation is carried out according to the literature.

Yield: 126 mg

ESI-MS: 493.3

The cleavage of the protective groups and the introduction of a benzyloxycarbonyl protective group is performed as described under 1.7.

In the course of the synthesis some of the described vinyloguous electron acceptor compounds showed to be not sufficiently stable in the presence of strong acids. Thus, the conditions described under 1.7 or 1.9 are not applicable for the synthesis of such Michael acceptors. In such a case which is presented by way of example for the compounds 3.7 to 3.9 a variation of the synthesis described under 1.16 can be carried out successfully as an alternative synthesis route (3.6). This yields compounds the further processing of which according to the methods described herein (FIG. 2) leads to more acid-labile Michael acceptors. FIG. 7 shows the preparation of a synthesis block with exocyclic double bond (3.7). The triphenylphosphonium salt needed therefore is not commercially available, but can be produced as described in literature (Baldwinn J. E., J. Org. Chem., 1971, 10, 1441-1443).

N$^\alpha$-tert.-butyloxycarbonyl, N$^\alpha$-benzyloxycarbonyl-[L-2-amino-5-oxo-valeric acid]-1-2-phenyl-2-propyl ester (compound 3.6)

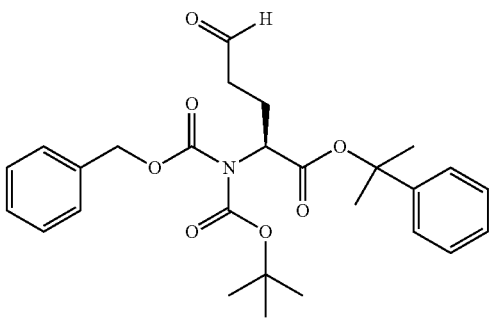 [SMILES: CC(C)(C)OC(=O)N(C(=O)OCc1ccccc1)[C@@H](CCC=O)C(=O)OC(C)(C)c1ccccc1]

2.95 g Z-Glu(OMe)-OH (10 mmol) are dissolved in 200 ml of absolute dichloromethane and cooled to 0° C. under nitrogen atmosphere. 2.88 g dicyclohexylcarbodiimide (14 mmol) and 122 mg N,N-dimethylamino-pyridine (1 mmol) are added. The mixture is stirred for 15 minutes at 0° C. and subsequently 1.63 g 2-phenyl-isopropanol (12 mmol) are added. After further 30 minutes the ice bath is removed and the reactive solution is stirred further on over night at room temperature. The precipitated solid is filtered off and the resulting crude product is purified by means of chromatography on silica gel (yield: 1.53 g).

The isopropylphenyl ester obtained this way (1.53 g, 3.7 mmol) is dissolved in 10 ml acetonitrile and consecutively 90 mg N,N-dimethylamino-pyridine (0.7 mmol) and 1.58 ml di-tert.butyl dicarbonate (Boc$_2$O, 7.4 mmol) are added. The mixture is stirred over night at room temperature under nitrogen atmosphere. The solvent is removed under vacuum and the oily residue is purified by means of chromatography on silica gel. This yields the pure intermediate (Z,Boc-Glu(OMe)-OiPrPh) as a colourless viscous oil. 1.1 g Z,Boc-Glu(OMe)-OiPrPh (2.14 mmol) are dissolved in 25 ml diethyl ether$_{abs}$ and cooled to −78° C. under argon atmosphere. 2.36 ml of an one-molar solution of diisobutylaluminium hydride in n-hexane is slowly added dropwise and subsequently stirred for 30 minutes. The reaction is quenched by adding 1 ml water and subsequently the solution is thawed to room temperature. The preparation is filtrated over diatomaceous earth and the filtrate is concentrated until drying. Chromatography on silica gel yields the pure aldehyde (Z,Boc-Glu(H)-OiPrPh, 3.6 Yield: 667 mg.

ESI-MS: 506.2 [M+Na]+, 406 [M-Boc-FNa]+

(L)-2-benzyloxycarbonylamino-5-[2-oxo-dihydro-furane-(3E)-ylidene]-valeric acid (compound 3.7)

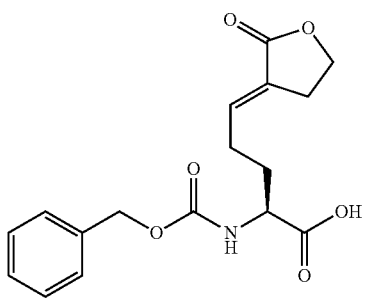 [SMILES: O=C(N[C@@H](CC/C=C1\CCOC1=O)C(=O)O)OCc1ccccc1]

12.4 mg NaH (60% in mineral oil, 0.3 mmol) are kept under argon atmosphere and a solution of 133 mg α-triphenylphosphonium-butyrolactone bromide (Baldwin, 1971) in 3.5 ml $DMF_{abs}$ is added. The mixture is stirred at room temperature until the gas formation ceases and subsequently 150 mg of the aldehyde 3.6 (0.3 mmol) dissolved in 0.5 ml $DMF_{abs}$ is added. After stirring over night the solvent is removed under vacuum and the obtained residue is residue is purified by means of chromatography on silica gel (yield: 112 mg).

By treatment with 2% TFA in dichloromethane the heavily acid-labile protective groups are removed and the compound given in the title is obtained in pure form by means of chromatography on silica gel (column: 29.5*2.3 cm, DCM/methanol=8/2).

Yield: 65 mg
ESI-MS: 356.0 [M+Na]$^+$ $N^\alpha$-benzyloxycarbonyl)-[(E)-(L)-7-amino-2-oxo-oct-3-ene-dicarboxyc acid]-1-ethyl ester (compound 3.8)

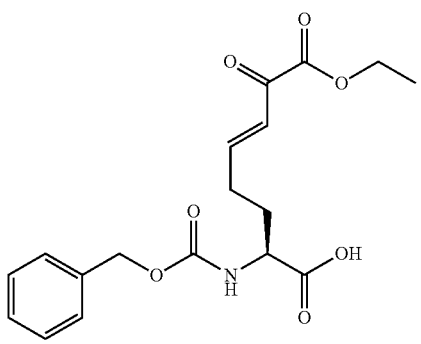 [SMILES: CCOC(=O)C(=O)/C=C/CC[C@H](NC(=O)OCc1ccccc1)C(=O)O]

556 mg $N^\alpha$-tert.-butyloxycarbonyl, N-benzyloxycarbonyl-L-2-amino-5-oxo-valeric acid-1-(2-phenylisopropyl ester, 3.6, 1.15 mmol) are kept in 20 ml dry xylol and a solution of 432 mg ethyl-(triphenylphosphoryliden) pyrovate (Sigma-Aldrich, 1.15 mmol) is added at room temperature under argon atmosphere. After stirring at 115° C. for four hours the solvent is removed under vacuum and the resulting oily residue is purified by means of chromatography on silica gel (column: 29*2.4 cm, petrol ether/ethyl acetate=99/1).

Compound 3.8 is prepared by stirring the precursor obtained above in dichloromethane with 1-2% TFA for one hour at room temperature. Purification is performed by means of chromatography on silica gel.

Yield: 324 mg
ESI-MS: 386.2 {M+Na}$^+$ $N^\alpha$-benzyloxycarbonyl-[(Z)-(L)-2-amino-7-oxo-oct-5-ene acid] (compound 3.9)

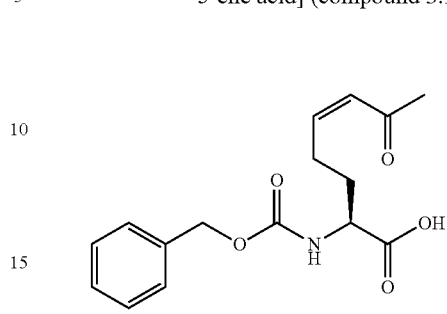

125 mg 3.6 (0.258 mmol) are dissolved in 3 ml dry benzene. 82 mg acetylene-triphenylphosphorane (0.258 mmol) are added to this solution. The mixture is stirred for 2 hours at 60° C. The solvent is removed under vacuum and the obtained residue is purified by means of chromatography on silica gel. Subsequent removal of the protective group by using 2% TFA in dichloromethane and purification by means of preparative HPLC yields compound 3.9.

(synergy max, 4 μm, 250*21.2 mm, A-eluent: 0.1% TFA/water, B-eluent: 90% AcCN/10% water/0.1% TFA. Gradient: 8 ml/min, 25% B on 100% B, 1%/min).

Yield: 58 mg
ESI-MS: 328.1 {M+Na}$^+$ $N^\alpha$-benzyloxycarbonyl-(Z)-(L)-2-amino-6-cyano-hex-5-ene acid (compound 3.10)

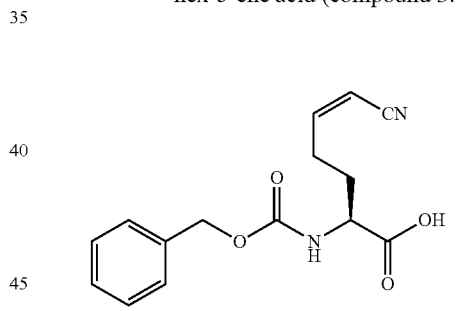

125 mg 3.6 (0.58 mmol) are dissolved in 3 ml dry benzene. 78 mg (triphenylphosphoranylidine)acetonitrile (Sigma-Aldrich, 0.258 mmol) are added to this solution. The mixture is stirred at 70° C. for four hours. The solvent is removed under vacuum and the obtained residue is purified by means of chromatography on silica gel. Subsequently the protective groups are removed by using 2% TFA in dichloromethane and purification by means of preparative HPLC yields compound 3.13.

Yield: 78 mg
ESI-MS: 311.2 {M+Na}$^+$

By using the corresponding phosphonates or phosphonium salts also vinylsulfones can be prepared via the Horner-Wadsworth-Emmons reaction (by way of example 3.11, 3.12a and 3.13). Of special interest are those vinyloguous sulfones that can be further diversified by the following reactions. Roush et al. describe such a synthesis pathway for inhibitors against cruazin and papain. (Roush W. R., Bioorg. Med. Chem. Lett., 2001, 11, 2759) (and references quoted therein); Roush W. R., J. Am. Chem. Soc., 1998, 120, 10994). There, starting with a vinyloguous sulfonic acid ester (see e.g. 3.12a in scheme 8) a sulfonic acid chloride (3.12.b) is generated and subsequently converted to a vinyloguous sulphonamide, a N-alkoxysulfonamide or a sulfonic acid ester with a different residue (scheme 8). Examples are given in 3.14 to 3.16.

Surprisingly, it resulted that such Michael acceptors having sulfonyl residues as electron-drawing group are also potent inhibitors of transglutaminases. An embodiment is given in 3.2.1.

N$^\alpha$-benzyloxycarbonyl-(E)-(L)-2-amino-6-methansulfonyl-hex-5-ene acid (compound 3.11)

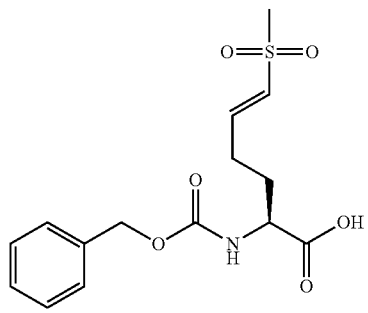 [SMILES: CS(=O)(=O)/C=C/CC[C@H](NC(=O)OCc1ccccc1)C(=O)O]

The preparation of compound 3.11 can be achieved with the methods described in 3.7. The reagent ((EtO)$_2$P(=O)SO$_2$Me) needed for the preparation of the vinyloguous sulfone can be obtained by an oxidation of the commercially available ((EtO)$_2$P(=O)SO$_2$Me), for example with meta-chlorobenzoic acid, a procedure known to the one skilled in the art.

Detailed Description of the Synthesis:

10 mg NaH (60% in mineral oil, 0.258 mmol) are dissolved in 5 ml DMF$_{abs}$ and 59 mg (EtO)$_2$P(=O)SO$_2$Me (0.258 mmol) are added under nitrogen atmosphere. After the gas formation has ceased 130 mg 3.6 (0.258 mmol) are added and the solution is stirred over night at room temperature. The solvent is removed under acuum and a solution of 1% TFA in dichloromethane is poured onto the obtained residue. After 30 minutes the solvent is concentrated under vacuum and the resulting residue is purified by means of chromatography on silica gel (column: 29*2.3 cm, dichloromethane/methanol 99/1).

Yield: 89 mg

ESI-MS: 364.2 [M+Na]$^+$

N$^\alpha$-benzyloxycarbonyl,N$^\alpha$-tert.butyloxycarbonyl-[(E)-(L)-2-amino-6-ethoxysulfonyl-hex-5-ene acid]-1-(2-phenyl-2-propyl ester) (compound 3.12a)

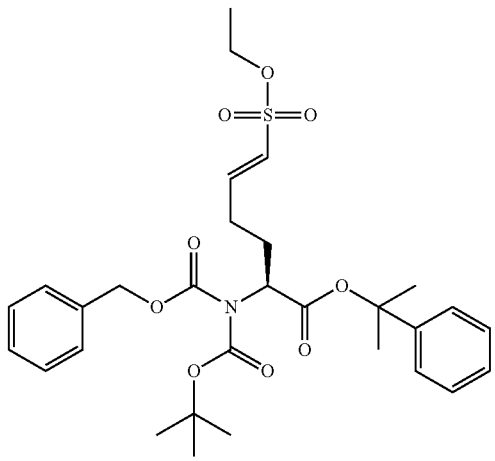 [SMILES: CCOS(=O)(=O)/C=C/CC[C@@H](C(=O)OC(C)(C)c1ccccc1)N(C(=O)OCc1ccccc1)C(=O)OC(C)(C)C]

To 119.8 mg NaH (3 mmol) a solution of 780 mg (3 mmol) ethyldiethylphosphorylmethane sulfonate (Carretero et al., 1987) in 20 ml DMF$_{abs}$ is added. After the gas formation has ceased a solution of 1.45 g 3.6 (3 mmol) solved in 10 ml DMF$_{abs}$ is added. The mixture is stirred over night at room temperature. The solvent is removed under vacuum and the obtained residue is purified by means of preparative HPLC. After removing the Z isomer compound 3.12.a is thus obtained in pure form (see scheme 8). (synergy max, 4 µm, 250*21.2 mm, A-eluent: 0.1% TFA/water, B-eluent: 90% AcCN/10% water/0.1% TFA.

Gradient: 8 ml/min, 40% B on 100% B, 1%/min).

Yield: 1.5 g

ESI-MS: 512.2 {M-Boc+Na}$^+$

N$^\alpha$-benzyloxycarbonyl,N-tert.butyloxycarbonyl-[(E)-(L)-2-amino-6-chlorosulfonyl-hex-5-ene acid]-1-(2-phenyl-2-propyl ester) (compound 3.12b)

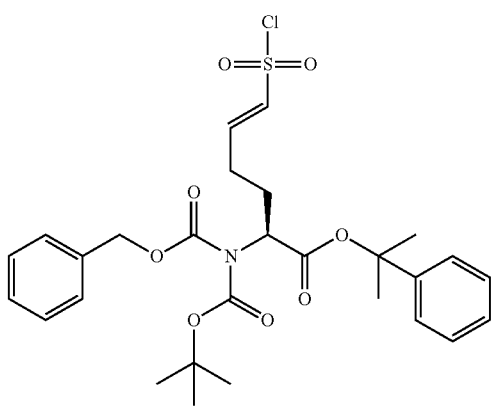 [SMILES: CC(C)(C)OC(=O)N(C(=O)OCc1ccccc1)[C@@H](CC/C=C/S(=O)(=O)Cl)C(=O)OC(C)(C)c1ccccc1]

1.47 g of compound 3.12a (2.5 mmol) are dissolved in 100 ml acetone and 941 mg tetrabutylammonium iodide (2.55 mmol) are added. The solution is heated under reflux until boiling over night. Subsequently the solvent is removed under vacuum and the tetraammonium salt (see scheme 8) is purified is purified by means of chromatography on silica gel (column: 2.5*27 cm, DCM/MeOH/TEA 8/2/0.1). The salt thus obtained (1.27 g) is dissolved in dry dichloromethane and a drop of $DMF_{abs}$ is added to the solution. Subsequently 235 mg triphosgene (0.8 mmol) are added and the mixture is stirred for one hour at room temperature under nitrogen atmosphere. The solution is washed two times each with 30 ml water, dried over $NaSO_4$ and the solvent is removed under vacuum. Thus the compound given in the title is obtained in a sufficiently pure form to perform the following reactions without a further purification.

Yield: 803 mg

ESI-MS: 502.1 {M-Boc+Na}$^+$

Instructions by way of examples for the preparation of vinyloguous vinylsulfones with alterating residue.

By using ((EtO)$_2$P(=O)SO$_2$Phe) compound 3.13 can be obtained on the same synthesis pathway as described for compound 3.11.

N$^\alpha$-benzyloxycarbonyl-(E)-(L)-2-amino-6-phenyl-sulfonyl-hex-5-ene acid (compound 3.13)

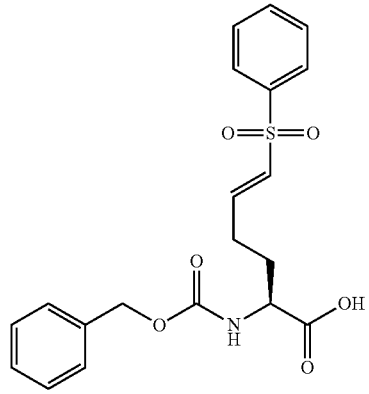 [SMILES: O=C(N[C@@H](CC/C=C/S(=O)(=O)c1ccccc1)C(=O)O)OCc1ccccc1]

ESI-MS: 426.1 [M+Na]$^+$

N$^\alpha$-benzyloxycarbonyl-((E)-(L)-2-amino-6-benzyloxysulfonyl)-hex-5-ene acid (compound 3.14)

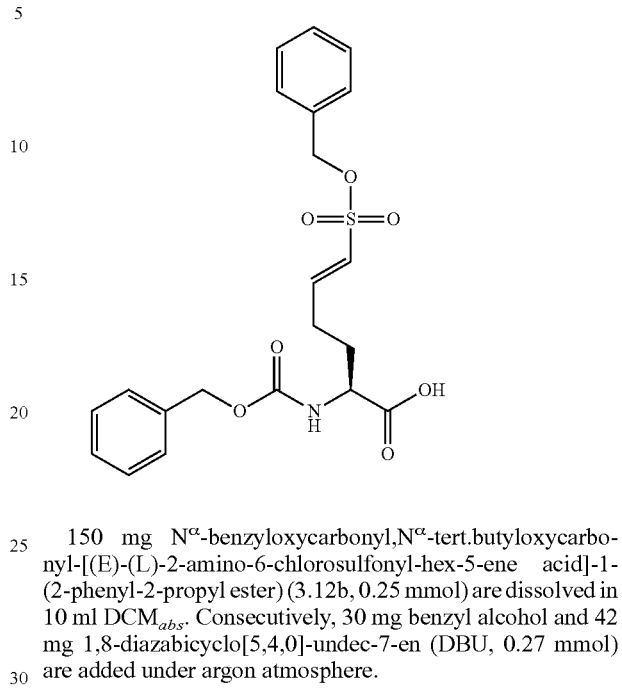

150 mg N$^\alpha$-benzyloxycarbonyl,N$^\alpha$-tert.butyloxycarbonyl-[(E)-(L)-2-amino-6-chlorosulfonyl-hex-5-ene acid]-1-(2-phenyl-2-propyl ester) (3.12b, 0.25 mmol) are dissolved in 10 ml $DCM_{abs}$. Consecutively, 30 mg benzyl alcohol and 42 mg 1,8-diazabicyclo[5,4,0]-undec-7-en (DBU, 0.27 mmol) are added under argon atmosphere.

The mixture is stirred over night at room temperature. 200 μl TFA are added to the solution which is stirred for another 30 minutes. The solvent is removed under vacuum and the oily residue is purified by means of preparative HPLC (synergy max, 4 μm, 250*21.2 mm, A-eluent: 0.1% TFA/water, B-eluent: 90% AcCN/10% water/0.1% TFA. Gradient: 8 ml/min, 40% B on 100% B, 1%/min).

Yield: 60.6 mg

ESI-MS: 456.2 {M+Na}$^+$

N$^\alpha$-benzyloxycarbonyl-[(E)-(L)-2-amino-6-dimethylsulfamoyl]-hex-5-ene acid (compound 3.15)

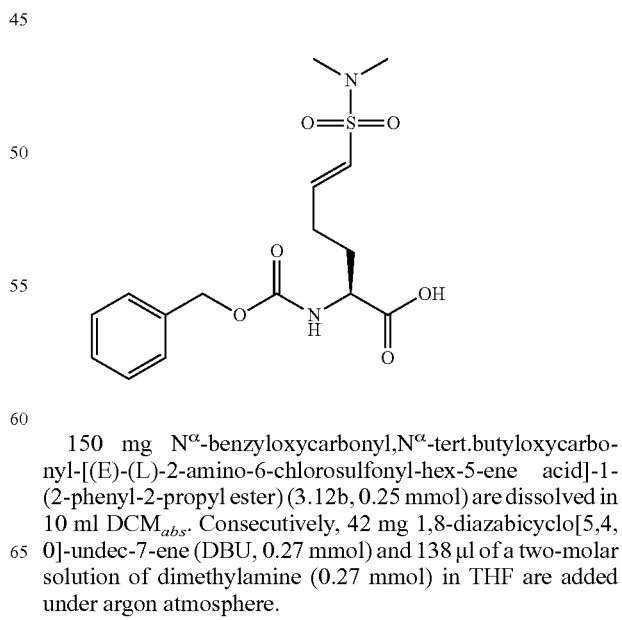

150 mg N$^\alpha$-benzyloxycarbonyl,N$^\alpha$-tert.butyloxycarbonyl-[(E)-(L)-2-amino-6-chlorosulfonyl-hex-5-ene acid]-1-(2-phenyl-2-propyl ester) (3.12b, 0.25 mmol) are dissolved in 10 ml $DCM_{abs}$. Consecutively, 42 mg 1,8-diazabicyclo[5,4,0]-undec-7-ene (DBU, 0.27 mmol) and 138 μl of a two-molar solution of dimethylamine (0.27 mmol) in THF are added under argon atmosphere.

The mixture is stirred over night at room temperature. 200 µl TFA are added to the solution which is stirred for another 30 minutes. The solvent is removed under vacuum and the resulting oily residue is purified by means of preparative HPLC (synergy max, 4 µm, 250*21.2 mm, A-eluent: 0.1% TFA/water, B-eluent: 90% AcCN/10% water/0.1% TFA. Gradient: 8 ml/min, 40% B on 100% B, 1%/min).

Yield: 66 mg
ESI-MS: 393.12 {M+Na}$^+$ $N^\alpha$-benzyloxycarbonyl-((E)-(L)-2-amino-6-benzyloxysulfamoyl)-hex-5-ene acid (compound 3.16)

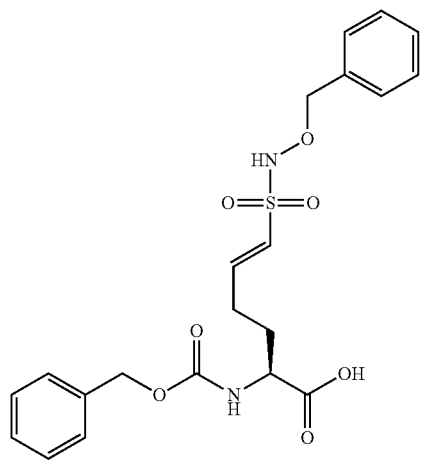 [SMILES: O=C(N[C@@H](CC/C=C/S(=O)(=O)NOCc1ccccc1)C(=O)O)OCc1ccccc1]

The compound given in the title is prepared according to the procedure described in 3.14 and 3.15 by using 44 mg O-benzylhydroxylamine hydrochloride (0.27 mmol) as nucleophile.

Yield: 53 mg
ESI-MS: 393.12 {M+Na}$^+$

According to the methods described in 1. and 2. the inhibitors listed in table 2 can be prepared from the pharmacophore-carrying amino acids described in 3. Additionally some embodiments are given in the following (3.2).

3.2 Presentation by Way of Examples of Inhibitors Containing Alternative Vinyloguous Electron Acceptor Groups $N^\alpha$-benzyloxycarbonyl-{[(E)-(L)-2-amino-6-methanesulfonyl]-hex-5-enyl}-L-glutaminyl-L-prolinyl-L-leucine methyl ester (compound 3.2.1)

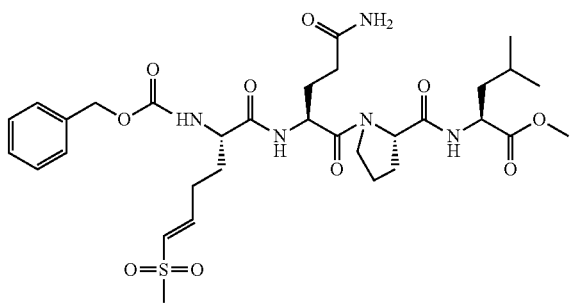 [SMILES: COC(=O)[C@H](CC(C)C)NC(=O)[C@@H]1CCCN1C(=O)[C@H](CCC(N)=O)NC(=O)[C@H](CC/C=C/S(C)(=O)=O)NC(=O)OCc1ccccc1]

27 mg $N^\alpha$-benzyloxycarbonyl-(E)-(L)-2-amino-6-methanesulfonyl-hex-5-ene acid (3.11, 79 µmol) are dissolved in 2.5 ml DMF. Consecutively, 30 mg HATU (79 µmol) and 27 ml DIPEA (158 µmol) are added and the resulting solution is added immediately to a solution of the trifluoroacetate salt of 79 µmol H-Gln-Pro-Leu-OMe (prepared according to method 1) in 5 ml DMF. Through continuous addition of DIPEA the pH is adjusted to 9. The processing is performed as described for compound 1: (synergy max, 4 µm, 250*21.2 mm, A-eluent: 0.1% TFA/water, B-eluent: 90% AcCN/10% water/0.1% TFA.

Gradient: 8 ml/min, 30% B on 100% B, 1%/min).
Yield: 40 mg
ESI-MS: 716.5 {M+Na}$^+$ $N^\alpha$-benzyloxycarbonyl-[(E)-(L)-2-amino-6-dimethylsulfamoyl)-hex-5-enyl]-L-glutaminyl-L-prolinyl-L-leucine methyl ester (compound 3.2.2)

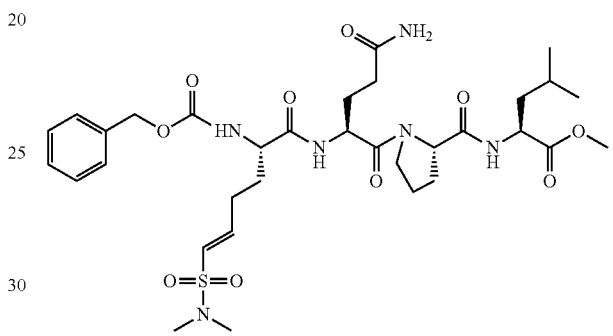

33 mg $N^\alpha$-benzyloxycarbonyl-[(E)-(L)-2-amino-6-dimethylsulfamoyl]-hex-5-ene acid (3.15, 89 µmol) are dissolved in 2.5 ml DMF. Consecutively, 34 mg HATU (89 µmol) and 30 µl DIPEA (158 µmol) are added and the resulting solution is added immediately to a solution of the trifluoroacetate salt of 89 µmol H-Gln-Pro-Leu-OMe (prepared according to method 1) in 5 ml DMF. Through continuous addition of DIPEA the pH is adjusted to 9. The processing is performed as described for compound 1: (synergy max, 4 µm, 250*21.2 mm, A-eluent: 0.1% TFA/water, B-eluent: 90% AcCN/10% water/0.1% TFA.

Gradient: 8 ml/min, 35% B on 100% B, 1%/min).
Yield: 42 mg
ESI-MS: 745.3 {M+Na}$^+$ $N^\alpha$-benzyloxycarbonyl-[(L)-2-amino-4-(3)-oxo-cyclopent-1-enyl]-butyryl-L-glutaminyl-L-prolinyl-L-leucine methyl ester (compound 3.2.3)

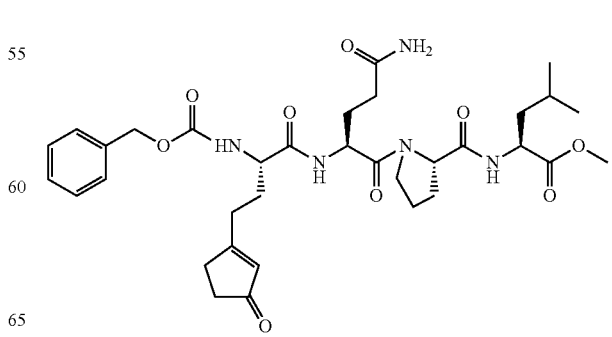

Compound 3.5 is deprotected as described under 1.7 and converted to the N^α-benzyloxycarbonyl-protected derivative. 30.3 mg N^α-benzyloxycarbony-[(L)-2-amino-4-(3)-oxo-cyclopent1-enyl]-butyric acid (0.1 mmol) are dissolved in 7.5 ml DMF. Consecutively, 38 mg HATU (0.1 mmol) and 51 μl DIPEA (0.3 mmol) are added and the resulting solution is added immediately to a solution of the trifluoroacetate salt of 0.1 mmol H-Gln-Pro-Leu-OMe (prepared according to method 1) in 7.5 ml DMF. Through continuous addition of DIPEA the pH is adjusted to 9. The processing is performed as described for compound 1: (synergy max, 4 μm, 250*21.2 mm, A-eluent: 0.1% TFA/water, B-eluent: 90% AcCN/10% water/0.1% TFA. Gradient: 8 ml/min, 5% B on 100% B, 1%/min).

Yield: 26 mg
ESI-MS: 692.2 {M+Na}+

N^α-benzyloxycarbonyl[(L)-2-amino-5-(2-oxo-dihydrofurane-(3E)-ylidene)]-pentanoyl-L-glutaminyl-L-prolinyl-L-leucine methyl ester (compound 3.2.4)

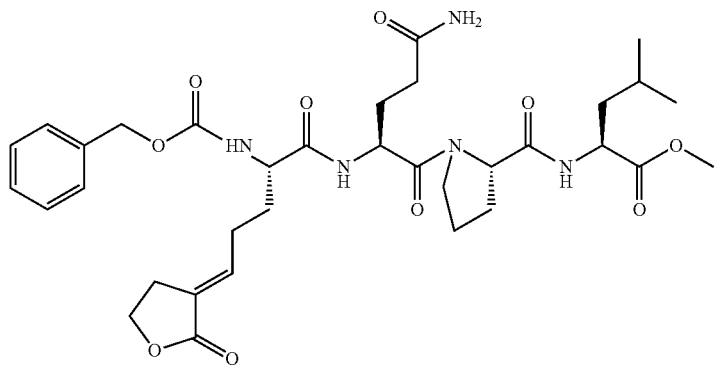 [SMILES: COC(=O)[C@H](CC(C)C)NC(=O)[C@@H]1CCCN1C(=O)[C@H](CCC(N)=O)NC(=O)[C@H](CC/C=C1\CCOC1=O)NC(=O)OCc1ccccc1]

58 mg (L)-2-benzyloxycarbonylamino-5-[-2-oxo-dihydrofurane-(3E)-ylidene]-valeric acid (3.7, 0.17 mmol) is dissolved in 10 ml DMF. Consecutively, 64 mg HATU (0.17 mmol) and 87 μl DIPEA (0.5 mmol) are added and the resulting solution is added immediately to a solution of the trifluoroacetate salt of 0.17 mmol H-Gln-Pro-Leu-OMe (prepared according to method 1) in 10 ml DMF. Through continuous addition of DIPEA the pH is adjusted to 9. The processing is performed as described for compound 1: (synergy max, 4 μm, 250*21.2 mm, A-eluent: 0.1% TFA/water, B-eluent: 90% AcCN/10% water/0.1% TFA. Gradient: 8 ml/min, 25% B on 100% B, 1%/min).

Yield: 46 mg
ESI-MS: 708.4 {M+Na}+

4. Variation of the C-Terminus

Obviously, the use of inventive transglutaminase inhibitors as active principles in the treatment of human diseases depends on the bioavailability and the metabolization of the compound. The metabolization of peptidic active principles is often relatively quick. Thus the effective doses is lowered. To counteract this process peptidic active principles are often converted into peptidomimetics. These mimetics may contain at the C-terminal end apart of the methyl esters described above other esters, primary, secondary and tertiary amides, as well as free carboxyc acids as C-terminal end group as a non-peptidic functional group. The solid phase synthesis of inventive inhibitors is shown in FIG. 9. A comprehensive listing of general synthesis instructions for solid phase systems of peptides can be found e.g. in *Fmoc Solid Phase Peptide Synthesis, A practical approach*, Chan, W. C., White P. D., Oxford University Press. As a concrete embodiment the synthesis of a C-terminal amide is given with compound 4.1. Secondary amides can be obtained by using corresponding amines in the first coupling step. (see as examples the synthesis of compounds 5 or 5.1.

By way of examples, tetrazoles or sulfonamides can be prepared as carbonyl surrogates (Johanson A. et al., Bioorg. & Med. Chem., 11, 2003, 2551-68, see FIG. 10).

Surprisingly, the resulting partially highly polar molecules are highly potent inhibitors of transglutaminases.

Some concrete embodiments are described in the following.

Example for a Solid Phase Synthesis of an Inhibitor

N^α-benzyloxycarbonyl-{[(E)-(L)-6-amino-hept-2-ene-dicarboxyc acid]-1-ethanoyl}-L-valinyl-L-(octahydroindol-2-carboxyl)-L-leucinylamide (compound 4.1)

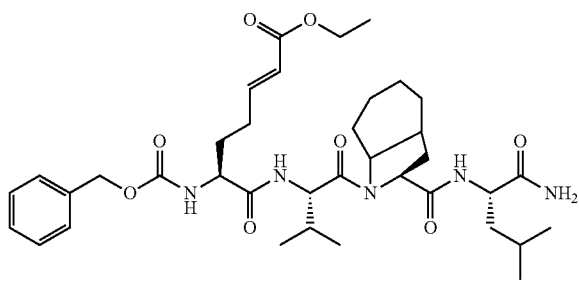

364 mg Sieber amide resin (0.2 mmol, Nova Biochem) are released from the Fmoc protective group by treatment with 20% piperidine in DMF, according to methods known by literature. The resulting amino group is coupled to Fmoc-Leu-OH by using 141 mg Fmoc-Leu-OH (0.4 mmol, Fluka), 126 mg TBTU (0.39 mmol, Fluka), 54 mg (0.4 mmol) and 136 µl DIPEA (0.8 mmol), according to methods known to the one skilled in the art. After one hour the reaction batch is filtered off and repeatedly washed thoroughly. The completeness of the coupling reaction is proven with the Kaiser test. The Fmoc protective group is cleaved by treating the polymeric carrier with 20% piperidine in DMF. The reaction solution is filtered off and the resin is thoroughly washed with DMF. The thus released amino group of the polymerically bound leucine is acylated with 157 mg Fmoc-L-octahydroindole-2-carboxyc acid (Fmoc-Oic-OH, 0.4 mmol) under the conditions cited above. The completeness of the reaction is proven with the Kaiser test. Subsequently the reaction batch is filtered off and the polymeric carrier is washed thoroughly with DMF. After cleaving the Fmoc protective group from Oic and washing the reaction solution the amino acid $N^\alpha$-benzyloxycarbonyl-{(E)-(L)-6-amino-hept-2-ene-dicarboxyc acid}-1-ethyl ester (1.7) whicxh carries the pharmacophore is coupled to the released amino group. Therefore, 134 mg 1.7 (0.4 mmol) are dissolved in DMF. Consecutively, 150 mg HATU (0.39 mmol) and 136 µl DIPEA are added and then added to the polymerically bound amine. After one hour the reaction solution is filtered off and the resin is washed thoroughly with DMF. The completeness of the reaction is proven with the Kaiser test.

The cleavage of the compound given in the title from the polymeric carrier is achieved through a 30 minutes treatment of the carrier material with a solution of 1% TFA in dichloromethane. The resulting product solution is concentrated under vacuum and the residue is purified by means of preparative HPLC (synergy max, 4 µm, 250*21.2 mm, A-eluent: 0.1% TFA/water, B-eluent: 90% AcCN/10% water/0.1% TFA. Gradient: 8 ml/min, 5% B on 100% B, 1%/min).

Yield: 78 mg
ESI-MS: 720.3 {M+Na}$^+$ $N^\alpha$-(piperidinyl-4-carbonyl)-{[(E)-(L)-2-amino-6-phenylsulfonyl]-hex-5-enyl}-L-phenylalaninyl-L-prolinyl-L-1-cyclopentylmethyl-2-oxo-2-(1H-tetrazole-5-yl)-ethylamide (compound 4.2)

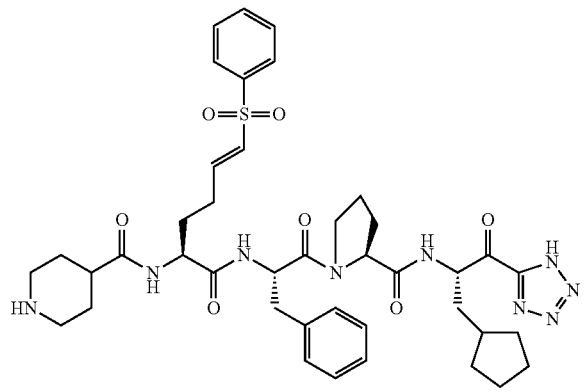 [SMILES: O=C(N[C@@H](CC/C=C/S(=O)(=O)c1ccccc1)C(=O)N[C@@H](Cc1ccccc1)C(=O)N1CCC[C@H]1C(=O)N[C@@H](CC1CCCC1)C(=O)c1nnn[nH]1)C1CCNCC1]

The synthesis goes convergently. (overview: See scheme 11). The pharmacophore-carrying amino acid ($N^\alpha$-(N-boc-(piperidinyl-4-carbonyl))-{[(E)-2-amino-6-phenylsulfonyl]-hex-5-ene acid, 4.2.1) is prepared as described under 3.11. Instead of Z—OSu N-boc-(piperidinyl-4-carboxyc acid) is used which can be prepared out of commercially piperidinyl-4-carboxyc acid by methods known to the one skilled in the art. L-1-cyclopentylmethyl-2-oxo-2-(1H-tetrazole-5-yl)ethylamide (4.2.2) can be prepared from the parental compound $N^\alpha$-tert.butyloxycarbonyl-β-cyclopentylalanine (Bachem) according to methods known from the literature (Johanson A. et al., Bioorg. & Med. Chem., 11, 2003, 2551-68). After cleavage of the boc protective group the hydrochloride of the amine 4.2.2 is obtained with a HCl/diethyl ether solution.

The formation of the compound given in the title is performed first at the solid phase: 0.5 g H-Pro-2ClTrt-resin (Fluka, 0.45 mmol) are coupled with 455 mg Fmoc-Phe-OH using 424 mg TBTU (1.32 mmol), 182 mg HOBt (1.35 mmol) and 483 µl DIPEA (2.7 mmol), according to methods known to the one skilled in the art and those lined out under 4.1. After a Kaiser test and washing the reaction solution with DMF the Fmoc protective group is cleaved with 20% piperidine in DMF and consecutively coupled with 342 mg (0.9 mmol) of the pharmacophore-carrying amino acid 4.2.1 using 283 mg TBTU (0.88 mmol) and 121 mg HOBt (0.9 mmol). The intermediate $N^\alpha$-(piperidinyl-4-carbonyl)-{[(E)-(L)-2-amino-6-phenylsulfonyl]-hex-5-enyl}-L-phenylalaninyl-L-proline (4.2.3) is cleaved from the polymeric carrier by treating the latter for 30 minutes with a solution of 1% TFA in dichloromethane. The filtrate is concentrated and the obtained residue is co-destilled repeatedly with methanol (yield: 134 mg).

To a solution of 72 mg 4.2.3 (0.12 mmol) in 5 ml DMF 38 mg TBTU (0.12 mmol), 16 mg HOBt (0.12 mmol) and 62 µl DIPEA (0.36 mmol) are added consecutively and the resulting solution is added immediately to a solution of 29.3 mg of the hydrochloride of compound 4.2.2 in 2 ml DMF, described above. After stirring for one hour at room temperature the solvent is removed under vacuum. From the resulting residue the boc protective group is cleaved by treatment with TFA/DCM (1/1) and the compound given in the title is purified by means of preparative HPLC. (synergy max, 4 µm, 250*21.2 mm, A-eluent: 0.1% TFA/water, B-eluent: 90% AcCN/10% water/0.1% TFA. Gradient: 8 ml/min, 5% B on 100% B, 1%/min).

Yield: 68 mg
ESI-MS: 816.3 {M-FH}$^+$ $N^\alpha$-benzyloxycarbonyl-[(E)-(L)-2-amino-6-benzyloxysulfonyl-hex-5-enyl]-L-valinyl-L-prolinylbenzylsulfonamide (compound 4.3)

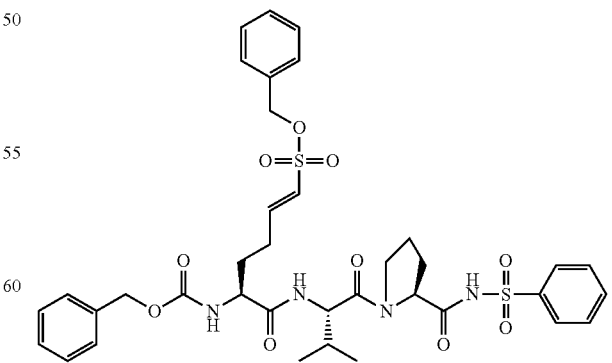

290 mg of the compound 4.3.1 (1 mmol, prepared according to methods known from the literature (Johanson A. et al., Bioorg. & Med. Chem., 11, 2003, 2551-2568, see scheme 10b)) are coupled with boc-valine according to methods known from the literature and those described above, with the aid of TBTU, HOBt and DIPEA in DMF. In order to purify the product the resulting residue is dissolved in ethyl acetate and washed consecutively with 10% citric acid, saturated NaHCO$_3$ solution and saturated NaCl solution and subsequently dried over Na$_2$SO$_4$ (yield: 342 mg). From 100 mg of the intermediate (0.22 mmol) the boc group is cleaved and the resulting amine is coupled with 98 mg (=0.22 mmol) of the pharmacophore-carrying amino acid 3.14, as described above.

The solvent is removed under vacuum and the compound given in the title is purified by means of preparative HPLC (synergy max, 4 µm, 250*21.2 mm, A-eluent: 0.1% TFA/water, B-eluent: 90% AcCN/10% water/0.1% TFA. Gradient: 8 ml/min, 5% B on 100% B, 1')/0/min).

Yield: 100 mg
ESI-MS: 791.3 {M+Na}$^+$

5. Conversion of Inhibitors into Peptidomimetics

Often peptidic active principles undergo in vivo a quick enzymatic degradation or other metabolization reactions. The metabolites thus generated often show a lower inhibitory activity and/or a lower selectivity towards the target. This degradation occurs mainly at the peptide backbone itself since there is a plethora of enzymes capable to hydrolyze peptidic bonds. In order to counteract this process, i.e. to reduce the in vivo degradation of the presented peptidic inhibitors, normally peptide-like or bioisosteric amino acid blocks are prepared. An isoster or bioisoster is a "group or molecule which displays chemical and physical properties triggering similar biologic effects" (see Thornber C. W., Chem. Soc. Rev., 8, 563-580). In principle, every group in a potent peptidic inhibitor can be exchanged when a bioisosteric group more stable in vivo can be found.

Therefore, some examples (but not limited to) of peptidomimetics and the synthesis of some commonly applied bioisosteric groups are described in the following.

Substitution of an Amide Bond Through a Secondary Amine (E)-(S)-6-[(S)-1-((S)-2-ethylcarbamoyl-pyrrolidine-1-carbonyl)-2-methyl-propylcarbamoyl]-6-(2-piperidine-4-yl-ethylamino)-hex-2-ene acid isopropyl ester (compound 5.1)

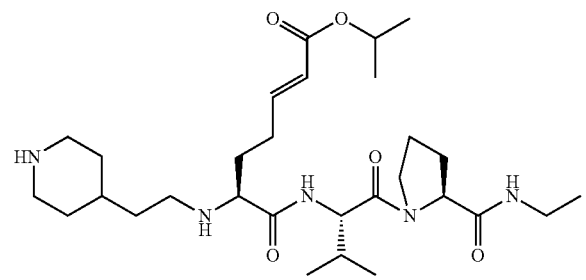 [SMILES: CCNC(=O)[C@@H]1CCCN1C(=O)[C@@H](NC(=O)[C@H](CC/C=C/C(=O)OC(C)C)NCCC1CCNCC1)C(C)C]

Reaction overview: see scheme 12
Detailed description of the synthesis:
Both partial molecules 5.1.5 and 5.1.6 are formed independently.

Starting with a 70% aqueous solution of ethylamine in water and boc-Pro-OH the synthesis of amine 5.1.6 is carried out as described for compound 5.a.

The partial molecule 5.1.5 is prepared as follows:

To a solution of 1 g B-boc-4-piperidineacetyl aldehyde (Aldrich, 4.4 mmol) in 30 ml dichloromethane$_{abs}$ 1.92 g H-Glu(OMe)-OtBu (Bachem, 8.8 mmol) and 4 g molecular sieve (4 Å) are added. A solution of 467 µl acetic acid (8.8 mmol) and 2.84 g sodium trisacetoxyboric hydride (13.2 mmol, Aldrich) in dichloromethane$_{abs}$ is added dropwise and the reaction solution is stirred for 36 hours at room temperature under protective gas. Judging by thin layer chromatogram no reactants are present anymore in the reaction batch after this time. The slightly opaque solution is filtrated over diatomaceous earth. The filtrate is diluted with 100 ml dichloromethane and washed with 40 ml 1 N NaOH. The organic phase is removed and the aqueous phase is reextracted three times with 20 l dichloromethane. The combined organic phases are dried over Na$_2$SO$_4$ and the solvent is removed under vacuum. The resulting crude product is dissolved in acetonitrile without further purification and converted to compound 5.1.3 by boc$_2$O and DMAP, under the assumption of a complete conversion. The reaction is carried out in the same way as in synthesis of 1.3. Purification is performed by means of chromatography on silica gel (column: 30*2.3 cm, petrol ether/ethyl acetate: 9/1, yield: 977 mg).

950 mg of the methyl ester (1.8 mmol) are dissolved in dry diethyl ether and reduced to the aldehyde 5.1.3 at 78° C., as described for the synthesis of 1.4. The conversion is complete and the crude product can be converted to the Michael acceptor under the conditions of the Wittig reaction without another chromatographic purification. Therefore, the crude product of the aldehyde 5.1.3 is dissolved in 20 ml benzene and 651 mg (2-propoxycarbonylmethylene)-triphenylphosphorane (1.8 mmol) are added at room temperature. At this temperature the mixture is stirred over night and subsequently the solvent is removed under vacuum. The compound is purified by means of chromatography on silica gel (column: 22*2.3 cm, petrol ether/ethyl acetate: 9/1, yield: 522 mg). The cleavage of all three protective groups is carried out as described by treatment with TFA/DCM (1/1) at room temperature. The subsequent purification can be performed by means of preparative HPLC. Synergy max, 4 µm, 250*21.2 mm, A-eluent: 0.1% TFA/water, B-eluent: 90% AcCN/10% water/0.1% TFA. Gradient: 8 ml/min, 5% B on 100% B, 1%/min). 211 mg of the free amino acid 5.1.4 are obtained.

200 mg 5.1.4 (0.55 mmol) are dissolved in DMF at room temperature and 248 mg boc-OSu (1.15 mmol) are added. The pH is adjusted with DIPEA to 8-9 and the solution is stirred over night at room temperature. After removing the solvent under vacuum and chromatography on silica gel (column: 20*1.3 cm, dichloromethane/methanol: 95/5) 178 mg of the purified compound 5.1.5 are obtained.

Preparation of Example 5.1

The coupling of the carboxyc acid 5.1.5 to the amine 5.1.6 is achieved without problems by using TBTU in the presence of HOBt. Therefore, 50 mg of the carboxyc acid (95 µmol) are dissolved in DMF. To this solution 29 mg TBTU, 13 mg HOBt and 40 µl DIPEA are added consecutively. Immediately after adding the base the solution is added to a solution of 33 mg of the trifluoroacetetate salt of 5.1.6 (95 µmol). The pH is adjusted with DIPEA to ~10 and after stirring for one hour at room temperature the solvent is removed under vacuum. The oily residue is taken up in 50 ml ethyl acetate and washed two times each with 10 ml of 10% citric acid in water and with saturated NaHCO$_3$ solution. From the resulting product both boc protective groups are cleaved by treatment with TFA in dichloromethane. The compound given in the title (5.1) can be obtained by means of preparative HPLC in purified form werden (synergy max, 4 μm, 250*21.2 mm, A-eluent: 0.1% TFA/water, B-eluent: 90% AcCN/10% water/0.1% TFA.

Gradient: 8 ml/min, 5% B on 100% B, 1%/min).

Yield: 19 mg

ESI-MS: 550.4 $\{M+H\}^+$

Substitution of an Amide Bond by a Ketomethylene or a Hydroxymethylene Group

A further option to stabilize the peptide backbone in vivo includes substituting the nitrogen atom of the amide bond by a carbon atom. The resulting compounds are tagged as hydroxymethylene or ketomethylene isosters to the amide bond. The synthesis is mostly performed through dipeptide analogues which are prepared separately and subsequently are integrated in the respective molecular environment. Such mimetics and analogues are discussed comprehensively on pages 17 to 19 herein. Surprisingly, inhibitors can be modified in such a way without diminishing their inhibitors potence.

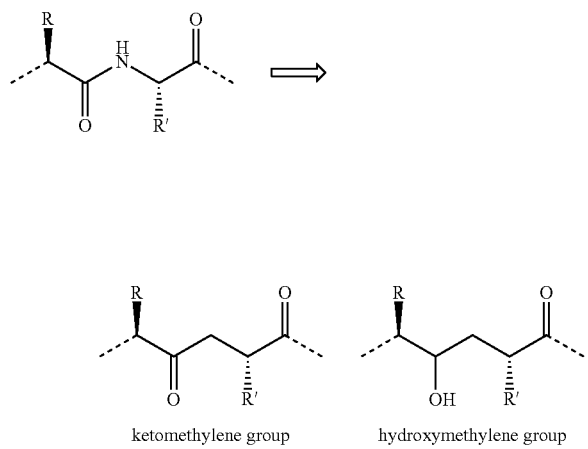

ketomethylene group    hydroxymethylene group

By way of example for this peptidomimetic modification of inventive inhibitors, but not limited to, the synthesis of compounds 5.2 to 5.4 is given in FIGS. 11 to 13. The preparation of inventive inhibitors 5.2 (FIG. 13) and 5.3 (a and b, respectively; FIG. 14) is carried out with a suitable isoxazole as dipeptide analogue.

Potent inhibitors are obtained preferably when residue A is a secondary substituted atom, preferably a carbon atom, to which the olefinic side chain is linked. To this preferably secondary substituted carbon atom preferably a nitrogen atom is bond. Surprisingly it was found that potent inhibitors can also be obtained when this nitrogen atom is substituted by other atoms, preferably carbon atoms, as shown by way of example in formula (II) with E=CH$_2$.

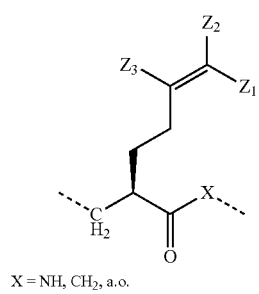

X = NH, CH$_2$, a.o.

A possible synthesis of peptidomimetic inhibitors in which this nitrogen is substituted is shown in FIG. 15. As an embodiment (but not limited to) compound 5.4 is given. As a concrete embodiment for the preparation of hydroxymethylene and ketomethylene isosters in different positions of inventive inhibitors the syntheses of compounds 5.3a & b and 5.4 are given.

General description of the synthesis of hydroxymethylene and ketomethylene bioisosters (schemes 11 and 12):

The preparation of hydroxymethylene and ketomethylene structural elements can be carried out for example via compound 5.2.1 described by Haug et al. and Litera et al. (Haug, B. E., et al.; Org. Lett., 2004, 6, 4783-4786, Litera, J.; et al. *Collet. Czech, Chem. Commun.*, 1998, 63, 231-244., see scheme 13).

By way of example, the synthesis sequence in scheme 13 starts with the lactone 5.2.1, described in literature. This lactone is preferably opened to the hydroxyethylene analogue with an amine, preferably a peptidic amino acid or a peptide, under heating treatment in DMF. The subsequent cyclization to the oxazolidinone is carried out with sodium hydride. The amide function of the oxazolidinone is protected with another boc group, as described in 1.3. The release of the primary alcohol can be achieved by methods known to the one skilled in the art by using tetrabutylammonium fluoride (TBAF) or in the case of racemization reactions by acetic acid in a THF/water mixture. The subsequent oxidation to the aldehyde is enabled by the variant according to Swern (Omura, K.; Swern, D. *Tetrahedron*, 1978, 34, 1651-1660.). Michael acceptor systems are obtained by converting a suitable aldehyde with a suitable phosphonium ylide in a Wittig reaction or a Horner-Wadworth-Emmons reaction (*JACS*, 1961, 83, 1733). As an example (but not limited to) (ethoxycarbonyl-methylene)-triphenylphosphorane is used, in analogy to compound 1.5 in scheme 11. Oxazolidinone is opened with TFA and the released β-amino alcohol (5.2.2) is derivatized at the nitrogen atom.

Inhibitors can also be obtained by converting isocyanates with the amino function to urea derivatives (see scheme 11, compound 5.2.a, instructions for example by: Davies, J. S., J. Chem. Soc. Perkin Trans 2, 1992, 1225-1231). With suitable active esters (as e.g. Z—OSu) derivatization of the free amino function in 5.2.2 and analogous compounds under formation of carbamates, or as described under 3. with carboxyc acid under formation of an amide bond, can be achieved. Examples (but not limited to) for the synthesis of ketomethylene analogues can be prepared from the hydroxymethylene derivatives via a subsequent oxidation according to the method of Dess-Martin (Dess, D. B; Martin, J. C. *JOC*, 1983, 48, 4155).

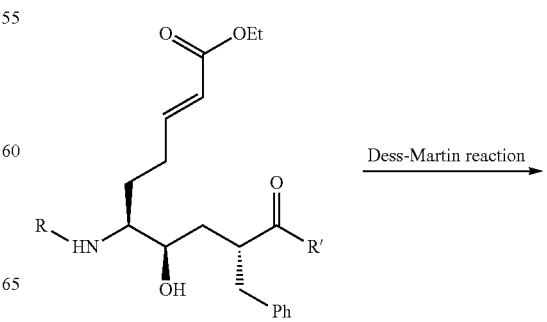

Dess-Martin reaction

-continued

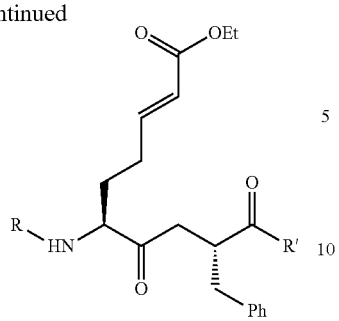

General synthesis instruction for hydroxymethylene and ketomethylene bioisosters (FIG. 15):

The preparation of inhibitors with E=CH₂ was performed via compound 5.4.1 described by Ghosh et al. and Brady et al. (Ghosh, A. K; JACS, 2000, 122, 3522; Brady, S. F., *Bioorg & Med. Chem. Lett.*, 2004, 14, 601). As an example (but not limited to) a synthesis sequence is given in FIG. 15.

General Description of the Synthesis (See FIG. 15)

The synthesis sequence starts with the lactone 5.4.1 described in literature (Ghosh, A. K; JACS, 2000, 122, 3522; Brady, S. F., *Bioorg & Med. Chem. Lett.*, 2004, 14, 601). This lactone is opened to the hydroxyethylene analogue with LiOH. The subsequent derivatization of the C-terminal carboxyl function was carried out preferably with amines. The subsequent oxidation of the secondary hydroxy function as well as of the primary alcohol is enabled by the variant of Swern. In turn, Michael acceptor systems are obtained when a suitable aldehyde is converted with a suitable phosphonium ylide in a Wittig reaction or a Horner-Wadworth-Emmons reaction. After cleavage of the boc group at the N-terminus the same consecutive reactions can occur at this nitrogen, as described herein elsewhere.

Embodiments

S)-2-[((S)-1-{(E)-2R,5S)-2-(4-fluorobenzyl)-9-methansulfonyl-5-[(5-methyl-isoxazol-3-carbonyl)-amino]-4-oxo-non-8-enoyl}-pyrrolidine-2-carbonyl)-amino]-4-methyl-valeric acid methyl ester
(compound 5.3.b)

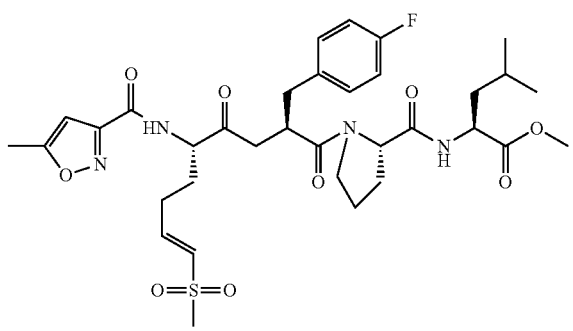

750 mg [(1S)-1-[(4R)-4-(4-fluoro)-benzyl-5-oxo-tetrahydro-furane-(2R)-2-yl]-4-(tert-butyl-dimethylsilanyloxy)-butyl]-carbamide acid-tert-butyl ester (5.3.1, see scheme 14, prepared according to Haug et al., *Org. Lett.*, 2004, 6, 4783-4786, 1.51 mmol) are dissolved in 20 ml THF and 759 mg H-Pro-Leu-OMe (3.14 mmol) are added. The reaction batch is adjusted to pH ~11 by adding DIPEA and heated to 40° C. for four hours. The solvent is removed under vacuum and the resulting oily residue is taken up in 200 ml ethyl acetate. The organic phase is washed with NaHCO₃ solution and saturated NaCl solution and dried over Na₂SO₄. 1.0 g od the crude product (5.3.2) are obtained which can be used for further conversions without additional purification.

To a solution of 1 g 5.3.2 (1.36 mmol) in 8 ml DMF$_{abs}$ 271 mg NaH (60% on mineral oil) are added under stirring. After stirring for three hours at room temperature 5 ml saturated NaCl solution are added and the mixture is extracted three times each with 20 ml ethyl acetate. The combined organic phases are dried over Na₂SO₄ and the solvent is removed under vacuum. The product (5.3.3) is purified by means of chromatography on silica gel (column: 21*2.3 cm, dichloromethane/methanol: 95/5, yield: 685 mg). 670 mg 5.3.3 (1 mmol) are dissolved in acetonitrile and the nitrogen is protected with a tert.-butyloxycarbonyl group, as described for compound 1.3. The purification of the product (5.3.4) is performed again by means of chromatography on silica gel (column: 26*2.3 cm, dichloromethane/methanol: 99/1, yield: 596 mg).

590 mg of the silyl ether 5.3.4 (0.77 mmol) are dissolved in 25 ml THF and 10 ml of a solution of acetic acid in THF and water (10/2/6) are added at room temperature. After stirring for one hour at room temperature the solvent is removed under vacuum and the resulting solid residue is purified by means of chromatography on silica gel (column: 21*1.2 cm, dichloromethane/methanol: 9/1, yield: 465 mg). The thus obtained primary alcohol is oxygenated to the aldehyde 5.3.5 in a Swern oxidation. Therefore, 100 mg oxalyl chloride (0.786 mmol) are dissolved in 5 ml dichloromethane. This solution is cooled to −60° C. under nitrogen atmosphere and subsequently a solution of 132 mg DMSO (1.7 mmol) in 2 ml dichloromethane is slowly added dropwise. The mixture is stirred for another 10 minutes at −60° C. and subsequently a solution of 460 mg (0.715 mmol) of the alcohol described above in 2 ml dichloromethane is added. After stirring for another 15 minutes at this temperature 3.5 g triethylamine (35 mmol) are added. The solution is stirred for five minutes at −60° C., then the cryostat is removed. The solution thaws to 0° C. during 30 minutes. At this temperature 10 ml water are added and the reaction batch is heavily stirred for ten minutes. The organic phase is removed and the aqueous phase is washed two times each with 10 ml dichloromethane. The combined organic phases are dried over Na₂SO₄ and concentrated for drying under vacuum. The resulting aldehyde 5.3.5 can be converted without further purification to the vinyloguous sulfone 5.3.6 in a Horner-Wadworth-Emmons reaction, as described for compound 3.11. The purification is performed by means of preparative chromatography (synergy max, 4 µm, 250*21.2 mm, A-eluent: 0.1% TFA/water, B-eluent: 90% AcCN/10% water/0.1% TFA. Gradient: 8 ml/min, 30% B on 100% B, 1')/0/min). Yield (5.3.6): 419 mg.

The treatment of 400 mg of the oxazolidinone 5.3.6 (0.55 mmol) in 15 ml of a solution of TFA/DCM (1/1) yields the amino alcohol 5.3.7 as TFA salt in a quantitative yield (400 mg). It can be used without another purification.

8.7 mg 5-methyl-isoxazole-4-carboxyc acid (69 µM, preparation: Street et al., J. Med. Chem., 2004, 3642-3657) are dissolved in 2 ml DMF and 26 mg HATU (138 µmol) and 23 µl DIPEA (140 µmol) are added. This solution is immediately added to a solution of 50 mg of the amino alcohol 5.3.7 (69 µmol) in 3 ml DMF. After stirring for 30 minutes at room temperature the reaction comes to an end. The solvent is removed under vacuum and the product is purified by means of preparative chromatography (synergy max, 4 µm, 250*21.2 mm, A-eluent: 0.1% TFA/water, B-eluent: 90% AcCN/10% water/0.1% TFA. Gradient: 8 ml/min, 5% B on 100% B, 1%/min).

Yield (5.3.a): 38 mg.
ESI-MS: 729.4 {M+Na}+

19 mg 5.3.a (27 µmol) are dissolved in 2 ml dichloromethane and 12.5 mg 1,1,1-tris(acetyloxy)-1,1-dihydro-1, 2-benziodoxole-3-(1H)-one (Dess-Martin Periodan, 29.7 µmol) in dichlormethane are added to this solution. The solution is stirred for 20 minutes at room temperature. The solvent is removed under vacuum and the compound given in the title is purified by means of preparative chromatography (synergy max, 4 µm, 250*21.2 mm, A-eluent: 0.1% TFA/water, B-eluent: 90% AcCN/10% water/0.1% TFA. Gradient: 8 ml/min, 30% B on 100% B, 1%/min).

Yield (5.3.b): 11 mg
ESI-MS: 727.4

(E)-(6R,9S)-9-benzyloxycarbonylamino-6-[2-(2-ethylcarbamoyl-octahydroindol-1-yl)-1-methyl-2-oxoethylcarbamoyl]-8-oxo-10-phenyl-dec-2-enylen acid-isopropyl ester (compound 5.4)

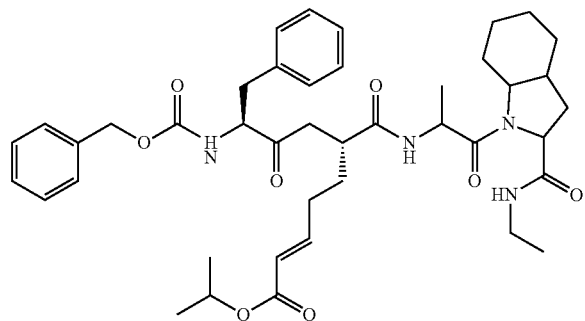 [SMILES: CCNC(=O)C1CC2CCCCC2N1C(=O)C(C)NC(=O)[C@H](CC/C=C/C(=O)OC(C)C)CC(=O)[C@H](Cc1ccccc1)NC(=O)OCc1ccccc1]

The synthesis starts with the lactone 5.4.1 known from literature (Ghosh, A. JACS, 2000, 122, 3522. Brady, S. F. Bioorg & Med. Chem. Lett., 2004, 14, 601). It was prepared as described therein. 363 mg 5.4.1 (1 mmol) are dissolved in 5 ml methanol and stirred over night at room temperature together with a 1.1 ml 1N LiOH solution. Subsequently the pH is adjusted to 3-4 with 1N HCl and the solvent is removed under vacuum. The resulting oily residue is taken up in 100 ml dichloromethane and washed two times with 10% citric acid and two times with saturated NaCl solution. After drying the organic phase over $Na_2SO_4$ and removing the solvent under vacuum 350 mg of the carboxyc acid 5.4.2 are obtained in pure form.

335 mg of the carboxyc acid 5.4.2 (0.87 mmol) are dissolved in 5 ml DMF and consecutively 276 mg TBTU (0.86 mmol), 118 mg HOBt and 451 µl DIPEA are added. To this solution a solution of 334 mg of the trifluoroacetate of the amine H-Ala-Oic-NHEt (0.87 mmol) are added immediately afterwards. After stirring for one hour at room temperature the solvent is removed under vacuum and the resulting solid residue is purified by means of preparative chromatography (synergy max, 4 µm, 250*21.2 mm, A-eluent: 0.1% TFA/water, B-eluent: 90% AcCN/10% water/0.1% TFA. Gradient: 8 ml/min, 30% B on 100% B, 1%/min). 409 mg of the diol 5.4.3 are obtained.

118 µl oxalyl chloride (1.38 mmol) are dissolved in 10 ml dichloromethane. This solution is cooled to −60° C. under nitrogen atmosphere and subsequently a solution of 212 µl DMSO (3 mmol) in 5 ml dichloromethane is slowly added dropwise. The solution is stirred for another ten minutes at −60° C. and subsequently a solution of 398 mh of the diol 5.4.3 described above (0.63 mmol) in 2 ml dichloromethane is added. After another 15 minutes of stirring at this temperature 6.2 g triethylamine (60 mmol) are added. The solution is stirred for five minutes at −60° C. and subsequently the cryostat is removed. The solution thaws to ca. 0° C. during 30 minutes. At this temperature 10 ml of water are added and the reaction batch is heavily stirred for ten minutes. The organic phase is removed and the aqueous phase is washed two times each with 10 ml dichloromethane. The combined organic phases are dried over $Na_2SO_4$ and concentrated for drying under vacuum. The resulting aldehyde 5.4.4 is pure according to HPLC and thin layer chromatography and can be used without further purification.

300 mg aldehyde 5.4.4 (0.48 mmol) are dissolved in 15 ml benzene and converted to the olefin 5.4.5, according to the instruction for the preparation of compound 3.3. The purification is perfomed by means of chromatography on silica gel (column: 20*2.3 cm, dichloromethane/methanol: 98/2, yield: 227 mg)

50 mg of the olefin 5.4.5 (70 µmol) are dissolved in 3 ml dichloromethane and 1.5 ml trifluoroacetic acid are added. After stirring for 45 minutes at room temperature 5 ml methanol are added to the solution and the mixture is concentrated for drying under vacuum.

The resulting residue is dissolved in 5 ml DMF and 17.4 mg N-(benzyloxycarbonyloxy)-succinimide (Z—OSu, 70 µmol, Fluka) are added. The Ph of the solution is adjusted to ~8-9 with DIPEA. The solution is stirred for two hours at room temperature and subsequently the solvent is removed under vacuum. By purification with preparative HPLC (synergy max, 4 µm, 250*21.2 mm, A-eluent: 0.1% TFA/water, B-eluent: 90% AcCN/10% water/0.1% TFA. Gradient: 8 ml/min, 30% B on 100% B, VA/min) the compound given in the title is obtained in pure form.

Yield: 30 mg
ESI-MS: 767.4 {M+Na}+

Substitution of an Amide Bond by a Hydroxyethylamino Group

The peptidomimetics described above are characterized by exchanging or removing respectively one atom of the amide bond. Thus a new chemical structure is generated which does not undergo metabolization, or at least to a much slower degree than the original peptide bond. This strategy to permit the least possible differences between a chemical and a bioisosteric structure safeguards that the compound obtained is still a potent inhibitor. Surprisingly it was found that even advanced structural modifications still yield potent inhibitors of transglutaminases. An example (but not limited to) for such a substitution is the hydroxyethylamino group.

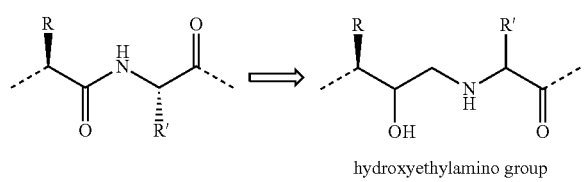

hydroxyethylamino group

General Description of the Synthesis of a Hydroxyethylamino Bioisoster

An example (but not limited to) for the synthesis of hydroxyethylamino bioisosters is described in FIG. 16. As embodiment the synthesis of compound 5.6 is given (see also FIG. 17).

For the preparation of hydroxyethylamino analogues of inventive inhibitors suitably substituted epoxides as e.g. compound 5.5.1 (Aldrich) are preferably reacted with amines. Preferably these amines are amino acids protected at the C-terminal.

Particularly preferred are peptides or peptidomimetics. Particularly the used amine may contain already an inventive pharmacophoric group, i.e. the double bond conjugated with an electron-drawing group. The secondary hydroxyl group in the resulting hydroxyethylamino analogue can be oxygenated to the ketone via a Dess-Martin reaction or a similar reaction. If necessary in the course of the synthesis the newly formed secondary amino function can be orthogonally protected as a boc group at this stage. After cleaving the boc protective group amines of the type 5.5.2 are obtained. If the inventive pharmacophoric group is not located in the immediate vicinity to the hydroxyethylamino bioisoster then the pharmacophore, as described above, can be integrated in form of the amine used for opening the epoxide or at the primary amino function, as described by way of example, but not limited that, in scheme 16. However, the pharmacophore-carrying side chain of inhibitors can be located at any position of the molecule. In scheme 17 the synthesis of the embodiment 5.6 is given. Here, a hydroxyethylaminpo bioisoster appears in the immediate vicinity of the inventive pharmacophoric group.

Piperidin-4-carbonyl-((E)-(S)-5-benzylsulfonyl-1-{2-[2-((S)-2-benzylsulfonylaminocarbonyl-octahydro-indole-1yl)-2-oxo-ethylamino]-acetyl}-4-enyl)-amide (compound 5.6)

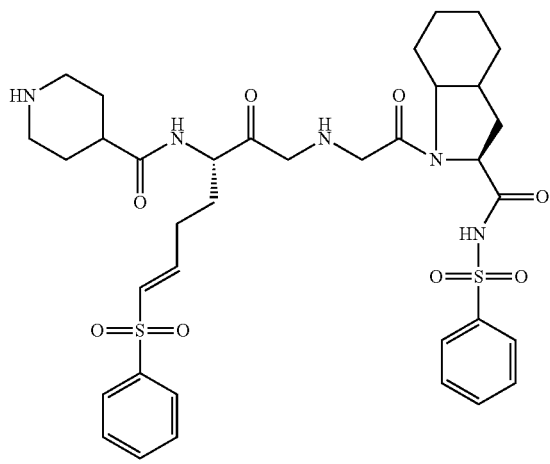

The epoxid needed (5.6.1, see scheme 17) is prepared as described in literature (Pico A. et al., J. Org. Chem., 2003, 68, 5075-5083). The amino component (N[(S)-1-(2-amino-acetyl)octahydro-indole-2-carbonyl]-benzylsulfonamide) is prepared in an analogous manner to the synthesis of compound 4.3.1 and the synthesis pathway described before in literature (Johanson A. et al., Bioorg. & Med. Chem., 11, 2003, 2551-2568).

980 mg 5.6.1 (2.83 mmol) are dissolved in 20 ml methanol and consecutively 1.03 g N[(S)-1-(2-amino-acetyl)octahydro-indole-2-carbonyl]-benzylsulfonamide (2.83 mmol) and 100 mg triethylamine (1 mmol) are added. The solution is boiled under reflux for five hours. The solvent is removed under vacuum and the resulting solid residue is purified by means of chromatography on silica gel (column: 32*3.5 cm, dichloromethane/methanol: 95/5. 1.12 g of compound 5.6.2 are obtained in pure form as white solid. 1.1 g of the compound 5.6.2 (1.54 mmol) are dissolved in THF and 2 ml of an one-molar solution of tetrabutylammonium fluoride (TBAF) in THF are added at room temperature. After stirring for 30 minutes at this temperature the solvent is removed under vacuum and the product (5.6.3) is purified by means of chromatography on silica gel (column: 26*2.8 cm, dichloromethane/methanol: 90/10, yield: 781 mg).

760 mg of the diol 5.6.3 (1.27 mmol) are dissolved in 15 ml dichloromethane and a solution of 1.18 g 1,1,1-tris(acetyloxy)-1,1-dihydro-1,2-benziodoxol-3-(1H)-one (Dess-Martin Periodan, 2.79 mmol) in dichlormethane is added. The solution is stirred for 30 minutes at room temperature. The solvent is removed under vacuum and the intermediate (5.6.4) is purified by means of chromatography on silica gel (column: 30*2.8 cm, dichloromethane/methanol: 98/2, yield: 474 mg).

257 mg $(EtO)_2P(=O)SO_2Phe$ (0.85 mmol) are dissolved in 10 ml $DMF_{abs}$ and 34 mg NaH (60% on mineral oil) are added at room temperature under nitrogen atmosphere.

After the gas production has ceased a solution of 460 mg 5.6.4 (0.77 mmol) in 10 ml $DMF_{abs}$ is added and the solution is stirred over night at room temperature. The solvent is removed under vacuum and the intermediate (5.6.4) is purified by means of preparative HPLC (synergy max, 4 μm, 250*21.2 mm, A-eluent: 0.1% TFA/water, B-eluent: 90% AcCN/10% water/0.1% TFA. Gradient: 8 ml/min, 25% B on 100% B, 1%/min). Yield: 498 mg.

The cleavage of the boc protective group by treatment with 10 ml of a solution of TFA/DCM=1/1 is achieved without problems and the resulting primary amine (5.6.5) can be used without further purification. The crude product of compound 5.6.5 is dissolved in 10 ml DMF and 195 mg N-boc-piperidine-4-carboxyc acid-N-hydroxysuccinimide (0.6 mmol) is added. The pH is adjusted to ~8-9 by adding DIPEA. After stirring for one hour at room temperature the reaction comes to an end. The solvent is removed under vacuum and the resulting oily residue is dissolved without further processing in a 10 ml solution of TFA/DCM=1/1. After stirring for 30 minutes at room temperature the reaction comes to an end. The solvent is removed under vacuum and the compound given in the title is purified by means of preparative HPLC.

Yield: 402 mg

ESI-MS: 742.3 {M+H}$^+$

A preferred form of the acceptor-substituted double bond is a Michael system from a carbonyl function in conjugation with a double bond displaying the following general structure [G]:

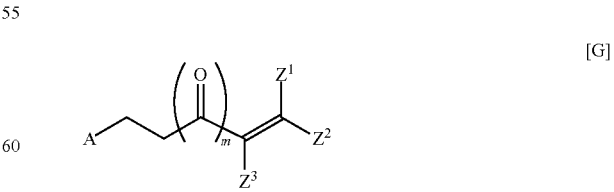

In one embodiment the atom which is bond via the A to the inventive pharmacophore is a nitrogen. To this preferably tertiary substituted nitrogen atom preferably a carbonyl group (C=O) is bond.

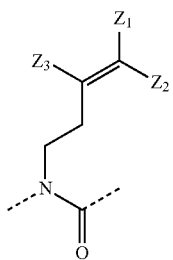

Surprisingly it was found that also inventive compounds substituted in such a way can inhibit transglutaminases potently.

General Description of Synthesis:

In FIG. 18 a synthesis sequence is shown as an example (but not limited to).

The preparation of inventive inhibitors is achieved starting from the compound 5.7.1 published by Hill et al. (Hill, R. D.; Vederas, J. C., JOC, 1999, 64, 9538-9546). By a reaction with bis-(pentafluorophenyl)carbonate in the presence of pyridine the pentafluorophenylester 5.7.2 is formed which reacts with alcoholates to differently protected esters, as e.g. 5.7.3. Before an aldehyde as for example 5.7.6 can be prepared, for example via an alcohol as 5.7.5, the second hydrazine nitrogen must be protected, as described herein. By way of example this protective group can be integrated through a reaction with di-tert.-butyl-bicarbonate in the presence of DMAP. After the dimethylamide 5.7.4 is reduced successfully to the alcohol 5.7.5 the alcohol can be oxygenated to the aldehyde 5.7.6, for example through a Swern oxidation. The further synthesis of inventive inhibitors can be performed starting from 5.7.6 according to the methods described herein (see e.g. compound 3.11). An embodiment is given with compound 5.7.

(E)-5-(N'-acetyl-N-carboxy-hydrazino)-[(pent-2-enoyl)-1-ethanoly]-valinyl-L-prolinyl-L-leucine methyl ester (compound 5.7)

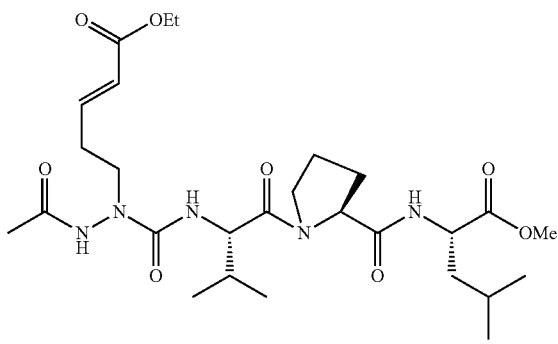 [SMILES: CCOC(=O)/C=C/CCN(NC(C)=O)C(=O)N[C@H](C(=O)N1CCC[C@H]1C(=O)N[C@@H](CC(C)C)C(=O)OC)C(C)C]

693 mg of the hydrazide 5.7.1 (4 mmol, scheme 18; Hill, R. D.; Vederas, J. C. JOC, 1999, 64, 9538-95469) are dissolved in 20 ml THF$_{abs}$ and 326 µl pyridine (4 mmol) are added. After two minutes 1.43 g bis-(pentafluorophenyl)carbonate (3.62 mmol, Fluka) are added and the solution is stirred over night at room temperature. The solvent is removed under vacuum and the residue is purified by means of chromatography on silica gel (column: 39*2.8 cm, dichloromethane/methanol: 95/5, yield: 1.24 g).

1.22 g of the pentafluorophenyl ester 5.7.2 (3.18 mmol) are dissolved again in 35 ml THF$_{abs}$. To this solution 540 mg potassium-2-phenyl-2-propanolate (3.1 mmol) is added. The solution is stirred for two hours at room temperature and the solvent is removed under vacuum. The resulting solid residue is taken up in 200 ml ethyl acetate and washed with a 10% Na$_2$CO$_3$ solution and a saturated NaCl solution. The organic phase is dried over Na$_2$SO$_4$. After removing the solvent under vacuum 628 mg of the 2-phenyl-2-propanol ester 5.7.3 are obtained. The crude product can be used for the following synthesis without further purification.

628 mg 5.7.3 (1.87 mmol) are dissolve din 20 ml acetonitrile and 817 mg di-tert.-butyl bicarbonate (3.74 mmol) and 46 mg DMAP (0.37 mmol) are added. The solution is stirred over night at room temperature and the solvent is removed under vacuum. The ensuing purification of compound 5.4.1 is performed by means of chromatography on silica gel (column: 32*2.2 cm, dichloromethane/methanol: 99/1, yield: 521 mg).

510 mg 5.4.1 (1.17 mmol) are dissolved in 20 ml methanol and 110 mg sodium borohydride (2.95 mmol) are added at 0° C. The solution is stirred at this temperature over night. Subsequently, 56 ml of a 1% citric acid solution are added to the reaction solution which then is thawed to room temperature. The aqueous phase is extracted five times each with 100 ml diethyl ether and the combined organic phases are dried over Na$_2$SO$_4$. This yields 388 mg of the alcohol 5.7.5 which is sufficiently pure for the consecutive reaction (Swern oxygenation to the aldehyde 5.7.6). Therefore, 137 mg oxalyl chloride (1.07 mmol) are dissolved in 5 ml dichloromethane. This solution is cooled to −60° C. under nitrogen atmosphere and subsequently a solution of 180 mg DMSO (2.33 mmol) in 2 ml dichloromethane is slowly added dropwise. The solution is stirred for another ten minutes at −60° C. and subsequently a solution of 388 mg (0.983 mmol) of the alcohol described above in 5 ml dichloromethane is added. After another 15 minutes of stirring at this temperature 4.8 g triethylamine (48 mmol) are added. The solution is stirred for five minutes at −60° C., then the cryostat is removed. The solution thaws to 0° C. during ca. 30 minutes. At this temperature 15 ml water are added and the reaction batch is heavily stirred for ten minutes. The organic phase is removed and the aqueous phase is washed two times each with 20 ml dichloromethane. The combined organic phases are dried over Na$_2$SO$_4$ and concentrated for drying under vacuum. After removing the solvent under vacuum 354 mg 5.7.6 are obtained. The aldehyde can be used for the following Wittig reaction without further purification. Therefore, 340 mg 5.7.6 (0.866 mmol) are dissolved in 15 ml benzene and 301 mg (0.866 mmol) (ethoxycarbonylmethylene)-triphenylphosphorane are added at room temperature. The solution is stirred over night at room temperature and subsequently the solvent is removed under vacuum. After purification by means of preparative HPLC (synergy max, 4 µm, 250*21.2 mm, A-eluent: 0.1% TFA/water, B-eluent: 90% AcCN/10% water/0.1% TFA. Gradient: 8 ml/min, 25% B on 100% B, VA/min) 300 mg of the pure olefin 5.7.7 are obtained.

From the purified product the acid-labile protective groups are cleaved by dissolving 290 mg of compound 5.7.7 (0.63 mmol) in 10 ml dichloromethane and adding consecutively 100 µl triisopropylsilane and 100 µl trifluoroacetic acid. After 30 minutes the solvent is removed under vacuum and the obtained residue is purified by means of preparative HPLC (synergy max, 4 µm, 250*21.2 mm, A-eluent: 0.1% TFA/water, B-eluent: 90% AcCN/10% water/0.1% TFA. Gradient: 8 ml/min, 5% B on 100% B, 1%/min). Thus 131 mg of the free carboxyc acid 5.7.8 are obtained.

50 mg 5.7.8 (0.2 mmol) are dissolved in 3 ml DMF. To this solution 77 mg (0.2 mmol) HATU and 68 µl DIPEA (0.4 mmol) are added. This solution is added immediately to a solution of 91 mg of the trifluoroacetate salt of H-Val-Pro-Leu-OMe in 2 ml DMF. After stirring for one hour at room temperature the solvent is removed under vacuum and the compound given in the title is purified by means of preparative HPLC (synergy max, 4 µm, 250*21.2 mm, A-eluent: 0.1% TFA/water, B-eluent: 90% AcCN/10% water/0.1% TFA. Gradient: 8 ml/min, 5% B on 100% B, 1%/min).

Yield: 78 mg
ESI-MS: 590.1 {M+Na}$^+$
(Compound 42)

Figure 3:
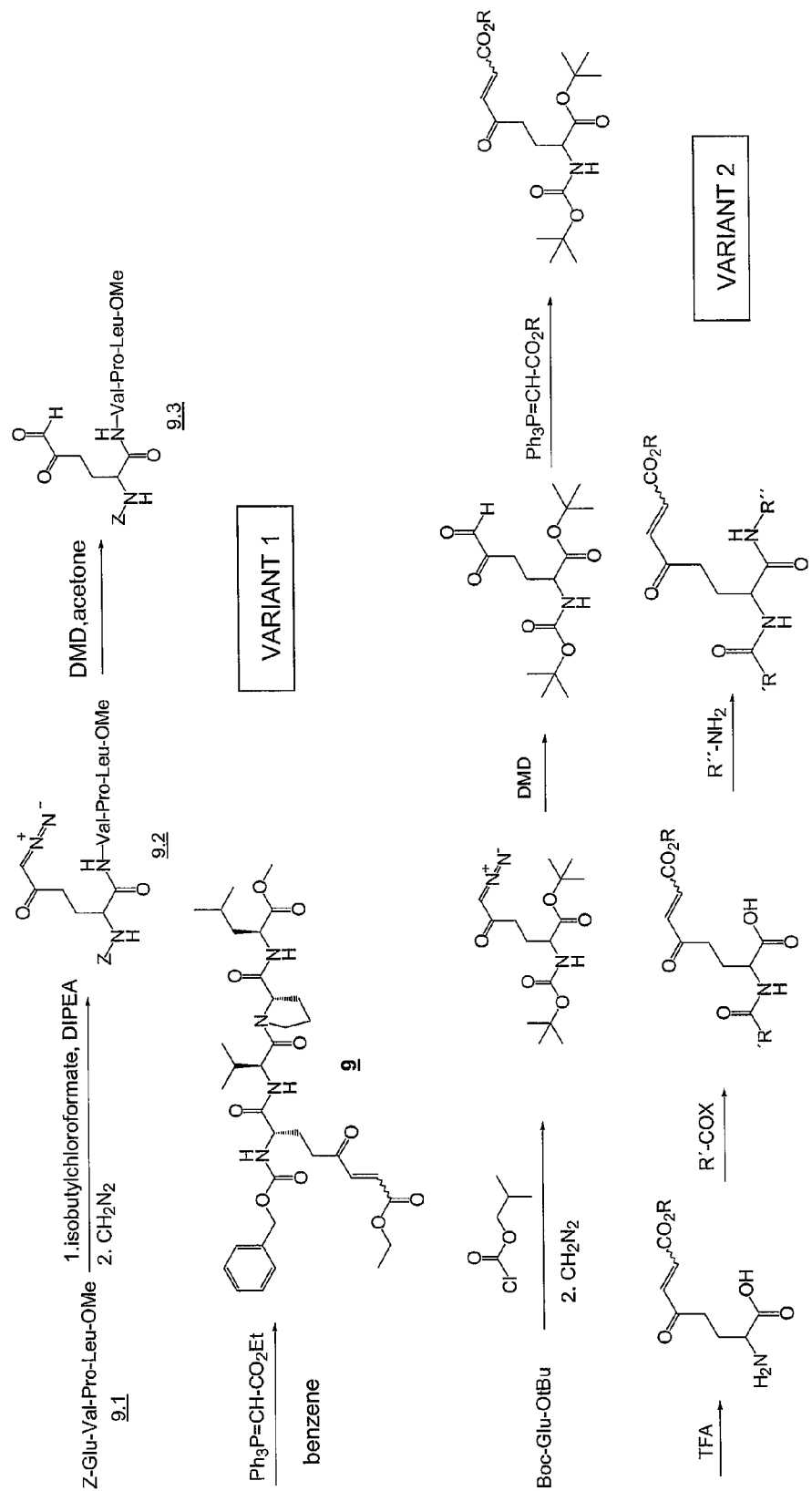
FIG. 3 shows two variants of a general synthesis of compounds using the example of L-2-amino-4-oxo-oct-2-ene-dicarboxylic acid ethyl ester wherein in variant 1 the modification of the side chain to an essential Michael system (i.e. of the acceptor-substituted double bond) is carried out at glutamic acid in the protected backbone after the synthesis of the backbone, and wherein in variant 2 as a first step an amino acid block is prepared with the essential Michael system (i.e. the acceptor-substituted double bond) and this block is linked at its C-terminus and/or N-terminus via an amide bond to further amino acids or oligopeptides.

Compound 42 was prepared according to the reaction scheme of FIG. 3 variant 2. This proves that backbones can be produced from completely non-proteinogenic amino acids.

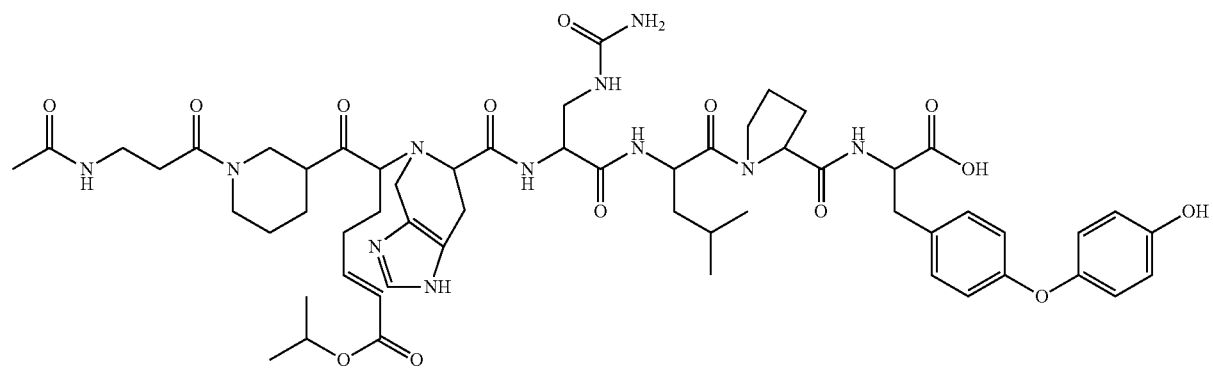

42

(Compound 43)

Compound 43 was prepared according to the reaction scheme of FIG. 3 variant 1. This proves that backbones can be produced from completely non-proteinogenic amino acids.

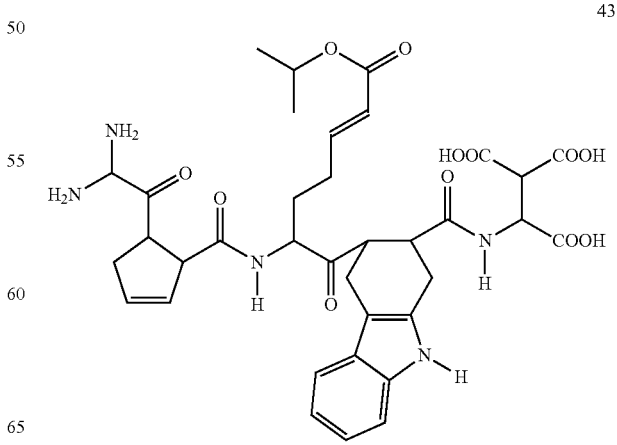

43

(Compound 44)

Compound 44 was prepared according to the reaction scheme of FIG. 3 variant 2. This proves that inventive backbones with 13 amino acids can be produced without a problem.

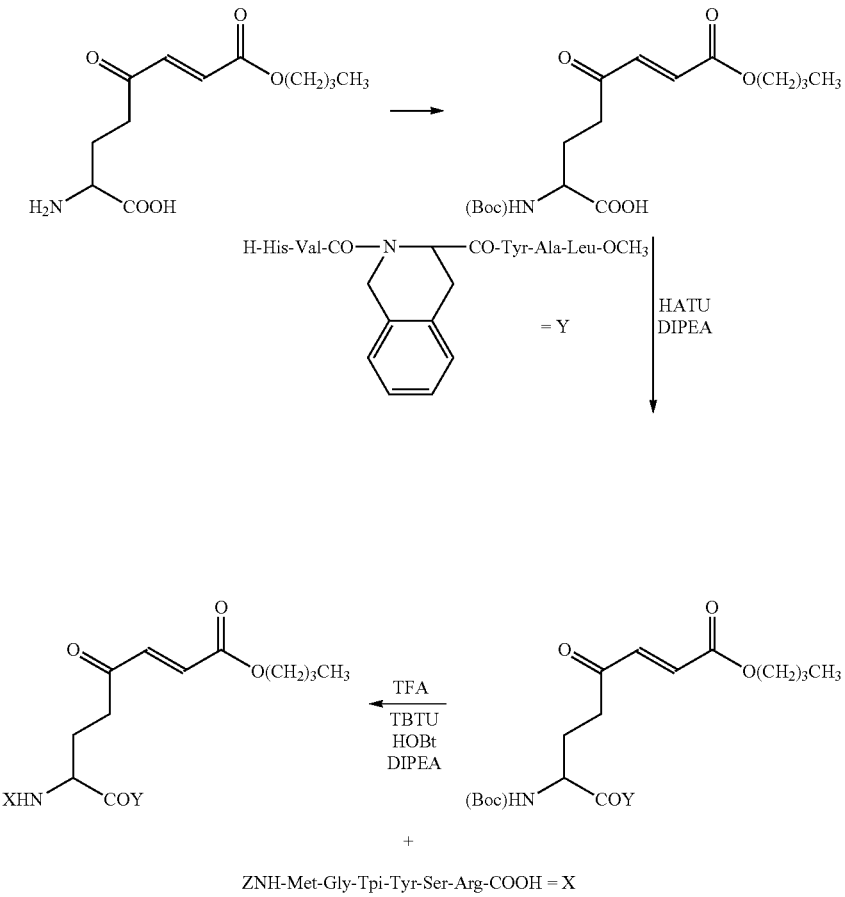

Compounds 43 and 44 showed an IC50 at TG2 of 5 μM and 15 μM, respectively.

Example of an In-Vivo Experiment in the Irish Setter

A 5 weeks old dog (Irish setter) was fed with a wheat-containing diet. The animal showed symptoms of diarrhea and a poor weight gain. By a jejunal biopsy a partial degradation of the intestinal villi and an increased number of intraepithelial lymphocytes were found.

This dog was fed before each meal with 75 mg/kg body weight transglutaminase inhibitor (1) in a acid-stable formulation. In the following a decrease of the diarrhea and an increase in body weight were observed. After two months it was shown by means of a biopsy that the intestinal villi displayed a normal length and that the number of intraepithelial lymphocytes was significantly reduced.

Example

Recombinant Production of TG6 and TG7

The genes encoding for TG6 and TG7 were amplified from TG6-cDNA and TG7-cDNA, respectively, with PCR according to standard procedures (both state-of-the-art according to U.S. Pat. No. 7,052,890). Through the primers used a NdeI restriction site and six histidine codons were inserted at the 5' end and a BgIII restriction site (TG6) and a HindIII restriction site (TG7) at the 3' end.

The Tg6 PCR product was treated with the restriction endonucleases NdeI and BgIII. In the NdeI and BamH I restricted vector pET 3a was inserted. The Tg7 PCR product was treated with the restriction endonucleases NdeI and HindIII. and in the likewise restricted vector pET 28b was inserted.

The *E. coli* strain BL21 (DE3) (Novagen, Darmstadt) was transformed with the obtained plasmids. A culture of one strain each was induced with IPTG and harvested. After cell disruption under high pressure homogenisation the disrupts were centrifuged and the supernatants were purified via metal ion affinity chromatography on HiTrap chelating HP columns (GE-Helathcare). The purified proteins TG6 and TG7 were analyzed by SDS-PAGE with Coomassie staining. All procedures used for the production of TG6 and TG7 are well known to the one skilled in the art.

The additional examples 10 to 43 of compounds according to the general formula (A) are prepared in analogous manner to the above experiment descriptions and have the following substitution patterns:

TABLE 1

| Compound Nr. | —NXX' | Y | Z | E/Z; m | ESI-MS [M + Na]+ | IC$_{50}$ value [TG2] | IC$_{50}$ value [FXIII] | IC$_{50}$ value [TG1] |
|---|---|---|---|---|---|---|---|---|
| 1 | Z*—NH | CO-Val-Pro-Leu-OMe | OCH$_2$CH$_3$ | 0; 0 | 681.4 | 30 nM | >50 μM | nd |
| 2 | Z*—NH | CO-Gln-Pro-Leu-OMe | OCH$_2$CH$_3$ | 0; 0 | 710.4 | 20 nM | >50 μM | nd |
| 3 | Z*—NH | CO-Phe-OMe | OCH$_2$CH$_3$ | 0; 0 | 519.2 | 8 μM | 2.5 μM | 200 nM |
| 4 | Z*—NH | Gln-Pro-Leu-OMe | OCH$_3$ | 0; 0 | 583.3 | 350 nM | >50 μM | nd |
| 5 | Z*—NH | Gln-Pro-isopropylamide | OCH$_2$CH$_3$ | 0; 0 | 623.5 | 125 nM | >50 μM | nd |
| 6 | (E)-(L)-6-(2-oxo-pyrrolidine-1-yl-) | Val-Pro-OMe | OCH$_2$CH$_3$ | 0; 0 | 502.3 | 15 μM | >50 μM | nd |
| 7 | Ac-Asn | Glu-Ala-Valin-OMe | OCH$_3$ | 0; 0 | 679.3 | >50 μM | 2 μM | >50 μM |
| 8 | Ac-Leu-Gly-Pro-Gly | Ser-Leu-Val-Ile-Gly-OMe | OCH$_2$CH$_3$ | 0; 0 | 1073.7 | >50 μM | 500 nM | >50 μM |
| 9 | Z*—NH | Val-Pro-Leu-OMe | OCH$_2$CH$_3$ | 0; 1 | 709.5 | 18 μM | nd | nd |
| 10 | Ac—NH | CO-Gln-Glu-Ala-OMe | OCH$_3$ | 0; 0 | 594.3 | 330 nM | nd | nd |
| 11 | Ac—NH | CO-Gln-Glu-OMe | OCH$_3$ | 0; 0 | 52.2 | 2.1 μM | nd | nd |
| 12 | Ac—NH | CO-Phe-Pro-Leu-OMe | OCH$_3$ | 0; 0 | 623.3 | 1.8 μM | nd | nd |
| 13 | Z*—NH | CO-Phe-Pro-Leu-OMe | OCH$_3$ | 0; 0 | 715.3 | 1.5 μM | nd | nd |
| 14 | Ac—NH | CO-(p-flouro-Phe)-Pro-Leu-OMe | OCH$_3$ | 0; 0 | 641.2 | 1.1 μM | nd | nd |
| 15 | Z*—NH | CO-(p-flouro-Phe)-Pro-Leu-OMe | OCH$_3$ | 0; 0 | 733.4 | 880 nM | nd | nd |
| 16 | (E)-(L)-6-(2-Oxo-pyrrolidine-1-yl-) | CO-Val-Pip-Leu-OMe | OCH$_2$CH$_3$ | 0; 0 | 615.4 | 22 μM | nd | nd |
| 17 | (E)-(L)-6-(2-Oxo-pyrrolidine-1-yl-) | CO-Chg-Pip-Leu-OMe | OCH$_2$CH$_3$ | 0; 0 | 655.4 | 35 μM | nd | nd |
| 18 | (E)-(L)-6-(2-Oxo-pyrrolidine-1-yl-) | CO-Chg-Pro-Leu-OMe | OCH$_2$CH$_3$ | 0; 0 | 641.5 | 28 μM | nd | nd |
| 19 | Z*—NH | CO-Gln-Pro-Tyr-OMe | OCH$_2$CH$_3$ | 0; 0 | 760.3 | 2.4 μM | nd | nd. |
| 20 | Z*-Phe-NH | CO-Gln-Pro-Leu-OMe | OCH$_2$CH$_3$ | 0; 0 | 857.5 | 2 μM | nd | nd |
| 21 | Z*-Gln-NH | CO-Leu-Pro-Gln-OMe | OCH$_2$CH$_3$ | 0; 0 | 838.3 | 3.2 μM | nd | nd |
| 22 | Ac—NH | CO-Gln-Pro-Leu-OMe | OCH$_2$CH$_4$ | 1; 0 | 646.2 | 70 nM | nd | nd |
| 23 | 5-methylisoxazole-3-carboxyc acid | CO-Gln-Pro-Leu-OMe | O—CH(CH$_3$)$_2$ | 1; 0 | 727.4 | 56 nM | nd | nd |
| 24 | 2-flouro-benzoic acid | CO-Val-4-fluoro-proline-O—CH(CH3)2 | OCH$_3$ | 1; 0 | 616.2 | 8 μM | nd | nd |
| 41 | Z*-Pro-Gln-Pro- | CO-Gln-Tic-Leu-OMe | O—CH$_2$Ph | 0; 0 | 1156.6 | 215 nM | nd | nd |
| 42 | Ac-β-Ala-(S)-piperidine-3-carbonyl | CO-L-spinacinyl-L-albizzinyl-Val-Pro-thyronine-OH | O—CH(CH$_3$)$_2$ | 0; 0 | 1140.4[M + H]+ | 4 μM | nd | nd |
| 43 | Agl-Dhp- | CO-Gln-Tpi-Gla-OH | O—CH(CH$_3$)$_2$ | 0; 0 | 740.3[M + H]+ | 1.9 μM | nd | nd |

The examples 3.2.1 to 3.2.11 of compounds according to the general formula [G] with m=0 are prepared from the compounds 3.1 to 3.12 according to the methods described under 1., 2. and 3.2 and show the following substitution pattern:

TABLE 2

| compound Nr. | —NXX' | Y | Z$_1$ | Z$_2$ | Z$_3$ | E/Z | ESI-MS [M + Na]$^+$ | IC$_{50}$ value [TG2] | IC$_{50}$ value [FXIII] | IC$_{50}$ value [TG1] |
|---|---|---|---|---|---|---|---|---|---|---|
| 3.2.1 | Z*—NH | CO-Gln-Pro-Leu-OMe | SO$_2$Me | H | H | 0 | 716.5 | 54 nM | >100 μM | 250 nM |
| 3.2.2 | Z*—NH | CO-Gln-Pro-Leu-OMe | SO$_2$N(CH$_3$)$_2$ | H | H | 0 | 745.3 | 760 nM | >100 μM | 1.3 μM |
| 3.2.3 | Z*—NH | CO-Gln-Pro-Leu-OMe | Z$_1$-Z$_3$ COCH$_2$CH$_2$ | H | ring structure (see column Z$_1$) | 0 | 692.2 | 18 μM | >100 μM | 14 μM |
| 3.2.4 | Z*—NH | CO-Gln-Pro-Leu-OMe | Z$_1$-Z$_2$ CO$_2$CH$_2$CH$_2$ | ring structure (see column Z$_1$) | H | 0 | 708.4 | 8.9 μM | >100 μM | 400 nM |
| 3.2.5 | Z*—NH | CO-Gln-Pro-Leu-OMe | CO$_2$H | H | H | 0 | 682.3 | 23 μM | >100 μM | n.b. |
| 3.2.6 | Ac—NH | CO-Gln-Asp-Pro-OMe | CONH—C$_5$H$_{11}$ | H | H | 0 | 661.4 | >100 μM | >100 μM | 23 μM |
| 3.2.7 | Z*—NH | CO-(p-Fluoro-Phe)-Pro-OH | CO$_2$—iPr | H | H | 0 | 634.4 | 1.5 μM | >100 μM | 3.7 μM |

TABLE 2-continued

| compound Nr. | —NXX' | Y | $Z_1$ | $Z_2$ | $Z_3$ | E/Z | ESI-MS $[M + Na]^+$ | $IC_{50}$ value | $IC_{50}$ value | $IC_{50}$ value |
|---|---|---|---|---|---|---|---|---|---|---|
| 3.2.8 | Z*—NH | CO-Phe-Pip-Leu-NH$_2$ | CO$_2$—Bn | H | H | 0 | 790.3 | 130 nM | >100 μM | 825 nM |
| 3.2.9 | Z*—NH | CO-Phe-OMe | COCO$_2$Et | H | H | 0 | 547.3 | 3.8 μM | >100 μM | 530 nM |
| 3.2.10 | Z*—NH | CO-Gln-Pro-Leu-OH | CO—CH$_3$ | H | H | 1 | 666.2 | 56 μM | nd | nd |
| 3.2.11 | Ac—NH | CO-Gln-Pro-Leu-OMe | CN | H | H | 1 | 663.3 | 43 μM | nd | nd |
| | | | Inhibitors of transglutaminases 3, 6 and 7 | | | | | | | |
| | | | | | | | | [TG3] | [TG6] | [TG7] |
| 3.2.12 | 4-methoxy-benzoic acid | CO-Leu-Pro-Tyr-NH—Et | 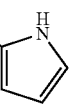 | H | H | 0 | 780.2 | 53 μM | 87 μM | 12 μM |
| 3.2.13 | Ac-Aib-Cph- | CO-Gln-Ile-Val-OH | C(O)—N(CH$_3$)$_2$ | H | H | 0 | 905.3 | >100 μM | 4 μM | 46 μM |
| 3.2.14 | Ac-Gln-Gln- | CO-Val-Hci-Gln-(4-hydroxy)-Tic-NH$_2$ | NO$_2$ | H | H | 0 | 1067.6 | 2.3 μM | >100 μM | >100 μM |
| 3.2.15 | GABA-Gly- | CO-Asp-Pro-Val-Tci-Gly-NH—CH$_2$—CH$_2$—SO$_3$H | CO$_2$Ph | H | H | 0 | 943.2 $[M + H]^+$ | 1.5 μM | 16 μM | 14 μM |
| 3.2.16 | Ac-β-chloralanine-thioproline- | CO-Gln-Cha-4-aminobenzoic acid | C(O)—Ph(4-NO$_2$) | H | H | 0 | 963.3 | 48 μM | 2 μM | 3.4 μM | legend to table 1:
Agl: α-aminoglycine
Dhp: 3,4-dehydroproline
Gla: γ-carboxyglutamic acid
Chg: cyclohexylglycine
Tpi: 1,2,3,4-tetrahydronorharman-3-carboxyc acid
Tic: 1,2,3,4-tetrahydroisochinoline-3-carboxyc acid
Pip: homoproline
Z*: benzyloxycarbonyl
nd: not determined

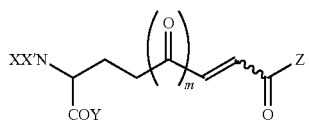

formula [A]

Only in compound 9 is m = 1, in all other cases m = 0
The given values refer for E/Z = 0 always to the respective E-isomer and for E/Z = 1 to the Z-isomer legend to table 2:
Aib: α-aminoisobutyric acid
Cph: 2,4-dichlorophenylalanine
Hci: homocitrulline
Tci: thiocitrulline
Cha: cyclohexylalanine
nd: not determined
Z*: benzyloxycarbonyl

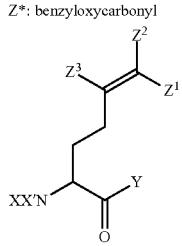

formula [G]

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method of inhibiting the biological activity of transglutaminases in a subject comprising administering to a subject an effective amount of a compound of the general structure [A*]:

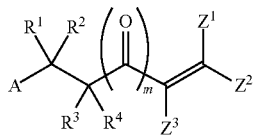

wherein the compound has at least one acceptor-substituted olefin with the residues $Z^1$, $Z^2$ and $Z^3$, which olefin is bound to an at least secondarily substituted group A via an ethylene group with the residues $R^1$, $R^2$, $R^3$ and $R^4$ or via a carbonyl ethylene group with the residues $R^1$, $R^2$, $R^3$ and $R^4$, wherein A represents a peptide residue, a peptide derivative or a peptidomimetic residue; wherein A has a secondarily or tertiarily substituted carbon atom to which the olefinic side chain and a carbonyl group are bound;

m is 0 or 1;

the residues $Z^1$, $Z^2$, $Z^3$ independently of each other represent the following groups: —H, —CO—($C_1$-$C_6$-Alkyl), —CO—$R^6$, —CO—$R^7$, —CO—($C_1$-$C_6$-Halogenalkyl), —CO—($C_3$-$C_{10}$-Heteroaryl), —CO—($C_6$-$C_{15}$-Aryl), —COO—($C_1$-$C_6$-Halogenalkyl), —COO—($C_3$-$C_{10}$-Heteroaryl), —COO—($C_6$-$C_{15}$-Aryl), —COO—($C_1$-$C_6$-Alkyl), —COO—$R^8$, —COO—$R^9$, —CN, —F, —Cl, —Br, —COOH, —CO—NH($C_1$-$C_6$-Alkyl), —CO—N($C_1$-$C_6$-Alkyl)($C_1$-$C_6$-Alkyl), —CO—$NR^{10}R^{11}$, —CO—$NH_2$, —CO—N($CR^{12}R^{13}R^{14}$)($CR^{15}R^{16}R^{17}$), —$CH_2CN$, —$CH_2F$, —$CHF_2$, —$CF_3$, —$OCF_3$, —$CH_2$—$CF_3$, —$CF_2$—$CF_3$, —$NO_2$, —CS—($C_1$-$C_6$-Alkyl), —CS—$R^{18}$, —CS—$R^{19}$, —CS—O—($C_1$-$C_6$-Alkyl), —CS—O—$R^{20}$, —CS—N($C_1$-$C_6$-Alkyl)($C_1$-$C_6$-Alkyl), —CS—O—$R^{21}$, —CS—$NR^{22}R^{23}$, —CS—$NH_2$, —CS—N($CR^{24}R^{25}R^{26}$)($CR^{27}R^{28}R^{29}$), —SO—$R^{30}$, —SO—$R^{31}$, —$SO_2$—$R^{32}$, —$SO_2$—$R^{33}$, —SO—$CR^{34}R^{35}R^{36}$, —SO—$CR^{37}R^{38}R^{39}$, —$SO_2$—$CR^{40}R^{41}R^{42}$, —$SO_2$—$CR^{43}R^{44}R^{45}$, —SO—N($C_1$-$C_6$-Alkyl)($C_1$-$C_6$-Alkyl), —SO—$NR^{46}R^{47}$, —SO—$NH_2$, —S O—N($CR^{48}R^{49}R^{50}$)($CR^{51}R^{52}R^{53}$), —$SO_2$—N($C_1$-$C_6$-Alkyl)($C_1$-$C_6$-Alkyl), —$SO_2$—$NR^{54}R^{55}$, —$SO_2$—$NH_2$, —$SO_2$—N($CR^{56}R^{57}R^{58}$)($CR^{59}R^{60}R^{61}$), —$SO_2$—OH, —$SO_2$—$OR^{62}$, —$SO_2$—$CR^{63}R^{64}R^{65}$, —$SO_2$—$OCR^{66}R^{67}R^{68}$, —O—P(O)(OH)$_2$, —O—P(O) ($OR^{69}$)($OR^{70}$), —O—P(O)(O—$C_1$-$C_6$-Alkyl)(O—$C_1$-$C_6$-Alkyl), —P(O)($OR^{71}$)($OR^{72}$), —P(O)(O—$C_1$-$C_6$-Alkyl) (O—$C_1$-$C_6$-Alkyl), —$CF_2$—P(O)($OR^{73}$)($OR^{74}$), —$CF_2$—P(O)(O—$C_1$-$C_6$-Alkyl)(O—$C_1$-$C_6$-Alkyl), wherein at least one of the residues $Z^1$, $Z^2$, $Z^3$ are different from hydrogen;

The residues $Z^1$ and $Z^2$ together may also represent a residue —CO—O—CO—$CH_2$—, —CO—O—$CH_2$—$CH_2$—, the residues $Z^2$ and $Z^3$ together may also form a residue —CO—Z'—$CH_2$—, —CO—O—$CH_2$—, —CO—O—$CH_2$—$CH_2$—, —CO—O—CO—, —CO—NH—CO— or —Z'—$CH_2$—$CH_2$—, wherein Z' represents one of the following groups: —$CH_2$—, —$CF_2$—, —$C_2H_4$—, —$CF_2$—$CH_2$—, —$CH_2$—$CH_2$—, —O—, —O—$CH_2$—, —NH— or —NH—$CH_2$—;

wherein the peptide residue is an amino acid chain of 1 to 6 amino acids or amino acid analogues wherein the amino acid analogues are selected from thiocarbonyl amino acids, β-amino acids, γ-amino acids, δ-amino acids,

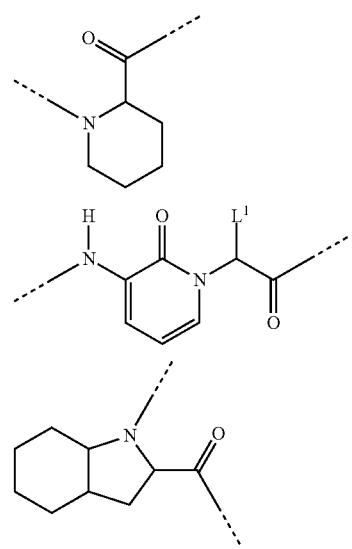

the peptidomimetic residue consists of 5 to 20 carbon atoms and the N-terminus of the peptidomimetic residue can carry an amino group, $C_1$-$C_{10}$ alkylamino group, $C_1$-$C_8$ alkyloxycarbonyl amino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group, wherein any of the $C_1$-$C_6$ alkoxy groups, $C_1$-$C_6$ alkyl groups, $C_1$-$C_{10}$ alkylamino groups, $C_1$-$C_8$ alkyloxycarbonyl amino groups, $C_6$-$C_{12}$ aralkyloxycarbonyl amino groups, $C_1$-$C_{10}$ dialkylamino groups, $C_2$-$C_6$ nitrogen heterocycles and $C_3$-$C_5$ nitrogen heteroaryl groups can be independently substituted with up to 5 residues selected from $R^{80}$, $R^{81}$, $R^{82}$, $R^{83}$, $R^{84}$, and wherein the peptidomimetic residue contains one of the following amino acid residues:

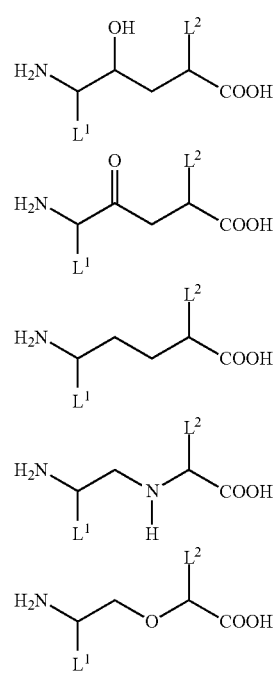

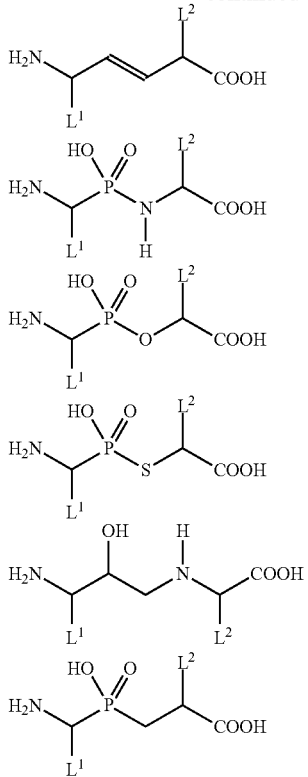

wherein $L^1$ and $L^2$ independently of each other represent a side chain residue of a natural amino acid or a residue $-R^{60}$, $-R^{61}$, $-CR^{62}R^{63}R^{64}$, $-CR^{65}R^{66}-CR^{67}R^{68}R^{69}$, $-CR^{70}R^{71}-CR^{72}R^{73}-CR^{74}R^{75}R^{76}$;

wherein the residues $R^1$-$R^{84}$ independently of each other represent the following groups:

—H, —OH, —OCH₃, —OC₂H₅, —OC₃H7, —O-cyclo-C₃H, —OCH(CH₃)₂, —OC(CH₃)₃, —OC₄H₉, —OPh, —OCH₂-Ph, —OCPh₃, —SH, —SCH₃, —SC₂H₅, —SC₃H₇, —S-cyclo-C₃H, —SCH(CH₃)₂, —SC(CH₃)₃, —NO₂, —F, —Cl, —Br, —I, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NH-COCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —S OCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—CO—NH-cyclo-C₃H₅, —NH—CO—NH[CH(CH₃)₂], —NH—CO—NH[C(CH₃)₃], —NH—CO—N(CH₃)₂, —NH—CO—N(C₂H₅)₂, —NH—CO—N(C₃H₇)₂, —NH—CO—N(cyclo-C₃H₅)₂, —NH—CO—N[CH(CH₃)₂]₂, —NH—CO—N[C(CH₃)₃]₂, —NH—CS—NH₂, —NH—CS—NHCH₃, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(CH₃)₂, —NH—CS—N(C₂H₅)₂, —NH—CS—N(C₃H₇)₂, —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —OC₆H₄—OCH₃, —NH—C(=NH)—NH-cyclo-C₃H₅, —NH—C(=NH)—NH[CH(CH₃)₂], —CF₂Cl, —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —OC₆H₄—CH₃, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NHC₃H₇, —O—CO—NH-cyclo-C₃H₅, —O—CO—NH[CH(CH₃)₂], —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃, —CH₂F, —CHF₂, —CF₃, —CH₂Cl, —CH₂Br, —CH₂J, —CH₂—CH₂F, —CH₂—CHF₂, —CH₂—CF₃, —CH₂—CH₂Cl, —CH₂—CH₂Br, —CH₂—CH₂J, cyclo-C₃H₅, cyclo-C₄H₇, cyclo-C₅H₉, cyclo-C₆H₁₁, cyclo-C₇H₁₃, cyclo-C₈H₁₅, -Ph, —CH₂-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —C₇H₁₅, —C₈H₁₇, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH—CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —CH₂—CH₂—CH₂—OCH₃, —C₂H₄—CH(CH₃)—CH=CH₂, —CH₂—CH(CH₃)—CH₂—CH=CH₂, —CH₂NH₂, —CH(CH₃)—C₂H₄—CH=CH₂, —C₂H₄—CH=C(CH₃)₂, —C₂H₄—C(CH₃)=CH—CH₃, —CH₂—CH(CH₃)—CH=CH—CH₃, —CH(CH₃)—CH₂—CH=CH—CH₃, —CH₂OH, —CH₂SH, —CH₂—CH=CH—CH(CH₃)₂, —CH₂—CH=C(CH₃)—C₂H₅, —CH₂—CH₂—CH₂NH₂, —CH₂—C(CH₃)=CH—C₂H₅, —CH(CH₃)—CH=CH—C₂H₅, —CH₂—CH₂NH₂, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —CH₂—CH₂SH, —CH(CH₃)—CH₂—C(CH₃)=CH₂, —CH(CH₃)—CH(CH₃)—CH=CH₂, —CH₂—CH₂—CH₂OH, —CH₂—C(CH₃)₂—CH=CH₂, —C(CH₃)₂—CH₂—CH=CH₂, —CH₂—C(CH₃)₂=C(CH₃)₂, —CH(CH₃)—CH=C(CH₃)₂, —C(CH₃)₂—CH=CH—CH₃, —CH₂—CH₂—CH₂SH, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —C₆H₄—OCH₃, —CH₂—CH=CH—CH₂—CH=CH₂, —CH=CH—C₂H₄—CH=CH₂, —C₆H₄—OH, —CH₂—CH=CH—CH=CH—CH₃, —CH=CH—CH₂—CH=CH—CH₃, —CH₂—CH₂—OCH₃, —CH=CH—CH=CH—C₂H₅, —CH₂—CH=CH—C(CH₃)=CH₂, —CH₂—CH₂OH, —CH₂—CH=C(CH₃)—CH=CH₂, —CH₂—C(CH₃)=CH—CH=CH₂, —CH₂—OCH₃, —CH(CH₃)—CH=CH—CH=CH₂, —CH=CH—CH₂—C(CH₃)=CH₂, —CH=CH—CH(CH₃)—CH=CH₂, —CH=C(CH₃)—CH₂—CH=CH₂, —C(CH₃)=CH—CH₂—CH=CH₂, —CH=CH—CH=C(CH₃)₂, —CH₂—C₆H₄—OCH₃, —CH=CH—C(CH₃)=CH—CH₃, —CH=C(CH₃)—CH=CH—CH₃, —CH₂—C₆H₄—OH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C≡C—C(CH₃)₃, —C₂H₄—CH(CH₃)—C≡CH, —CH₂—CH(CH₃)—CH₂—C≡CH, —CH₂—C≡C—CH(CH₃)₂, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —C≡C—CH(CH₃)—C₂H₅, —CH=C(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃;

and stereoisomeric forms, E/Z isomers, enantiomers, enantiomeric mixtures, diastereomers, diastereomeric mixtures, racemates, tautomers, anomers, keto-enol forms, betaine forms, solvates, hydrates as well as pharmacologically acceptable salts of the aforementioned compounds.

2. The method of claim 1, wherein the compound has the following general structure [B]:

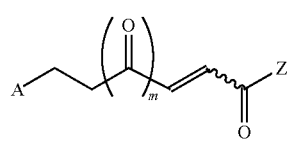

wherein

Z represents a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group and m is 0 or 1; and A represents a peptide residue, a peptide derivative or a peptidomimetic residue as defined in claim 9, wherein A has a secondarily or tertiarily substituted carbon atom to which the olefinic side chain and a carbonyl group are bound.

3. The method of claim 2, wherein the compound has the following general structure [C], [D], [E] or [F]:

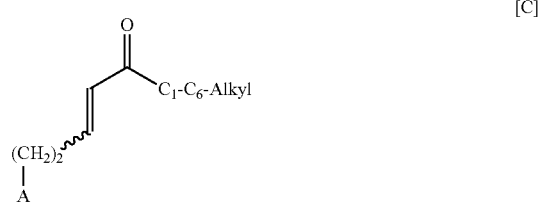

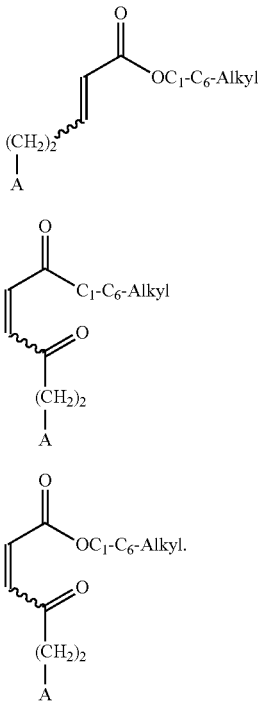

4. The method of claim 1, wherein A represents a peptide residue, a peptide derivative or a peptidomimetic residue as defined in claim 1, having at least one carbonyl group and up to 80 carbon atoms, wherein A has a secondarily or tertiarily substituted carbon atom to which the olefinic side chain and a carbonyl group are bound.

5. The method of claim 1 wherein A represents one of the following groups:
—S—$CR^{75}R^{76}R^{77}$, —S—CO—$CR^{75}R^{76}R^{77}$, —S—CO—Y, —S-E-X, —S-E-CHQ-X, —S-E-CHQ-$R^{75}$, —S-E-CHQ-NXX', —S—CHQ-X, —S—CHQ-$R^{75}$, —S—CHQ-NXX', —S—$CR^{75}R^{76}$—NXX', —NH—$CR^{75}R^{76}R^{77}$, —$NR^{78}$—$CR^{75}R^{76}R^{77}$, —NH—CO—$CR^{75}R^{76}R^{77}$, —$NR^{78}$—CO—$CR^{75}R^{76}R^{77}$, —NH—CO—Y, —$NR^{78}$—CO—Y, —NH-E-X, —$NR^{78}$-E-X, —NH-E-CHQ-X, —$NR^{78}$-E-CHQ-X, —NH-E-CHQ-$R^{75}$, —$NR^{78}$-E-CHQ-$R^{75}$, —NH-E-CHQ-NXX', —$NR^{78}$-E-CHQ-NXX', —NH—CHQ-X, —$NR^{78}$—CHQ-X, —NH—CHQ-$R^{75}$, —$NR^{78}$—CHQ-$R^{75}$, —NH—CHQ-NXX', —$NR^{78}$—CHQ-NXX', —NH—$CR^{75}R^{76}$—NXX', —$NR^{78}$—$CR^{75}R^{76}$—NXX', —$CR^{75}R^{76}R^{77}$, —$CR^{78}R^{79}$—CO—$CR^{75}R^{76}R^{77}$, —$CR^{78}R^{79}$—CO—Y, —$CR^{78}R^{79}$—X, —$CR^{78}R^{79}$—NXX', —$CR^{78}R^{79}$-E-X, —$CR^{78}R^{79}$-E-NXX', —$CR^{78}R^{79}$(-E-CHQ-X), —$CR^{78}R^{79}$(-E-CHQ-$R^{75}$), —$CR^{78}R^{79}$(-E-CHQ-NXX'), —$CR^{78}R^{79}$(—CHQ-X), —$CR^{78}R^{79}$(—CHQ-$R^{75}$), —$CR^{78}R^{79}$(—CHQ-NXX'), —$CR^{78}R^{79}$(—$CR^{75}Rv^{6}$-NXX'), —$CR^{78}$(—CO—Y)(—X), —$CR^{78}$(—CO—Y)(—NXX'), —$CR^{78}$(—CO—Y)(-E-X), —$CR^{78}$(—CO—Y)(-E-NXX'), —$CR^{78}$(—CO—Y)(-E-CHQ-X), —$CR^{78}$(—CO—Y)(-E-CHQ-$R^{75}$), —$CR^{78}$ (—CO—Y)(-E-CHQ-NXX'), —$CR^{78}$(—CO—Y) (—CHQ-X), —$CR^{78}$(—CO—Y)(—CHQ-$R^{75}$), —$CR^{78}$(—CO—Y)(—CHQ-NXX'), —$CR^{78}$(—CO—Y)(—$CR^{75}R^{76}$-NXX'), —$CR^{78}$(—X)(—CO—NX"-$CR^{79}Q'$-CO—Y), —$CR^{78}$(—NXX')(—CO—NX"—$CR^{79}Q'$-CO—Y);

E represents the following group —$CH_2$—, —$CF_2$—, —$C_2H_4$—, —$CH_2$—$CF_2$—, —$CF_2$—$CH_2$—, —CH=CH—, —CH(OH)—$CH_2$—, —C(=O)—$CH_2$—, —$CH_2$—NH—, —$CH_2$—O—, —CH(OH)—$CH_2$—NH—, —P(=O)(OH)—NH—, —P(=O)(OH)—O—, —P(=O)(OH)—S—, —P(=O)(OH)—$CH_2$—, —CH(OH)—$CH_2$—NH—, —C(=O)—NH—, —C(=O)—O— oder —C(=O)—NX"—;

Q and Q' independently of each other represent a side chain residue of a natural amino acid; or Q together with X" forms a propylenyl residue; or Q" together with X" forms a propylenyl residue;

Y represents a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group or Y represents a peptide residue of up to 6 amino acids and bound via an amide bond, the C-terminal carbonyl function of which peptide residue carries a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group; or Y represents a peptidomimetic residue of up to 30 carbon atoms and X" represents hydrogen or a $C_1$-$C_6$ alkyl group; and —NXX' is a amino group, —NH—CHO, $C_1$-$C_{10}$ alkylamino group, $C_1$-$C_8$ alkoxycarbonylamino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group; or the group —NXX' is part of a peptidomimetic residue of up to 30 carbon atoms or X' represents hydrogen or a $C_1$-$C_6$ alkyl group; and X represents a peptide residue of up to 6 amino acids and bound via an amide bond, the N-terminus of which peptide residue carries an amino group, —NH—CHO, $C_1$-$C_{10}$ alkylamino group, $C_1$-$C_8$ alkoxycarbonylamino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group; wherein any of the $C_1$-$C_6$ alkoxy groups, $C_1$-$C_6$ alkyl groups, $C_1$-$C_{10}$ alkylamino groups, $C_1$-$C_8$ alkoxycarbonylamino groups, $C_6$-$C_{12}$ aralkyloxycarbonyl amino group, $C_1$-$C_{10}$ dialkylamino groups, $C_2$-$C_6$ nitrogen heterocycles as well as $C_3$-$C_5$ nitrogen heteroaryl groups can be independently substituted with up to 5 residues selected from $R^{80}$, $R^{81}$, $R^{82}R^{83}$, $R^{84}$, wherein the residues $R^{75}$—$R^{84}$ independently of each other represent the following groups: —H, —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —OPh, —$OCH_2$-Ph, —$OCPh_3$, —SH, —$SCH_3$, —$SC_2H_5$, —$SC_3H_7$, —S-cyclo-$C_3H$, —$SCH(CH_3)_2$, —$SC(CH_3)_3$, —$NO_2$, —F, —Cl, —Br, —I, —$N_3$, —CN, —OCN, —NCO, —SCN, —NCS, —CHO, —$COCH_3$, —$COC_2H_5$, —$COC_3H_7$, —CO-cyclo-$C_3H_5$, —$COCH(CH_3)_2$, —$COC(CH_3)_3$, —COOH, —COCN, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —$CONH[CH(CH_3)_2]$, —$CONH[C(CH_3)_3]$, —$CON(CH_3)_2$, —$CON(C_2H_5)_2$, —$CON(C_3H_7)_2$, —$CON(cyclo-C_3H_5)_2$, —$CON[CH(CH_3)_2]_2$, —$CON[C(CH_3)_3]_2$, —$NHCOCH_3$, —$NHCOC_2H_5$, —$NHCOC_3H_7$, —NHCO-cyclo-C₃HS, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —OCF₃, —OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—CO—NH-cyclo-C₃H₅, —NH—CO—NH[CH(CH₃)₂], —NH—CO—NH[C(CH₃)₃], —NH—CO—N(CH₃)₂, —NH—CO—N(C₂H₅)₂, —NH—CO—N(C₃H₇)₂, —NH—CO—N(cyclo-C₃Hs)₂, —NH—CO—N[CH(CH₃)₂]₂, —NH—CO—N[C(CH₃)₃]₂, —NH—CS—NH₂, —NH—CS—NHCH₃, —NH—CS—NHC₂H₅, —NH—CS—NHC₃H₇, —NH—CS—NH-cyclo-C₃Hs, —NH—CS—NH[CH(CH₃)₂], —NH—CS—NH[C(CH₃)₃], —NH—CS—N(CH₃)₂, —NH—CS—N(C₂H₅)₂, —NH—CS—N(C₃H₇)₂, —NH—CS—N(cyclo-C₃Hs)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —OC₆H₄—OCH₃, —NH—C(=NH)—NH-cyclo-C₃H₅, —NH—C(=NH)—NH[CH(CH₃)₂], —CF₂Cl, —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H)₂, —OC₆H₄—CH₃, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NHC₃H₇, —O—CO—NH-cyclo-C₃H₅, —O—CO—NH[CH(CH₃)₂], —O—CO—NH[C(CH₃)₃], —O—CO—N(CH₃)₂, —O—CO—N(C₂H₅)₂, —O—CO—N(C₃H₇)₂, —O—CO—N(cyclo-C₃H)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃Hs, —O—CO—OCH(CH₃)₂, —O—CO—OC(CH₃)₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-C₅H₉, cyclo-C₆H₁₁, cyclo-C₇H₁₃, cyclo-C₈H₁₅, -Ph, —CH₂-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —C₇H₁₅, —C₈H₁₇, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —CH₂—CH₂—CH₂—OCH₃, —C₂H₄—CH(CH₃)—CH=CH₂, —CH₂—CH(CH₃)—CH₂—CH=CH₂, —CH₂NH₂, —CH(CH₃)—C₂H₄—CH=CH₂, —C₂H₄—CH=C(CH₃)₂, —C₂H₄—C(CH₃)=CH—CH₃, —CH₂—C(CH₃)₂—CH=CH—CH₃, —CH(CH₃)—CH₂—CH=CH—CH₃, —CH₂OH, —CH₂SH, —CH₂—CH=CH—CH(CH₃)₂, —CH₂—CH=C(CH₃)—C₂H₅, —CH₂—CH₂—CH₂NH₂, —CH₂—C(CH₃)=CH—C₂H₅, —CH(CH₃)—CH=CH—C₂H₅, —CH₂—CH₂NH₂, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —CH₂—CH₂SH, —CH(CH₃)—CH₂—C(CH₃)=CH₂, —CH(CH₃)—CH(CH₃)—CH=CH₂, —CH₂—CH₂—CH₂OH, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH₂—CH₂—CH₂SH, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —C₆H₄—OCH₃, —CH₂—CH=CH—CH₂—CH=CH₂, —CH=CH—C₂H₄—CH=CH₂, —C₆H₄—OH, —CH₂—CH=CH—CH=CH—CH₃, —CH=CH—CH₂—CH=CH—CH₃, —CH₂—CH₂—OCH₃, —CH=CH—CH=CH—C₂H₅, —CH₂—CH=CH—C(CH₃)=CH₂, —CH₂—CH₂OH, —CH₂—CH=C(CH₃)—CH=CH₂, —CH₂—C(CH₃)=CH—CH=CH₂, —CH₂—OCH₃, —CH(CH₃)—CH=CH—CH=CH₂, —CH=CH—CH₂—C(CH₃)=CH₂, —CH=CH—CH(CH₃)—CH=CH₂, —CH=C(CH₃)—CH₂—CH=CH₂, —C(CH₃)=CH—CH₂—CH=CH₂, —CH₂—CH=C(CH₃)₂, —CH₂—C₆H₄—OCH₃, —CH=CH—C(CH₃)=CH—CH₃, —CH=C(CH₃)—CH=CH—CH₃, —CH₂—C₆H₄—OH, —C(CH₃)=CH—CH=CH—CH₃, —CH=C(CH₃)—C(CH₃)=CH₂, —C(CH₃)=C(CH₃)—CH=CH₂, —C(CH₃)=C(CH₃)—CH=CH₂, —C(CH₃)=C(CH₃)—CH=CH₂, —CH=CH—CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —C$_2$H$_4$—CH(CH$_3$)—C≡CH, —CH$_2$—CH(CH$_3$)—CH$_2$—C≡CH, —CH$_2$—C≡C—CH(CH$_3$)$_2$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH$_3$, —CH$_2$—CH(C≡CH)$_2$, —CH(C≡CH)—C≡C—CH$_3$.

6. The method of claim 1, wherein residue A comprises at least two natural or synthetic amino acids linked to each other.

7. A method of inhibiting the biological activity of transglutaminases in a subject comprising administering to a subject an effective amount of a compound which has one of the following general formulas (I), (II) or (III):

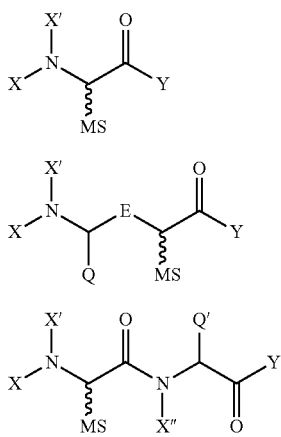

MS is the Michael system of the following structure

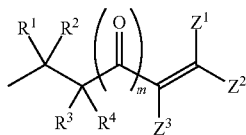

and

E represents the following group —CH$_2$—, —CF$_2$—, —C$_2$H$_4$—, —CH$_2$—CF$_2$, —CF$_2$—CH$_2$—, —CH=CH—, —CH(OH)—CH$_2$—, —C(=O)—CH$_2$—, —CH$_2$—NH—, —CH$_2$—O—, —CH(OH)—CH$_2$—NH—, —P(=O)(OH)—NH—, —P(=O)(OH)—O—, —P(=O)(OH)—S—, —P(=O)(OH)—CH$_2$—, —CH(OH)—CH$_2$—NH—, —C(=O)—NH—, —C(=O)—O— or —C(=O)—NX″—;

m is 0 or 1;

the residues $Z^1$, $Z^2$, $Z^3$ independently of each other represent the following groups:

—H, —CO—($C_1$-$C_6$ alkyl), —CO—$R^6$, —CO—$R^7$, —CO—($C_1$-$C_6$ halogenalkyl), —CO—($C_3$-$C_{10}$ heteroaryl), —CO—($C_6$-$C_{15}$ aryl), —COO—($C_1$-$C_6$ halogenalkyl), —COO—($C_3$-$C_{10}$ heteroaryl), —COO—($C_6$-$C_{15}$ aryl), —COO—($C_1$-$C_6$ alkyl), —COO—$R^8$, —COO—$R^9$, —CN, —F, —Cl, —COOH, —CO—NH($C_1$-$C_6$ alkyl), —CO—N($C_1$-$C_6$ alkyl)(C—$C_6$ alkyl), —CO—NR$^{10}$R$^{11}$, —CO—NH$_2$, —CO—N(CR$^{12}$R$^{13}$R$^{14}$)(CR$^{15}$R$^{16}$R$^{17}$), —CH$_2$CN, —CH$_2$F, —CHF$_2$, —CF$_3$, —OCF$_3$, —CH$_2$—CF$_3$, —CF$_2$—CF$_3$, —NO$_2$, —CS—($C_1$-$C_6$ alkyl), —CS—$R^{18}$, —CS—$R^{19}$, —CS—O—($C_1$-$C_6$ alkyl), —CS—O—$R^{20}$, —CS—O—$R^{21}$, —CS—N($C_1$-$C_6$ alkyl)($C_1$-$C_6$ alkyl), —CS—NR$^{22}$R$^{23}$, —CS—NH$_2$, —CS—N(CR$^{24}$R$^{25}$R$^{26}$)(CR$^{27}$R$^{28}$R$^{29}$), —SO—$R^{30}$, —SO—$R^{31}$, —SO$_2$—$R^{32}$, —SO$_2$—$R^{33}$, —SO—CR$^{34}$R$^{35}$R$^{36}$, —SO—CR$^{37}$R$^{38}$R$^{39}$, —SO$_2$—CR$^{40}$R$^{41}$R$^{42}$, —SO$_2$—CR$^{43}$R$^{44}$R$^{45}$, —SO—N($C_1$-$C_6$ alkyl)($C_1$-$C_6$ alkyl), —SO—NR$^{46}$R$^{47}$, —SO—NH$_2$, —SO—N(CR$^{48}$R$^{49}$R$^{50}$)(CR$^{51}$R$^{52}$R$^{53}$), —SO$_2$—N($C_1$-$C_6$ alkyl)($C_1$-$C_6$ alkyl), —SO$_2$—NR$^{54}$R$^{55}$, —SO$_2$—NH$_2$ —SO$_2$—N(CR$^{56}$R$^{57}$R$^{58}$)(CR$^{59}$R$^{60}$R$^{61}$), —SO$_2$—OH, —SO$_2$—OR$^{62}$, —SO$_2$—C R$^{63}$R$^{64}$R$^{65}$, —SO$_2$—OCR$^{66}$R$^{67}$R$^{68}$, —O—P(O)(OH)$_2$, —O—P(O)(OR$^{69}$)(OR$^{70}$), —O—P(O)(O—$C_1$-$C_6$ alkyl)(O—$C_1$-$C_6$ alkyl), —P(O)(OR$^{71}$)(OR$^{72}$), —P(O)(O—$C_1$-$C_6$ alkyl)(O—$C_1$-$C_6$ alkyl), —CF$_2$—P(O)(OR$^{73}$)(OR$^{74}$), —CF$_2$—P(O)(O—$C_1$-$C_6$ alkyl)(O—$C_1$-$C_6$ alkyl), wherein at least one of the residues $Z^1$, $Z^2$, $Z^3$ is different from hydrogen;

the residues $Z^1$ and $Z^2$ together may also represent a residue —CO—O—CO—CH$_2$—, —CO—O—CH$_2$—CH$_2$, the residues $Z^2$ and $Z^3$ together may also represent a residue —CO—Z′—CH$_2$—, —CO—O—CH$_2$—, —CO—CH$_2$—CH$_2$, —CO—O—CO—, —CO—NH—CO— or —Z′—CH$_2$—CH$_2$, wherein Z′ represents one of the following groups: —CH$_2$—, —CF$_2$—, —C$_2$H$_4$—CF$_2$—CH$_2$—, —CH$_2$—CH$_2$—, —O—, —O—CH$_2$—, —NH— or —NH—CH$_2$—;

Q and Q′ independently of each other represent a side chain residue of a natural amino acid; or Q together with X′ forms a propylenyl residue; or Q′ together with X″ forms a propylenyl residue;

Y represents a hydroxy group, amino group, $C_1$-$C_6$ alkylamino group, $C_1$-$C_6$ dialkylamino group, $C_1$-$C_6$ alkoxy group, $C_6$-$C_{19}$ aryloxy group, $C_1$-$C_6$ alkyl group, $C_1$-$C_6$ halogenalkyl group, $C_3$-$C_{10}$ heteroaryl group or a $C_6$-$C_{15}$ aryl group; or Y represents a peptide residue as defined in claim 1 of up to 6 amino acids and bound via an amide bond, the C-terminal carbonyl function of which peptide residue carries a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$n heteroaryl group or a $C_6$-$C_{15}$ aryl group; or Y represents a peptidomimetic residue as defined in claim 1 of up to 60 carbon atoms and X" represents hydrogen or a $C_1$-$C_6$ alkyl group; and —NXX' is an amino group, $C_1$-$C_{10}$ alkylamino group, $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group; or the group —NXX' is part of a peptidomimetic residue as defined in claim 1 of up to 60 carbon atoms or X' represents hydrogen or a $C_1$-$C_6$ alkyl group; and X represents a peptide residue of up to 6 amino acids and bound via an amide bond, the N-terminus of which peptide residue carries an amino group, $C_1$-$C_{10}$ alkylamino group, $C_1$-$C_8$-alkyloxycarbonylamino group $C_6$-$C_{12}$ aralkyloxycarbonyl amino group, $C_1$-$C_{10}$ dialkylamino group, $C_2$-$C_6$ nitrogen heterocycle or a $C_3$-$C_5$ nitrogen heteroaryl group; wherein any of the $C_1$-$C_6$ alkoxy groups, $C_1$-$C_6$ alkyl groups, $C_1$-$C_{10}$ alkylamino groups, $C_1$-$C_8$-alkyloxycarbonylamino groups, $C_6$-$C_{12}$ aralkyloxycarbonyl amino group, $C_1$-$C_{10}$ dialkylamino groups, $C_2$-$C_6$ nitrogen heterocycles as well as $C_3$-$C_5$-nitrogen heteroaryl groups can be independently substituted with up to 5 residues selected from $R^{80}$, $R^{81}$, $R^{82}$, $R^{83}$, $R^{84}$, wherein the residues $R^1$—$R^{84}$ independently of each other represent the following groups: —H, —OH, —$OCH_3$, —$OC_2H_5$, $OC_3H_7$, —O-cyclo-$C_3H_5$, —$OCH(CH_3)_2$, —$OC(CH_3)_3$, —$OC_4H_9$, —OPh, —$OCH_2$-Ph, —$OCPh_3$, —SH, —$SCH_3$, —$SC_2H_5$, —$SC_3H_7$, —S-cyclo-$C_3H_5$, —$SCH(CH_3)_2$, —$SC(CH_3)_3$, —$NO_2$, —F, —Cl, —Br, —I, —$N_3$, —CN, —OCN, —NCO, —SCN, —NCS, —CHO, —$COCH_3$, —$COC_2H_5$, —$COC_3H_7$, —CO-cyclo-$C_3H_5$, —$COCH(CH_3)_2$, —$COC(CH_3)_3$, —COOH, —COCN, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —$CONH[CH(CH_3)_2]$, —$CONH[C(CH_3)_3]$, —$CON(CH_3)_2$, —$CON(C_2H_5)_2$, —$CON(C_3H_7)_2$, —CON(cyclo-$C_3H_5)_2$, —$CON[CH(CH_3)_2]_2$, —$CON[C(CH_3)_3]_2$, —$NHCOCH_3$, —$NHCOC_2H_5$, —$NHCOC_3H_7$, —NHCO-cyclo-$C_3H_5$, —NHCO—$CH(CH_3)_2$, —NHCO—$C(CH_3)_3$, —NHCO—$OCH_3$, —NHCO—$OC_2H_5$, —NHCO—$OC_3H_7$, —NHCO—O-cyclo-$C_3H_5$, —NHCO—$OCH(CH_3)_2$, —NHCO—$OC(CH_3)_3$, —$NH_2$, —$NHCH_3$, —$NHC_2H_5$, —$NHC_3H_7$, —NH-cyclo-$C_3H_5$, —$NHCH(CH_3)_2$, —$NHC(CH_3)_3$, —$N(CH_3)_2$, —$N(C_2H_5)_2$, —$N(C_3H_7)_2$, —N(cyclo-$C_3H_5)_2$, —$N[CH(CH_3)_2]_2$, —$N[C(CH_3)_3]_2$, —$SOCH_3$, —$SOC_2H_5$, —$SOC_3H_7$, —SO-cyclo-$C_3H_5$, —$SOCH(CH_3)_2$, —$SOC(CH_3)_3$, —$SO_2CH_3$, —$SO_2C_2H_5$, —$SO_2C_3H_7$, —$SO_2$-cyclo-$C_3H_5$, —$SO_2CH(CH_3)_2$, —$SO_2C(CH_3)_3$, —$SO_3H$, —$SO_3CH_3$, —$SO_3C_2H_5$, —$SO_3C_3H_7$, —$SO_3$-cyclo-$C_3H_5$, —$SO_3CH(CH_3)_2$, —$SO_3C(CH_3)_3$, —$OCF_3$, —$OC_2F_5$, —O—$COOCH_3$, —O—$COOC_2H_5$, —O—$COOC_3H_7$, —O—COO—cyclo-$C_3H_5$, —O—$COOCH(CH_3)_2$, —O—$COOC(CH_3)_3$, —NH—CO—$NH_2$, —NH—CO—$NHCH_3$, —NH—CO—$NHC_2H_5$, —NH—CO—$NHC_3H_7$, —NH—CO—NH-cyclo-$C_3H_5$, —NH—CO—$NH[CH(CH_3)_2]$, —NH—CO—$NH[C(CH_3)_3]$, —NH—CO—$N(CH_3)_2$, —NH—CO—$N(C_2H_5)_2$, —NH—CO—$N(C_3H_7)_2$, —NH—CO—N(cyclo-$C_3H_5)_2$, —NH—CO—$N[CH(CH_3)_2]_2$, —NH—CO—$N[C(CH_3)_3]_2$, —NH—CS—$NH_2$, —NH—CS—$NHCH_3$, —NH—CS—$NHC_2H_5$, —NH—CS—$NHC_3H_7$, —NH—CS—NH-cyclo-$C_3H_5$, —NH—CS—$NH[CH(CH_3)_2]$, —NH—CS—$NH[C(CH_3)_3]$, —NH—CS—$N(CH_3)_2$, —NH—CS—$N(C_2H_5)_2$, —NH—CS—$N(C_3H_7)_2$, —NH—CS—N(cyclo-$C_3H_5)_2$, —NH—CS—$N[CH(CH_3)_2]_2$, —NH—CS—$N[C(CH_3)_3]_2$, —NH—C(=NH)—$NH_2$, —NH—C(=NH)—$NHCH_3$, —NH—C(=NH)—$NHC_2H_5$, —NH—C(=NH)—$NHC_3H_7$, —$OC_6H_4$—$OCH_3$, —NH—C(=NH)—NH-cyclo-$C_3H_5$, —NH—C(=NH)—$NH[CH(CH_3)_2]$, —$CF_2Cl$, —NH—C(=NH)—$NH[C(CH_3)_3]$, —NH—C(=NH)—$N(CH_3)_2$, —NH—C(=NH)—$N(C_2H_5)_2$, —NH—C(=NH)—$N(C_3H_7)_2$, —NH—C(=NH)—N(cyclo-$C_3H_5)_2$, —$OC_6H_4$—$CH_3$, —NH—C(=NH)—$N[CH(CH_3)_2]_2$, —NH—C(=NH)—$N[C(CH_3)_3]_2$, —O—CO—$NH_2$, —O—CO—$NHCH_3$, —O—CO—$NHC_2H_5$, —O—CO—$NHC_3H_7$, —O—CO—NH-cyclo-$C_3H_5$, —O—CO—$NH[CH(CH_3)_2]$, —O—CO—$NH[C(CH_3)_3]$, —O—CO—$N(CH_3)_2$, —O—CO—$N(C_2H_5)_2$, —O—CO—$N(C_3H_7)_2$, —O—CO—N(cyclo-$C_3H_5)_2$, —O—CO—$N[CH(CH_3)_2]_2$, —O—CO—$N[C(CH_3)_3]_2$, —O—CO—$OCH_3$, —O—CO—$OC_2H_5$, —O—CO—$OC_3H_7$, —O—CO—O-cyclo-$C_3H_5$, —O—CO—$OCH(CH_3)_2$, —O—CO—$OC(CH_3)_3$, —$CH_2F$, —$CHF_2$, —$CF_3$, —$CH_2Cl$, —$CH_2Br$, —$CH_2I$, —$CH_2$—$CH_2F$, —CH—$CHF_2$, —$CH_2$—$CF_3$, —$CH_2$—$CH_2Cl$, —$CH_2$—$CH_2Br$, —$CH_2$—$CH_2I$, cyclo-$C_3H_5$, cyclo-$C_4H_7$, cyclo-$C_5H_9$, cyclo-$C_6H_{11}$, cyclo-$C_7H_{13}$, cyclo-$C_8H_{15}$, -Ph, —$CH_2$-Ph, —$CPh_3$, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —CH=$CH_2$, —$CH_2$—CH=$CH_2$, —C($CH_3$)=$CH_2$, —CH=CH—$CH_3$, —$C_2H_4$—CH=$CH_2$, —$C_7H_{15}$, —$C_8H_{17}$, —$CH_2$—CH=CH—$CH_3$, —CH=CH—$C_2H_5$, —$CH_2$—C($CH_3$)=$CH_2$, —CH($CH_3$)—CH=CH, —CH=C($CH_3$)_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$C_2H_4$—C($CH_3$)=$CH_2$, —$CH_2$—CH($CH_3$)—CH=$CH_2$, —CH($CH_3$)—$CH_2$—CH=$CH_2$, —$CH_2$—CH=C($CH_3$)_2$, —$CH_2$—C($CH_3$)=CH—$CH_3$, —CH($CH_3$)—CH=CH—$CH_3$, —CH=CH—CH($CH_3$)_2$, —CH=C($CH_3$)—$C_2H_5$, —C($CH_3$)=CH—$C_2H_5$, —C($CH_3$)=C($CH_3$)_2$, —C($CH_3$)_2$—CH=$CH_2$, —CH($CH_3$)—C($CH_3$)=$CH_2$, —C($CH_3$)=CH—CH=$CH_2$, —CH=C($CH_3$)—CH=$CH_2$, —CH=CH—C($CH_3$)=$CH_2$, —$C_4H_8$—CH=$CH_2$, —$C_3H_6$—CH=CH—$CH_3$, —$C_2H_4$—CH=CH—$C_2H_5$, —$CH_2$—CH=CH—$C_3H_7$, —CH=CH—$C_4H_9$, —$C_3H_6$—C($CH_3$)=$CH_2$, —$CH_2$—$CH_2$—$CH_2$—$OCH_3$, —$C_2H_4$—CH($CH_3$)—

CH=CH$_2$, —CH$_2$—CH(CH$_3$)—CH$_2$—CH=CH$_2$, —CH$_2$NH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$OH, —CH$_2$SH, —CH$_2$—CH=CH—CH(CH$_3$)$_2$, —CH$_2$—CH=C(CH$_3$)—C$_2$H$_5$, —CH$_2$—CH$_2$—CH$_2$NH$_2$, —CH$_2$—C(CH$_3$)=CH—C$_2$H$_5$, —CH(CH$_3$)—CH=CH—C$_2$H$_5$, —CH$_2$—CH$_2$NH$_2$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH$_2$—CH$_2$SH, —CH(CH$_3$)—CH$_2$—C(CH$_3$)=CH$_2$, —CH(CH$_3$)—CH(CH$_3$)—CH=CH$_2$, —CH$_2$—CH$_2$—CH$_2$OH, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH$_2$—CH$_2$—CH$_2$SH, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$), —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —C$_6$H$_4$—OCH$_3$, —CH$_2$—CH=CH—CH=CH$_2$, —CH=CH—C$_2$H$_4$—CH=CH$_2$, —C$_6$H$_4$—OH, —CH$_2$—CH=CH—CH=CH—CH$_3$, —CH=CH—CH$_2$—CH=CH—CH$_3$, —CH$_2$—CH$_2$—OCH$_3$, —CH=CH—CH=CH—C$_2$H$_5$, —CH$_2$—CH=CH—C(CH$_3$)=CH$_2$, —CH$_2$—CH$_2$OH, —CH$_2$—CH=C(CH$_3$)—CH=CH$_2$, —CH$_2$C(CH$_3$)=CH—CH=CH$_2$, —CH$_2$—OCH$_3$, —CH(CH$_3$)—CH=CH—CH=CH$_2$, —CH=CH—CH=C(CH$_3$)=CH$_2$, —CH=CH—CH(CH$_3$)—CH=CH$_2$, —CH=C(CH$_3$)—CH$_2$—CH=CH$_2$, —C(CH$_3$)=CH—CH$_2$—CH=CH$_2$, —CH=CH—CH=C(CH$_3$)$_2$, —CH$_2$—C$_6$H$_4$—OCH$_3$, —CH=CH—C(CH$_3$)=CH—CH$_3$, —CH=C(CH$_3$)—CH=CH—CH$_3$, —CH$_2$—C$_6$H$_4$—OH, —C(CH$_3$)=CH—CH=CH—CH$_3$, —CH=C(CH$_3$)—C(CH$_3$)=CH$_2$, —C(CH$_3$)=CH—C(CH$_3$)CH$_2$, —C(CH$_3$)=C(CH$_3$—CH=CH$_2$, —CH=CH—CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —C$_2$H$_4$—CH(CH$_3$)—C≡CH, —CH$_2$—CH(CH$_3$)—CH$_2$—C≡CH, —CH$_2$—C≡C—CH(CH$_3$)$_2$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(C$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH, —CH$_2$—CH(C≡CH)$_2$, —CH(C≡CH)—C≡C—CH$_3$;

and stereoisomeric forms, E/Z isomers, enantiomers, enantiomeric mixtures, diastereomers, diastereomeric mixtures, racemates, tautomers, anomers, keto-enol forms, betaine forms, solvates, hydrates as well as pharmacologically acceptable salts of the aforementioned compounds.

8. The method of claim 7, wherein MS has the following meaning:

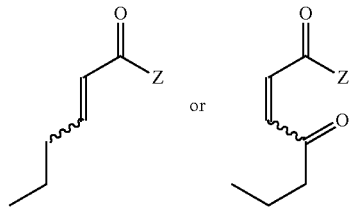

and wherein

Z represents a hydroxy group, amino group, $C_1$-$C_6$ alkylamino group, $C_1$-$C_6$ dialkylamino group, $C_1$-$C_6$ alkoxy group, $C_1$-$C_6$ alkyl group, $C_1$-$C_6$ halogenalkyl group, $C_3$-$C_{10}$ heteroaryl group or a $C_6$-$C_{15}$ aryl group.

9. A method of inhibiting the biological activity of transglutaminases in a subject comprising administering to the subject an effective amount of a compound of the general structure [A*] as defined in claim 1 for the treatment or prophylaxis of coeliac disease, fibroses, thrombosis, neurodegenerative diseases, Huntington's disease, Parkinson's disease, Alzheimer's disease, cataract, acne, psoriasis, skin aging, candidosis and other transglutaminase dependent diseases.

* * * * *